US012600783B2

(12) United States Patent
Bray et al.

(10) Patent No.: US 12,600,783 B2
(45) Date of Patent: Apr. 14, 2026

(54) ANTI-NEW YORK ESOPHAGEAL SQUAMOUS CELL CARCINOMA 1 (NY-ESO-1) ANTIGEN-BINDING PROTEINS AND METHODS OF USE THEREOF

(71) Applicant: Regeneron Pharmaceuticals, Inc., Tarrytown, NY (US)

(72) Inventors: Kevin A. Bray, Tarrytown, NY (US); Frank Delfino, Tarrytown, NY (US); David Dilillo, Tarrytown, NY (US); Matthew C. Franklin, Tarrytown, NY (US); Jessica Kirshner, Tarrytown, NY (US); Douglas MacDonald, Tarrytown, NY (US)

(73) Assignee: Regeneron Pharmaceuticals, Inc., Tarrytown, NY (US)

( * ) Notice: Subject to any disclaimer, the term of this patent is extended or adjusted under 35 U.S.C. 154(b) by 1111 days.

(21) Appl. No.: 17/622,307

(22) PCT Filed: Jul. 2, 2020

(86) PCT No.: PCT/US2020/040642
§ 371 (c)(1),
(2) Date: Dec. 23, 2021

(87) PCT Pub. No.: WO2021/003357
PCT Pub. Date: Jan. 7, 2021

(65) Prior Publication Data
US 2022/0251215 A1 Aug. 11, 2022

Related U.S. Application Data

(60) Provisional application No. 63/021,826, filed on May 8, 2020, provisional application No. 63/020,177, filed on May 5, 2020, provisional application No. 62/870,232, filed on Jul. 3, 2019.

(51) Int. Cl.
| | |
|---|---|
| *C07K 16/28* | (2006.01) |
| *A61K 31/7088* | (2006.01) |
| *A61K 40/11* | (2025.01) |
| *A61K 40/31* | (2025.01) |
| *A61K 40/42* | (2025.01) |
| *A61P 35/00* | (2006.01) |
| *C07K 16/30* | (2006.01) |

(52) U.S. Cl.
CPC ...... *C07K 16/2833* (2013.01); *A61K 31/7088* (2013.01); *A61K 40/11* (2025.01); *A61K 40/31* (2025.01); *A61K 40/4269* (2025.01); *A61P 35/00* (2018.01); *C07K 16/3076* (2013.01); *A61K 2239/31* (2023.05); *A61K 2239/38* (2023.05); *A61K 2239/57* (2023.05); *C07K 2317/24* (2013.01); *C07K 2317/32* (2013.01); *C07K 2317/34* (2013.01); *C07K 2317/622* (2013.01); *C07K 2317/71* (2013.01); *C07K 2317/92* (2013.01); *C07K 2319/03* (2013.01)

(58) Field of Classification Search
CPC ........... C07K 16/2833; C07K 16/3076; C07K 2317/24; C07K 2317/32; C07K 2317/34; C07K 2317/622; C07K 2317/71; C07K 2317/92; C07K 2319/03; C07K 14/7051; C07K 14/70521; C07K 14/70578; C07K 2317/565; C07K 2319/33; C07K 2319/74; C07K 2319/02; A61K 31/7088; A61K 40/11; A61K 40/31; A61K 40/4269; A61K 2239/31; A61K 2239/38; A61K 2239/57; A61K 45/06; A61K 2039/505; A61K 2121/00; A61K 2300/00; A61P 35/00; C12N 5/0636; C12N 2510/00
See application file for complete search history.

(56) References Cited

U.S. PATENT DOCUMENTS

| | | |
|---|---|---|
| 2003/0175250 A1 | 9/2003 | Jager et al. |
| 2016/0081314 A1 | 3/2016 | Thurston et al. |
| 2018/0037104 A1 | 2/2018 | Al et al. |
| 2018/0258187 A1 | 9/2018 | Cheung et al. |
| 2018/0371049 A1 | 12/2018 | Boulter et al. |
| 2019/0002522 A1 | 1/2019 | Odunsi et al. |

FOREIGN PATENT DOCUMENTS

| | | |
|---|---|---|
| EP | 4144370 A1 | 3/2023 |
| WO | WO-2005/113595 A2 | 12/2005 |
| WO | WO-2008/110372 A1 | 9/2008 |
| WO | WO-2010/106431 A2 | 9/2010 |
| WO | WO-2016/210365 A2 | 12/2016 |
| WO | WO-2018/132739 A2 | 7/2018 |

(Continued)

OTHER PUBLICATIONS

Chen et al., "A testicular antigen aberrantly expressed in human cancers detected by autologous antibody screening", Proc. Natl. Acad. Sci., vol. 94, pp. 1914-1918 (1997).

(Continued)

*Primary Examiner* — Julie Wu
*Assistant Examiner* — Amber K Faust
(74) *Attorney, Agent, or Firm* — McCarter & English, LLP; Marcie B. Clarke, Esq.; Deborah L. Nagle

(57) ABSTRACT

The present disclosure provides antigen-binding proteins that specifically bind to an H LA-displayed New York esophageal squamous cell carcinoma 1 (NY-ESO-1) peptide, and therapeutic and diagnostic methods of using those binding proteins. The antigen-binding proteins of the present disclosure bind with a high degree of specificity to HLA-displayed NY-ESO-1 and do not bind to HLA-displayed peptides that differ by 2, 3, 4, 5 or more amino acids.

46 Claims, 3 Drawing Sheets

Specification includes a Sequence Listing.

(56) References Cited

FOREIGN PATENT DOCUMENTS

| WO | WO-2019/084538 A1 | 5/2019 |
| WO | WO-2021016585 A1 | 1/2021 |
| WO | WO-2021/226063 A1 | 11/2021 |

OTHER PUBLICATIONS

Stockert et al., "A Survey of the Humoral Immune Response of Cancer Patients to a Panel of Human Tumor Antigens," J. Exp. Med., vol. 187(8), pp. 1349-1354 (1998).

Irving et al., "Interplay between T cell receptor binding kinetics and the level of cognate peptide presented by major histocompatibility complexes governs CD 8+ T cell responsiveness" J Biol Chem, (May 1, 2012), vol. 287, No. 27, doi:10.1074/jbc.M112.357673, pp. 23068-23078.

Dhanik et al., "In-silico discovery of cancer-specific peptide-HLA complexes for targeted therapy" BMC Bioinformatics, (Jul. 20, 2016), vol. 17, doi:10.1186/s12859-016-1150-2, pp. 1-14.

Dunbar et al., Examining Variable Domain Orientations in Antigen Receptors Gives Insight into TCR-Like Antibody Design# PLoS Comput Biol, (Sep. 18, 2014), vol. 10, No. 9, doi:10.1371/journal. pcbi.1003852, pp. 1-10.

Maus et al., "An MHC-restricted antibody-based chimeric antigen receptor requires TCR-like affinity to maintain antigen specificity" Mol Ther Oncolytics, (Jan. 11, 2017), vol. 3, doi:10.1038/mto.2016. 23, pp. 1-9.

Stewart-Jones et al., "Rational development of high-affinity T-cell receptor-like Antibodies", Proc Natl Acad Sci U S A . Apr. 7, 2009:106(14):5784-8.

Zoete et al., "Structure-Based, Rational Design of T Cell Receptors", Front Immunol, (20130912), vol. 4, doi:10.3389/fimmu.2013. 00268, pp. 1-19.

Robbins, et al: "Tumor regression in patients with metastatic synovial cell sarcoma and melanoma using genetically engineered lymphocytes reactive with NYESO-1". J Clin Oncol. Mar. 1, 2011;29(7):917-24.

Romero, et al. "CD8+ T-Cell Response to NY-ESO-1: Relative Antigenicity and in Vitro Immunogenicity of Natural and Analogue Sequences" (2001) Clin Cancer Res 7(3, Suppl):766S-772S).

Derre, et al. "Distinct sets of ab TCRs confer similar recognition of tumor antigen NY-ESO-1157-165 by interacting with its central Met/Trp residues" (2008) Proc Natl Acad Sci USA 105(39):15010-150150.

International Search Report and Written Opinion from PCT/US2020/040642, mailed Oct. 22, 2020.

ANTI-NEW YORK ESOPHAGEAL SQUAMOUS CELL CARCINOMA 1 (NY-ESO-1) ANTIGEN-BINDING PROTEINS AND METHODS OF USE THEREOF

RELATED APPLICATIONS

The instant application is a 35 U.S.C. § 371 national stage filing of International Application No. PCT/US2020/040642, filed on Jul. 2, 2020, which claims priority to U.S. Provisional Patent Application No. 62/870,232, filed on Jul. 3, 2019, U.S. Provisional Patent Application No. 63/020,177, filed on May 5, 2020, and U.S. Provisional Patent Application No. 63/021,826, filed on May 8, 2020. The entire contents of each of the foregoing are incorporated herein by reference.

SEQUENCE LISTING

The instant application contains a Sequence Listing which has been filed electronically in ASCII format and is hereby incorporated by reference in its entirety. Said ASCII copy, created on Jul. 2, 2020 is named 118003_10520_SL.txt and is 245,227 bytes in size.

FIELD

The present disclosure is related to antigen-binding proteins that specifically bind to an HLA-displayed New York esophageal squamous cell carcinoma 1 (NY-ESO-1) peptide, and therapeutic and diagnostic methods of using those binding proteins.

BACKGROUND

New York esophageal squamous cell carcinoma 1 (NY-ESO-1) is a cancer-testis antigen (CTAs) also referred to as CTAG1B. Expression of NY-ESO-1, encoded by the CTAG1B gene, is restricted to germ cells. NY-ESO-1 is, however, frequently re-expressed aberrantly by different tumor types. The main protein product of the CTAG1B gene is a 180 amino acid long 18 KDa protein, with a glycine-rich N-terminal region and an extremely hydrophobic C-terminal region. The function of NY-ESO-1, however, remains unclear.

Spontaneous CD8+ and CD4+ T-cell responses to NY-ESO-1 in cancer patients have been observed and analyzed (Jager, E. et al. (1998) *J Exp Med* 187:265-270; Jager, E. et al. (2000) *J Exp Med* 191:628-630). In particular, it was found that NY-ESO-1 peptides 157-165, 157-167 and 155-163 are restricted by HLA-A2 in tumor reactive CD8+ T cell lines, and peptide 56-62 is recognized by HLA-A31 CD8+ T cells (Jager et al. (1998) *J. Exp Med* 187:265-270; Wang, R. F. et al. (1998) *J. Immunol* 161:3598-3606). Several epitopes restricted by HLA-DR4 in CD4 T cell responses have also been demonstrated, and responses against peptide 157-170 were restricted by HLA-DP4, an allele found in the majority of Caucasians (Jager et al. (2000) *J Exp Med* 191:625-630; Zang et al. (2001) *Proc Natl Acd Sci USA* 98:3964-3969).

The ability of NY-ESO-1 to elicit spontaneous humoral and cellular immune responses, together with its restricted expression pattern have rendered it a good candidate target for cancer therapy. Although the NY-ESO-1 antigen has been evaluated as a cancer vaccine candidate, few complete humoral and cellular immune responses have been obtained. Indeed, the use of NY-ESO-1 as a therapeutic target is challenging because of the difficulty in designing antigen-binding proteins that target HLA-presented antigens and the need to avoid off-target binding, so as to prevent nonspecific binding that may lead to decreased therapeutic efficacy and/or increased adverse effects (e.g., nonspecific cytotoxicity that diminishes tumor cell killing activity and/or causes side effects in subjects).

Accordingly, there is an unmet need in the art for new therapeutic strategies to target NY-ESO-1 with high specificity and to treat NY-ESO-1-associated cancers.

BRIEF SUMMARY

The present disclosure provides antigen-binding proteins that specifically bind to a conformational epitope of an HLA-displayed New York esophageal squamous cell carcinoma 1 (NY-ESO-1) peptide. The antigen-binding proteins of the present disclosure bind with a high degree of specificity to HLA-displayed NY-ESO-1 and do not bind to HLA-displayed peptides that differ by 2, 3, 4, 5 or more amino acids. The antigen-binding proteins of the present disclosure allow for specific targeting of NY-ESO-1 peptide-presenting cells (i.e., cells presenting on their surface a NY-ESO-1 peptide bound to an MHC molecule, e.g., HLA-A2), such as cancer cells expressing NY-ESO-1 and, in some embodiments, stimulating T cell activation, e.g., to stimulate T cell-mediated killing of such cells. Furthermore, when fused to a detectable moiety, the antigen-binding proteins of the present disclosure allow for diagnosis and prognosis of NY-ESO-1-positive diseases or disorders with high sensitivity to changes in the number and distribution of NY-ESO-1 peptide-presenting cells, a more relevant measure of disease progression than circulating NY-ESO-1 levels.

The antigen-binding proteins of the disclosure may be antibodies, such as full-length (for example, an IgG1 or IgG4 antibody) antibodies, or may comprise only an antigen-binding portion of an antibody (for example, a Fab, F(ab')₂ or scFv fragment), and may be modified to affect functionality, e.g., to eliminate residual effector functions (Reddy et al., 2000, *J. Immunol.* 164:1925-1933). In some embodiments, the antigen-binding proteins of the disclosure may be antibodies, or antigen-binding fragments thereof. In certain embodiments, the antigen-binding proteins may be bispecific.

In a first aspect, the present disclosure provides recombinant antigen-binding proteins that bind specifically to a conformational epitope of an HLA-displayed New York esophageal squamous cell carcinoma 1 (NY-ESO-1) peptide, such as a HLA-displayed peptide comprising amino acid residues 157-165 of NY-ESO-1. In certain embodiments, the antigen-binding proteins are antibodies. In some embodiments, the antibodies are fully human.

Exemplary anti-HLA-A2:NY-ESO-1 antigen-binding proteins of the present disclosure are listed in Tables 1 and 2 herein. Table 1 sets forth the amino acid sequence identifiers of the heavy chain variable regions (HCVRs), light chain variable regions (LCVRs), heavy chain complementarity determining regions (HCDR1, HCDR2 and HCDR3), and light chain complementarity determining regions (LCDR1, LCDR2 and LCDR3) of the exemplary anti-HLA-A2:NY-ESO-1 antibodies. Table 2 sets forth the nucleic acid sequence identifiers of the HCVRs, LCVRs, HCDR1, HCDR2 HCDR3, LCDR1, LCDR2 and LCDR3 of the exemplary anti-HLA-A2:NY-ESO-1 antibodies.

The present disclosure provides antigen-binding proteins comprising an HCVR comprising an amino acid sequence selected from any of the HCVR amino acid sequences listed in Table 1, or a substantially similar sequence thereof having at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, at least 99.9%, or 100% sequence identity thereto. In some embodiments, an antigen-binding protein with sequence identity less than 100% comprises CDR sequences from an HCVR of Table 1. For example, such an antigen-binding protein can comprise those CDR sequences but have differences in a framework region as compared to the HCVR of Table 1.

The present disclosure also provides antigen-binding proteins comprising an LCVR comprising an amino acid sequence selected from any of the LCVR amino acid sequences listed in Table 1, or a substantially similar sequence thereof having at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, at least 99.9%, or 100% sequence identity thereto. In some embodiments, an antigen-binding protein with sequence identity less than 100% comprises CDR sequences from an LCVR of Table 1. For example, such an antigen-binding protein can comprise those CDR sequences but have differences in a framework region as compared to the LCVR of Table 1.

The present disclosure also provides antigen-binding proteins comprising an HCVR and an LCVR amino acid sequence pair (HCVR/LCVR) comprising any of the HCVR amino acid sequences listed in Table 1 paired with any of the LCVR amino acid sequences listed in Table 1. According to certain embodiments, the present disclosure provides antigen-binding proteins comprising an HCVR/LCVR amino acid sequence pair contained within any of the exemplary anti-HLA-A2:NY-ESO-1 antigen-binding proteins listed in Table 1. In certain embodiments, the HCVR/LCVR amino acid sequence pair is selected from the group consisting of SEQ ID NOs: 2/10, 22/30, 42/50, 62/70, 82/90, 102/110, 122/130, 142/150, 162/170, 180/186, 196/203, 211/219, and 230/238. In certain embodiments, the HCVR/LCVR amino acid sequence pair is selected from one of SEQ ID NOs: 2/10 (e.g., mAb24955N), 22/30 (e.g., mAb24956N), 42/50 (e.g., mAb24958N), and 62/70 (e.g., mAb24959N).

In certain embodiments, the present disclosure provides anti-HLA-A2:NY-ESO-1 antigen-binding proteins comprising a HCVR and a LCVR, said HCVR comprising an amino acid sequence listed in Table 1 having no more than five amino acid substitutions, and said LCVR comprising an amino acid sequence listed in Table 1 having no more than five amino acid substitutions. For example, the present disclosure provides anti-HLA-A2:NY-ESO-1 antigen-binding proteins comprising a HCVR and a LCVR, said HCVR comprising an amino acid sequence of SEQ ID NO: 2 having no more than five amino acid substitutions, and said LCVR comprising an amino acid sequence of SEQ ID NO: 10 having no more than five amino acid substitutions. In another exemplary embodiment, the present disclosure provides anti-HLA-A2:NY-ESO-1 antigen-binding proteins comprising a HCVR and a LCVR, said HCVR comprising an amino acid sequence of SEQ ID NO: 2 having at least one amino acid substitution, and said LCVR comprising an amino acid sequence of SEQ ID NO: 10 having at least one amino acid substitution.

The present disclosure also provides antigen-binding proteins comprising a heavy chain CDR1 (HCDR1) comprising an amino acid sequence selected from any of the HCDR1 amino acid sequences listed in Table 1 or a substantially similar sequence thereof having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98% or at least 99% sequence identity.

The present disclosure also provides antigen-binding proteins comprising a heavy chain CDR2 (HCDR2) comprising an amino acid sequence selected from any of the HCDR2 amino acid sequences listed in Table 1 or a substantially similar sequence thereof having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98% or at least 99% sequence identity.

The present disclosure also provides antigen-binding proteins comprising a heavy chain CDR3 (HCDR3) comprising an amino acid sequence selected from any of the HCDR3 amino acid sequences listed in Table 1 or a substantially similar sequence thereof having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98% or at least 99% sequence identity.

The present disclosure also provides antigen-binding proteins comprising a light chain CDR1 (LCDR1) comprising an amino acid sequence selected from any of the LCDR1 amino acid sequences listed in Table 1 or a substantially similar sequence thereof having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98% or at least 99% sequence identity.

The present disclosure also provides antigen-binding proteins comprising a light chain CDR2 (LCDR2) comprising an amino acid sequence selected from any of the LCDR2 amino acid sequences listed in Table 1 or a substantially similar sequence thereof having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98% or at least 99% sequence identity.

The present disclosure also provides antigen-binding proteins comprising a light chain CDR3 (LCDR3) comprising an amino acid sequence selected from any of the LCDR3 amino acid sequences listed in Table 1 or a substantially similar sequence thereof having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98% or at least 99% sequence identity.

The present disclosure also provides antigen-binding proteins comprising a HCDR3 and a LCDR3 amino acid sequence pair (HCDR3/LCDR3) comprising any of the HCDR3 amino acid sequences listed in Table 1 paired with any of the LCDR3 amino acid sequences listed in Table 1. According to certain embodiments, the present disclosure provides antigen-binding proteins, comprising an HCDR3/LCDR3 amino acid sequence pair contained within any of the exemplary anti-HLA-A2:NY-ESO-1 antigen-binding proteins listed in Table 1. In certain embodiments, the HCDR3/LCDR3 amino acid sequence pair is selected from the group consisting of SEQ ID NOs: 8/16 (e.g., mAb24955N), 28/36 (e.g., mAb24956N), 48/56 (e.g., mAb25958N), and 68/76 (e.g., mAb24959N).

The present disclosure also provides antigen-binding proteins comprising a HCVR and a LCVR, said HCVR comprising HCDR1 comprising an amino acid sequence differing from an amino acid sequence listed in Table 1 by 1 amino acid, HCDR2 comprising an amino acid sequence differing from an amino acid sequence listed in Table 1 by 1 amino acid, and HCDR3 comprising an amino acid sequence differing from an amino acid sequence listed in Table 1 by 1 amino acid. In certain embodiments, the present disclosure provides antigen-binding proteins comprising a HCVR and a LCVR, said LCVR comprising LCDR1 comprising an amino acid sequence differing from an amino acid sequence listed in Table 1 by 1 amino acid, LCDR2 comprising an amino acid sequence differing from an amino acid sequence listed in Table 1 by 1 amino acid, and LCDR3 comprising an amino acid sequence differing from an amino acid sequence listed in Table 1 by 1 amino acid. For example, the present disclosure provides anti-HLA-A2:NY-ESO-1 antigen-binding proteins comprising a HCVR and a LCVR, said HCVR comprising HCDR1 comprising an amino acid sequence of SEQ ID NO: 4 or an amino acid sequence differing from SEQ ID NO: 4 by 1 amino acid, HCDR2 comprising an amino acid sequence of SEQ ID NO: 6 or an amino acid sequence differing from SEQ ID NO: 6 by 1 amino acid, and HCDR3 comprising an amino acid sequence of SEQ ID NO: 8 or an amino acid sequence differing from SEQ ID NO: 8 by 1 amino acid. In another exemplary embodiment, the present disclosure provides antigen-binding proteins comprising a HCVR and a LCVR, said LCVR comprising LCDR1 comprising an amino acid sequence of SEQ ID NO: 12 or an amino acid sequence differing from SEQ ID NO: 12 by 1 amino acid, LCDR2 comprising an amino acid sequence of SEQ ID NO: 14 or an amino acid sequence differing from SEQ ID NO: 14 by 1 amino acid, and LCDR3 comprising an amino acid sequence of SEQ ID NO: 16 or an amino acid sequence differing from SEQ ID NO: 16 by 1 amino acid.

The present disclosure also provides antigen-binding proteins comprising a set of six CDRs (i.e., HCDR1-HCDR2-HCDR3-LCDR1-LCDR2-LCDR3) contained within any of the exemplary antigen-binding proteins listed in Table 1. In certain embodiments, the HCDR1-HCDR2-HCDR3-LCDR1-LCDR2-LCDR3 amino acid sequence set is selected from the group consisting of SEQ ID NOs: 4-6-8-12-14-16 (e.g., mAb24955N), 24-26-28-32-34-36 (e.g., mAb24956N), 44-46-48-52-54-56 (e.g., mAb24958N), and 64-66-68-72-74-76 (e.g., mAb24959N).

In a related embodiment, the present disclosure provides antigen-binding proteins comprising a set of six CDRs (i.e., HCDR1-HCDR2-HCDR3-LCDR1-LCDR2-LCDR3) contained within an HCVR/LCVR amino acid sequence pair as defined by any of the exemplary antigen-binding proteins listed in Table 1. For example, the present disclosure includes antigen-binding proteins comprising the HCDR1-HCDR2-HCDR3-LCDR1-LCDR2-LCDR3 amino acid sequences set contained within an HCVR/LCVR amino acid sequence pair selected from the group consisting of SEQ ID NOs: 2/10 (e.g., mAb24955N), 22/30 (e.g., mAb24956N), 42/50 (e.g., mAb24958N), and 62/70 (e.g., mAb24959N).

Methods and techniques for identifying CDRs within HCVR and LCVR amino acid sequences are well known in the art and can be used to identify CDRs within the specified HCVR and/or LCVR amino acid sequences disclosed herein. Exemplary conventions that can be used to identify the boundaries of CDRs include, e.g., the Kabat definition, the Chothia definition, and the AbM definition. In general terms, the Kabat definition is based on sequence variability, the Chothia definition is based on the location of the structural loop regions, and the AbM definition is a compromise between the Kabat and Chothia approaches. See, e.g., Kabat, "Sequences of Proteins of Immunological Interest," National Institutes of Health, Bethesda, Md. (1991); Al-Lazikani et al., *J. Mol. Biol.* 273:927-948 (1997); and Martin et al., *Proc. Natl. Acad. Sci. USA* 86:9268-9272 (1989). Public databases are also available for identifying CDR sequences within an antigen-binding protein.

The present disclosure includes anti-HLA-A2:NY-ESO-1 antigen-binding proteins having a modified glycosylation pattern. In some embodiments, modification to remove undesirable glycosylation sites may be useful, or an antibody lacking a fucose moiety present on the oligosaccharide chain, for example, to increase antibody dependent cellular cytotoxicity (ADCC) function (see Shield et al. (2002) *JBC* 277:26733). In other applications, modification of galactosylation can be made in order to modify complement dependent cytotoxicity (CDC).

In certain embodiments, the antigen-binding proteins of the present disclosure are monoclonal antibodies comprising a HCVR and a LCVR amino acid sequence pair (HCVR/LCVR) comprising any of the HCVR amino acid sequences listed in Table 1 paired with any of the LCVR amino acid sequences listed in Table 1. In certain embodiments, the monoclonal antibodies comprise a Fc domain of an isotype selected from the group consisting of IgA, IgD, IgE, IgG, IgG1, IgG2, IgG3, IgG4, IgM and a variant thereof.

The present disclosure provides antigen-binding proteins, or antigen-binding fragments thereof, comprising a heavy chain comprising an amino acid sequence selected from any of the HC amino acid sequences listed in Table 3, or a substantially similar sequence thereof having at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98% or at least 99% sequence identity thereto. In some embodiments, an antigen-binding protein with sequence identity less than 100% comprises CDR sequences from an HC of Table 3. For example, such an antigen-binding protein can comprise those CDR sequences but have differences in a framework region as compared to the HC of Table 3.

The present disclosure also provides antigen-binding proteins, or antigen-binding fragments thereof, comprising a light chain comprising an amino acid sequence selected from any of the LC amino acid sequences listed in Table 3, or a substantially similar sequence thereof having at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98% or at least 99% sequence identity thereto. In some embodiments, an antigen-binding protein with sequence identity less than 100% comprises CDR sequences from an LC of Table 3. For example, such an antigen-binding protein can comprise those CDR sequences but have differences in a framework region as compared to the LC of Table 3.

The present disclosure also provides antigen-binding proteins, or antigen-binding fragments thereof, comprising a HC and a LC amino acid sequence pair (HC/LC) comprising any of the HC amino acid sequences listed in Table 3 paired with any of the LC amino acid sequences listed in Table 3. According to certain embodiments, the present disclosure provides antibodies, or antigen-binding fragments thereof, comprising an HC/LC amino acid sequence pair contained within any of the exemplary anti-NY-ESO-1 antibodies listed in Table 3. In certain embodiments, the HC/LC amino acid sequence pair is selected from the group consisting of SEQ ID NOs: 18/20, 38/40, 58/60, and 78/80. In certain embodiments, the HC/LC amino acid sequence pair is selected from the group consisting of SEQ ID NOs: 18/20, 38/40, 58/60, and 78/80.

In one aspect, the present disclosure provides antigen-binding proteins or antigen-binding fragments thereof that bind to a HLA-peptide complex wherein the antigen-binding protein or antigen-binding fragment thereof contacts at least 60%, at least 70%, at least 80% or at least 90% of the amino acid residues of the peptide that is comprised in the HLA-peptide complex. In certain embodiments, the antigen-binding protein or antigen-binding fragment thereof "covers" or contacts all of the amino acid residues of the peptide comprised in the HLA-peptide complex. In certain embodiments, the antigen-binding protein or antigen-binding fragment thereof binds to a HLA-peptide complex with high affinity and specificity, wherein the antigen-binding protein or antigen-binding fragment thereof contacts the entire length of the displayed peptide. "Contact", as used herein includes direct or water-mediated hydrogen bonds, charge-charge interactions, or hydrophobic/van der Waals interactions. In one embodiment, the antigen-binding protein or antigen-binding fragment thereof binds to HLA-A2-NY-ESO-1 157-165 peptide complex wherein the antigen-binding protein binds to at least 3 of 9 amino acid residues of peptide 157-165 (SEQ ID NO: 269) and to HLA-A2 such that the antigen-binding protein is roughly centered on the peptide in the HLA-A2 peptide-binding groove, thereby "covering" (physically blocking) the HLA-A2-peptide complex. In another embodiment, the antigen-binding protein or antigen-binding fragment thereof binds to HLA-A2-NY-ESO-1 157-165 peptide complex wherein the antigen-binding protein binds to at least 3 of 9 amino acid residues of peptide 157-165 (SEQ ID NO: 270 or 291) and to HLA-A2 such that the antigen-binding protein is roughly centered on the peptide in the HLA-A2 peptide-binding groove, thereby "covering" (physically blocking) the HLA-A2-peptide complex. In certain embodiments, the antigen-binding protein or antigen-binding fragment thereof comprises the CDRs of a HCVR and the CDRs of a LCVR, wherein the HCVR and LCVR each has an amino acid sequence selected from the HCVR and LCVR sequences listed in Table 1. In one embodiment, the antigen-binding protein is fully human. In certain embodiments, the fully human antigen-binding proteins are not obtained using phage display methods and technologies. In some embodiments, the antigen-binding proteins comprise a light chain variable region of the IGKV1-39 sub-type. In some embodiments, the antigen-binding proteins comprise a light chain variable region of the IGKJ1 sub-type.

In certain embodiments, the present disclosure provides antigen-binding proteins or antigen-binding fragments thereof that bind to HLA-A2:NY-ESO-1 157-165 peptide complex, wherein the antigen-binding protein binds to one or more amino acids of SEQ ID NO: 269. In one embodiment, the antigen-binding protein binds to at least 3 amino acids of SEQ ID NO: 269.

In certain embodiments, the present disclosure provides antigen-binding proteins or antigen-binding fragments thereof that bind to HLA-A2:NY-ESO-1 157-165 peptide complex, wherein the antigen-binding protein binds to one or more amino acids of SEQ ID NO: 270 or 291. In one embodiment, the antigen-binding protein binds to at least 3 amino acids of SEQ ID NO: 270 or 291. In one embodiment, the antigen-binding protein binds to one or more amino acids selected from the group consisting of M160, W161, and Q164 of SEQ ID NO: 270.

In certain embodiments, the present disclosure provides antigen-binding protein that binds specifically to a conformational epitope of an HLA-displayed New York esophageal squamous cell carcinoma 1 (NY-ESO-1) peptide, wherein the conformational epitope comprises one or more amino acids of SEQ ID NO: 269.

In certain embodiments, the present disclosure provides antigen-binding protein that binds specifically to a conformational epitope of an HLA-displayed New York esophageal squamous cell carcinoma 1 (NY-ESO-1) peptide, wherein the conformational epitope comprises one or more amino acids of SEQ ID NO: 270 or 291. In the certain embodiments, the conformational epitope comprises one or more amino acids selected from the group consisting of M160, W161, and Q164 of SEQ ID NO: 270 or 291.

The present disclosure also provides for antigen-binding proteins that compete for specific binding to HLA-A2:NY-ESO-1 with an antigen-binding protein comprising the CDRs of a HCVR and the CDRs of a LCVR, wherein the HCVR and LCVR each has an amino acid sequence selected from the HCVR and LCVR sequences listed in Table 1.

The present disclosure also provides antigen-binding proteins that cross-compete for binding to HLA-A2:NY-ESO-1 with a reference antigen-binding protein comprising the CDRs of a HCVR and the CDRs of a LCVR, wherein the HCVR and LCVR each has an amino acid sequence selected from the HCVR and LCVR sequences listed in Table 1.

The present disclosure also provides antigen-binding proteins that bind to the same epitope as a reference antigen-binding protein comprising the CDRs of a HCVR and the CDRs of a LCVR, wherein the HCVR and LCVR each has an amino acid sequence selected from the HCVR and LCVR sequences listed in Table 1. In certain embodiments, the present disclosure provides antigen-binding proteins that bind to the same epitope as a reference antigen-binding protein comprising the CDRs of a HCVR and the CDRs of a LCVR, wherein the HCVR is selected from the group consisting of SEQ ID NOs: 2, 22, 42, and 62, and the LCVR is selected from the group consisting of SEQ ID Nos: 10, 30, 50, and 70.

In one embodiment, the disclosure provides a recombinant antigen-binding protein that binds specifically to a conformational epitope of an HLA-A2 presented New York esophageal squamous cell carcinoma 1 (NY-ESO-1) peptide, wherein the antigen-binding protein has a property selected from the group consisting of: (a) binds monomeric HLA-A2:NY-ESO-1 157-165 peptide complex (C165 or V165) with a binding dissociation equilibrium constant ($K_D$) of less than about 1 nM as measured in a surface plasmon resonance assay at 25° C.; (b) binds to HLA-A2:NY-ESO-1 157-165 peptide complex expressing cells with an $EC_{50}$ less than about 10 nM and does not bind to cells expressing predicted off-target peptides as determined by flow cytometry assay; and (c) the epitope comprises one or more amino acids of SEQ ID NO: 269, 270, or 291. As disclosed elsewhere herein, an "off-target peptide" refers to a peptide that differs by 2, 3, 4, 5 or more amino acids from a target peptide (e.g., NY-ESO-1 157-165 peptide (SEQ ID NO: 269 and/or SEQ ID NO:270 or 291)).

In a second aspect, the present disclosure provides nucleic acid molecules encoding anti-HLA-A2:NY-ESO-1 antigen-binding proteins. For example, the present disclosure provides nucleic acid molecules encoding any of the HCVR amino acid sequences listed in Table 1; in certain embodiments the nucleic acid molecule comprises a polynucleotide sequence selected from any of the HCVR nucleic acid sequences listed in Table 2, or a substantially similar sequence thereof having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98% or at least 99% sequence identity thereto.

The present disclosure also provides nucleic acid molecules encoding any of the LCVR amino acid sequences listed in Table 1; in certain embodiments the nucleic acid molecule comprises a polynucleotide sequence selected from any of the LCVR nucleic acid sequences listed in Table 2, or a substantially similar sequence thereof having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98% or at least 99% sequence identity thereto.

The present disclosure also provides nucleic acid molecules encoding any of the HCDR1 amino acid sequences listed in Table 1; in certain embodiments the nucleic acid molecule comprises a polynucleotide sequence selected from any of the HCDR1 nucleic acid sequences listed in Table 2, or a substantially similar sequence thereof having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98% or at least 99% sequence identity thereto.

The present disclosure also provides nucleic acid molecules encoding any of the HCDR2 amino acid sequences listed in Table 1; in certain embodiments the nucleic acid molecule comprises a polynucleotide sequence selected from any of the HCDR2 nucleic acid sequences listed in Table 2, or a substantially similar sequence thereof having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98% or at least 99% sequence identity thereto.

The present disclosure also provides nucleic acid molecules encoding any of the HCDR3 amino acid sequences listed in Table 1; in certain embodiments the nucleic acid molecule comprises a polynucleotide sequence selected from any of the HCDR3 nucleic acid sequences listed in Table 2, or a substantially similar sequence thereof having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98% or at least 99% sequence identity thereto.

The present disclosure also provides nucleic acid molecules encoding any of the LCDR1 amino acid sequences listed in Table 1; in certain embodiments the nucleic acid molecule comprises a polynucleotide sequence selected from any of the LCDR1 nucleic acid sequences listed in Table 2, or a substantially similar sequence thereof having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98% or at least 99% sequence identity thereto.

The present disclosure also provides nucleic acid molecules encoding any of the LCDR2 amino acid sequences listed in Table 1; in certain embodiments the nucleic acid molecule comprises a polynucleotide sequence selected from any of the LCDR2 nucleic acid sequences listed in Table 2, or a substantially similar sequence thereof having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98% or at least 99% sequence identity thereto.

The present disclosure also provides nucleic acid molecules encoding any of the LCDR3 amino acid sequences listed in Table 1; in certain embodiments the nucleic acid molecule comprises a polynucleotide sequence selected from any of the LCDR3 nucleic acid sequences listed in Table 2, or a substantially similar sequence thereof having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98% or at least 99% sequence identity thereto.

The present disclosure also provides nucleic acid molecules encoding an HCVR, wherein the HCVR comprises a set of three CDRs (i.e., HCDR1-HCDR2-HCDR3), wherein the HCDR1-HCDR2-HCDR3 amino acid sequence set is as defined by any of the exemplary anti-HLA-A2:NY-ESO-1 antigen-binding proteins listed in Table 1.

The present disclosure also provides nucleic acid molecules encoding an LCVR, wherein the LCVR comprises a set of three CDRs (i.e., LCDR1-LCDR2-LCDR3), wherein the LCDR1-LCDR2-LCDR3 amino acid sequence set is as defined by any of the exemplary anti-HLA-A2:NY-ESO-1 antigen-binding proteins listed in Table 1.

The present disclosure also provides nucleic acid molecules encoding both an HCVR and an LCVR, wherein the HCVR comprises an amino acid sequence of any of the HCVR amino acid sequences listed in Table 1, and wherein the LCVR comprises an amino acid sequence of any of the LCVR amino acid sequences listed in Table 1. In certain embodiments, the nucleic acid molecule comprises a polynucleotide sequence selected from any of the HCVR nucleic acid sequences listed in Table 2, or a substantially similar sequence thereof having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98% or at least 99% sequence identity thereto, and a polynucleotide sequence selected from any of the LCVR nucleic acid sequences listed in Table 2, or a substantially similar sequence thereof having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98% or at least 99% sequence identity thereto. In certain embodiments according to this aspect of the disclosure, the nucleic acid molecule encodes an HCVR and LCVR, wherein the HCVR and LCVR are both derived from the same anti-HLA-A2:NY-ESO-1 antigen-binding protein listed in Table 1.

The present disclosure provides nucleic acid molecules encoding any of the heavy chain amino acid sequences listed in Table 3. The present disclosure also provides nucleic acid molecules encoding any of the light chain amino acid sequences listed in Table 3.

The present disclosure also provides nucleic acid molecules encoding both heavy chain (HC) and a light chain (LC), wherein the HC comprises an amino acid sequence of any of the HC amino acid sequences listed in Table 3, and wherein the LC comprises an amino acid sequence of any of the LC amino acid sequences listed in Table 3.

In a related aspect, the present disclosure provides recombinant expression vectors capable of expressing a polypeptide comprising a heavy and/or or light chain variable region of an anti-HLA-A2:NY-ESO-1 antigen-binding protein. For example, the present disclosure includes recombinant expression vectors comprising any of the nucleic acid molecules mentioned above, i.e., nucleic acid molecules encoding any of the HCVR, LCVR, and/or CDR sequences as set forth in Table 1. The present disclosure also provides recombinant expression vectors capable of expressing a polypeptide comprising a heavy and/or light chain of an anti-HLA-A2:NY-ESO-1 antigen-binding protein. For example, the present disclosure includes recombinant expression vectors comprising any of the nucleic acid molecules mentioned above, i.e., nucleic acid molecules encoding any of the heavy chain or light chain sequences as set forth in Table 2. Also included within the scope of the present disclosure are host cells into which such vectors have been introduced, as well as methods of producing the antigen-binding proteins by culturing the host cells under conditions permitting production of the antigen-binding proteins, and recovering the antigen-binding proteins so produced.

In a third aspect, the present disclosure provides a pharmaceutical composition comprising a therapeutically effective amount of a recombinant antigen-binding protein that binds specifically to a conformational epitope of an HLA-A2 presented NY-ESO-1 peptide (e.g., a peptide comprising amino acid residues 157-165 of NY-ESO-1), and a pharmaceutically acceptable carrier. In a related aspect, the disclosure features a composition which is a combination of an anti-HLA-A2:NY-ESO-1 antigen-binding protein and a second therapeutic agent. In one embodiment, the second therapeutic agent is any agent that is advantageously combined with an anti-HLA-A2:NY-ESO-1 antigen-binding protein. Exemplary agents that may be advantageously combined with an anti-HLA-A2:NY-ESO-1 antigen-binding protein include, without limitation, other agents that modulate immune cell activation. Additional therapies that can be used in combination with the anti-HLA-A2:NY-ESO-1 antigen-binding proteins of the present disclosure are disclosed elsewhere herein.

In a fourth aspect, the disclosure provides methods to treat a subject having a NY-ESO-1-associated disease or disorder, such as a NY-ESO-1-positive cancer. The methods include administering a therapeutically effective amount of an anti-HLA-A2:NY-ESO-1 antigen-binding protein of the disclosure or a pharmaceutical composition of the disclosure to the subject in need thereof. The disorder treated is any disease or condition which is improved, ameliorated, inhibited or prevented by the antigen-binding proteins and compositions provided herein. In certain embodiments, the antigen-binding protein (or pharmaceutical composition) of the disclosure is administered in combination with a second therapeutic agent to the subject in need thereof. The second therapeutic agent may be selected from the group consisting of an antibody to a T cell co-inhibitor, an antibody to a tumor cell antigen, an antibody to a T cell receptor, a cytotoxic agent, an anti-cancer drug, an anti-inflammatory drug (e.g., corticosteroids), chemotherapeutic agent, surgery, radiation therapy, an immunosuppressant and any other drug or therapy known in the art. In certain embodiments, the second therapeutic agent may be an agent that helps to counteract or reduce any possible side effect(s) associated with antigen-binding protein of the disclosure, if such side effect(s) should occur.

In certain embodiments, the present disclosure provides methods for suppressing growth of a NY-ESO-1-associated cancer. For example, the present disclosure provides methods to suppress tumor growth due to a primary tumor or a metastatic tumor in a subject. In certain embodiments, the present disclosure provides methods to enhance survival (e.g., progression-free survival or overall survival) of a subject with a NY-ESO-1-associated cancer. Examples of cancer include, but are not limited to, a liposarcoma, a neuroblastoma, a myeloma, a metastatic melanoma, a synovial sarcoma, a bladder cancer, an esophageal cancer, a hepatocellular cancer, a head and neck cancer, a non-small cell lung cancer, an ovarian cancer, a prostate cancer, a breast cancer, astrocytic tumor, glioblastoma multiforme, anaplastic astrocytoma, brain tumor, fallopian tube cancer, ovarian epithelial cancer, primary peritoneal cavity cancer, advanced solid tumors, soft tissue sarcoma, melanoma, a sarcoma, myelodysplastic syndrome, acute myeloid leukemia, Hodgkin lymphoma, non-Hodgkin lymphoma, Hodgkin disease, multiple myeloma, synovial sarcoma, metastatic solid tumors, esophageal cancer, rhabdomyosarcoma, advanced myxoid, round cell liposarcoma, metastatic melanoma, or recurrent non-small cell lung cancer.

In certain embodiments, the present disclosure provides methods for inhibiting or suppressing growth of established tumors. The methods comprise administering to a subject in need thereof a pharmaceutical composition comprising a therapeutically effective amount of an antigen-binding protein of the present disclosure. In certain embodiments, the antigen-binding protein is administered in combination with a second therapeutic agent.

The antigen-binding protein, e.g., antibody, or antigen-binding fragment thereof, may be administered subcutaneously, intravenously, intradermally, intraperitoneally, orally, intramuscularly, or intracranially. The antigen-binding protein, e.g., antibody or antigen-binding fragment thereof, may be administered at a dose of about 0.1 mg/kg of body weight to about 100 mg/kg of body weight of the subject.

In a fifth aspect, the present disclosure provides an isolated nucleic acid molecule encoding a chimeric antigen receptor (CAR), or a cell expressing such a CAR (e.g., a cell expressing the CAR on its surface). The CAR may include an extracellular binding domain that specifically binds to a conformational epitope of an HLA-displayed New York esophageal squamous cell carcinoma 1 (NY-ESO-1) peptide, e.g., amino acid residues 157-165 of NY-ESO-1, a transmembrane domain, and an intracellular signaling domain. In one embodiment, the extracellular binding domain is an anti-HLA-A2:NY-ESO-1 antigen-binding protein or an antigen-binding fragment thereof. Exemplary anti-HLA-A2:NY-ESO-1 antigen-binding proteins of the present disclosure are any of the antigen-binding proteins described herein.

For example, in certain embodiments, the antigen-binding protein suitable for use in the CARs of the disclosure comprises three heavy chain complementarity determining regions (CDRs) (HCDR1, HCDR2 and HCDR3) contained within any one of the heavy chain variable region (HCVR)

sequences listed in Table 1; and three light chain CDRs (LCDR1, LCDR2 and LCDR3) contained within any one of the light chain variable region (LCVR) sequences listed in Table 1.

In other embodiments, the antigen-binding protein suitable for use in the CARs of the disclosure comprises a HCVR having an amino acid sequence selected from the group consisting of HCVR sequences listed in Table 1; and/or a LCVR having an amino acid sequence selected from the group consisting of LCVR sequences listed in Table 1.

In some embodiments, the antigen-binding protein suitable for use in the CARs of the disclosure comprises (a) a HCVR having an amino acid sequence selected from the group consisting of HCVR sequences listed in Table 1; and (b) a LCVR having an amino acid sequence selected from the group consisting of LCVR sequences listed in Table 1.

In one embodiment, the antigen-binding protein suitable for use in the CARs of the disclosure comprises (a) a HCDR1 domain having an amino acid sequence selected from the group consisting of SEQ ID NOs: 4, 24, 44, 64, 84, 104, 124, 144, 164, 213, and 232; (b) a HCDR2 domain having an amino acid sequence selected from the group consisting of SEQ ID NOs: 6, 26, 46, 66, 86, 106, 126, 146, 166, 182, 199, 215, and 234; (c) a HCDR3 domain having an amino acid sequence selected from the group consisting of SEQ ID NOs: 8, 28, 48, 68, 88, 108, 128, 148, 168, 184, 201, 217, and 236; (d) a LCDR1 domain having an amino acid sequence selected from the group consisting of SEQ ID NOs: 12, 32, 52, 72, 92, 112, 132, 152, 172, 188, 221, and 240; (e) a LCDR2 domain having an amino acid sequence selected from the group consisting of SEQ ID NOs: 14, 34, 54, 74, 94, 114, 134, 154, 174, and 242; and (f) a LCDR3 domain having an amino acid sequence selected from the group consisting of SEQ ID NOs: 16, 36, 56, 76, 96, 116, 136, 156, 190, 205, 224, and 244.

In further embodiment, the antigen-binding protein suitable for use in the CARs of the disclosure comprises a HCVR/LCVR amino acid sequence pair selected from the group consisting of SEQ ID NOs: 2/10, 22/30, 42/50, 62/70, 82/90, 102/110, 122/130, 142/150, 162/170, 180/186, 196/203, 211/219, and 230/238.

In some embodiments the antigen-binding protein for use in the CARs of the present disclosure is an scFv.

In other aspects, the present disclosure provides vectors comprising the isolated CAR nucleic acid molecules; and immune effector cells comprising such vectors.

In yet other aspects of the present disclosure, methods for treating a subject having a NY-ESO-1-associated disease or disorder, such as a NY-ESO-1-positive cancer, e.g., a liposarcoma, a neuroblastoma, a myeloma, a metastatic melanoma, a synovial sarcoma, a bladder cancer, an esophageal cancer, a hepatocellular cancer, a head and neck cancer, a non-small cell lung cancer, an ovarian cancer, a prostate cancer, a breast cancer, astrocytic tumor, glioblastoma multiforme, anaplastic astrocytoma, brain tumor, fallopian tube cancer, ovarian epithelial cancer, primary peritoneal cavity cancer, advanced solid tumors, soft tissue sarcoma, melanoma, a sarcoma, myelodysplastic syndrome, acute myeloid leukemia, Hodgkin lymphoma, non-Hodgkin lymphoma, Hodgkin disease, multiple myeloma, synovial sarcoma, metastatic solid tumors, esophageal cancer, rhabdomyosarcoma, advanced myxoid, round cell liposarcoma, metastatic melanoma, or recurrent non-small cell lung cancer, are provided. The methods include administering to the subject a population of immune effector cells comprising a CAR of the disclosure.

In some aspects, the present disclosure provides methods for detecting NY-ESO-1-positive cells, e.g., in a subject or in a sample obtained from a subject. The methods include contacting a cell, such as a cell sample obtained from a subject, or administering to a subject, an antigen-binding protein of the disclosure comprising a detectable moiety, and detecting the presence of the detectable moiety.

Other embodiments will become apparent from a review of the ensuing detailed description.

DETAILED DESCRIPTION

Figure 1A:
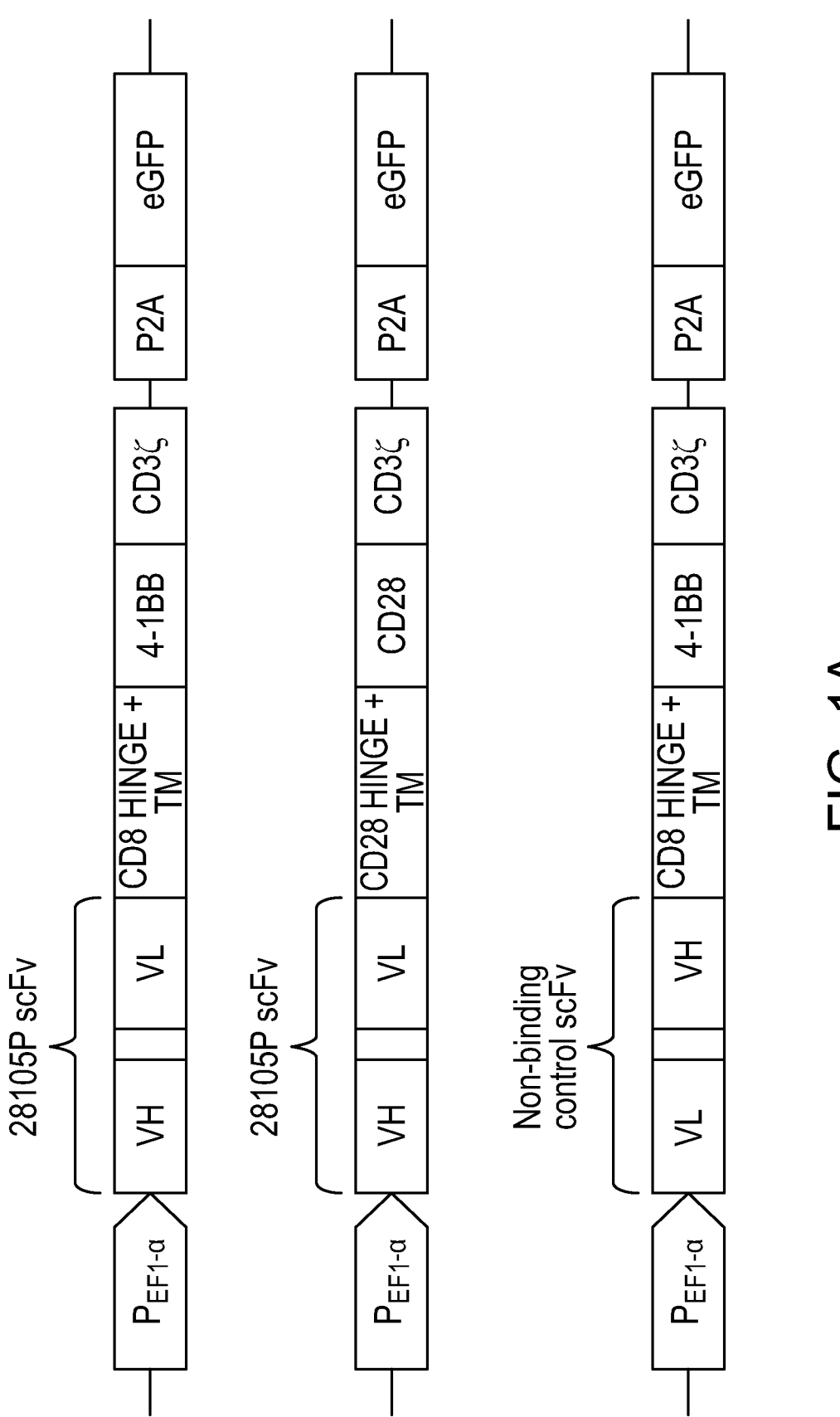
FIG. 1A depicts diagrams of three different CAR constructs, including promoters and vector elements.

Before the present methods are described, it is to be understood that this disclosure is not limited to particular methods, and experimental conditions described, as such methods and conditions may vary. It is also to be understood that the terminology used herein is for the purpose of describing particular embodiments only, and is not intended to be limiting, since the scope of the present disclosure will be limited only by the appended claims.

Unless defined otherwise, all technical and scientific terms used herein have the same meaning as commonly understood by one of ordinary skill in the art to which this disclosure belongs. Although any methods and materials similar or equivalent to those described herein can be used in the practice or testing of the present disclosure, preferred methods and materials are now described. All publications mentioned herein are incorporated herein by reference in their entirety.

The terms "NY-ESO-1," NY-ESO-1," "New York esophageal squamous cell carcinoma 1," and "CTAG1B" refer to the well-known cancer-testis antigen (CTA) that is re-expressed in numerous cancer types and encoded by the CTAG1B gene.

The amino acid sequence of full-length NY-ESO-1 is provided in Gen Bank as accession number NP_001318.1 (SEQ ID NO:271). The term "NY-ESO-1" includes recombinant NY-ESO-1 or a fragment thereof. The term also encompasses NY-ESO-1 or a fragment thereof coupled to, for example, histidine tag, mouse or human Fc, or a signal sequence such as ROR1. In certain embodiments, the term comprises NY-ESO-1 or a fragment thereof in the context of HLA-A2, linked to HLA-A2 or as displayed by HLA-A2.

In certain embodiments, a NY-ESO-1 peptide includes amino acids 157-165 of SEQ ID NO: 271 (SLLMWITQC (SEQ ID NO:269)) and is referred to herein as "NY-ESO-1_157-165C peptide" or "NY-ESO-1 (157-165) peptide" (excepting wherein "NY-ESO-1 (157-165) peptide is further clarified as having a C or a V at position 165). In other embodiments, a NY-ESO-1 peptide includes amino aid residues 157-165 of SEQ ID NO: 271 in which the cysteine at residue 165 has been substituted with a valine (SLMMWITQV (SEQ ID NO:270)) and is referred to herein as "NY-ESO-1_157-165V peptide" or "NY-ESO-1 (157-165V peptide), or otherwise denoted with "C165V" or "V165." For simplicity, it will be understood that, unless specified, the terms "NY-ESO-1_157-165 peptide," "NY-ESO-1 (157-165)," and "a peptide comprising amino acid residues 157-165 of NY-ESO-1" encompass both of a NY-ESO-1_157-165C peptide and a NY-ESO-1_157-165V peptide.

The term "HLA" refers to the human leukocyte antigen (HLA) system or complex, which is a gene complex encoding the major histocompatibility complex (MHC) proteins in humans. These cell-surface proteins are responsible for the regulation of the immune system in humans. HLAs corresponding to MHC class I (A, B, and C) present peptides from inside the cell.

The term "HLA-A" refers to the group of human leukocyte antigens (HLA) that are coded for by the HLA-A locus. HLA-A is one of three major types of human MHC class I cell surface receptors. The receptor is a heterodimer, and is composed of a heavy α chain and smaller β chain. The α chain is encoded by a variant HLA-A gene, and the β chain (β2-microglobulin) is an invariant β2 microglobulin molecule.

The term "HLA-A2" is one particular class I major histocompatibility complex (MHC) allele group at the HLA-A locus; the α chain is encoded by the HLA-A*02 gene and the β chain is encoded by the β2-microglobulin or B2M locus.

The term "antigen-binding protein," "binding protein" or "binding molecule," as used herein includes molecules that contain at least one antigen-binding site that specifically binds to a molecule of interest, such as a conformational epitope of an HLA-A2 presented New York esophageal squamous cell carcinoma 1 peptide (NY-ESO-1 peptide), e.g., a HLA-A2-displayed peptide comprising amino acid residues 157-165. A binding protein may be an antibody, such as a full-length antibody, or an antigen-binding fragment of an antibody, or a chimeric antigen receptor (CAR), or any other polypeptide, e.g., a receptor-antibody (Rab) protein.

The term "HLA-A2:NY-ESO-1 antigen-binding protein" or "HLA-A2:NY-ESO-1 antigen-binding protein," or the like, refers to an antigen-binding protein, such as an antibody, or antigen-binding portion thereof, that specifically binds to a conformational epitope by the presentation of a peptide fragment of NY-ESO-1, e.g., amino acid residues 157-165, by HLA-A2. In certain embodiments, the conformational epitope is created on the surface of a cell by the HLA-A2-presented NY-ESO-1 peptide. As used herein, the term "HLA-A2:NY-ESO-1 157-165 peptide complex," or the like, refers to a complex between HLA-A2 and an NY-ESO-1 polypeptide, wherein the HLA-A2 presents amino acid residues 157-165 of NY-ESO-1. In this context, the NY-ESO-1 can be a full length NY-ESO-1 polypeptide or a truncated version, so long as amino acids 157-165 (with reference to SEQ ID NO: 271) are present in the NY-ESO-1 polypeptide and presented by the HLA-A2. For the avoidance of doubt, the term "NY-ESO-1 157-165 peptide" encompasses peptides as short as 157-165 of NY-ESO-1 (with respect to SEQ ID NO: 271) or longer, up to and include a full length NY-ESO-1 protein (e.g., of the sequence of SEQ ID NO: 271).

The term "epitope" refers to an antigenic determinant that interacts with a specific antigen-binding site in the variable region of an antigen-binding protein known as a paratope. A single antigen may have more than one epitope. Thus, different antigen-binding proteins may bind to different areas on an antigen and may have different biological effects. The term "epitope" also refers to a site on an antigen to which B and/or T cells respond. It also refers to a region of an antigen that is bound by an antigen-binding protein. Epitopes may be defined as structural or functional. Functional epitopes are generally a subset of the structural epitopes and have those residues that directly contribute to the affinity of the interaction. Epitopes may also be "conformational," that is, composed of non-linear amino acids. In certain embodiments, epitopes may include determinants that are chemically active surface groupings of molecules such as amino acids, sugar side chains, phosphoryl groups, or sulfonyl groups, and, in certain embodiments, may have specific three-dimensional structural characteristics, and/or specific charge characteristics. In some embodiments, an antigen-binding protein of the present disclosure interacts with a conformational epitope of an HLA-A2:NY-ESO-1 peptide complex. In some embodiments, this conformational epitope comprises one or more amino acids (e.g., one, two, or three amino acids) corresponding to M160, W161, and Q164 of SEQ ID NO: 271. To determine amino acids that correspond to one or more of M160, W161, or Q164, a sequence alignment can be performed as described herein. In some embodiments, an antigen-binding protein of the present disclosure binds specifically to an HLA-A2:NY-ESO-1 peptide complex comprising amino acids corresponding to amino acids 157-165 of SEQ ID NO: 271, as determined by X-ray crystallography at a resolution of 4.0 Å or higher. For the avoidance of doubt, a resolution of 4.0 Å or higher encompasses a resolution of 3.9 Å or higher, 3.8 Å or higher, 3.7 Å or higher, 3.6 Å or higher, 3.5 Å or higher, 3.4 Å or higher, 3.3 Å or higher, 3.2 Å or higher, 3.1 Å or higher, 3.0 Å or higher, 2.9 Å or higher, 2.8 Å or higher, 2.7 Å or higher, 2.6 Å or higher, 2.5 Å or higher, 2.4 Å or higher, 2.3 Å or higher, 2.2 Å or higher, 2.1 Å or higher, 2.0 Å or higher, 1.9 Å or higher, 1.8 Å or higher, 1.7 Å or higher, 1.6 Å or higher, 1.5 Å or higher, 1.4 Å or higher, 1.3 Å or higher, 1.2 Å or higher, 1.1 Å or higher, 1.0 Å or higher, 0.9 Å or higher, 0.8 Å or higher, 0.7 Å or higher, 0.6 Å or higher, or 0.5 Å or higher.

In some embodiments, a binding protein is an antibody, or an antigen-binding fragment thereof, such as a full-length antibody, or antigen-binding fragment thereof.

The term "antibody", as used herein, is intended to refer to immunoglobulin molecules comprised of four polypeptide chains, two heavy (H) chains and two light (L) chains inter-connected by disulfide bonds (i.e., "full antibody molecules"), as well as multimers thereof (e.g. IgM) or antigen-binding fragments thereof. Each heavy chain is comprised of a heavy chain variable region ("HCVR" or "$V_H$") and a heavy chain constant region (comprised of domains $C_H1$, $C_H2$ and $C_H3$). Each light chain is comprised of a light chain variable region ("LCVR or "$V_L$") and a light chain constant region ($C_L$). The $V_H$ and $V_L$ regions can be further subdivided into regions of hypervariability, termed complementarity determining regions (CDR), interspersed with regions that are more conserved, termed framework regions (FR). Each $V_H$ and $V_L$ is composed of three CDRs and four FRs, arranged from amino-terminus to carboxy-terminus in the following order: FR1, CDR1, FR2, CDR2, FR3, CDR3, FR4. In certain embodiments, the FRs of the antibody (or antigen-binding fragment thereof) may be identical to the human germline sequences, or may be naturally or artificially modified. An amino acid consensus sequence may be defined based on a side-by-side analysis of two or more CDRs.

Substitution of one or more CDR residues or omission of one or more CDRs is also possible. Antigen binding proteins, such as antibodies, have been described in the scientific literature in which one or two CDRs can be dispensed with for binding. Padlan et al. (1995 *FASEB J.* 9:133-139) analyzed the contact regions between antibodies and their antigens, based on published crystal structures, and concluded that only about one fifth to one third of CDR residues actually contact the antigen. Padlan also found many antibodies in which one or two CDRs had no amino acids in contact with an antigen (see also, Vajdos et al. 2002 *J Mol Biol* 320:415-428).

CDR residues not contacting antigen can be identified based on previous studies (for example residues H60-H65 in CDRH2 are often not required), from regions of Kabat CDRs lying outside Chothia CDRs, by molecular modeling and/or empirically. If a CDR or residue(s) thereof is omitted, it is usually substituted with an amino acid occupying the corresponding position in another human antibody sequence or a consensus of such sequences. Positions for substitution within CDRs and amino acids to substitute can also be selected empirically. Empirical substitutions can be conservative or non-conservative substitutions.

The anti-HLA-A2:NY-ESO-1 antigen-binding proteins, e.g., fully human anti-HLA-A2:NY-ESO-1 monoclonal antibodies, or antigen-binding fragments thereof, or CARs, disclosed herein may comprise one or more amino acid substitutions, insertions and/or deletions in the framework and/or CDR regions of the heavy and light chain variable domains as compared to the corresponding germline sequences. Such mutations can be readily ascertained by comparing the amino acid sequences disclosed herein to germline sequences available from, for example, public antibody sequence databases. The present disclosure includes antigen-binding proteins, e.g., antibodies, or antigen-binding fragments thereof, or CARs, which are derived from any of the amino acid sequences disclosed herein, wherein one or more amino acids within one or more framework and/or CDR regions are mutated to the corresponding residue(s) of the germline sequence from which the antigen-binding protein was derived, or to the corresponding residue(s) of another human germline sequence, or to a conservative amino acid substitution of the corresponding germline residue(s) (such sequence changes are referred to herein collectively as "germline mutations"). A person of ordinary skill in the art, starting with the heavy and light chain variable region sequences disclosed herein, can easily produce numerous antigen-binding proteins, e.g., antibodies, or antigen-binding fragments thereof, or CARs, which comprise one or more individual germline mutations or combinations thereof. In certain embodiments, all of the framework and/or CDR residues within the $V_H$ and/or $V_L$ domains are mutated back to the residues found in the original germline sequence from which the antigen-binding protein, e.g., antibody, was derived. In other embodiments, only certain residues are mutated back to the original germline sequence, e.g., only the mutated residues found within the first 8 amino acids of FR1 or within the last 8 amino acids of FR4, or only the mutated residues found within CDR1, CDR2 or CDR3. In other embodiments, one or more of the framework and/or CDR residue(s) are mutated to the corresponding residue(s) of a different germline sequence (i.e., a germline sequence that is different from the germline sequence from which the antibody was originally derived). Furthermore, the antigen-binding proteins, e.g., antibodies, or antigen-binding fragments thereof, or CARs, of the present disclosure may contain any combination of two or more germline mutations within the framework and/or CDR regions, e.g., wherein certain individual residues are mutated to the corresponding residue of a particular germline sequence while certain other residues that differ from the original germline sequence are maintained or are mutated to the corresponding residue of a different germline sequence. Once obtained, antigen-binding proteins, e.g., antibodies and antigen-binding fragments, that contain one or more germline mutations can be easily tested for one or more desired property such as, improved binding specificity, increased binding affinity, improved or enhanced antagonistic or agonistic biological properties (as the case may be), reduced immunogenicity, etc. Antigen binding proteins, e.g., antibodies, or antigen-binding fragments thereof, or CARs, obtained in this general manner are encompassed within the present disclosure.

The present disclosure also includes antigen-binding proteins, e.g., fully human anti-HLA-A2:NY-ESO-1 monoclonal antibodies, or antigen-binding fragments thereof, or CARs, comprising variants of any of the HCVR, LCVR, and/or CDR amino acid sequences disclosed herein having one or more conservative substitutions. For example, the present disclosure includes anti-HLA-A2:NY-ESO-1 antigen-binding proteins having HCVR, LCVR, and/or CDR amino acid sequences with, e.g., 10 or fewer, 8 or fewer, 6 or fewer, 4 or fewer, etc. conservative amino acid substitutions relative to any of the HCVR, LCVR, and/or CDR amino acid sequences disclosed herein.

The term "human antibody", as used herein, is intended to include antibodies having variable and constant regions derived from human germline immunoglobulin sequences. The human monoclonal antibodies (mAbs) of the disclosure may include amino acid residues not encoded by human germline immunoglobulin sequences (e.g., mutations introduced by random or site-specific mutagenesis in vitro or by somatic mutation in vivo), for example in the CDRs and in particular CDR3. However, the term "human antibody", as used herein, is not intended to include mAbs in which CDR sequences derived from the germline of another mammalian species (e.g., mouse), have been grafted onto human FR sequences. The term includes antibodies recombinantly produced in a non-human mammal, or in cells of a non-human mammal. The term is not intended to include antibodies isolated from or generated in a human subject.

The term "recombinant", as used herein, refers to antigen-binding proteins, e.g., antibodies or antigen-binding fragments thereof, of the disclosure created, expressed, isolated or obtained by technologies or methods known in the art as recombinant DNA technology which include, e.g., DNA splicing and transgenic expression. The term refers to antigen-binding proteins, e.g., antibodies expressed in a non-human mammal (including transgenic non-human mammals, e.g., transgenic mice), or a cell (e.g., CHO cells) expression system or isolated from a recombinant combinatorial human antibody library.

As used herein, the terms "chimeric antigen receptor" or "CAR", used interchangeably herein, refer to a recombinant fused protein comprising an extracellular domain capable of binding to an antigen (e.g., a conformational epitope of an HLA-A2 displayed NY-ESO-1 peptide, e.g., a peptide comprising amino acid residues 157-165 of NY-ESO-1), a transmembrane domain, and at least one intracellular signaling domain.

An "immune effector cell," as used herein, refers to any cell of the immune system that has one or more effector functions (e.g., cytotoxic cell killing activity, secretion of cytokines, induction of ADCC and/or CDC). In one embodiment, the immune effector cells used with the CARs as described herein are T lymphocytes, in particular cytotoxic T cells (CTLs; CD8+ T cells) and helper T cells (HTLs; CD4+ T cells). Other populations of T cells are also useful herein, for example näive T cells and memory T cells. As would be understood by the skilled person, other cells may also be used as immune effector cells with the CARs as described herein. In particular, immune effector cells also include NK cells, NKT cells, neutrophils, and macrophages. Immune effector cells also include progenitors of effector cells wherein such progenitor cells can be induced to differentiate into immune effector cells in vivo or in vitro. Thus, in this regard, immune effector cell includes progenitors of immune effectors cells such as hematopoietic stem cells (HSCs) contained within the CD34+ population of cells derived from cord blood, bone marrow or mobilized peripheral blood which upon administration in a subject differentiate into mature immune effector cells, or which can be induced in vitro to differentiate into mature immune effector cells.

As disclosed herein, the term "off-target peptide" refers to a peptide that differs by 2, 3, 4, 5 or more amino acids from a target peptide (e.g., NY-ESO-1_157-165 peptide). In certain embodiments, the term includes a peptide that differs by less than or equal to 3 amino acids than the target peptide. For example, for a 9-mer peptide, if 2, 3, or 4 amino acids are not identical to the target peptide, it is considered an "off-target" peptide. In certain embodiments, amino acid identity is expressed in terms of 'degree of similarity' (DoS). If 6 amino acids within a 9-mer peptide are identical, the DoS is 6. In certain embodiments, a peptide with DoS 6 is considered an "off-target" peptide. The term "off-target" peptide also refers to a peptide that is similar to the target peptide based on sequence homology, is predicted to bind to HLA-A2 and is comprised in a protein that is expressed in essential, normal tissues.

The term "specifically binds," or "binds specifically to", or the like, means that an antigen-binding protein, e.g., antibody, or antigen-binding fragments thereof, or CAR, forms a complex with an antigen that is relatively stable under physiologic conditions. Specific binding can be characterized by an equilibrium dissociation constant of at least about $1\times10^{-8}$ M or less (e.g., a smaller $K_D$ denotes a tighter binding). Methods for determining whether two molecules specifically bind are well known in the art and include, for example, equilibrium dialysis, surface plasmon resonance, and the like. As described herein, antigen-binding proteins, e.g., antibodies, have been identified by surface plasmon resonance, e.g., BIACORE™, which bind specifically to a conformational epitope of an HLA-A2 presented New York esophageal squamous cell carcinoma 1 (NY-ESO-1) peptide, e.g., a peptide comprising amino acid residues 157-165 of NY-ESO-1.

The term "high affinity" antigen-binding protein, e.g., antibody, refers to those antigen-binding proteins, e.g., mAbs, having a binding affinity to conformational epitope of an HLA-A2 presented NY-ESO-1 peptide, e.g., a peptide comprising amino acid residues 157-165 of NY-ESO-1, expressed as $K_D$, of at least $10^{-8}$ M; preferably $10^{-9}$M; more preferably $10^{-10}$ M, even more preferably $10^{-11}$ M, even more preferably $10^{-12}$ M, as measured by surface plasmon resonance, e.g., BIACORE™ or solution-affinity ELISA.

By the term "slow off rate", "Koff" or "kd" is meant an antigen-binding protein that dissociates from HLA-A2:NY-ESO-1, with a rate constant of $1\times10^{-3}$ s$^{-1}$ or less, preferably $1\times10^{-4}$s$^{-1}$ or less, as determined by surface plasmon resonance, e.g., BIACORE™.

The terms "antigen-binding portion" of an antigen-binding protein (e.g., antibody), "antigen-binding fragment" of an antigen-binding protein (e.g., antibody), and the like, as used herein, include any naturally occurring, enzymatically obtainable, synthetic, or genetically engineered polypeptide or glycoprotein that specifically binds an antigen to form a complex. The terms "antigen-binding fragment" of an antibody, or "antibody fragment", as used herein, refers to one or more fragments of an antibody that retain the ability to bind to conformational epitope of an HLA-A2 presented NY-ESO-1 peptide, e.g., a peptide comprising amino acid residues 157-165 of NY-ESO-1 coupled to HLA-A2.

In specific embodiments, antigen-binding proteins, e.g., antibody or antibody fragments, or CARs, of the disclosure may be conjugated to a moiety such as a ligand, a detectable moiety, or a therapeutic moiety ("immunoconjugate"), such as a cytotoxin, a second anti-HLA-A2:NY-ESO-1 antigen-binding protein, an antibody to a tumor-specific antigen, an anti-cancer drug, or any other therapeutic moiety useful for treating a disease or condition including NY-ESO-1-associated disease or disorder, such as an NY-ESO-1-positive cancer.

An "isolated antigen-binding protein", e.g., an isolated antibody, as used herein, is intended to refer to an antigen-binding protein, e.g., antibody, that is substantially free of other antigen-binding proteins, e.g., antibodies (Abs), having different antigenic specificities (e.g., an isolated antibody that specifically binds HLA-A2:NY-ESO-1, or a fragment thereof, is substantially free of antigen-binding proteins, e.g., antibodies, that specifically bind antigens other than a conformational epitope of an HLA-A2 presented NY-ESO-1 peptide.

The term "surface plasmon resonance", as used herein, refers to an optical phenomenon that allows for the analysis of real-time biomolecular interactions by detection of alterations in protein concentrations within a biosensor matrix, for example using the BIACORE™ system (Pharmacia Biosensor AB, Uppsala, Sweden and Piscataway, N.J.).

The term "$K_D$", as used herein, is intended to refer to the equilibrium dissociation constant of a particular antigen-binding protein-antigen interaction.

The term "cross-competes", as used herein, means an antigen-binding protein, e.g., antibody or antigen-binding fragment thereof, binds to an antigen and inhibits or blocks the binding of another antigen-binding protein, e.g., antibody or antigen-binding fragment thereof. The term also includes competition between two antigen-binding proteins, e.g., antibodies, in both orientations, i.e., a first antigen-binding protein, e.g., antibody, that binds and blocks binding of second antigen-binding protein, e.g., antibody, and vice-versa. In certain embodiments, the first antigen-binding protein, e.g., antibody, and second antigen-binding protein, e.g., antibody, may bind to the same epitope. Alternatively, the first and second antigen-binding proteins, e.g., antibodies, may bind to different, but overlapping epitopes such that binding of one inhibits or blocks the binding of the second, e.g., via steric hindrance. Cross-competition between antigen-binding proteins, e.g., antibodies, may be measured by methods known in the art, for example, by a real-time, label-free bio-layer interferometry assay. Cross-competition between two antigen-binding proteins, e.g., antibodies, may be expressed as the binding of the second antigen-binding protein, e.g., antibody, that is less than the background signal due to self-self binding (wherein first and second antigen-binding proteins, e.g., antibodies, is the same antigen-binding protein, e.g., antibody). Cross-competition between 2 antigen-binding proteins, e.g., antibodies, may be expressed, for example, as % binding of the second antigen-binding protein, e.g., antibody, that is less than the baseline self-self background binding (wherein first and second antigen-binding proteins, e.g., antibodies is the same antigen-binding protein, e.g., antibody).

The term "substantial identity" or "substantially identical," when referring to a nucleic acid or fragment thereof, indicates that, when optimally aligned with appropriate nucleotide insertions or deletions with another nucleic acid (or its complementary strand), there is nucleotide sequence identity in at least about 90%, and more preferably at least about 95%, 96%, 97%, 98% or 99% of the nucleotide bases, as measured by any well-known algorithm of sequence identity, as discussed below. A nucleic acid molecule having substantial identity to a reference nucleic acid molecule may, in certain instances, encode a polypeptide having the same or substantially similar amino acid sequence as the polypeptide encoded by the reference nucleic acid molecule.

Sequence identity can be calculated using an algorithm, for example, the Needleman Wunsch algorithm (Needleman and Wunsch 1970, *J. Mol. Biol.* 48: 443-453) for global alignment, or the Smith Waterman algorithm (Smith and Waterman 1981, *J. Mol. Biol.* 147: 195-197) for local alignment. Another preferred algorithm is described by Dufresne et al in *Nature Biotechnology* in 2002 (vol. 20, pp. 1269-71) and is used in the software GenePAST (GQ Life Sciences, Inc. Boston, MA).

As applied to polypeptides, the term "substantial similarity" or "substantially similar" means that two peptide sequences, when optimally aligned, such as by the programs GAP or BESTFIT using default gap weights, share at least 90% sequence identity, even more preferably at least 95%, 96%, 97%, 98% or 99% sequence identity. Preferably, residue positions, which are not identical, differ by conservative amino acid substitutions. A "conservative amino acid substitution" is one in which an amino acid residue is substituted by another amino acid residue having a side chain (R group) with similar chemical properties (e.g., charge or hydrophobicity). In general, a conservative amino acid substitution will not substantially change the functional properties of a protein. In cases where two or more amino acid sequences differ from each other by conservative substitutions, the percent or degree of similarity may be adjusted upwards to correct for the conservative nature of the substitution. Means for making this adjustment are well known to those of skill in the art. See, e.g., Pearson (1994) *Methods Mol. Biol.* 24: 307-331, which is herein incorporated by reference. Examples of groups of amino acids that have side chains with similar chemical properties include 1) aliphatic side chains: glycine, alanine, valine, leucine and isoleucine; 2) aliphatic-hydroxyl side chains: serine and threonine; 3) amide-containing side chains: asparagine and glutamine; 4) aromatic side chains: phenylalanine, tyrosine, and tryptophan; 5) basic side chains: lysine, arginine, and histidine; 6) acidic side chains: aspartate and glutamate, and 7) sulfur-containing side chains: cysteine and methionine. Preferred conservative amino acids substitution groups are: valine-leucine-isoleucine, phenylalanine-tyrosine, lysine-arginine, alanine-valine, glutamate-aspartate, and asparagine-glutamine. Alternatively, a conservative replacement is any change having a positive value in the PAM250 log-likelihood matrix disclosed in Gonnet et al. (1992) *Science* 256:

1443 45, herein incorporated by reference. A "moderately conservative" replacement is any change having a nonnegative value in the PAM250 log-likelihood matrix.

Sequence similarity for polypeptides is typically measured using sequence analysis software. Protein analysis software matches similar sequences using measures of similarity assigned to various substitutions, deletions and other modifications, including conservative amino acid substitutions. For instance, GCG software contains programs such as GAP and BESTFIT which can be used with default parameters to determine sequence homology or sequence identity between closely related polypeptides, such as homologous polypeptides from different species of organisms or between a wild type protein and a mutein thereof. See, e.g., GCG Version 6.1. Polypeptide sequences also can be compared using FASTA with default or recommended parameters; a program in GCG Version 6.1. FASTA (e.g., FASTA2 and FASTA3) provides alignments and percent sequence identity of the regions of the best overlap between the query and search sequences (Pearson (2000) supra). Sequences also can be compared using the Smith-Waterman homology search algorithm using an affine gap search with a gap open penalty of 12 and a gap extension penalty of 2, BLOSUM matrix of 62. Another preferred algorithm when comparing a sequence of this disclosure to a database containing a large number of sequences from different organisms is the computer program BLAST, especially BLASTP or TBLASTN, using default parameters. See, e.g., Altschul et al. (1990) *J. Mol. Biol.* 215: 403-410 and (1997) Nucleic Acids Res. 25:3389-3402, each of which is herein incorporated by reference.

By the phrase "therapeutically effective amount" is meant an amount that produces the desired effect for which it is administered. The exact amount will depend on the purpose of the treatment, and will be ascertainable by one skilled in the art using known techniques (see, for example, Lloyd (1999) *The Art, Science and Technology of Pharmaceutical Compounding*).

As used herein, the term "subject" refers to an animal, preferably a mammal, in need of amelioration, prevention and/or treatment of a disease or disorder such as an NY-ESO-1-associated disease or disorder, such as an NY-ESO-1-associated cancer (e.g., an NY-ESO-1-positive cancer). The term includes human subjects who have or are at risk of having NY-ESO-1-associated disease or disorder, such as an NY-ESO-1-associated cancer or metastatic NY-ESO-1-associated cancer.

As used herein, "anti-cancer drug" means any agent useful to treat or ameliorate or inhibit cancer including, but not limited to, cytotoxins and agents such as antimetabolites, alkylating agents, anthracyclines, antibiotics, antimitotic agents, procarbazine, hydroxyurea, asparaginase, corticosteroids, cyclophosphamide, mytotane (O,P'-(DDD)), biologics (e.g., antibodies and interferons) and radioactive agents. As used herein, "a cytotoxin or cytotoxic agent", also refers to a chemotherapeutic agent and means any agent that is detrimental to cells. Examples include Taxol® (paclitaxel), temozolomide, cytochalasin B, gramicidin D, ethidium bromide, emetine, cisplatin, mitomycin, etoposide, tenoposide, vincristine, vinbiastine, coichicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof.

As used herein, the term "anti-viral drug" refers to any drug or therapy used to treat, prevent, or ameliorate a viral infection in a host subject. The term "anti-viral drug"

includes, but is not limited to zidovudine, lamivudine, abacavir, ribavirin, lopinavir, efavirenz, cobicistat, tenofovir, rilpivirine, analgesics and corticosteroids.

An immunogen comprising any one of the following can be used to generate antigen-binding proteins, e.g., antibodies, to a conformational epitope of an HLA-A2 presented NY-ESO-1 peptide, e.g., a peptide comprising amino acid residues 157-165 of NY-ESO-1 linked to HLA-A2. In certain embodiments, the antigen-binding proteins, e.g., antibodies, of the disclosure can be obtained from mice immunized with a full length native NY-ESO-1 protein (See, GenBank Accession No. NP_001318.1) (SEQ ID NO: 271) or a recombinant NY-ESO-1 peptide (e.g., a peptide comprising amino acids residues 157-165 (SLLMWITQC; SEQ ID NO: 269) of GenBank Accession No. NP_001318.1 (SEQ ID NO: 271) or that sequence with a C165V substitution (SLMMWITQV; SEQ ID NO: 270) of GenBank Accession, bound to an HLA protein such as HLA-A2.

Alternatively, NY-ESO-1 or a fragment thereof may be produced using standard biochemical techniques and modified in the context of HLA-A2 and used as immunogen.

In some embodiments, the immunogen may be a recombinant NY-ESO-1 peptide (which may be a recombinant NY-ESO-1 peptide presented by an HLA) expressed in E. coli or in any other eukaryotic or mammalian cells such as Chinese hamster ovary (CHO) cells.

In certain embodiments, antigen-binding proteins that bind specifically a conformational epitope of an HLA-A2 presented NY-ESO-1 peptide may be prepared using the polypeptides described above, or fragments thereof. In some embodiments, an HLA-A2 presented NY-ESO-1 peptide can +extend beyond the designated regions by about 5 to about 20 amino acid residues from either, or both, the N or C terminal ends of the regions described herein. In certain embodiments, any combination of the above-noted regions or fragments thereof may be used in the preparation of HLA-A2:NY-ESO-1 specific antigen-binding proteins, e.g., antibodies.

The peptides may be modified to include addition or substitution of certain residues for tagging or for purposes of conjugation to carrier molecules, such as, KLH. For example, a cysteine may be added at either the N terminal or C terminal end of a peptide, or a linker sequence may be added to prepare the peptide for conjugation to, for example, KLH for immunization.

Non-limiting, exemplary in vitro assays for measuring binding activity are illustrated in Examples herein. In Example 3, the binding affinities and kinetic constants of human anti-HLA-A2:NY-ESO-1 specific antigen-binding proteins, e.g., antibodies were determined by surface plasmon resonance and the measurements were conducted on a Biacore 4000 or T200 instrument. Example 4 describes the binding of the antibodies to cells overexpressing fragments of NY-ESO-1.

The antigen-binding proteins, e.g., antibodies, specific for HLA-A2:NY-ESO-1 may contain no additional labels or moieties, or they may contain an N-terminal or C-terminal label or moiety. In one embodiment, the label or moiety is biotin. In a binding assay, the location of a label (if any) may determine the orientation of the peptide relative to the surface upon which the peptide is bound. For example, if a surface is coated with avidin, a peptide containing an N-terminal biotin will be oriented such that the C-terminal portion of the peptide will be distal to the surface. In one embodiment, the label may be a radionuclide, a fluorescent dye or a MRI-detectable label. In certain embodiments, such labeled antigen-binding proteins may be used in diagnostic assays including imaging assays.

Antigen Binding Proteins

The present disclosure provides antigen-binding proteins that include antibodies, or antigen-binding fragments thereof, and CARs (e.g., nucleic acid molecules encoding a CAR of the disclosure) (described below). Unless specifically indicated otherwise, the term "antibody," as used herein, shall be understood to encompass antibody molecules comprising two immunoglobulin heavy chains and two immunoglobulin light chains (i.e., "full antibody molecules") as well as antigen-binding fragments thereof. The terms "antigen-binding portion" of an antibody, "antigen-binding fragment" of an antibody, and the like, as used herein, include any naturally occurring, enzymatically obtainable, synthetic, or genetically engineered polypeptide or glycoprotein that specifically binds an antigen to form a complex. The terms "antigen-binding fragment" of an antibody, or "antibody fragment", as used herein, refers to one or more fragments of an antibody that retain the ability to specifically bind to a conformational epitope of an HLA-A2 presented NY-ESO-1 peptide. An antigen-binding protein, such as an antibody fragment, may include a Fab fragment, a F(ab')2 fragment, a Fv fragment, a dAb fragment, a fragment containing a CDR, or an isolated CDR. Antigen binding proteins, such as antigen-binding fragments of an antibody, may be derived, e.g., from full antibody molecules using any suitable standard techniques such as proteolytic digestion or recombinant genetic engineering techniques involving the manipulation and expression of DNA encoding antibody variable and (optionally) constant domains. Such DNA is known and/or is readily available from, e.g., commercial sources, DNA libraries (including, e.g., phage-antibody libraries), or can be synthesized. The DNA may be sequenced and manipulated chemically or by using molecular biology techniques, for example, to arrange one or more variable and/or constant domains into a suitable configuration, or to introduce codons, create cysteine residues, modify, add or delete amino acids, etc.

Non-limiting examples of antigen-binding fragments of an antibody, include: (i) Fab fragments; (ii) F(ab')2 fragments; (iii) Fd fragments; (iv) Fv fragments; (v) single-chain Fv (scFv) molecules; (vi) dAb fragments; and (vii) minimal recognition units consisting of the amino acid residues that mimic the hypervariable region of an antibody (e.g., an isolated complementarity determining region (CDR) such as a CDR3 peptide), or a constrained FR3-CDR3-FR4 peptide. Other engineered molecules, such as domain-specific antibodies, single domain antibodies, domain-deleted antibodies, chimeric antibodies, CDR-grafted antibodies, diabodies, triabodies, tetrabodies, minibodies, nanobodies (e.g. monovalent nanobodies, bivalent nanobodies, etc.), small modular immunopharmaceuticals (SMIPs), and shark variable IgNAR domains, are also encompassed within the expression "antigen-binding fragment," as used herein.

An antigen-binding fragment of an antigen-binding protein (e.g., antibody), will typically comprise at least one variable domain. The variable domain may be of any size or amino acid composition and will generally comprise at least one CDR, which is adjacent to or in frame with one or more framework sequences. In antigen-binding proteins having a VH domain associated with a VL domain, the VH and VL domains may be situated relative to one another in any suitable arrangement. For example, the variable region may be dimeric and contain VH-VH, VH-VL or VL-VL dimers. Alternatively, the antigen-binding fragment of an antibody may contain a monomeric VH or VL domain.

In certain embodiments, an antigen-binding fragment of an antibody may contain at least one variable domain covalently linked to at least one constant domain. Non-limiting, exemplary configurations of variable and constant domains that may be found within an antigen-binding frag-ment of an antigen-binding protein of the present disclosure include: (i) $V_H$-$C_H1$; (ii) $V_H$-$C_H2$; (iii) $V_H$-$C_H3$; (iv) $V_H$-$C_H1$-$C_H2$; (v) $V_H$-$C_H1$-$C_H2$-$C_H3$; (vi) $V_H$-$C_H2$-$C_H3$; (vii) $V_H$-$C_H1$; (viii) $V_L$-$C_H1$; (ix) $V_L$-$C_H2$; (x) $V_L$-$C_H3$; (xi) $V_L$-$C_H1$-$C_H2$; (xii) $V_L$-$C_H1$-$C_H2$-$C_H3$; (xiii) $V_L$-$C_H2$-$C_H3$; and (xiv) $V_L$-$C_L$. In any configuration of variable and constant domains, including any of the exemplary configu-rations listed above, the variable and constant domains may be either directly linked to one another or may be linked by a full or partial hinge or linker region. A hinge region may consist of at least 2 (e.g., 5, 10, 15, 20, 40, 60 or more) amino acids, which result in a flexible or semi-flexible linkage between adjacent variable and/or constant domains in a single polypeptide molecule. Moreover, an antigen-binding fragment of an antibody, of the present disclosure may comprise a homo-dimer or hetero-dimer (or other multimer) of any of the variable and constant domain configurations listed above in non-covalent association with one another and/or with one or more monomeric $V_H$ or $V_L$ domain (e.g., by disulfide bond(s)).

As with full antibody molecules, antigen-binding pro-teins, e.g., antigen-binding fragments of an antibody, may be mono-specific or multi-specific (e.g., bi-specific). A multi-specific antigen-binding fragment of an antibody will typi-cally comprise at least two different variable domains, wherein each variable domain is capable of specifically binding to a separate antigen or to a different epitope on the same antigen. Any multi-specific antibody format, including the exemplary bi-specific antibody formats disclosed herein, may be adapted for use in the context of an antigen-binding fragment of an antibody of the present disclosure using routine techniques available in the art.

Preparation of Antigen-Binding Proteins

Methods for generating antigen-binding proteins, such as human antibodies, in transgenic mice are known in the art. Any such known methods can be used in the context of the present disclosure to make human antibodies that specifi-cally bind to a conformational epitope of an HLA-A2 presented New York esophageal squamous cell carcinoma 1 peptide (NY-ESO-1 peptide).

Using VELOCIMMUNE® technology (see, for example, U.S. Pat. No. 6,596,541, Regeneron Pharmaceuticals, VELOCIMMUNE®) or any other known method for gen-erating antigen-binding proteins, e.g., monoclonal antibod-ies, high affinity antigen-binding proteins, e.g., chimeric antibodies, to conformational epitope of an HLA-A2 pre-sented NY-ESO-1 peptide, are initially isolated having a human variable region and a mouse constant region. The VELOCIMMUNE® technology involves generation of a transgenic mouse having a genome comprising human heavy and light chain variable regions operably linked to endogenous mouse constant region loci such that the mouse produces an antigen-binding protein, e.g., antibody, com-prising a human variable region and a mouse constant region in response to antigenic stimulation. The DNA encoding the variable regions of the heavy and light chains of the antibody are isolated and operably linked to DNA encoding the human heavy and light chain constant regions. The DNA is then expressed in a cell capable of expressing the fully human antibody.

Generally, a VELOCIMMUNE® mouse is challenged with the antigen of interest, and lymphatic cells (such as B-cells) are recovered from the mice that express antigen-binding proteins, e.g., antibodies. The lymphatic cells may be fused with a myeloma cell line to prepare immortal hybridoma cell lines, and such hybridoma cell lines are screened and selected to identify hybridoma cell lines that produce antibodies specific to the antigen of interest. DNA encoding the variable regions of the heavy chain and light chain may be isolated and linked to desirable isotypic constant regions of the heavy chain and light chain. Such an antigen-binding protein may be produced in a cell, such as a CHO cell. Alternatively, DNA encoding the antigen-specific antigen-binding proteins, e.g., chimeric antibodies, or the variable domains of the light and heavy chains may be isolated directly from antigen-specific lymphocytes.

Initially, high affinity antigen-binding proteins, e.g., chi-meric antibodies, are isolated having a human variable region and a mouse constant region. As in the experimental section below, the antigen-binding proteins are characterized and selected for desirable characteristics, including affinity, selectivity, epitope, etc. The mouse constant regions are replaced with a desired human constant region to generate the antigen-binding proteins, e.g., fully human antibodies, of the disclosure, for example wild-type or modified IgG1 or IgG4. While the constant region selected may vary accord-ing to specific use, high affinity antigen-binding and target specificity characteristics reside in the variable region.

Bioequivalents

The anti-HLA-A2:NY-ESO-1 antigen-binding proteins of the present disclosure encompass proteins having amino acid sequences that vary from those of the described anti-gen-binding proteins, e.g., antibodies, but that retain the ability to bind a conformational epitope of an HLA-A2 presented NY-ESO-1 peptide. Such variant antigen-binding proteins comprise one or more additions, deletions, or substitutions of amino acids when compared to parent sequence, but exhibit biological activity that is essentially equivalent to that of the described antigen-binding proteins. Likewise, the antigen-binding protein-encoding DNA sequences of the present disclosure encompass sequences that comprise one or more additions, deletions, or substitu-tions of nucleotides when compared to the disclosed sequence, but that encode an antigen-binding protein that is essentially bioequivalent to an antigen-binding protein of the disclosure.

Two antigen-binding proteins, or antibodies, are consid-ered bioequivalent if, for example, they are pharmaceutical equivalents or pharmaceutical alternatives whose rate and extent of absorption do not show a significant difference when administered at the same molar dose under similar experimental conditions, either single dose or multiple doses. Some antigen-binding proteins or antibodies will be considered equivalents or pharmaceutical alternatives if they are equivalent in the extent of their absorption but not in their rate of absorption and yet may be considered bioequivalent because such differences in the rate of absorp-tion are intentional and are reflected in the labeling, are not essential to the attainment of effective body drug concen-trations on, e.g., chronic use, and are considered medically insignificant for the particular drug product studied.

In one embodiment, two antigen-binding proteins (or antibodies) are bioequivalent if there are no clinically mean-ingful differences in their safety, purity, or potency.

In one embodiment, two antigen-binding proteins (or antibodies) are bioequivalent if a patient can be switched one or more times between the reference product and the biological product without an expected increase in the risk of adverse effects, including a clinically significant change in immunogenicity, or diminished effectiveness, as compared to continued therapy without such switching.

In one embodiment, two antigen-binding proteins (or antibodies) are bioequivalent if they both act by a common mechanism or mechanisms of action for the condition or conditions of use, to the extent that such mechanisms are known.

Bioequivalence may be demonstrated by in vivo and/or in vitro methods. Bioequivalence measures include, e.g., (a) an in vivo test in humans or other mammals, in which the concentration of the antigen-binding protein or its metabolites is measured in blood, plasma, serum, or other biological fluid as a function of time; (b) an in vitro test that has been correlated with and is reasonably predictive of human in vivo bioavailability data; (c) an in vivo test in humans or other mammals in which the appropriate acute pharmacological effect of the antigen-binding protein (or its target) is measured as a function of time; and (d) in a well-controlled clinical trial that establishes safety, efficacy, or bioavailability or bioequivalence of an antigen-binding protein.

Bioequivalent variants of the antigen-binding proteins (or antibodies) of the disclosure may be constructed by, for example, making various substitutions of residues or sequences or deleting terminal or internal residues or sequences not needed for biological activity. For example, cysteine residues not essential for biological activity can be deleted or replaced with other amino acids to prevent formation of unnecessary or incorrect intramolecular disulfide bridges upon renaturation. In other contexts, bioequivalent antigen-binding proteins may include antigen-binding protein variants comprising amino acid changes, which modify the glycosylation characteristics of the antigen-binding proteins, e.g., mutations that eliminate or remove glycosylation.

Anti-HLA-A2:NY-ESO-1 Antigen Binding-Proteins Comprising Fc Variants

According to certain embodiments of the present disclosure, anti-HLA-A2:NY-ESO-1 antigen-binding proteins, e.g., antibodies, are provided comprising an Fc domain comprising one or more mutations which enhance or diminish antigen-binding protein binding to the FcRn receptor, e.g., at acidic pH as compared to neutral pH. For example, the present disclosure includes anti-HLA-A2:NY-ESO-1 antigen-binding proteins comprising a mutation in the $C_H2$ or a $C_H3$ region of the Fc domain, wherein the mutation(s) increases the affinity of the Fc domain to FcRn in an acidic environment (e.g., in an endosome where pH ranges from about 5.5 to about 6.0). Such mutations may result in an increase in serum half-life of the antigen-binding protein when administered to an animal. Non-limiting examples of such Fc modifications include, e.g., a modification at position 250 (e.g., E or Q); 250 and 428 (e.g., L or F); 252 (e.g., L/Y/F/W or T), 254 (e.g., S or T), and 256 (e.g., S/R/Q/E/D or T); or a modification at position 428 and/or 433 (e.g., H/L/R/S/P/Q or K) and/or 434 (e.g., A, W, H, F or Y [N434A, N434W, N434H, N434F or N434Y]); or a modification at position 250 and/or 428; or a modification at position 307 or 308 (e.g., 308F, V308F), and 434. In one embodiment, the modification comprises a 428 L (e.g., M428L) and 434S (e.g., N434S) modification; a 428 L, 259I (e.g., V259I), and 308F (e.g., V308F) modification; a 433K (e.g., H433K) and a 434 (e.g., 434Y) modification; a 252, 254, and 256 (e.g., 252Y, 254T, and 256E) modification; a 250Q and 428L modification (e.g., T250Q and M428L); and a 307 and/or 308 modification (e.g., 308F or 308P). In yet another embodiment, the modification comprises a 265 Å (e.g., D265A) and/or a 297 Å (e.g., N297A) modification.

For example, the present disclosure includes anti-HLA-A2:NY-ESO-1 antigen-binding proteins comprising an Fc domain comprising one or more pairs or groups of mutations selected from the group consisting of: 250Q and 248L (e.g., T250Q and M248L); 252Y, 254T and 256E (e.g., M252Y, S254T and T256E); 428L and 434S (e.g., M428L and N434S); 257I and 311I (e.g., P257I and Q311I); 257I and 434H (e.g., P257I and N434H); 376V and 434H (e.g., D376V and N434H); 307 Å, 380 Å and 434 Å (e.g., 1307 Å, E380 Å and N434 Å); and 433K and 434F (e.g., H433K and N434F). In one embodiment, the present disclosure includes anti-HLA-A2:NY-ESO-1 antigen-binding proteins comprising an Fc domain comprising a S108P mutation in the hinge region of IgG4 to promote dimer stabilization. All possible combinations of the foregoing Fc domain mutations, and other mutations within the antigen-binding protein variable domains disclosed herein, are contemplated within the scope of the present disclosure.

The present disclosure also includes anti-HLA-A2:NY-ESO-1 antigen-binding proteins comprising a chimeric heavy chain constant ($C_H$) region, wherein the chimeric $C_H$ region comprises segments derived from the $C_H$ regions of more than one immunoglobulin isotype. For example, the antigen-binding proteins of the disclosure may comprise a chimeric $C_H$ region comprising part or all of a $C_H2$ domain derived from a human IgG1, human IgG2 or human IgG4 molecule, combined with part or all of a $C_H3$ domain derived from a human IgG1, human IgG2 or human IgG4 molecule. According to certain embodiments, the antigen-binding proteins of the disclosure comprise a chimeric $C_H$ region having a chimeric hinge region. For example, a chimeric hinge may comprise an "upper hinge" amino acid sequence (amino acid residues from positions 216 to 227 according to EU numbering) derived from a human IgG1, a human IgG2 or a human IgG4 hinge region, combined with a "lower hinge" sequence (amino acid residues from positions 228 to 236 according to EU numbering) derived from a human IgG1, a human IgG2 or a human IgG4 hinge region. According to certain embodiments, the chimeric hinge region comprises amino acid residues derived from a human IgG1 or a human IgG4 upper hinge and amino acid residues derived from a human IgG2 lower hinge. An antigen-binding protein comprising a chimeric $C_H$ region as described herein may, in certain embodiments, exhibit modified Fc effector functions without adversely affecting the therapeutic or pharmacokinetic properties of the antigen-binding protein. (See, e.g., U.S. Patent Publication No. 20140243504, the disclosure of which is hereby incorporated by reference in its entirety).

Biological Characteristics of the Antigen-Binding Proteins

In general, the antigen-binding proteins of the present disclosure function by binding to a conformational epitope of an HLA-A2 presented New York esophageal squamous cell carcinoma 1 (NY-ESO-1) peptide.

The present disclosure includes anti-HLA-A2:NY-ESO-1 antigen-binding proteins that bind NY-ESO-1 peptide in the context of HLA-A2 with high specificity. The anti-HLA-A2:NY-ESO-1 antigen-binding proteins do not bind to the NY-ESO-1 peptide in the absence of HLA-A2. Further, the anti-HLA-A2:NY-ESO-1 antigen-binding proteins do not bind to an off-target peptide in the context of HLA-A2.

The present disclosure includes anti-HLA-A2:NY-ESO-1 antigen-binding proteins that bind a monomeric HLA-A2:NY-ESO-1 (157-165) peptide (wherein the NY-ESO-1 157-165 peptide can comprise either C165 or V165; i.e., the antigen-binding proteins of the present disclosure can be specific for either form, or nonspecific with respect to which form) with high affinity. For example, the present disclosure includes antigen-binding proteins that bind monomeric HLA-A2:157-165 peptide (optionally with the C165V substitution) (e.g., at 25° C. or at 37° C.) with a $K_D$ of less than about 1 nM as measured by surface plasmon resonance, e.g., using the assay format as defined in Example 3 herein. In certain embodiments, the antigen-binding proteins bind monomeric HLA-A2:NY-ESO-1_157-165 peptide with a $K_D$ of less than about 1 nM, less than about 0.5 nM, less than about 0.1 nM, less than about 0.05 nM or less than about 0.04 nM, as measured by surface plasmon resonance, e.g., using the assay format as defined in Example 3 herein, or a substantially similar assay.

The present disclosure also includes antigen-binding proteins that bind to a cell expressing an HLA-A2:NY-ESO-1: 157-165 peptide complex (wherein the NY-ESO-1_157-165 peptide can comprise either C165 or V165; i.e., the antigen-binding proteins of the present disclosure can be specific for either form, or nonspecific with respect to which form) with an $EC_{50}$ less than about 10 nM and do not bind to cells expressing predicted off-target peptides as determined by a flow cytometry assay, as defined in Examples 4 and 5 herein, or a substantially similar assay. In certain embodiments, the antigen-binding proteins bind to a cell expressing an HLA-A2:NY-ESO-1_157-165 peptide with an $EC_{50}$ less than about less than about 10 nM, less than about 5 nM, less than about 2 nM, less than about 1 nM, or less than about 0.5 nM, and do not bind to cells expressing predicted off-target peptides as determined by a flow cytometry assay, as defined in Example 4 and 5 herein, or a substantially similar assay. e.g., using the assay format in Examples 4 and 5 herein, or a substantially similar assay.

In certain embodiments, the antigen-binding proteins of the present disclosure are useful in inhibiting the growth of a tumor or delaying the progression of cancer when administered prophylactically to a subject in need thereof and may increase survival of the subject. For example, the administration of an antigen-binding protein of the present disclosure may lead to shrinking of a primary tumor and may prevent metastasis or development of secondary tumors. In certain embodiments, the antigen-binding proteins of the present disclosure are useful in inhibiting the growth of a tumor when administered therapeutically to a subject in need thereof and may increase survival of the subject. For example, the administration of a therapeutically effective amount of an antigen-binding protein of the disclosure to a subject may lead to shrinking and disappearance of an established tumor in the subject.

In one embodiment, the disclosure provides an isolated recombinant antigen-binding protein thereof that binds to a conformational epitope of an HLA-A2 presented NY-ESO-1 peptide, wherein the antigen-binding protein exhibits one or more of the following characteristics: (i) comprises a HCVR having an amino acid sequence selected from the group consisting of SEQ ID NO: 2, 22, 42, 62, 82, 102, 122, 142, 162, 180, 196, 211, and 230, or a substantially similar sequence thereof having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98% or at least 99% sequence identity; (ii) comprises a LCVR having an amino acid sequence selected from the group consisting of SEQ ID NO: 10, 30, 50, 70, 90, 110, 130, 150, 170, 186, 203, 219, and 238, or a substantially similar sequence thereof having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98% or at least 99% sequence identity; (iii) comprises a HCDR3 domain having an amino acid sequence selected from the group consisting of SEQ ID NO: 8, 28, 48, 68, 88, 108, 128, 148, 168, 184, 201, 217, and 236, or a substantially similar sequence thereof having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98% or at least 99% sequence identity; and a LCDR3 domain having an amino acid sequence selected from the group consisting of SEQ ID NO: 16, 36, 56, 76, 96, 116, 136, 156, 190, 205, 224, and 244, or a substantially similar sequence thereof having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98% or at least 99% sequence identity; (iv) comprises a HCDR1 domain having an amino acid sequence selected from the group consisting of SEQ ID NO: 4, 24, 44, 64, 84, 104, 124, 144, 164, 213, and 232, or a substantially similar sequence thereof having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98% or at least 99% sequence identity; a HCDR2 domain having an amino acid sequence selected from the group consisting of SEQ ID NO: 6, 26, 46, 66, 86, 106, 126, 146, 166, 215, and 234, or a substantially similar sequence thereof having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98% or at least 99% sequence identity; a LCDR1 domain having an amino acid sequence selected from the group consisting of SEQ ID NO: 12, 32, 52, 72, 92, 112, 132, 152, 172, 188, 221, and 240, or a substantially similar sequence thereof having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98% or at least 99% sequence identity; and a LCDR2 domain having an amino acid sequence selected from the group consisting of SEQ ID NO: 14, 34, 54, 74, 94, 114, 134, 154, 174, and 242, or a substantially similar sequence thereof having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98% or at least 99% sequence identity; (v) binds monomeric HLA-A2:NY-ESO-1 157-165 (C165 or V165) peptide complex with a binding dissociation equilibrium constant (KD) of less than about 1 nM as measured in a surface plasmon resonance assay at 25° C.; (vi) binds monomeric HLA-A2: NY-ESO-1 157-165 (C165 or V165) peptide complex with a binding dissociation equilibrium constant (KD) of less than about 1 nM as measured in a surface plasmon resonance assay at 25° C.; (vii) binds to HLA-A2:NY-ESO-1 157-165 (C165 or V165) peptide complex expressing cells with an $EC_{50}$ less than about 10 nM; and (viii) does not bind to a HLA-A2-displayed off-target peptide wherein the peptide differs by 2, 3, 4, 5 or more amino acids from SEQ ID NO: 271.

The antigen-binding proteins of the present disclosure may possess one or more of the aforementioned biological characteristics, or any combinations thereof. Other biological characteristics of the antigen-binding proteins of the present disclosure will be evident to a person of ordinary skill in the art from a review of the present disclosure including the working Examples herein.

Epitope Mapping and Related Technologies

The present disclosure includes anti-HLA-A2:NY-ESO-1 antigen-binding proteins which interact with one or more amino acids found within one or more domains of the HLA-A2 displayed NY-ESO-1 peptide. The epitope may consist of a plurality of non-contiguous amino acids (or amino acid sequences) located within either or both of the aforementioned domains of the NY-ESO-1 molecule (e.g. a conformational epitope).

Various techniques known to persons of ordinary skill in the art can be used to determine whether an antigen-binding protein "interacts with one or more amino acids" within a polypeptide or protein. Exemplary techniques include, for example, routine cross-blocking assays, such as that described in Antibodies, Harlow and Lane (Cold Spring Harbor Press, Cold Spring Harbor, NY). Other methods include alanine scanning mutational analysis, peptide blot analysis (Reineke (2004) *Methods Mol. Biol.* 248: 443-63), peptide cleavage analysis crystallographic studies and NMR analysis. In addition, methods such as epitope excision, epitope extraction and chemical modification of antigens can be employed (Tomer (2000) *Prot. Sci.* 9: 487-496). Another method that can be used to identify the amino acids within a polypeptide with which an antigen-binding protein interacts is hydrogen/deuterium exchange detected by mass spectrometry. In general terms, the hydrogen/deuterium exchange method involves deuterium-labeling the protein of interest, followed by binding the antigen-binding protein to the deuterium-labeled protein. Next, the protein/antigen-binding protein complex is transferred to water and exchangeable protons within amino acids that are protected by the antigen-binding protein complex undergo deuterium-to-hydrogen back-exchange at a slower rate than exchangeable protons within amino acids that are not part of the interface. As a result, amino acids that form part of the protein/antigen-binding protein interface may retain deuterium and therefore exhibit relatively higher mass compared to amino acids not included in the interface. After dissociation of the antigen-binding protein, the target protein is subjected to protease cleavage and mass spectrometry analysis, thereby revealing the deuterium-labeled residues which correspond to the specific amino acids with which the antigen-binding protein interacts. See, e.g., Ehring (1999) *Analytical Biochemistry* 267: 252-259; Engen and Smith (2001) *Anal. Chem.* 73: 256A-265A.

The term "epitope" refers to a site on an antigen to which B and/or T cells respond. B-cell epitopes can be formed both from contiguous amino acids or noncontiguous amino acids juxtaposed by tertiary folding of a protein. Epitopes formed from contiguous amino acids are typically retained on exposure to denaturing solvents, whereas epitopes formed by tertiary folding are typically lost on treatment with denaturing solvents. An epitope typically includes at least 3, and more usually, at least 5 or 8-10 amino acids in a unique spatial conformation.

Modification-Assisted Profiling (MAP), also known as Antigen Structure-based Antibody Profiling (ASAP) is a method that categorizes large numbers of monoclonal antigen-binding proteins, e.g., antibodies (mAbs), directed against the same antigen according to the similarities of the binding profile of each antibody to chemically or enzymatically modified antigen surfaces (see US 2004/0101920, herein specifically incorporated by reference in its entirety). Each category may reflect a unique epitope either distinctly different from or partially overlapping with epitope represented by another category. This technology allows rapid filtering of genetically identical antigen-binding proteins, such that characterization can be focused on genetically distinct antigen-binding proteins. When applied to hybridoma screening, MAP may facilitate identification of rare hybridoma clones that produce antigen-binding proteins having the desired characteristics. MAP may be used to sort the antigen-binding proteins of the disclosure into groups of antigen-binding proteins binding different epitopes.

The present disclosure includes anti-HLA-A2:NY-ESO-1 antigen-binding proteins that bind to the same epitope, or a portion of the epitope, as any of the specific exemplary antigen-binding proteins described herein in Table 1, or an antigen-binding protein having the CDR sequences of any of the exemplary antigen-binding proteins described in Table 1. Likewise, the present disclosure also includes anti-HLA-A2:NY-ESO-1 antigen-binding proteins that compete for binding to HLA-A2:NY-ESO-1 or a fragment thereof with any of the specific exemplary antigen-binding proteins described herein in Table 1, or an antigen-binding protein having the CDR sequences of any of the exemplary antigen-binding proteins described in Table 1.

One can easily determine whether an antigen-binding protein binds to the same epitope as, or competes for binding with, a reference anti-HLA-A2:NY-ESO-1 antigen-binding protein by using routine methods known in the art. For example, to determine if a test antigen-binding protein binds to the same epitope as a reference anti-HLA-A2:NY-ESO-1 antigen-binding protein of the disclosure, the reference antigen-binding protein is allowed to bind to a HLA-A2:NY-ESO-1 protein or peptide under saturating conditions. Next, the ability of a test antigen-binding protein to bind to the HLA-A2:NY-ESO-1 molecule is assessed. If the test antigen-binding protein is able to bind to HLA-A2:NY-ESO-1 following saturation binding with the reference anti-HLA-A2:NY-ESO-1 antigen-binding protein, it can be concluded that the test antigen-binding protein binds to a different epitope than the reference anti-HLA-A2:NY-ESO-1 antigen-binding protein. On the other hand, if the test antigen-binding protein is not able to bind to the HLA-A2:NY-ESO-1 protein following saturation binding with the reference anti-HLA-A2:NY-ESO-1 antigen-binding protein, then the test antigen-binding protein may bind to the same epitope as the epitope bound by the reference anti-HLA-A2:NY-ESO-1 antigen-binding protein of the disclosure.

To determine if an antigen-binding protein competes for binding with a reference anti-HLA-A2:NY-ESO-1 antigen-binding protein, the above-described binding methodology is performed in two orientations: In a first orientation, the reference antigen-binding protein is allowed to bind to a HLA-A2:NY-ESO-1 protein under saturating conditions followed by assessment of binding of the test antigen-binding protein to the HLA-A2:NY-ESO-1 molecule. In a second orientation, the test antigen-binding protein is allowed to bind to a HLA-A2:NY-ESO-1 molecule under saturating conditions followed by assessment of binding of the reference antigen-binding protein to the HLA-A2:NY-ESO-1 molecule. If, in both orientations, only the first (saturating) antigen-binding protein is capable of binding to the HLA-A2:NY-ESO-1 molecule, then it is concluded that the test antigen-binding protein and the reference antigen-binding protein compete for binding to HLA-A2:NY-ESO-1. As will be appreciated by a person of ordinary skill in the art, an antigen-binding protein that competes for binding with a reference antigen-binding protein may not necessarily bind to the identical epitope as the reference antigen-binding protein, but may sterically block binding of the reference antigen-binding protein by binding an overlapping or adjacent epitope.

Two antigen-binding proteins bind to the same or overlapping epitope if each competitively inhibits (blocks) binding of the other to the antigen. That is, a 1-, 5-, 10-, 20- or 100-fold excess of one antigen-binding protein inhibits binding of the other by at least 50% but preferably 75%, 90% or even 99% as measured in a competitive binding assay (see, e.g., Junghans et al., *Cancer Res.* 1990 50:1495-1502). Alternatively, two antigen-binding proteins have the same epitope if essentially all amino acid mutations in the antigen that reduce or eliminate binding of one antigen-binding protein reduce or eliminate binding of the other. Two antigen-binding proteins have overlapping epitopes if some amino acid mutations that reduce or eliminate binding of one antigen-binding protein reduce or eliminate binding of the other.

Additional routine experimentation (e.g., peptide mutation and binding analyses) can then be carried out to confirm whether the observed lack of binding of the test antigen-binding protein is in fact due to binding to the same epitope as the reference antigen-binding protein or if steric blocking (or another phenomenon) is responsible for the lack of observed binding. Experiments of this sort can be performed using ELISA, RIA, surface plasmon resonance, flow cytometry or any other quantitative or qualitative antigen-binding protein-binding assay available in the art.

Immunoconjugates

The disclosure encompasses anti-HLA-A2:NY-ESO-1 antigen-binding proteins conjugated to a therapeutic moiety ("immunoconjugate"), such as a cytotoxin or a chemotherapeutic agent to treat cancer. As used herein, the term "immunoconjugate" refers to an antigen-binding protein which is chemically or biologically linked to a cytotoxin, a radioactive agent, a cytokine, an interferon, a target or reporter moiety, such as a detectable moiety, an enzyme, a toxin, a peptide or protein or a therapeutic agent. The antigen-binding protein may be linked to the cytotoxin, radioactive agent, cytokine, interferon, target or reporter moiety, enzyme, toxin, peptide or therapeutic agent at any location along the molecule so long as the antigen-binding protein is able to bind its target. Examples of immunoconjugates include antigen-binding protein-drug conjugates and antigen-binding protein-toxin fusion proteins. In one embodiment, the agent may be a second different antibody to NY-ESO-1 or HLA-A2:NY-ESO-1. In certain embodiments, the antigen-binding protein may be conjugated to an agent specific for a tumor cell. The type of therapeutic moiety that may be conjugated to the anti-HLA-A2:NY-ESO-1 antigen-binding protein and will take into account the condition to be treated and the desired therapeutic effect to be achieved. Examples of suitable agents for forming immunoconjugates are known in the art; see for example, PCT Publication No. WO 05/103081.

Chimeric Antigen Receptors (CAR)

Chimeric antigen receptors (CARs) redirect T cell specificity toward antibody-recognized antigens expressed on the surface of cancer cells, while T cell receptors (TCRs) extend the range of targets to include intracellular tumor antigens. CAR redirected T cells specific for the B cell differentiation antigen CD19 have shown dramatic efficacy in the treatment of B cell malignancies, while TCR-redirected T cells have shown benefits in patients suffering from solid cancer. Stauss et al. describe strategies to modify therapeutic CARs and TCRs, for use in the treatment of cancer, for example, to enhance the antigen-specific effector function and limit toxicity of engineered T cells (*Current Opinion in Pharmacology* 2015, 24:113-118).

One aspect of the disclosure includes a chimeric antigen receptor (CAR) which is specific for a NY-ESO-1 peptide displayed on the surface of tumor cells by HLA-A2, such as a peptide comprising amino acid residues 157-165 of NY-ESO-1. In one embodiment of the present disclosure, a CAR as described herein comprises an extracellular target-specific binding domain, a transmembrane domain, an intracellular signaling domain (such as a signaling domain derived from CD3zeta or FcRgamma), and/or one or more co-stimulatory signaling domains derived from a co-stimulatory molecule, such as, but not limited to, CD28, CD137, CD134 or CD278. In one embodiment, the CAR includes a hinge or spacer region between the extracellular binding domain and the transmembrane domain, such as a CD8alpha hinge or a CD28 hinge. In another embodiment of the present disclosure, a CAR as described herein comprises an extracellular target-specific binding domain, and a T cell receptor constant domain ("T-body construct"). In some embodiments, a hinge/transmembrane domain comprises the amino acid sequence of SEQ ID NO: 296. In some embodiments, a hinge region comprises a CD28 sequence of SEQ ID NO: 305. In some embodiments, a transmembrane domain comprises a CD28 sequence of SEQ ID NO: 304. In some embodiments, a 4-1 BB costimulatory domain comprises the amino acid sequence of SEQ ID NO: 297. In some embodiments, a CD28 costimulatory domain comprises the amino acid sequence of SEQ ID NO: 299. In some embodiments, the CD3zeta signaling domain comprises the amino acid sequence of SEQ ID NO: 298.

It is to be understood that, for use in any of the CARs described herein, the extracellular target-specific binding domain may comprise a Fab, a Fab', a (Fab')₂, an Fv, or a single chain Fv (scFv) of an antigen-binding protein of the disclosure.

As used herein, the binding domain or the extracellular domain of the CAR provides the CAR with the ability to bind to the target antigen of interest. A binding domain can be any protein, polypeptide, oligopeptide, or peptide that possesses the ability to specifically recognize and bind to a biological molecule (e.g., a cell surface receptor or tumor protein, or a component thereof). A binding domain includes any naturally occurring, synthetic, semi-synthetic, or recombinantly produced binding partner for a biological molecule of interest. For example, and as further described herein, a binding domain may be antibody light chain and heavy chain variable regions, or the light and heavy chain variable regions can be joined together in a single chain and in either orientation (e.g., VL-VH or VH-VL). A variety of assays are known for identifying binding domains of the present disclosure that specifically bind with a particular target, including Western blot, ELISA, flow cytometry, or surface plasmon resonance analysis (e.g., using BIACORE analysis), and are described herein. The target may be any antigen of clinical interest against which it would be desirable to trigger an effector immune response that results in tumor killing. In one embodiment, the target antigen of the binding domain of the chimeric antigen receptor is a conformational epitope of an HLA-A2 presented NY-ESO-1 peptide on the surface of tumor cells, such as a peptide comprising amino acid residues 157-165 of NY-ESO-1.

Illustrative binding domains include antigen-binding proteins, such as antigen-binding fragments of an antibody, such as scFv, scTCR, extracellular domains of receptors, ligands for cell surface molecules/receptors, or receptor binding domains thereof, and tumor binding proteins. In certain embodiments, the antigen-binding domains included in a CAR of the disclosure can be a variable region (Fv), a CDR, a Fab, an scFv, a VH, a VL, a domain antibody variant (dAb), a camelid antibody (VHH), a fibronectin 3 domain variant, an ankyrin repeat variant and other antigen-specific binding domain derived from other protein scaffolds.

In one embodiment, the binding domain of the CAR is an anti-HLA-A2:NY-ESO-1 single chain antibody (scFv), and may be a murine, human or humanized scFv. Single chain antibodies may be cloned from the V region genes of a hybridoma specific for a desired target. A technique which can be used for cloning the variable region heavy chain (VH) and variable region light chain (VL) has been described, for example, in Orlandi et al., *PNAS,* 1989; 86: 3833-3837. Thus, in certain embodiments, a binding domain comprises an antibody-derived binding domain but can be a non-antibody derived binding domain. An antibody-derived binding domain can be a fragment of an antibody or a genetically engineered product of one or more fragments of the antibody, which fragment is involved in binding with the antigen.

In certain embodiments, the CARs of the present disclosure may comprise a linker between the various domains, added for appropriate spacing and conformation of the molecule. For example, in some embodiments, there may be a linker between the binding domain VH and VL regions which may be 1-10 amino acids long. In other embodiments, the linker between any of the domains of the chimeric antigen receptor may be between 1-20 or 20 amino acids long. In this regard, the linker may be 1, 2, 3, 4, 5, 6, 7, 8, 9, 10, 11, 12, 13, 14, 15, 16, 17, 18, 19 or 20 amino acids long. In further embodiments, the linker may be 21, 22, 23, 24, 25, 26, 27, 28, 29 or 30 amino acids long. Ranges including the numbers described herein are also included herein, e.g., a linker 10-30 amino acids long.

In certain embodiments, linkers suitable for use in the CAR described herein are flexible linkers. Suitable linkers can be readily selected and can be of any of a suitable of different lengths, such as from 1 amino acid (e.g., Gly) to 20 amino acids, from 2 amino acids to 15 amino acids, from 3 amino acids to 12 amino acids, including 4 amino acids to 10 amino acids, 5 amino acids to 9 amino acids, 6 amino acids to 8 amino acids, or 7 amino acids to 8 amino acids, and may be 1, 2, 3, 4, 5, 6, or 7 amino acids.

Exemplary flexible linkers include glycine polymers (G)n, glycine-serine polymers (G)nS, where n is an integer of at least one (e.g., 1, 2, 3, 4, 5, 6, 7, 8, 9, 10, or more), glycine-alanine polymers, alanine-serine polymers, and other flexible linkers known in the art. In addition, linkers may comprise multiple units of the aforementioned sequences, e.g., ((G)nS)m), wherein n is an integer of at least one (e.g., 1, 2, 3, 4, 5, 6, 7, 8, 9, 10, or more) and m is an integer of at least one (e.g., 1, 2, 3, 4, 5, 6, 7, 8, 9, 10, or more). In some embodiments, n is 4, and a linker comprises the sequence GGGGS (SEQ ID NO: 295). In some embodiments, n is 4 and m is 3, and a linker comprises the sequence GGGGSGGGGSGGGGS (SEQ ID NO: 303). Glycine and glycine-serine polymers are relatively unstructured, and therefore may be able to serve as a neutral tether between domains of fusion proteins such as the CARs described herein. Glycine accesses significantly more phi-psi space than even alanine, and is much less restricted than residues with longer side chains (see Scheraga, *Rev. Computational Chem.* 11173-142 (1992)). The ordinarily skilled artisan will recognize that design of a CAR can include linkers that are all or partially flexible, such that the linker can include a flexible linker as well as one or more portions that confer less flexible structure to provide for a desired CAR structure.

The binding domain of the CAR may be followed by a "spacer," or, "hinge," which refers to the region that moves the antigen-binding domain away from the effector cell surface to enable proper cell/cell contact, antigen-binding and activation (Patel et al., Gene Therapy, 1999; 6: 412-419). The hinge region in a CAR is generally between the transmembrane (TM) and the binding domain. In certain embodiments, a hinge region is an immunoglobulin hinge region and may be a wild type immunoglobulin hinge region or an altered wild type immunoglobulin hinge region. Other exemplary hinge regions used in the CARs described herein include the hinge region derived from the extracellular regions of type 1 membrane proteins such as CD8alpha, CD4, CD28, and CD7, which may be wild-type hinge regions from these molecules or may be altered. In one embodiment, the hinge region comprises a CD8alpha hinge.

The "transmembrane," region or domain is the portion of the CAR that anchors the extracellular binding portion to the plasma membrane of the immune effector cell, and facilitates binding of the binding domain to the target antigen. The transmembrane domain may be a CD3zeta transmembrane domain, however, other transmembrane domains that may be employed include those obtained from CD8alpha, CD4, CD28, CD45, CD9, CD16, CD22, CD33, CD64, CD80, CD86, CD134, CD137, and CD154. In one embodiment, the transmembrane domain is the transmembrane domain of CD137. In certain embodiments, the transmembrane domain is synthetic in which case it would comprise predominantly hydrophobic residues such as leucine and valine.

The "intracellular signaling domain," refers to the part of the chimeric antigen receptor protein that participates in transducing the message of effective CAR binding to a target antigen into the interior of the immune effector cell to elicit effector cell function, e.g., activation, cytokine production, proliferation and cytotoxic activity, including the release of cytotoxic factors to the CAR-bound target cell, or other cellular responses elicited with antigen-binding to the extracellular CAR domain. The term "effector function" refers to a specialized function of the cell. Effector function of the T cell, for example, may be cytolytic activity or help or activity including the secretion of a cytokine. Thus, the term "intracellular signaling domain" refers to the portion of a protein which transduces the effector function signal and that directs the cell to perform a specialized function. While usually the entire intracellular signaling domain can be employed, in many cases it is not necessary to use the entire domain. To the extent that a truncated portion of an intracellular signaling domain is used, such truncated portion may be used in place of the entire domain as long as it transduces the effector function signal. The term intracellular signaling domain is meant to include any truncated portion of the intracellular signaling domain sufficient to transducing effector function signal. The intracellular signaling domain is also known as the, "signal transduction domain," and is typically derived from portions of the human CD3 or FcRy chains.

It is known that signals generated through the T cell receptor alone are insufficient for full activation of the T cell and that a secondary, or costimulatory signal is also required. Thus, T cell activation can be said to be mediated by two distinct classes of cytoplasmic signaling sequences: those that initiate antigen dependent primary activation through the T cell receptor (primary cytoplasmic signaling sequences) and those that act in an antigen independent manner to provide a secondary or costimulatory signal (secondary cytoplasmic signaling sequences). Primary cytoplasmic signaling sequences regulate primary activation of the T cell receptor complex either an inhibitory way, or in an inhibitory way. Primary cytoplasmic signaling sequences that act in a costimulatory manner may contain signaling motifs which are known as immunoreceptor tyrosine-based activation motif or ITAMs.

Examples of ITAM containing primary cytoplasmic signaling sequences that are of particular used in the disclosure include those derived from TCRzeta, FcRgamma, FcRbeta, CD3gamma, CD3delta, CD3epsilon, CD5, CD22, CD79a, CD79b and CD66d. In certain particular embodiments, the intracellular signaling domain of the anti-HLA-A2:NY-ESO-1 CARs described herein are derived from CD3zeta or FcRgamma.

As used herein, the term, "co-stimulatory signaling domain," or "co-stimulatory domain", refers to the portion of the CAR comprising the intracellular domain of a co-stimulatory molecule. Co-stimulatory molecules are cell surface molecules other than antigen receptors or Fc receptors that provide a second signal required for efficient activation and function of T lymphocytes upon binding to antigen. Examples of such co-stimulatory molecules include CD27, CD28, 4-1BB (CD137), OX40 (CD134), CD30, CD40, PD-1, ICOS (CD278), LFA-1, CD2, CD7, LIGHT, NKD2C, B7-H2 and a ligand that specifically binds CD83. Accordingly, while the present disclosure provides exemplary costimulatory domains derived from CD3zeta, CD28, and 4-1 BB, other costimulatory domains are contemplated for use with the CARs described herein. The inclusion of one or more co-stimulatory signaling domains may enhance the efficacy and expansion of T cells expressing CAR receptors. The intracellular signaling and co-stimulatory signaling domains may be linked in any order in tandem to the carboxyl terminus of the transmembrane domain.

Although scFv-based CARs engineered to contain a signaling domain from CD3 or FcRgamma have been shown to deliver a potent signal for T cell activation and effector function, they are not sufficient to elicit signals that promote T cell survival and expansion in the absence of a concomitant co-stimulatory signal. Other CARs containing a binding domain, a hinge, a transmembrane and the signaling domain derived from CD3zeta or FcRgamma together with one or more co-stimulatory signaling domains (e.g., intracellular co-stimulatory domains derived from CD28, CD137, CD134 and CD278) may more effectively direct antitumor activity as well as increased cytokine secretion, lytic activity, survival and proliferation in CAR expressing T cells in vitro, and in animal models and cancer patients (Milone et al., *Molecular Therapy*, 2009; 17: 1453-1464; Zhong et al., *Molecular Therapy*, 2010; 18: 413-420; Carpenito et al., *PNAS*, 2009; 106:3360-3365).

In one embodiment, the HLA-A2:NY-ESO-1 CARs of the disclosure comprise (a) an anti-HLA-A2:NY-ESO-1 scFv as a binding domain (e.g., an scFv having binding regions (e.g., CDRs or variable domains) from any one or more of the HLA-A2:NY-ESO-1 antibodies described in Table 1) (b) a hinge region derived from human CD8alpha, (c) a human CD8alpha transmembrane domain, and (d) a human T cell receptor CD3 zeta chain (CD3) intracellular signaling domain, and optionally one or more co-stimulatory signaling domains derived from CD28, CD137, CD134, and CD278. In one embodiment, the different protein domains are arranged from amino to carboxyl terminus in the following order: binding domain, hinge region and transmembrane domain. The intracellular signaling domain and optional co-stimulatory signaling domains are linked to the transmembrane carboxy terminus in any order in tandem to form a single chain chimeric polypeptide. In one embodiment, a nucleic acid construct encoding an HLA-A2:NY-ESO-1 CAR is a chimeric nucleic acid molecule comprising a nucleic acid molecule comprising different coding sequences, for example, (5' to 3') the coding sequences of a human anti-HLA-A2:NY-ESO-1 scFv, a human CD8alpha-hinge, a human CD8alpha transmembrane domain, a CD137 co-stimulatory domain, and a CD3zeta intracellular signaling domain. In another embodiment, a nucleic acid construct encoding an HLA-A2:NY-ESO-1 CAR is a chimeric nucleic acid molecule comprising a nucleic acid molecule comprising different coding sequences, for example, (5' to 3') the coding sequences of a human anti-HLA-A2:NY-ESO-1 scFv, a human CD8alpha-hinge, a human CD8alpha transmembrane domain, a CD137 co-stimulatory domain, and a CD3zeta co-stimulatory domain. In certain embodiments, a nucleic acid construct encoding an HLA-A2:NY-ESO-1 CAR is a chimeric nucleic acid molecule comprising a nucleic acid molecule comprising different coding sequences, for example, (5' to 3') the coding sequences of a human anti-HLA-A2:NY-ESO-1 scFv, a human CD8alpha-hinge, a human CD8alpha transmembrane domain, a CD137 co-stimulatory domain, and a CD3zeta co-stimulatory domain, wherein the anti-HLA-A2:NY-ESO-1 scFv comprises a $V_H$ selected from the group consisting of SEQ ID Nos: 2, 22, 42, 62, 82, 102, 122, 142, 162, 180, 196, 211, 230, and 250, or wherein the anti-HLA-A2:NY-ESO-1 scFv comprises a $V_L$ selected from the group consisting of SEQ ID Nos: 10, 30, 50, 70, 90, 110, 130, 150, 170, 186, 203, 219, 238, and 258, or wherein the anti-HLA-A2:NY-ESO-1 scFv comprises a $V_H/V_L$ pair selected from the group consisting of SEQ ID Nos: 2/10, 22/30, 42/50, 62/70, 82/90, 102/110, 122/130, 142/150, 162/170, 180/186, 196/203, 211/219, 230/238, and 250/258. In some embodiments, In some embodiments, the present disclosure includes a nucleic acid molecule that encodes for a HLA-A2:NY-ESO-1 CAR selected from the group consisting of the sequences of Table 2.

In certain embodiments, the polynucleotide encoding the CAR described herein is inserted into a vector. The term "vector" as used herein refers to a vehicle into which a polynucleotide encoding a protein may be covalently inserted so as to bring about the expression of that protein and/or the cloning of the polynucleotide. Such vectors may also be referred to as "expression vectors". The isolated polynucleotide may be inserted into a vector using any suitable methods known in the art, for example, without limitation, the vector may be digested using appropriate restriction enzymes and then may be ligated with the isolated polynucleotide having matching restriction ends. Expression vectors have the ability to incorporate and express heterologous or modified nucleic acid sequences coding for at least part of a gene product capable of being transcribed in a cell. In most cases, RNA molecules are then translated into a protein. Expression vectors can contain a variety of control sequences, which refer to nucleic acid sequences necessary for the transcription and possibly translation of an operatively linked coding sequence in a particular host organism. In addition to control sequences that govern transcription and translation, vectors and expression vectors may contain nucleic acid sequences that serve other functions as well and are discussed infra. An expression vector may comprise additional elements, for example, the expression vector may have two replication systems, thus allowing it to be maintained in two organisms, for example in human cells for expression and in a prokaryotic host for cloning and amplification.

The expression vector may have the necessary 5' upstream and 3' downstream regulatory elements such as promoter sequences such as CMV, PGK and EF1alpha promoters, ribosome recognition and binding TATA box, and 3' UTR AAUAAA transcription termination sequence for the efficient gene transcription and translation in its respective host cell. Other suitable promoters include the constitutive promoter of simian virus 40 (SV40) early promoter, mouse mammary tumor virus (MMTV) promoter, HIV LTR promoter, MoMuLV promoter, avian leukemia virus promoter, EBV immediate early promoter, and rous sarcoma virus promoter. Human gene promoters may also be used, including, but not limited to the actin promoter, the myosin promoter, the hemoglobin promoter, and the creatine kinase promoter. In certain embodiments inducible promoters are also contemplated as part of the vectors expressing chimeric antigen receptor. This provides a molecular switch capable of turning on expression of the polynucleotide sequence of interest or turning off expression. Examples of inducible promoters include, but are not limited to a metallothionine promoter, a glucocorticoid promoter, a progesterone promoter, or a tetracycline promoter.

The expression vector may have additional sequence such as 6×-histidine (SEQ ID NO:292), c-Myc, and FLAG tags which are incorporated into the expressed CARs. Thus, the expression vector may be engineered to contain 5' and 3' untranslated regulatory sequences that sometimes can function as enhancer sequences, promoter regions and/or terminator sequences that can facilitate or enhance efficient transcription of the nucleic acid(s) of interest carried on the expression vector. An expression vector may also be engineered for replication and/or expression functionality (e.g., transcription and translation) in a particular cell type, cell location, or tissue type. Expression vectors may include a selectable marker for maintenance of the vector in the host or recipient cell.

Examples of vectors are plasmid, autonomously replicating sequences, and transposable elements. Additional exemplary vectors include, without limitation, plasmids, phagemids, cosmids, artificial chromosomes such as yeast artificial chromosome (YAC), bacterial artificial chromosome (BAC), or P1-derived artificial chromosome (PAC), bacteriophages such as lambda phage or M13 phage, and animal viruses. Examples of categories of animal viruses useful as vectors include, without limitation, retrovirus (including lentivirus), adenovirus, adeno-associated virus, herpesvirus (e.g., herpes simplex virus), poxvirus, baculovirus, papillomavirus, and papovavirus (e.g., SV40). Examples of expression vectors are Lenti-X™ Bicistronic Expression System (Neo) vectors (Clontrch), pClneo vectors (Promega) for expression in mammalian cells; pLenti4/V5-DEST™, pLenti6/V5-DEST™, and pLenti6.2N5-GW/lacZ (Invitrogen) for lentivirus-mediated gene transfer and expression in mammalian cells. The coding sequences of the CARs disclosed herein can be ligated into such expression vectors for the expression of the chimeric protein in mammalian cells.

In certain embodiments, the nucleic acids encoding the CAR of the present disclosure are provided in a viral vector. A viral vector can be those derived from retrovirus, lentivirus, or foamy virus. As used herein, the term, "viral vector," refers to a nucleic acid vector construct that includes at least one element of viral origin and has the capacity to be packaged into a viral vector particle. The viral vector can contain the coding sequence for a the various chimeric proteins described herein in place of nonessential viral genes. The vector and/or particle can be utilized for the purpose of transferring DNA, RNA or other nucleic acids into cells either in vitro or in vivo. Numerous forms of viral vectors are known in the art.

In certain embodiments, the viral vector containing the coding sequence for a CAR described herein is a retroviral vector or a lentiviral vector. The term "retroviral vector" refers to a vector containing structural and functional genetic elements that are primarily derived from a retrovirus. The term "lentiviral vector" refers to a vector containing structural and functional genetic elements outside the LTRs that are primarily derived from a lentivirus.

The retroviral vectors for use herein can be derived from any known retrovirus (e.g., type c retroviruses, such as Moloney murine sarcoma virus (MoMSV), Harvey murine sarcoma virus (HaMuSV), murine mammary tumor virus (MuMTV), gibbon ape leukemia virus (GaLV), feline leukemia virus (FLV), spumavirus, Friend, Murine Stem Cell Virus (MSCV) and Rous Sarcoma Virus (RSV)). Retroviruses" of the disclosure also include human T cell leukemia viruses, HTLV-1 and HTLV-2, and the lentiviral family of retroviruses, such as Human Immunodeficiency Viruses, HIV-1, HIV-2, simian immunodeficiency virus (SIV), feline immunodeficiency virus (FIV), equine immunodeficiency virus (EIV), and other classes of retroviruses.

A lentiviral vector for use herein refers to a vector derived from a lentivirus, a group (or genus) of retroviruses that give rise to slowly developing disease. Viruses included within this group include HIV (human immunodeficiency virus; including HIV type 1, and HIV type 2); visna-maedi; a caprine arthritis-encephalitis virus; equine infectious anemia virus; feline immunodeficiency virus (FIV); bovine immune deficiency virus (BIV); and simian immunodeficiency virus (SIV). Preparation of the recombinant lentivirus can be achieved using the methods according to Dull et al. and Zufferey et al. (Dull et al., *J. Virol.*, 1998; 72: 8463-8471 and Zufferey et al., *J. Virol.* 1998; 72:9873-9880).

Retroviral vectors (i.e., both lentiviral and non-lentiviral) for use in the present disclosure can be formed using standard cloning techniques by combining the desired DNA sequences in the order and orientation described herein (Current Protocols in Molecular Biology, Ausubel, F. M. et al. (eds.) Greene Publishing Associates, (1989), Sections 9.10-9.14 and other standard laboratory manuals; Eglitis, et al. (1985) *Science* 230:1395-1398; Danos and Mulligan (1988) *Proc. Natl. Acad. Sci. USA* 85:6460-6464; Wilson et al. (1988) *Proc. Natl. Acad. Sci. USA* 85:3014-3018; Armentano et al. (1990) *Proc. Natl. Acad. Sci. USA* 87:6141-6145; Huber et al. (1991) *Proc. Natl. Acad. Sci. USA* 88:8039-8043; Ferry et al. (1991) *Proc. Natl. Acad. Sci. USA* 88:8377-8381; Chowdhury et al. (1991) *Science* 254:1802-1805; van Beusechem et al. (1992) Proc. Natl. Acad. Sci. USA 89:7640-7644; Kay et al. (1992) Human Gene Therapy 3:641-647; Dai et al. (1992) Proc. Natl. Acad. Sci. USA 89:10892-10895; Hwu et al. (1993) J. Immunol 150:4104-4115; U.S. Pat. Nos. 4,868,116; 4,980,286; PCT Application WO 89/07136; PCT Application WO 89/02468; PCT Application WO 89/05345; and PCT Application WO 92/07573).

Suitable sources for obtaining retroviral (i.e., both lentiviral and non-lentiviral) sequences for use in forming the vectors include, for example, genomic RNA and cDNAs available from commercially available sources, including the Type Culture Collection (ATCC), Rockville, Md. The sequences also can be synthesized chemically.

For expression of a HLA-A2:NY-ESO-1 CAR, the vector may be introduced into a host cell to allow expression of the polypeptide within the host cell. The expression vectors may contain a variety of elements for controlling expression, including without limitation, promoter sequences, transcription initiation sequences, enhancer sequences, selectable markers, and signal sequences. These elements may be selected as appropriate by a person of ordinary skill in the art, as described above. For example, the promoter sequences may be selected to promote the transcription of the polynucleotide in the vector. Suitable promoter sequences include, without limitation, T7 promoter, T3 promoter, SP6 promoter, beta-actin promoter, EF1a promoter, CMV promoter, and SV40 promoter. Enhancer sequences may be selected to enhance the transcription of the polynucleotide. Selectable markers may be selected to allow selection of the host cells inserted with the vector from those not, for example, the selectable markers may be genes that confer antibiotic resistance. Signal sequences may be selected to allow the expressed polypeptide to be transported outside of the host cell.

For cloning of the polynucleotide, the vector may be introduced into a host cell (an isolated host cell) to allow replication of the vector itself and thereby amplify the copies of the polynucleotide contained therein. The cloning vectors may contain sequence components generally include, without limitation, an origin of replication, promoter sequences, transcription initiation sequences, enhancer sequences, and selectable markers. These elements may be selected as appropriate by a person of ordinary skill in the art. For example, the origin of replication may be selected to promote autonomous replication of the vector in the host cell.

In certain embodiments, the present disclosure provides isolated host cells containing the vectors provided herein. The host cells containing the vector may be useful in expression or cloning of the polynucleotide contained in the vector. Suitable host cells can include, without limitation, prokaryotic cells, fungal cells, yeast cells, or higher eukaryotic cells such as mammalian cells. Suitable prokaryotic cells for this purpose include, without limitation, eubacteria, such as Gram-negative or Gram-positive organisms, for example, Enterobacteriaceae such as *Escherichia*, e.g., *E. coli, Enterobacter, Erwinia, Klebsiella, Proteus, Salmonella*, e.g., *Salmonella typhimurium, Serratia*, e.g., *Serratia marcescans*, and *Shigella*, as well as Bacilli such as *B. subtilis* and *B. licheniformis, Pseudomonas* such as *P. aeruginosa*, and *Streptomyces*.

The CARs of the present disclosure are introduced into a host cell using transfection and/or transduction techniques known in the art. As used herein, the terms, "transfection," and, "transduction," refer to the processes by which an exogenous nucleic acid sequence is introduced into a host cell. The nucleic acid may be integrated into the host cell DNA or may be maintained extrachromosomally. The nucleic acid may be maintained transiently or a may be a stable introduction. Transfection may be accomplished by a variety of means known in the art including but not limited to calcium phosphate-DNA co-precipitation, DEAE-dextran-mediated transfection, polybrene-mediated transfection, electroporation, microinjection, liposome fusion, lipofection, protoplast fusion, retroviral infection, and biolistics. Transduction refers to the delivery of a gene(s) using a viral or retroviral vector by means of viral infection rather than by transfection. In certain embodiments, retroviral vectors are transduced by packaging the vectors into virions prior to contact with a cell. For example, a nucleic acid encoding an anti-HLA-A2:NY-ESO-1 CAR carried by a retroviral vector can be transduced into a cell through infection and pro virus integration.

As used herein, the term "genetically engineered" or "genetically modified" refers to the addition of extra genetic material in the form of DNA or RNA into the total genetic material in a cell. The terms, "genetically modified cells," "modified cells," and, "redirected cells," are used interchangeably.

In particular, a CAR of the present disclosure is introduced and expressed in immune effector cells so as to redirect their specificity to a target antigen of interest, e.g., a conformational epitope of an HLA-A2 displayed NY-ESO-1 peptide, e.g., amino acid residues 157-165.

The present disclosure provides methods for making the immune effector cells which express the CAR as described herein. In one embodiment, the method comprises transfecting or transducing immune effector cells isolated from a subject, such as a subject having a NY-ESO-1-associate disease or disorder, such that the immune effector cells express one or more CAR as described herein. In certain embodiments, the immune effector cells are isolated from an individual and genetically modified without further manipulation in vitro. Such cells can then be directly re-administered into the same individual (as for autologous therapy) or into a different individual (as for allogeneic therapy). In further embodiments, the immune effector cells are first activated and stimulated to proliferate in vitro prior to being genetically modified to express a CAR. In this regard, the immune effector cells may be cultured before or after being genetically modified (i.e., transduced or transfected to express a CAR as described herein).

Prior to in vitro manipulation or genetic modification of the immune effector cells described herein, the source of cells may be obtained from a subject. In particular, the immune effector cells for use with the CARs as described herein comprise T cells. Such recombinant T cells are referred to herein as "T-bodies."

In one embodiment of the present disclosure, a T-body includes a CAR of the disclosure comprising an extracellular target-specific binding domain, a transmembrane domain, an intracellular signaling domain (such as a signaling domain derived from CD3zeta or FcRgamma), and/or one or more co-stimulatory signaling domains derived from a co-stimulatory molecule, such as, but not limited to, CD28, CD137, CD134 or CD278. In another embodiment of the present disclosure, a T-body includes a CAR of the disclosure comprising an extracellular target-specific binding domain, a transmembrane domain, a hinge or spacer region between the extracellular binding domain and the transmembrane domain, an intracellular signaling domain (such as a signaling domain derived from CD3zeta or FcRgamma), and/or one or more co-stimulatory signaling domains derived from a co-stimulatory molecule. In yet another embodiment of the present disclosure, a T-body includes a T-body construct CAR comprising an extracellular target-specific binding domain, and a T cell receptor constant domain. The extracellular target-specific binding domain suitable for use in a T-body comprising any of the CARs described herein may comprise a Fab, a Fab', a (Fab')$_2$, an Fv, or a single chain Fv (scFv) of an antigen-binding protein of the disclosure.

T cells can be obtained from a number of sources, including peripheral blood mononuclear cells, bone marrow, lymph nodes tissue, cord blood, thymus issue, tissue from a site of infection, ascites, pleural effusion, spleen tissue, and tumors. In certain embodiments, T cell can be obtained from a unit of blood collected from the subject using any number of techniques known to the skilled person, such as FICOLL separation. In one embodiment, cells from the circulating blood of an individual are obtained by apheresis. The apheresis product typically contains lymphocytes, including T cells, monocytes, granulocyte, B cells, other nucleated white blood cells, red blood cells, and platelets. In one embodiment, the cells collected by apheresis may be washed to remove the plasma fraction and to place the cells in an appropriate buffer or media for subsequent processing. In one embodiment of the disclosure, the cells are washed with PBS. In an alternative embodiment, the washed solution lacks calcium and may lack magnesium or may lack many if not all divalent cations. As would be appreciated by those of ordinary skill in the art, a washing step may be accomplished by methods known to those in the art, such as by using a semiautomated flowthrough centrifuge. After washing, the cells may be resuspended in a variety of biocompatible buffers or other saline solution with or without buffer. In certain embodiments, the undesirable components of the apheresis sample may be removed in the cell directly resuspended culture media.

In certain embodiments, T cells are isolated from peripheral blood mononuclear cells (PBMCs) by lysing the red blood cells and depleting the monocytes, for example, by centrifugation through a PERCOLL™ gradient. A specific subpopulation of T cells, such as CD28+, CD4+, CD8+, CD45RA+, and CD45RO+ T cells, can be further isolated by positive or negative selection techniques. For example, enrichment of a T cell population by negative selection can be accomplished with a combination of antibodies directed to surface markers unique to the negatively selected cells. One method for use herein is cell sorting and/or selection via negative magnetic immunoadherence or flow cytometry that uses a cocktail of monoclonal antibodies directed to cell surface markers present on the cells negatively selected. For example, to enrich for CD4+ cells by negative selection, a monoclonal antibody cocktail typically includes antibodies to CD14, CD20, CD11b, CD16, HLA-DR, and CD8. Flow cytometry and cell sorting may also be used to isolate cell populations of interest for use in the present disclosure.

PBMC may be used directly for genetic modification with the CARs using methods as described herein. In certain embodiments, after isolation of PBMC, T lymphocytes are further isolated and in certain embodiments, both cytotoxic and helper T lymphocytes can be sorted into naive, memory, and effector T cell subpopulations either before or after genetic modification and/or expansion. CD8+ cells can be obtained by using standard methods. In some embodiments, CD8+ cells are further sorted into naive, central memory, and effector cells by identifying cell surface antigens that are associated with each of those types of CD8+ cells. In embodiments, memory T cells are present in both CD62L+ and CD62L-subsets of CD8+ peripheral blood lymphocytes. PBMC are sorted into CD62L-CD8+ and CD62L+CD8+ fractions after staining with anti-CD8 and anti-CD62L antibodies. In some embodiments, the expression of phenotypic markers of central memory TCM include CD45RO, CD62L, CCR7, CD28, CD3, and CD127 and are negative for granzyme B. In some embodiments, central memory T cells are CD45RO+, CD62L+, CD8+ T cells. In some embodiments, effector T cells are negative for CD62L, CCR7, CD28, and CD127, and positive for granzyme B and perforin. In some embodiments, naive CD8+ T lymphocytes are characterized by the expression of phenotypic markers of naive T cells including CD62L, CCR7, CD28, CD3, CD 127, and CD45RA.

In certain embodiments, CD4+ T cells are further sorted into subpopulations. For example, CD4+ T helper cells can be sorted into naive, central memory, and effector cells by identifying cell populations that have cell surface antigens. CD4+ lymphocytes can be obtained by standard methods. In some embodiments, naive CD4+ T lymphocytes are CD45RO−, CD45RA+, CD62L+CD4+ T cell. In some embodiments, central memory CD4+ cells are CD62L positive and CD45RO positive. In some embodiments, effector CD4+ cells are CD62L and CD45RO negative.

The immune effector cells, such as T cells, can be genetically modified following isolation using known methods, or the immune effector cells can be activated and expanded (or differentiated in the case of progenitors) in vitro prior to being genetically modified. In another embodiment, the immune effector cells, such as T cells, are genetically modified with the chimeric antigen receptors described herein (e.g., transduced with a viral vector comprising a nucleic acid encoding a CAR) and then are activated and expanded in vitro. Methods for activating and expanding T cells are known in the art and are described, for example, in U.S. Pat. Nos. 6,905,874; 6,867,041; 6,797,514; WO2012079000, US 2016/0175358. Generally, such methods include contacting PBMC or isolated T cells with a stimulatory agent and costimulatory agent, such as anti-CD3 and anti-CD28 antibodies, generally attached to a bead or other surface, in a culture medium with appropriate cytokines, such as IL-2. Anti-CD3 and anti-CD28 antibodies attached to the same bead serve as a "surrogate" antigen presenting cell (APC). In other embodiments, the T cells may be activated and stimulated to proliferate with feeder cells and appropriate antibodies and cytokines using methods such as those described in U.S. Pat. Nos. 6,040,177; 5,827,642; and WO2012129514.

The disclosure provides a population of modified immune effector cells for the treatment of a NY-ESO-1-associated disease or disorder, e.g., cancer, the modified immune effector cells comprising an HLA-A2:NY-ESO-1 CAR as disclosed herein.

CAR-expressing immune effector cells prepared as described herein can be utilized in methods and compositions for adoptive immunotherapy in accordance with known techniques, or variations thereof that will be apparent to those skilled in the art based on the instant disclosure. See, e.g., U.S. Patent Application Publication No. 2003/0170238 to Gruenberg et al; see also U.S. Pat. No. 4,690,915 to Rosenberg.

In some embodiments, the cells are formulated by first harvesting them from their culture medium, and then washing and concentrating the cells in a medium and container system suitable for administration (a "pharmaceutically acceptable" carrier) in a treatment-effective amount. Suitable infusion medium can be any isotonic medium formulation, typically normal saline, Normosol R (Abbott) or Plasma-Lyte A (Baxter), but also 5% dextrose in water or Ringer's lactate can be utilized. The infusion medium can be supplemented with human serum albumin.

A treatment-effective amount of cells in the composition is at least 2 cells (for example, at least 1 CD8+ central memory T cell and at least 1 CD4+ helper T cell subset) or is more typically greater than $10^2$ cells, and up to $10^6$ up to and including $10^8$ or $10^9$ cells and can be more than $10^{10}$ cells. The number of cells will depend upon the ultimate use for which the composition is intended as will the type of cells included therein.

The cells may be autologous or heterologous to the patient undergoing therapy. If desired, the treatment may also include administration of mitogens (e.g., PHA) or lympho-kines, cytokines, and/or chemokines (e.g., IFN-γ, IL-2, IL-12, TNF-α, IL-18, and TNF-β, GM-CSF, IL-4, IL-13, Flt3-L, RANTES, MIP1α, etc.) as described herein to enhance induction of the immune response.

The CAR expressing immune effector cell populations of the present disclosure may be administered either alone, or as a pharmaceutical composition in combination with diluents and/or with other components such as IL-2 or other cytokines or cell populations. Briefly, pharmaceutical com-positions of the present disclosure may comprise a CAR-expressing immune effector cell population, such as T cells, as described herein, in combination with one or more pharmaceutically or physiologically acceptable carriers, diluents or excipients. Such compositions may comprise buffers such as neutral buffered saline, phosphate buffered saline and the like; carbohydrates such as glucose, mannose, sucrose or dextrans, mannitol; proteins; polypeptides or amino acids such as glycine; antioxidants; chelating agents such as EDTA or glutathione; adjuvants (e.g., aluminum hydroxide); and preservatives. Compositions of the present disclosure are preferably formulated for intravenous admin-istration.

The anti-tumor immune response induced in a subject by administering CAR expressing T cells described herein using the methods described herein, or other methods known in the art, may include cellular immune responses mediated by cytotoxic T cells capable of killing infected cells, regu-latory T cells, and helper T cell responses. Humoral immune responses, mediated primarily by helper T cells capable of activating B cells thus leading to antibody production, may also be induced. A variety of techniques may be used for analyzing the type of immune responses induced by the compositions of the present disclosure, which are well described in the art; e.g., *Current Protocols in Immunology*, Edited by: John E. Coligan, Ada M. Kruisbeek, David H. Margulies, Ethan M. Shevach, Warren Strober (2001) John Wiley & Sons, NY, N.Y.

Thus, the present disclosure provides for methods of treating an individual diagnosed with or suspected of hav-ing, or at risk of developing, a NY-ESO-1-associated disease or disorder, e.g., NY-ESO-1-positive cancer, comprising administering the individual a therapeutically effective amount of the CAR-expressing immune effector cells as described herein.

In one embodiment, the disclosure provides a method of treating a subject diagnosed with an NY-ESO-1-positive cancer comprising removing immune effector cells from a subject diagnosed with an NY-ESO-1-positive cancer, genetically modifying said immune effector cells with a vector comprising a nucleic acid encoding a chimeric anti-gen receptor of the present disclosure, thereby producing a population of modified immune effector cells, and admin-istering the population of modified immune effector cells to the same subject. In one embodiment, the immune effector cells comprise T cells.

The methods for administering the cell compositions described herein includes any method which is effective to result in reintroduction of ex vivo genetically modified immune effector cells that either directly express a CAR of the disclosure in the subject or on reintroduction of the genetically modified progenitors of immune effector cells that on introduction into a subject differentiate into mature immune effector cells that express the CAR. One method comprises transducing peripheral blood T cells ex vivo with a nucleic acid construct in accordance with the disclosure and returning the transduced cells into the subject.

Therapeutic Administration and Formulations

The disclosure provides therapeutic compositions com-prising the anti-HLA-A2:NY-ESO-1 antigen-binding pro-teins, e.g., antibodies, or antigen-biding fragments thereof, or CARs, of the present disclosure. Therapeutic composi-tions in accordance with the disclosure will be administered with suitable carriers, excipients, and other agents that are incorporated into formulations to provide improved transfer, delivery, tolerance, and the like. A multitude of appropriate formulations can be found in the formulary known to all pharmaceutical chemists: Remington's Pharmaceutical Sci-ences, Mack Publishing Company, Easton, PA These for-mulations include, for example, powders, pastes, ointments, jellies, waxes, oils, lipids, lipid (cationic or anionic) con-taining vesicles (such as LIPOFECTIN™), DNA conju-gates, anhydrous absorption pastes, oil-in-water and water-in-oil emulsions, emulsions carbowax (polyethylene glycols of various molecular weights), semi-solid gels, and semi-solid mixtures containing carbowax. See also Powell et al. "Compendium of excipients for parenteral formulations" PDA (1998) *J Pharm Sci Technol* 52:238-311.

The dose of the antigen-binding protein, e.g., antibody, or antigen-biding fragments thereof, may vary depending upon the age and the size of a subject to be administered, target disease, conditions, route of administration, and the like. When an antigen-binding protein of the present disclosure is used for treating a disease or disorder in an adult patient, or for preventing such a disease, it is advantageous to admin-ister the antigen-binding protein, e.g., antibody, or antigen-biding fragments thereof, of the present disclosure normally at a single dose of about 0.1 to about 60 mg/kg body weight, more preferably about 5 to about 60, about 20 to about 50, about 10 to about 50, about 1 to about 10, or about 0.8 to about 11 mg/kg body weight. Depending on the severity of the condition, the frequency and the duration of the treat-ment can be adjusted. In certain embodiments, the antigen-binding protein, e.g., antibody, or antigen-biding fragments thereof, of the disclosure can be administered as an initial dose of at least about 0.1 mg to about 800 mg, about 1 to about 500 mg, about 5 to about 300 mg, or about 10 to about 200 mg, to about 100 mg, or to about 50 mg. In certain embodiments, the initial dose may be followed by admin-istration of a second or a plurality of subsequent doses of the antigen-binding protein, e.g., antibody, or antigen-biding fragments thereof, in an amount that can be approximately the same or less than that of the initial dose, wherein the subsequent doses are separated by at least 1 day to 3 days; at least one week, at least 2 weeks; at least 3 weeks; at least 4 weeks; at least 5 weeks; at least 6 weeks; at least 7 weeks; at least 8 weeks; at least 9 weeks; at least 10 weeks; at least 12 weeks; or at least 14 weeks.

Various delivery systems are known and can be used to administer the pharmaceutical composition of the disclo-sure, e.g., encapsulation in liposomes, microparticles, microcapsules, recombinant cells capable of expressing mutant viruses, receptor mediated endocytosis (see, e.g., Wu et al. (1987) *J. Biol. Chem.* 262:4429-4432). Methods of introduction include, but are not limited to, intradermal, transdermal, intramuscular, intraperitoneal, intravenous, subcutaneous, intranasal, epidural and oral routes. The com-position may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local. The pharmaceutical composition can be also delivered in a vesicle, in particular a liposome (see, for example, Langer (1990) *Science* 249: 1527-1533).

The use of nanoparticles to deliver the antigen-binding proteins, e.g., antibody, or antigen-biding fragments thereof, of the present disclosure is also contemplated herein. Antigen binding protein-conjugated nanoparticles may be used both for therapeutic and diagnostic applications. Antigen binding protein-conjugated nanoparticles and methods of preparation and use are described in detail by Arruebo, M., et al. 2009 ("Antibody-conjugated nanoparticles for biomedical applications" in *J. Nanomat.* Volume 2009, Article ID 439389, 24 pages, doi: 10.1155/2009/439389), incorporated herein by reference. Nanoparticles may be developed and conjugated to antigen-binding proteins contained in pharmaceutical compositions to target tumor cells or autoimmune tissue cells or virally infected cells. Nanoparticles for drug delivery have also been described in, for example, U.S. Pat. No. 8,257,740, or U.S. Pat. No. 8,246,995, each incorporated herein in its entirety.

In certain situations, the pharmaceutical composition can be delivered in a controlled release system. In one embodiment, a pump may be used. In another embodiment, polymeric materials can be used. In yet another embodiment, a controlled release system can be placed in proximity of the composition's target, thus requiring only a fraction of the systemic dose.

The injectable preparations may include dosage forms for intravenous, subcutaneous, intracutaneous, intracranial, intraperitoneal and intramuscular injections, drip infusions, etc. These injectable preparations may be prepared by methods publicly known. For example, the injectable preparations may be prepared, e.g., by dissolving, suspending or emulsifying the antigen-binding protein or its salt described above in a sterile aqueous medium or an oily medium conventionally used for injections. As the aqueous medium for injections, there are, for example, physiological saline, an isotonic solution containing glucose and other auxiliary agents, etc., which may be used in combination with an appropriate solubilizing agent such as an alcohol (e.g., ethanol), a polyalcohol (e.g., propylene glycol, polyethylene glycol), a nonionic surfactant (e.g., polysorbate 80, HCO-50 (polyoxyethylene (50 mol) adduct of hydrogenated castor oil)), etc. As the oily medium, there are employed, e.g., sesame oil, soybean oil, etc., which may be used in combination with a solubilizing agent such as benzyl benzoate, benzyl alcohol, etc. The injection thus prepared is preferably filled in an appropriate ampoule.

A pharmaceutical composition of the present disclosure can be delivered subcutaneously or intravenously with a standard needle and syringe. In addition, with respect to subcutaneous delivery, a pen delivery device readily has applications in delivering a pharmaceutical composition of the present disclosure. Such a pen delivery device can be reusable or disposable. A reusable pen delivery device generally utilizes a replaceable cartridge that contains a pharmaceutical composition. Once all of the pharmaceutical composition within the cartridge has been administered and the cartridge is empty, the empty cartridge can readily be discarded and replaced with a new cartridge that contains the pharmaceutical composition. The pen delivery device can then be reused. In a disposable pen delivery device, there is no replaceable cartridge. Rather, the disposable pen delivery device comes prefilled with the pharmaceutical composition held in a reservoir within the device. Once the reservoir is emptied of the pharmaceutical composition, the entire device is discarded.

Numerous reusable pen and autoinjector delivery devices have applications in the subcutaneous delivery of a pharmaceutical composition of the present disclosure. Examples include, but certainly are not limited to AUTOPEN™ (Owen Mumford, Inc., Woodstock, UK), DISETRONIC™ pen (Disetronic Medical Systems, Burghdorf, Switzerland), HUMALOG MIX 75/25™ pen, HUMALOG™ pen, HUMALIN 70/30™ pen (Eli Lilly and Co., Indianapolis, IN), NOVOPEN™ I, II and III (Novo Nordisk, Copenhagen, Denmark), NOVOPEN JUNIOR™ (Novo Nordisk, Copenhagen, Denmark), BD™ pen (Becton Dickinson, Franklin Lakes, N.J.), OPTIPEN™, OPTIPEN PRO™, OPTIPEN STARLET™, and OPTICLIK™ (Sanofi-Aventis, Frankfurt, Germany), to name only a few. Examples of disposable pen delivery devices having applications in subcutaneous delivery of a pharmaceutical composition of the present disclosure include, but certainly are not limited to the SOLOSTAR™ pen (Sanofi-Aventis), the FLEXPEN™ (Novo Nordisk), and the KWIKPEN™ (Eli Lilly), the SURECLICK™ Autoinjector (Amgen, Thousand Oaks, CA), the PENLET™ (Haselmeier, Stuttgart, Germany), the EPIPEN (Dey, L. P.) and the HUMIRA™ Pen (Abbott Labs, Abbott Park, IL), to name only a few.

Advantageously, the pharmaceutical compositions for oral or parenteral use described above are prepared into dosage forms in a unit dose suited to fit a dose of the active ingredients. Such dosage forms in a unit dose include, for example, tablets, pills, capsules, injections (ampoules), suppositories, etc. The amount of the antigen-binding protein contained is generally about 5 to about 500 mg per dosage form in a unit dose; especially in the form of injection, it is preferred that the antigen-binding protein is contained in about 5 to about 100 mg and in about 10 to about 250 mg for the other dosage forms.

Therapeutic Uses of the Antigen-Binding Proteins

The antibodies of the disclosure are useful, inter alia, for the treatment, prevention and/or amelioration of any disease or disorder associated with or mediated by NY-ESO-1. For example, the present disclosure provides methods for treating a NY-ESO-1-associated disease or disorder, such as an NY-ESO-1-associated cancer (e.g., a NY-ESO-1-positive cancer) (tumor growth inhibition) by administering an anti-HLA-A2:NY-ESO-1 antigen-binding protein (or pharmaceutical composition comprising an anti-HLA-A2:NY-ESO-1 antigen-binding protein) as described herein to a patient in need of such treatment, and anti-HLA-A2:NY-ESO-1 antigen-binding proteins (or pharmaceutical composition comprising an anti-HLA-A2:NY-ESO-1 antigen-binding protein) for use in the treatment of a NY-ESO-1-associated cancer (tumor growth inhibition). The antigen-binding proteins of the present disclosure are useful for the treatment, prevention, and/or amelioration of disease or disorder or condition such as an NY-ESO-1-associated cancer and/or for ameliorating at least one symptom associated with such disease, disorder or condition. In the context of the methods of treatment described herein, the anti-HLA-A2:NY-ESO-1 antigen-binding protein may be administered as a monotherapy (i.e., as the only therapeutic agent) or in combination with one or more additional therapeutic agents (examples of which are described elsewhere herein).

In some embodiments, the antibodies described herein are useful for treating subjects suffering from primary or recurrent cancer, including, but not limited to, NY-ESO-1-associated cancer, e.g., a liposarcoma, a neuroblastoma, a myeloma, a metastatic melanoma, a synovial sarcoma, a bladder cancer, an esophageal cancer, a hepatocellular cancer, a head and neck cancer, a non-small cell lung cancer, an ovarian cancer, a prostate cancer, a breast cancer, astrocytic tumor, glioblastoma multiforme, anaplastic astrocytoma, brain tumor, fallopian tube cancer, ovarian epithelial cancer, primary peritoneal cavity cancer, advanced solid tumors, soft tissue sarcoma, melanoma, a sarcoma, myelodysplastic syndrome, acute myeloid leukemia, Hodgkin lymphoma, non-Hodgkin lymphoma, Hodgkin disease, multiple myeloma, synovial sarcoma, metastatic solid tumors, esophageal cancer, rhabdomyosarcoma, advanced myxoid, round cell liposarcoma, metastatic melanoma, or recurrent non-small cell lung cancer.

The antigen-binding proteins may be used to treat early stage or late-stage symptoms of the NY-ESO-1-associated cancer. In one embodiment, an antibody or fragment thereof of the disclosure may be used to treat advanced or metastatic cancer. The antigen-binding proteins are useful in reducing or inhibiting or shrinking tumor growth. In certain embodiments, treatment with an antigen-binding protein of the disclosure leads to more than 40% regression, more than 50% regression, more than 60% regression, more than 70% regression, more than 80% regression or more than 90% regression of a tumor in a subject. In certain embodiments, the antigen-binding proteins may be used to prevent relapse of a tumor. In certain embodiments, the antigen-binding proteins are useful in extending progression-free survival or overall survival in a subject with NY-ESO-1-associated cancer. In some embodiments, the antibodies are useful in reducing toxicity due to chemotherapy or radiotherapy while maintaining long-term survival in a patient suffering from NY-ESO-1-associated cancer.

One or more antibodies of the present disclosure may be administered to relieve or prevent or decrease the severity of one or more of the symptoms or conditions of the disease or disorder.

It is also contemplated herein to use one or more antibodies of the present disclosure prophylactically to patients at risk for developing a disease or disorder such as NY-ESO-1-associated disease or disorder, such as an NY-ESO-1-associated cancer.

In a further embodiment of the disclosure, the present antibodies are used for the preparation of a pharmaceutical composition for treating patients suffering from NY-ESO-1-associated disease or disorder, such as an NY-ESO-1-associated cancer. In another embodiment of the disclosure, the present antibodies are used as adjunct therapy with any other agent or any other therapy known to those skilled in the art useful for treating NY-ESO-1-associated cancer.

Combination Therapies and Formulations

Combination therapies may include an anti-HLA-A2:NY-ESO-1 antigen-binding protein of the disclosure, such as a CAR of the disclosure (e.g., an immune effector cell comprising a CAR of the disclosure) or a pharmaceutical composition of the disclosure, and any additional therapeutic agent that may be advantageously combined with an antigen-binding protein of the disclosure. The antigen-binding proteins of the present disclosure may be combined synergistically with one or more anti-cancer drugs or therapy used to treat or inhibit an NY-ESO-1-associated disease or disorder, such as NY-ESO-1-positive cancer, e.g., a liposarcoma, a neuroblastoma, a myeloma, a metastatic melanoma, a synovial sarcoma, a bladder cancer, an esophageal cancer, a hepatocellular cancer, a head and neck cancer, a non-small cell lung cancer, an ovarian cancer, a prostate cancer, a breast cancer, astrocytic tumor, glioblastoma multiforme, anaplastic astrocytoma, brain tumor, fallopian tube cancer, ovarian epithelial cancer, primary peritoneal cavity cancer, advanced solid tumors, soft tissue sarcoma, melanoma, a sarcoma, myelodysplastic syndrome, acute myeloid leukemia, Hodgkin lymphoma, non-Hodgkin lymphoma, Hodgkin disease, multiple myeloma, synovial sarcoma, metastatic solid tumors, esophageal cancer, rhabdomyosarcoma, advanced myxoid, round cell liposarcoma, metastatic melanoma, or recurrent non-small cell lung cancer.

It is contemplated herein to use the anti-HLA-A2:NY-ESO-1 antigen-binding proteins of the disclosure in combination with immunostimulatory and/or immunosupportive therapies to inhibit tumor growth, and/or enhance survival of cancer patients. The immunostimulatory therapies include direct immunostimulatory therapies to augment immune cell activity by either "releasing the brake" on suppressed immune cells or "stepping on the gas" to activate an immune response. Examples include targeting other checkpoint receptors, vaccination and adjuvants. The immunosupportive modalities may increase antigenicity of the tumor by promoting immunogenic cell death, inflammation or have other indirect effects that promote an anti-tumor immune response. Examples include radiation, chemotherapy, anti-angiogenic agents, and surgery.

In various embodiments, one or more antigen-binding proteins of the present disclosure may be used in combination with a PD-1 inhibitor (e.g., an anti-PD-1 antibody such as nivolumab, pembrolizumab, pidilizumab, BGB-A317 or REGN2810), a PD-L1 inhibitor (e.g., an anti-PD-L1 antibody such as avelumab, atezolizumab, durvalumab, MDX-1105, or REGN3504), a CTLA-4 inhibitor (e.g., ipilimumab), a TIM3 inhibitor, a BTLA inhibitor, a TIGIT inhibitor, a CD47 inhibitor, a GITR inhibitor, an antagonist of another T cell co-inhibitor or ligand (e.g., an antibody to CD-28, 2B4, LY108, LAIR1, ICOS, CD160 or VISTA), an indoleamine-2,3-dioxygenase (IDO) inhibitor, a vascular endothelial growth factor (VEGF) antagonist (e.g., a "VEGF-Trap" such as aflibercept or other VEGF-inhibiting fusion protein as set forth in U.S. Pat. No. 7,087,411, or an anti-VEGF antibody or antigen-binding fragment thereof (e.g., bevacizumab, or ranibizumab) or a small molecule kinase inhibitor of VEGF receptor (e.g., sunitinib, sorafenib, or pazopanib)), an Ang2 inhibitor (e.g., nesvacumab), a transforming growth factor beta (TGFβ) inhibitor, an epidermal growth factor receptor (EGFR) inhibitor (e.g., erlotinib, cetuximab), a CD20 inhibitor (e.g., an anti-CD20 antibody such as rituximab), an antibody to a tumor-specific antigen (e.g., CA9, CA125, melanoma-associated antigen 3 (MAGE3), carcinoembryonic antigen (CEA), vimentin, tumor-M2-PK, prostate-specific antigen (PSA), mucin-1, MART-1, and CA19-9), a vaccine (e.g., *Bacillus* Calmette-Guerin, a cancer vaccine), an adjuvant to increase antigen presentation (e.g., granulocyte-macrophage colony-stimulating factor), a bispecific antibody (e.g., CD3×CD20 bispecific antibody, or PSMA×CD3 bispecific antibody), a cytotoxin, a chemotherapeutic agent (e.g., dacarbazine, temozolomide, cyclophosphamide, docetaxel, doxorubicin, daunorubicin, cisplatin, carboplatin, gemcitabine, methotrexate, mitoxantrone, oxaliplatin, paclitaxel, and vincristine), cyclophosphamide, radiotherapy, surgery, an IL-6R inhibitor (e.g., sarilumab), an IL-4R inhibitor (e.g., dupilumab), an IL-10 inhibitor, a cytokine such as IL-2, IL-7, IL-21, and IL-15, an antibody-drug conjugate (ADC) (e.g., anti-CD19-DM4 ADC, and anti-DS6-DM4 ADC), an anti-inflammatory drug (e.g., corticosteroids, and non-steroidal anti-inflammatory drugs), a dietary supplement such as anti-oxidants or any other therapy care to treat cancer. In certain embodiments, the anti-HLA-A2:NY-ESO-1 antigen-binding protein of the present disclosure may be used in combination with cancer vaccines including dendritic cell vaccines, oncolytic viruses, tumor cell vaccines, etc. to augment the anti-tumor response. Examples of cancer vaccines that can be used in combination with anti-HLA-A2:NY-ESO-1 antigen-binding proteins of the present disclosure include MAGE3 vaccine for melanoma and bladder cancer, MUC1 vaccine for breast cancer, EGFRv3 (e.g., Rindopepimut) for brain cancer (including glioblastoma multiforme), or ALVAC-CEA (for CEA+ cancers).

In certain embodiments, the anti-HLA-A2:NY-ESO-1 antigen-binding proteins of the disclosure may be administered in combination with radiation therapy in methods to generate long-term durable anti-tumor responses and/or enhance survival of patients with cancer. In some embodiments, the anti-HLA-A2:NY-ESO-1 antigen-binding proteins of the disclosure may be administered prior to, concomitantly or after administering radiation therapy to a cancer patient. For example, radiation therapy may be administered in one or more doses to tumor lesions followed by administration of one or more doses of anti-HLA-A2: NY-ESO-1 antigen-binding proteins of the disclosure. In some embodiments, radiation therapy may be administered locally to a tumor lesion to enhance the local immunogenicity of a patient's tumor (adjuvinating radiation) and/or to kill tumor cells (ablative radiation) followed by systemic administration of an anti-HLA-A2:NY-ESO-1 antigen-binding protein of the disclosure. For example, intracranial radiation may be administered to a patient with brain cancer (e.g., glioblastoma multiforme) in combination with systemic administration of an anti-HLA-A2:NY-ESO-1 antigen-binding protein of the disclosure. In certain embodiments, the anti-HLA-A2:NY-ESO-1 antigen-binding proteins of the disclosure may be administered in combination with radiation therapy and a chemotherapeutic agent (e.g., temozolomide) or a VEGF antagonist (e.g., aflibercept).

The additional therapeutically active agent(s)/ component(s) may be administered prior to, concurrent with, or after the administration of the anti-HLA-A2:NY-ESO-1 antigen-binding proteins of the present disclosure. For purposes of the present disclosure, such administration regimens are considered the administration of an anti-HLA-A2: NY-ESO-1 antigen-binding protein "in combination with" a second therapeutically active component.

The additional therapeutically active component(s) may be administered to a subject prior to administration of an anti-HLA-A2:NY-ESO-1 antigen-binding protein of the present disclosure. For example, a first component may be deemed to be administered "prior to" a second component if the first component is administered 1 week before, 72 hours before, 60 hours before, 48 hours before, 36 hours before, 24 hours before, 12 hours before, 6 hours before, 5 hours before, 4 hours before, 3 hours before, 2 hours before, 1 hour before, 30 minutes before, 15 minutes before, 10 minutes before, 5 minutes before, or less than 1 minute before administration of the second component. In other embodiments, the additional therapeutically active component(s) may be administered to a subject after administration of an anti-HLA-A2:NY-ESO-1 antigen-binding protein of the present disclosure. For example, a first component may be deemed to be administered "after" a second component if the first component is administered 1 minute after, 5 minutes after, 10 minutes after, 15 minutes after, 30 minutes after, 1 hour after, 2 hours after, 3 hours after, 4 hours after, 5 hours after, 6 hours after, 12 hours after, 24 hours after, 36 hours after, 48 hours after, 60 hours after, 72 hours after, or 1 week after administration of the second component. In yet other embodiments, the additional therapeutically active component(s) may be administered to a subject concurrent with administration of an anti-HLA-A2:NY-ESO-1 antigen-binding protein of the present disclosure. "Concurrent" administration, for purposes of the present disclosure, includes, e.g., administration of an anti-HLA-A2:NY-ESO-1 antigen-binding protein and an additional therapeutically active component to a subject in a single dosage form (e.g., co-formulated), or in separate dosage forms administered to the subject within about 30 minutes or less of each other. If administered in separate dosage forms, each dosage form may be administered via the same route (e.g., both the anti-HLA-A2:NY-ESO-1 antigen-binding protein and the additional therapeutically active component may be administered intravenously, subcutaneously, etc.); alternatively, each dosage form may be administered via a different route (e.g., the anti-HLA-A2:NY-ESO-1 antigen-binding protein may be administered intravenously, and the additional therapeutically active component may be administered subcutaneously). In any event, administering the components in a single dosage form, in separate dosage forms by the same route, or in separate dosage forms by different routes are all considered "concurrent administration," for purposes of the present disclosure. For purposes of the present disclosure, administration of an anti-HLA-A2:NY-ESO-1 antigen-binding protein "prior to", "concurrent with," or "after" (as those terms are defined herein above) administration of an additional therapeutically active component is considered administration of an anti-HLA-A2:NY-ESO-1 antigen-binding protein "in combination with" an additional therapeutically active component).

The present disclosure includes pharmaceutical compositions in which an anti-HLA-A2:NY-ESO-1 antigen-binding protein of the present disclosure is co-formulated with one or more of the additional therapeutically active component (s) as described elsewhere herein using a variety of dosage combinations.

Administrative Regimens

According to certain embodiments of the present disclosure, multiple doses of an anti-HLA-A2:NY-ESO-1 antigen-binding protein (or a pharmaceutical composition comprising a combination of an anti-HLA-A2:NY-ESO-1 antigen-binding protein and any of the additional therapeutically active agents mentioned herein) may be administered to a subject over a defined time course. The methods according to this aspect of the disclosure comprise sequentially administering to a subject multiple doses of an anti-HLA-A2:NY-ESO-1 antigen-binding protein of the disclosure. As used herein, "sequentially administering" means that each dose of anti-HLA-A2:NY-ESO-1 antigen-binding protein is administered to the subject at a different point in time, e.g., on different days separated by a predetermined interval (e.g., hours, days, weeks or months). The present disclosure includes methods which comprise sequentially administering to the patient a single initial dose of an anti-HLA-A2: NY-ESO-1 antigen-binding protein, followed by one or more secondary doses of the anti-HLA-A2:NY-ESO-1 antigen-binding protein, and optionally followed by one or more tertiary doses of the anti-HLA-A2:NY-ESO-1 antigen-binding protein. The anti-HLA-A2:NY-ESO-1 antigen-binding protein may be administered at a dose between 0.1 mg/kg to 100 mg/kg body weight of the subject.

The terms "initial dose," "secondary doses," and "tertiary doses," refer to the temporal sequence of administration of the anti-HLA-A2:NY-ESO-1 antigen-binding protein of the disclosure. Thus, the "initial dose" is the dose which is administered at the beginning of the treatment regimen (also referred to as the "baseline dose"); the "secondary doses"

are the doses which are administered after the initial dose; and the "tertiary doses" are the doses which are administered after the secondary doses. The initial, secondary, and tertiary doses may all contain the same amount of anti-HLA-A2:NY-ESO-1 antigen-binding protein, but generally may differ from one another in terms of frequency of administration. In certain embodiments, however, the amount of anti-HLA-A2:NY-ESO-1 antigen-binding protein contained in the initial, secondary and/or tertiary doses varies from one another (e.g., adjusted up or down as appropriate) during the course of treatment. In certain embodiments, two or more (e.g., 2, 3, 4, or 5) doses are administered at the beginning of the treatment regimen as "loading doses" followed by subsequent doses that are administered on a less frequent basis (e.g., "maintenance doses").

In certain embodiments, the amount of anti-HLA-A2:NY-ESO-1 antigen-binding protein contained in the initial, secondary and/or tertiary doses may be sub-optimal or sub-therapeutic. As used herein, the terms "sub-therapeutic" or "sub-optimal" refer to an antibody dose administered at too low a level to produce a therapeutic effect or below the level necessary to treat a disease such as cancer.

In certain exemplary embodiments of the present disclosure, each secondary and/or tertiary dose is administered 1 to 26 (e.g., 1, 1½, 2, 2½, 3, 3½, 4, 4½, 5, 5½, 6, 6½, 7, 7½, 8, 8½, 9, 9½, 10, 10½, 11, 11½, 12, 12½, 13, 13½, 14, 14½, 15, 15½, 16, 16½, 17, 17½, 18, 18½, 19, 19½, 20, 20½, 21, 21½, 22, 22½, 23, 23½, 24, 24½, 25, 25½, 26, 26½, or more) weeks after the immediately preceding dose. The phrase "the immediately preceding dose," as used herein, means, in a sequence of multiple administrations, the dose of anti-HLA-A2:NY-ESO-1 antigen-binding protein which is administered to a patient prior to the administration of the very next dose in the sequence with no intervening doses.

The methods according to this aspect of the disclosure may comprise administering to a patient any number of secondary and/or tertiary doses of an anti-HLA-A2:NY-ESO-1 antigen-binding protein. For example, in certain embodiments, only a single secondary dose is administered to the patient. In other embodiments, two or more (e.g., 2, 3, 4, 5, 6, 7, 8, or more) secondary doses are administered to the patient. Likewise, in certain embodiments, only a single tertiary dose is administered to the patient. In other embodiments, two or more (e.g., 2, 3, 4, 5, 6, 7, 8, or more) tertiary doses are administered to the patient.

In embodiments involving multiple secondary doses, each secondary dose may be administered at the same frequency as the other secondary doses. For example, each secondary dose may be administered to the patient 1 to 2 weeks or 1 to 2 months after the immediately preceding dose. Similarly, in embodiments involving multiple tertiary doses, each tertiary dose may be administered at the same frequency as the other tertiary doses. For example, each tertiary dose may be administered to the patient 2 to 12 weeks after the immediately preceding dose. In certain embodiments, the frequency at which the secondary and/or tertiary doses are administered to a patient can vary over the course of the treatment regimen. The frequency of administration may also be adjusted during the course of treatment by a physician depending on the needs of the individual patient following clinical examination.

Diagnostic Uses of the Antigen Binding Proteins

The anti-HLA-A2:NY-ESO-1 antigen-binding proteins of the present disclosure may be used to detect and/or measure NY-ESO-1 in a sample, e.g., for diagnostic purposes. Some embodiments contemplate the use of one or more antigen-binding proteins of the present disclosure in assays to detect a disease or disorder such as NY-ESO-1-associated disease or disorder, such as an NY-ESO-1-positive cancer. Exemplary diagnostic assays for NY-ESO-1 may comprise, e.g., contacting a sample, obtained from a subject (e.g., a patient), with an anti-HLA-A2:NY-ESO-1 antigen-binding protein of the disclosure, wherein the anti-HLA-A2:NY-ESO-1 antigen-binding protein is labeled with a detectable label or reporter molecule or used as a capture ligand to selectively isolate NY-ESO-1 from subject samples. Alternatively, an unlabeled anti-HLA-A2:NY-ESO-1 antigen-binding protein can be used in diagnostic applications in combination with a secondary antigen-binding protein, e.g., antibody, which is itself detectably labeled. The detectable label or reporter molecule can be a radioisotope, such as $^{3}H$, $^{14}C$, $^{32}P$, $^{35}S$, or $^{125}I$; a fluorescent or chemiluminescent moiety such as fluorescein isothiocyanate, or rhodamine; or an enzyme such as alkaline phosphatase, β-galactosidase, horseradish peroxidase, or luciferase. Specific exemplary assays that can be used to detect or measure NY-ESO-1 in a sample include enzyme-linked immunosorbent assay (ELISA), radioimmunoassay (RIA), and fluorescence-activated cell sorting (FACS).

Samples that can be used in NY-ESO-1 diagnostic assays according to the present disclosure include any tissue or fluid sample obtainable from a subject, which contains detectable quantities of either NY-ESO-1 protein, or fragments thereof, under normal or pathological conditions. Generally, levels of NY-ESO-1 in a particular sample obtained from a healthy patient (e.g., a patient not afflicted with a NY-ESO-1-associated disease or disorder, e.g., NY-ESO-1-positive cancer) will be measured to initially establish a baseline, or standard, level of NY-ESO-1. This baseline level of NY-ESO-1 can then be compared against the levels of NY-ESO-1 measured in samples obtained from individuals suspected of having a cancer-related condition, or symptoms associated with such condition.

The antigen-binding proteins specific for NY-ESO-1 may contain no additional labels or moieties, or they may contain an N-terminal or C-terminal label or moiety. In one embodiment, the label or moiety is biotin. In a binding assay, the location of a label (if any) may determine the orientation of the peptide relative to the surface upon which the peptide is bound. For example, if a surface is coated with avidin, a peptide containing an N-terminal biotin will be oriented such that the C-terminal portion of the peptide will be distal to the surface.

Aspects of the disclosure relate to use of the disclosed antigen-binding proteins as markers for predicting prognosis of NY-ESO-1-positive cancer in patients. Antigen binding proteins of the present disclosure may be used in diagnostic assays to evaluate prognosis of cancer in a patient and to predict survival.

EXAMPLES

The following examples are put forth so as to provide those of ordinary skill in the art with a complete disclosure and description of how to make and use the methods and compositions of the invention, and are not intended to limit the scope of what the inventors regard as their invention. Efforts have been made to ensure accuracy with respect to numbers used (e.g., amounts, temperature, etc.) but some experimental errors and deviations should be accounted for. Unless indicated otherwise, parts are parts by weight, molecular weight is average molecular weight, temperature is in degrees Centigrade, room temperature is about 25° C., and pressure is at or near atmospheric.

Example 1: Generation of Human Antibodies to HLA-A2:NY-ESO-1_157-165

Human antibodies to HLA-A2:NY-ESO-1 were generated using an HLA-A2-coupled NY-ESO-1 peptide fragment of GenBank Accession NP_001318.1 (SEQ ID NO: 271) that includes amino acids 157-165 having the cysteine (C) at position 165 substituted with a valine (V) (SLLMWITQV; "NY-ESO-1_V"); SEQ ID NO: 291). The immunogen was administered directly, with an adjuvant to stimulate the immune response, to a VELOCIMMUNE® mouse (i.e., an engineered mouse comprising DNA encoding human Immunoglobulin heavy and kappa light chain variable regions), e.g., as described in U.S. Pat. No. 8,502,018. The antibody immune response was monitored by an HLA-A2:NY-ESO-1-specific immunoassay. When a desired immune response was achieved splenocytes were harvested and fused with mouse myeloma cells to preserve their viability and form hybridoma cell lines. The hybridoma cell lines were screened and selected to identify cell lines that produce HLA-A2:NY-ESO-1-specific antibodies. Using this technique, and the immunogen described above, several anti-NY-ESO-1 chimeric antibodies (i.e., antibodies possessing human variable domains and mouse constant domains) were obtained.

Anti-HLA-A2:NY-ESO-1 antibodies were also isolated directly from antigen-positive B cells (from either of the immunized mice) without fusion to myeloma cells, as described in U.S. Pat. No. 7,582,298, herein specifically incorporated by reference in its entirety. Using this method, several fully human anti-HLA-A2:NY-ESO-1 antibodies (i.e., antibodies possessing human variable domains and human constant domains) were obtained.

Exemplary antibodies generated according to the foregoing methods were designated as follows: mAb24955N; mAb24956N; mAb24958N; mAb24959N; mAb28042P; mAb28035P; mAb28037P2; mAb28075P; mAb28105P; mAb28113P; mAb28128P; mAb29814P; mAb24955N; and mAb29822P2.

The biological properties of the exemplary antibodies generated in accordance with the methods of this Example are described in detail in the Examples set forth below.

Example 2: Heavy and Light Chain Variable Region Amino Acid and Nucleotide Sequences Table 1 sets forth the amino acid sequence identifiers of the heavy and light chain variable regions, CDRs, and heavy and light chains of selected anti-HLA-A2:NY-ESO-1 antibodies of the present disclosure. The corresponding nucleic acid sequence identifiers are set forth in Table 2.

TABLE 1

Amino Acid Sequence Identifiers

| Antibody Designation | SEQ ID NOs: | | | | | | | |
|---|---|---|---|---|---|---|---|---|
| | HCVR | HCDR1 | HCDR2 | HCDR3 | LCVR | LCDR1 | LCDR2 | LCDR3 |
| mAb24955N | 2 | 4 | 6 | 8 | 10 | 12 | 14 | 16 |
| mAb24956N | 22 | 24 | 26 | 28 | 30 | 32 | 34 | 36 |
| mAb24958N | 42 | 44 | 46 | 48 | 50 | 52 | 54 | 56 |
| mAb24959N | 62 | 64 | 66 | 68 | 70 | 72 | 74 | 76 |
| mAb28042P | 82 | 84 | 86 | 88 | 90 | 92 | 94 | 96 |
| mAb28035P | 102 | 104 | 106 | 108 | 110 | 112 | 114 | 116 |
| mAb28037P2 | 122 | 124 | 126 | 128 | 130 | 132 | 134 | 136 |
| mAb28075P | 142 | 144 | 146 | 148 | 150 | 152 | 154 | 156 |
| mAb28105P | 162 | 164 | 166 | 168 | 170 | 172 | 174 | 156 |
| mAb28113P | 180 | 144 | 182 | 184 | 186 | 188 | 154 | 190 |
| mAb28128P | 196 | 164 | 199 | 201 | 203 | 172 | 174 | 205 |
| mAb29814P | 211 | 213 | 215 | 217 | 219 | 221 | 174 | 224 |
| mAb24955N2 | 230 | 232 | 234 | 236 | 238 | 240 | 242 | 244 |
| mAb29822P2 | 250 | 252 | 254 | 256 | 258 | 260 | 262 | 264 |

TABLE 2

Nucleic Acid Sequence Identifiers

| Antibody Designation | SEQ ID NOs: | | | | | | | |
|---|---|---|---|---|---|---|---|---|
| | HCVR | HCDR1 | HCDR2 | HCDR3 | LCVR | LCDR1 | LCDR2 | LCDR3 |
| mAb24955N | 1 | 3 | 5 | 7 | 9 | 11 | 13 | 15 |
| mAb24956N | 21 | 23 | 25 | 27 | 29 | 31 | 33 | 35 |
| mAb24958N | 41 | 43 | 45 | 47 | 49 | 51 | 53 | 55 |
| mAb24959N | 61 | 63 | 65 | 67 | 69 | 71 | 73 | 75 |
| mAb28042P | 81 | 83 | 85 | 87 | 89 | 91 | 93 | 95 |
| mAb28035P | 101 | 103 | 105 | 107 | 109 | 111 | 113 | 115 |
| mAb28037P2 | 121 | 123 | 125 | 127 | 129 | 131 | 133 | 135 |
| mAb28075P | 141 | 143 | 145 | 147 | 149 | 151 | 153 | 155 |
| mAb28105P | 161 | 163 | 165 | 167 | 169 | 171 | 173 | 155 |

TABLE 2-continued

| Nucleic Acid Sequence Identifiers | | | | | | | |
|---|---|---|---|---|---|---|---|
| Antibody | | | | SEQ ID NOs: | | | |
| Designation | HCVR | HCDR1 | HCDR2 | HCDR3 | LCVR | LCDR1 | LCDR2 | LCDR3 |

| Antibody Designation | HCVR | HCDR1 | HCDR2 | HCDR3 | LCVR | LCDR1 | LCDR2 | LCDR3 |
|---|---|---|---|---|---|---|---|---|
| mAb28113P | 179 | 143 | 181 | 183 | 185 | 187 | 153 | 189 |
| mAb28128P | 195 | 197 | 198 | 200 | 202 | 171 | 173 | 204 |
| mAb29814P | 210 | 212 | 214 | 216 | 218 | 220 | 222 | 223 |
| mAb24955N2 | 229 | 231 | 233 | 235 | 237 | 239 | 241 | 243 |
| mAb29822P2 | 249 | 251 | 253 | 255 | 257 | 259 | 261 | 263 |

Antibodies are typically referred to herein according to the following nomenclature: Fc prefix (e.g. "mAb" etc.), followed by a numerical identifier (e.g. "17670," "17930," etc., as shown in Table 1), followed by a "P," "N," or "N2" suffix. Thus, according to this nomenclature, an antibody may be referred to herein as, e.g., "mAb17670P," "mAb17930N," "mAb17368N2," etc. As will be appreciated by a person of ordinary skill in the art, an antibody having a particular Fc isotype can be converted to an antibody with a different Fc isotype (e.g., an antibody with a mouse IgG1 Fc can be converted to an antibody with a human IgG4, etc.), but in any event, the variable domains (including the CDRs)—which are indicated by the numerical identifiers shown in Table 1—will remain the same, and the binding properties to antigen are expected to be identical or substantially similar regardless of the nature of the Fc domain.

In certain embodiments, selected antibodies with a mouse IgG1 Fc were converted to antibodies with human IgG4 Fc. In certain embodiments, the antibody comprises a human IgG4 Fc with 2 or more amino acid changes as disclosed in U.S. Patent Publication No. 20100331527 (herein incorporated in its entirety). In one embodiment, the IgG4 Fc domain comprises a serine to proline mutation in the hinge region (S108P) to promote dimer stabilization.

Table 3 sets forth the amino acid sequence identifiers of heavy chain and light chain sequences of selected antibodies of the present disclosure.

TABLE 3

| Heavy chain and light chain sequence identifiers | | | | | |
|---|---|---|---|---|---|
| | SEQ ID Nos (polypeptide) | | SEQ ID NOs (DNA) | | |
| Antibody Designation | Heavy Chain | Light Chain | Heavy Chain | Light Chain | Fc Isotype |
| mAb24955N | 18 | 20 | 17 | 19 | IgG4 with reduced effector function* |
| mAb24956N | 38 | 40 | 37 | 39 | IgG4 with reduced effector function* |
| mAb24958N | 58 | 60 | 57 | 59 | IgG4 with reduced effector function* |
| mAb24959N | 78 | 80 | 77 | 79 | IgG4 with reduced effector function* |
| mAb28042P | 98 | 100 | 97 | 99 | IgG4 with reduced effector function* |
| mAb28035P | 118 | 120 | 117 | 119 | IgG4 with reduced effector function* |
| mAb28037P2 | 138 | 140 | 137 | 139 | IgG4 with reduced effector function* |
| mAb28075P | 158 | 160 | 157 | 159 | IgG4 with reduced effector function* |
| mAb28105P | 176 | 178 | 175 | 177 | IgG4 with reduced effector function* |

TABLE 3-continued

| Heavy chain and light chain sequence identifiers | | | | | |
|---|---|---|---|---|---|
| | SEQ ID Nos (polypeptide) | | SEQ ID NOs (DNA) | | |
| Antibody Designation | Heavy Chain | Light Chain | Heavy Chain | Light Chain | Fc Isotype |
| mAb28113P | 192 | 194 | 191 | 193 | IgG4 with reduced effector function* |
| mAb28128P | 207 | 209 | 206 | 208 | IgG4 with reduced effector function* |
| mAb29814P | 226 | 228 | 225 | 227 | IgG4 with reduced effector function* |
| mAb24955N2 | 246 | 248 | 245 | 247 | IgG2a |
| mAb29822 | 266 | 268 | 265 | 267 | IgG4 with reduced effector function* |

*As described in, for example, U.S. Pat. No. 9,359,437.

Example 3: Surface Plasmon Resonance Derived Binding Affinities and Kinetic Constants of Human Monoclonal Anti-HLA-A2:NY-ESO-1 Monospecific Antibodies Binding affinities and kinetic constants of human anti-HLA-A2:NY-ESO-1 antibodies were determined via real-time surface plasmon resonance (SPR; Biacore 4000 by GE Healthcare Life Sciences, or MASS-1 by Sierra Sensors) at 25° C. and 37° C. The anti-HLA-A2: NY-ESO-1 antibodies tested in this example were bivalent monospecific binders to HLA-A2: NY-ESO-1 (expressed with a constant region (e.g., a hIgG4 constant region) with reduced effector function (e.g., as described in U.S. Pat. No. 9,359,437), with a hIgG2a constant region, with a mIgG2a constant region, or with a mIgG1 constant region). Reference Antibodies 1, 2, and 3 were generated from the antibodies described in Stewart-Jones et al., Proc Natl Acad Sci USA 106(14):5784-5788 (2009) and in International Patent Publication No. WO2010106431. Ref Ab 1 comprises the VH and VL domains from the 3M4E5 antibody described in those publications with a human IgG1 Fc and a human lambda light chain; Ref Ab 2 comprises the 3M4E5 VH domain and the T1 Fab $V_L$ domain from the publications with a human IgG1 Fc and a human lambda light chain; Ref Ab 3 comprises the 3M4E5 VH domain and the T1 Fab VL domain from the publications with a human IgG4 with reduced effector function Fc (as described in U.S. Pat. No. 9,359,437) and a human lambda VL domain. Antibodies were captured onto a CM5 Biacore sensor surface (GE Healthcare Life Sciences) derivatized via amine coupling with a monoclonal anti-human Fc antibody (Jackson Immunoresearch) or a high-capacity amine sensor surface (Sierra Sensors) derivatized via amine coupling with polyclonal anti-mouse Fc antibody (GE Life Sciences). Various concentrations of monomeric HLA-A2:NY-ESO-1(156-165) (SEQ ID NO: 270 or 291; V at position 165) peptide complex, 2906 (SEQ ID NO: 272); were injected over the anti-HLA-A2:(NY-ESO-1 antibody captured surface at a flow rate of 504/ minute (MASS-1) or 304/minute (Biacore 4000). Antibody-reagent association was monitored for 4-5 minutes and the dissociation was monitored for 10 minutes. All binding studies were performed in HBS-ET buffer (0.01 M HEPES pH 7.4, 0.15M NaCl, 3 mM EDTA, 0.05% v/v Surfactant P20).

Kinetic association (ka) and dissociation (kd) rate constants were determined by fitting the real-time sensorgrams to a 1:1 binding model using Scrubber 2.0c curve fitting software. Binding dissociation equilibrium constants (KD) and dissociative half-lives (t½) were calculated from the kinetic rate constants as:

$$K_D(M)=(kd/ka), \text{ and } t½(min)=((\ln_{(2)})/(60*kd))$$

Binding kinetic parameters for the monospecific anti-HLA-A2:NY-ESO-1 antibodies to monomeric HLA-A2:NY-ESO-1 peptide complex are shown below in Table 4.

TABLE 4

Biacore binding affinities of anti-HLA-
A2: NY-ESO-1 antibodies at 25° C.

| | 25° C. | | | |
|---|---|---|---|---|
| Antibody | ka (1/Ms) | kd (1/s) | KD (M) | t½ (min) |
| mAbm24955N | 5.69E+05 | 1.29E−03 | 2.27E−09 | 9.0 |
| mAb24956N | 9.43E+05 | 3.65E−04 | 3.87E−10 | 31.6 |
| mAb24958N | 6.37E+04 | 1.77E−04 | 2.77E−09 | 65.4 |
| mAb24959N | 4.21E+05 | 5.17E−04 | 1.23E−09 | 22.3 |
| mAb28035P | 4.45E+05 | 1.52E−04 | 3.42E−10 | 75.9 |
| mAb28037P2 | 4.43E+05 | 3.07E−04 | 6.92E−10 | 37.7 |
| mAb28042P | 3.62E+05 | 1.99E−04 | 5.50E−10 | 58.0 |
| mAb28075P | 9.07E+05 | 3.52E−04 | 3.88E−10 | 32.8 |
| mAb28105P | 4.76E+05 | 1.84E−04 | 3.86E−10 | 62.8 |
| mAb28113P | 5.10E+05 | 3.26E−04 | 6.39E−10 | 35.5 |
| mAb28128P | 1.16E+06 | 1.85E−04 | 1.60E−10 | 62.5 |
| Ref Ab 1 | 4.77E+05 | 2.19E−03 | 4.60E−9 | 5.3 |
| Ref Ab 2 | 6.81E+05 | 6.69E−04 | 9.82E−10 | 17.3 |
| Ref Ab 3 | 7.35E+05 | 7.05E−04 | 9.58E−10 | 16.4 |

TABLE 5

Biacore binding affinities of anti-HLA-
A2: NY-ESO-1 antibodies at 37° C.

| | 37° C. | | | |
|---|---|---|---|---|
| Antibody | ka (1/Ms) | kd (1/s) | KD (M) | t½ (min) |
| mAb28035P | 6.69E+05 | 2.53E−04 | 3.78E−10 | 45.7 |
| mAb28037P2 | 6.64E+05 | 1.83E−03 | 2.76E−09 | 6.3 |
| mAb28042P | 5.61E+05 | 1.17E−03 | 2.09E−09 | 9.9 |
| mAb28075P | 1.26E+06 | 1.27E−03 | 1.00E−09 | 9.1 |
| mAb28105P | 9.23E+05 | 5.41E−04 | 5.86E−10 | 21.3 |
| mAb28113P | 7.51E+05 | 1.46E−03 | 1.94E−09 | 7.9 |
| mAb28128P | 1.50E+06 | 4.41E−04 | 2.93E−10 | 26.2 |
| Ref Ab 1 | 8.81E+05 | 4.82E−03 | 5.47E−09 | 2.4 |
| Ref Ab 2 | 1.36E+06 | 1.84E−03 | 1.41E−09 | 6.3 |
| Ref Ab 3 | 1.16E+06 | 1.94E−03 | 1.72E−09 | 6.0 |

The data demonstrate that a majority of the anti-HLA-A2: NY-ESO-1 antibodies tested selectively bound to soluble HLA-A2:NY-ESO-1 peptide complex, some displaying nanomolar or sub-nanomolar affinity, and that many had higher affinity for the complex than the reference antibodies.

Example 4: FACS Binding of
Anti-HLA-A2:NY-ESO-1 Antibodies Against T2
Cells Pulsed with NY-ESO-1_157-165 Peptide Relative binding of NY-ESO-1:157-165 antibodies was assessed by flow cytometry on T2 (174 CEM.T2) cells pulsed with an NY-ESO-1_157-165 (C165) peptide (SEQ ID NO: 269). To pulse, T2 cells (174 CEM.T2) were re-suspended in AIM V medium at a density of $1\times10^6$ cells/ml (Gibco. Cat #31035-025). Cells were pulsed by adding 10 µg/ml hB2M (EMD Millipore Cat #475828) and 100 µg/ml of the indicated peptide. T2 cells were then incubated overnight at 37° C., washed in staining buffer and subsequently stained.

To stain the cells, the cells were harvested from the flasks using cell dissociation buffer (Millipore, Cat #S-004-C) and counted. Cells were plated in staining buffer (PBS, without Calcium and Magnesium (Corning, Ref #21-031-CV)+2% FBS (Seradigm, Lot #238615) at a density of 200,000 cells per well in a 96 well V-Bottom plate and stained with three-fold serial dilutions (1.7 pM-100 nM) of primary antibodies for 30 minutes at 4° C. Following primary antibody incubation, cells were washed once in staining buffer, and stained with an APC conjugated secondary antibody (Jackson ImmunoResearch, Cat #109-136-170) at 5 µg/ml for 30 minutes at 4° C. Cells were then washed and fixed using a 50% solution of BD Cytofix (BD, Cat #554655). Samples were analyzed on an intellicyt iQue flow cytometer to calculate mean fluorescence intensity (MFI). MFI values were plotted in Graphpad Prism using a four-parameter logistic equation over a 12-point response curve to calculate $EC_{50}$ values. The secondary antibody alone (i.e. no primary antibody) for each dose-response curve is also included in the analysis as a continuation of the three-fold serial dilution and is represented as the lowest dose. Ref Ab 2 and Ref Ab 3, as described above, were used as controls. $EC_{50}$ values (M) are shown in Table 6.

TABLE 6

FACS binding of anti-HLA-A2: NY-ESO-1 antibodies

| Antibody | T2 Pulsed NY-ESO-1__157-165) $EC_{50}$ (M) |
|---|---|
| mAb24955N | 6.00E−10 |
| mAb24956N | 4.70E−10 |
| mAb24958N | 1.90E−08 |
| mAb24959N | 1.10E−09 |
| mAb28035P | 2.70E−09 |
| mAb28037P2 | 7.80E−10 |
| mAb28042P | 1.60E−09 |
| mAb28075P | 3.80E−10 |
| mAb28105P | 1.80E−09 |
| mAb28113P | 6.00E−10 |
| mAb28128P | 3.20E−10 |
| mAb29814P | 1.10E−09 |
| mAb29822P2 | 5.40E−09 |
| Ref Ab 2 | 2.20E−10 |
| Ref Ab 3 | 4.90E−10 |

Example 5: FACS Binding of
Anti-HLA-A2:NY-ESO-1 Antibodies Against T2
Cells Pulsed With Predicted Off-Target Peptides Binding specificity of NY-ESO-1:157-165 antibodies was assessed by flow cytometry on T2 (174 CEM.T2) cells pulsed with NY-ESO-1(157-165) peptide (C165; SEQ ID NO: 269) or predicted off-target peptides (Table 7). To pulse, T2 cells (174 CEM.T2) were re-suspended in AIM V medium at a density of 1×10⁶ cells/ml (Gibco. Cat #31035-025). Cells were pulsed by adding 10 μg/ml hB2M (EMD Millipore Cat #475828) and 100 μg/ml of the indicated peptide. T2 cells were then incubated overnight at 37° C., washed in staining buffer and stained with the indicated antibodies at a concentration of 10 μg/ml following the protocol described above in Example 4. MFI values were calculated and presented as a ratio of T2 pulsed cells to unpulsed cells. The results of these assays are presented in Table 8. Effective peptide loading was determined by comparing the increase in HLA-A2 surface staining from a pulsed cell line to an unpulsed cell line using an anti-HLA-A2 antibody. Any increase of 1.4 fold or greater was considered to be loaded with peptide. Loading could not be confirmed for one peptide (ITCH (807-815)); however the two comparator NY-ESO-1 mAbs Ref Ab 1 and Ref Ab 2, as described above, bound to cells pulsed with this peptide, indicating that some amount of peptide had loaded onto the cells.

TABLE 7

| NY-ESO-1 157-165 peptide and predicted off-target peptides. | |
|---|---|
| Peptide Name | Peptide Amino Acid Sequence |
| NY-ESO-1:157-165, wt | SLLMWITQC (SEQ ID NO: 269) |
| BCL9L: 1351-1359 | SLLMWLTPL (SEQ ID NO: 273) |
| GRID1: 7-15 | WLLPWICQC (SEQ ID NO: 274) |
| EARS2: 306-314 | SLLDIITNC (SEQ ID NO: 275) |
| ZDHHC1 (376-384) | LLAMWGPQA (SEQ ID NO: 276) |
| ITCH (807-815) | KQIMWFWQF (SEQ ID NO: 277) |
| MAGEH1: 90-98 | SLLMSILAL (SEQ ID NO: 278) |
| FBXL22: 4-12 | LLTMHITQL (SEQ ID NO: 279) |
| URB1: 1853-1861 | SLLTWILHI (SEQ ID NO: 280) |
| NY-ESO-1:157-165, C165V | SLLMWITQV (SEQ ID NO: 281) |
| NY-ESO-1:157-165, C165V, S157A | ALLMWITQV (SEQ ID NO: 282) |
| NY-ESO-1:157-165, C165V, L158A | SALMWITQV (SEQ ID NO: 283) |
| NY-ESO-1:157-165, C165V, L159A | SLAMWITQV (SEQ ID NO: 284) |
| NY-ESO-1:157-165, C165V, M160A | SLLAWITQV (SEQ ID NO: 285) |
| NY-ESO-1:157-165, C165V, W161A | SLLMAITQV (SEQ ID NO: 286) |
| NY-ESO-1:157-165, C165V, I162A | SLLMWATQV (SEQ ID NO: 287) |
| NY-ESO-1:157-165, C165V, T163A | SLLMWIAQV (SEQ ID NO: 288) |
| NY-ESO-1:157-165, C165V, Q164A | SLLMWITAV (SEQ ID NO: 289) |
| NY-ESO-1:157-165, C165A | SLLMWITQA (SEQ ID NO: 290) |

TABLE 8

Ratio of anti-HLA-A2:NY-ESO-1 antibodies binding T2 Cells
Pulsed with Off-Target Peptide to Unpulsed Cells

| Antibody | Ratio NY-ESO-1:157-165 wt to Unpulsed | Ratio BCL9L:1351-1359 to Unpulsed | Ratio GRID1:7-15 to Unpulsed | Ratio EARS2:306-314 to Unpulsed | Ratio ZDHHC1 (376-384) to Unpulsed |
|---|---|---|---|---|---|
| mAb24955N | 110.1 | 0.4 | 1.1 | 0.6 | 0.4 |
| mAb24956N | 124.8 | 0.4 | 1 | 0.6 | 0.4 |
| mAb24958N | 98.6 | 0.4 | 0.7 | 0.6 | 0.4 |
| mAb24959N | 131 | 80.7 | 3.2 | 0.6 | 0.4 |
| mAb28035P | 131.4 | 170.1 | 1.4 | 0.6 | 0.9 |
| mAb28037P2 | 136.6 | 52.3 | 0.7 | 0.6 | 0.5 |
| mAb28042P | 134.2 | 46.5 | 17.4 | 0.6 | 0.5 |
| mAb28075P | 58.8 | 1.5 | 1.4 | 0.5 | 0.4 |
| mAb28105P | 126.4 | 0.4 | 0.7 | 0.6 | 0.5 |
| mAb28113P | 114.7 | 1 | 0.9 | 0.5 | 0.4 |
| mAb28128P | 138.4 | 3 | 1.6 | 0.6 | 1.6 |
| mAb29814P | 124 | 150.1 | 1.6 | 0.6 | 0.6 |

TABLE 8-continued

Ratio of anti-HLA-A2:NY-ESO-1 antibodies binding T2 Cells
Pulsed with Off-Target Peptide to Unpulsed Cells

| | | | | | |
|---|---|---|---|---|---|
| mAb29822P2 | 36.7 | 0.8 | 0.7 | 0.5 | 0.3 |
| anti-NY-ESO-1 3M4E5_VH.hIgG1 T1_Fab_VL.hLambda_opt | 102.2 | 146.9 | 22.8 | 0.6 | 25.6 |
| anti-NY-ESO-1 3M4E5_VH.hIgG4s T1_Fab_VL.hLambda_opt | 137.6 | 174.3 | 21 | 0.7 | 30.3 |
| human IgG4s) Isotype control | 0.7 | 1.4 | 0.7 | 0.6 | 1 |
| anti-HLA-A2 | 2.1 | 2.8 | 1.4 | 2.6 | 1.8 |
| human IgG2a Isotype control | 0.6 | 1.1 | 1.7 | 1.9 | 1.1 |
| human IgG1 Isotope control | 0.8 | 1.1 | 0.8 | 0.6 | 0.8 |
| Anti-hFC | 0.7 | 0.4 | 0.8 | 0.6 | 0.5 |
| Anti-mFC | 1.9 | 0.8 | 1.0 | 0.9 | 1.0 |
| Unstained | 0.9 | 0.9 | 1.1 | 1.1 | 1.1 |

| Antibody | Ratio ITCH (807-815) to Unpulsed | Ratio MAGEH1:90-98 to Unpulsed | Ratio FBXL22:4-12 to Unpulsed | Ratio URB1:1853-1861 to Unpulsed |
|---|---|---|---|---|
| mAb24955N | 1 | 0.5 | 0.5 | 0.6 |
| mAb24956N | 0.9 | 0.4 | 0.5 | 0.5 |
| mAb24958N | 1 | 0.5 | 0.5 | 0.6 |
| mAb24959N | 0.9 | 0.4 | 0.5 | 0.6 |
| mAb28035P | 1 | 0.4 | 0.5 | 0.5 |
| mAb28037P2 | 1.3 | 0.4 | 0.5 | 0.6 |
| mAb28042P | 0.7 | 0.4 | 0.5 | 0.5 |
| mAb28075P | 1 | 0.5 | 0.5 | 0.5 |
| mAb28105P | 1 | 0.5 | 0.5 | 0.6 |
| mAb28113P | 0.9 | 0.4 | 0.5 | 0.6 |
| mAb28128P | 1 | 0.5 | 1.3 | 0.6 |
| mAb29814P | 0.9 | 0.4 | 0.5 | 7.9 |
| mAb29822P2 | 0.8 | 0.4 | 0.4 | 0.4 |
| anti-NY-ESO-1 3M4E5_VH.hIgG1 T1_Fab_VL.hLambda_opt | 10.5 | 0.6 | 1.1 | 141.8 |
| anti-NY-ESO-1 3M4E5_VH.hIgG4s T1_Fab_VL.hLambda_opt | 9.4 | 0.6 | 0.8 | 171.9 |
| human IgG4s) Isotype control | 1 | 0.5 | 0.6 | 2.4 |
| anti-HLA-A2 | 0.5 | 2.3 | 2.2 | 2.9 |
| human IgG2a Isotype control | 0.8 | 1.7 | 1.5 | 2.1 |
| human IgG1 Isotope control | 0.9 | 0.5 | 0.6 | 1.5 |
| Anti-hFC | 1 | 0.6 | 0.6 | 0.7 |
| Anti-mFC | 1.1 | 0.7 | 0.9 | 0.9 |
| Unstained | 1 | 1.1 | 1 | 0.8 |

As seen in Table 8, a number of the antibodies tested were identified as having no significant binding on T2 cells pulsed with any of the predicted off-target peptides, especially in comparison to the two comparator antibodies, which had significant binding to multiple off-target peptides. Nonspecific binding may lead to decreased therapeutic efficacy and/or increased adverse effects (e.g., nonspecific cytotoxicity that diminishes tumor cell killing activity and/or causes side effects in subjects). Thus, the identification of antigen-binding proteins (e.g., antibodies) which have minimal off-target binding can be beneficial in developing therapeutics that target MAGE-A4, as described herein.

Alanine scanning was performed to determine which residues in the NY-ESO-1(157-165) peptide were important for cell binding. T2 cells were pulsed with alanine scanning peptides (Table 7) and stained with the NY-ESO-1 (157-165) antibodies as described above. Fold change over unpulsed cells is displayed in table 9. All peptides loaded effectively as determined by HLA.A2 surface staining (described above) except NY-ESO-1:157-165, C165V, S157 Å and NY-ESO-1:157-165, C165V, I162A. The following residues were important for binding of the anti-NY-ESO-1 mAbs tested (defined as a 90% or greater reduction in binding): leucine 158, tryptophan 161, threonine 163, and glutamine 164. Threonine 163 and glutamine 164 were dispensable for binding of the comparator monoclonal antibody Ref Ab 3, as described above. Methionine 160 was particularly important for binding of mAb24956N, mAb24958N, and mAb28105P.

TABLE 9

Ratio of anti-HLA-A2:NY-ESO-1 antibodies binding T2 Cells
Pulsed with Alanine Scanning Peptides to Unpulsed Cells

| mAb | NY-ESO-1 (SLLMWITQV (SEQ ID NO: 281)) | S157A (ALLMWITQV (SEQ ID NO: 282)) | L158A (SALMWITQV (SEQ ID NO: 283)) | L159A (SLAMWITQV (SEQ ID NO: 284)) | M160A (SLLAWITQV (SEQ ID NO: 285)) |
|---|---|---|---|---|---|
| mAb24955N | 29.8 | 0.5 | 0.6 | 23.0 | 16.3 |
| mAb24956N | 32.6 | 0.4 | 0.4 | 27.8 | 0.7 |
| mAb24958N | 46.8 | 1.2 | 8.6 | 29.8 | 2.0 |
| mAb28075P | 29.3 | 1.6 | 5.1 | 25.0 | 27.1 |
| mAb28105P | 35.4 | 2.5 | 7.7 | 40.1 | 8.5 |
| mAb28113P | 44.6 | 2.5 | 7.6 | 34.5 | 27.9 |
| mAb29822P2 | 5.3 | 0.3 | 0.3 | 10.3 | 10.3 |
| Ref Ab 3 | 67.2 | 3.6 | 11.3 | 51.8 | 68.0 |
| anti-HLA-A2 | 3.4 | 1.2 | 2.7 | 4.1 | 3.9 |
| human IgG4 with reduced effector function isotype control | 0.5 | 0.4 | 0.4 | 0.4 | 0.5 |
| Anti-mouse FC | 0.5 | 0.3 | 0.3 | 0.3 | 0.4 |
| Anti-human FC | 0.8 | 1.2 | 0.7 | 0.7 | 0.6 |
| Viability | 0.9 | 0.9 | 0.8 | 0.8 | 0.8 |

| mAb | W161A (SLLMATQV (SEQ ID NO: 286)) | I162A (SLLMWATQV (SEQ ID NO: 287)) | T163A (SLLMWIAQV (SEQ ID NO: 288)) | Q164A (SLLMWITAV (SEQ ID NO: 289)) | C165A (SLLMWITQA (SEQ ID NO: 290)) |
|---|---|---|---|---|---|
| mAb24955N | 0.4 | 1.1 | 0.9 | 1.0 | 66.1 |
| mAb24956N | 0.4 | 0.7 | 1.7 | 0.8 | 53.5 |
| mAb24958N | 0.4 | 0.3 | 0.4 | 2.0 | 45.2 |
| mAb28075P | 0.4 | 2.3 | 7.5 | 2.1 | 25.4 |
| mAb28105P | 0.4 | 5.2 | 14.2 | 3.2 | 62.1 |
| mAb28113P | 0.4 | 5.0 | 16.0 | 9.1 | 45.1 |
| mAb29822P2 | 0.4 | 0.3 | 0.4 | 0.4 | 14.2 |
| Ref Ab 3 | 0.4 | 7.4 | 47.0 | 67.1 | 68.1 |
| anti-HLA-A2 | 3.5 | 1.3 | 3.1 | 3.4 | 3.5 |
| human IgG4 with reduced effector function isotype control | 0.4 | 0.4 | 0.4 | 0.4 | 0.4 |
| Anti-mouse FC | 0.4 | 0.3 | 0.3 | 0.4 | 0.4 |
| Anti-human FC | 0.7 | 0.6 | 0.7 | 0.8 | 0.8 |
| Viability | 0.9 | 0.8 | 0.8 | 0.9 | 0.9 |

Example 6: Reformatting Anti-HLA-A2:NY-ESO-1 Antibodies into ScFv for Use in Chimeric Antigen Receptors Four NY-ESO-1(157-165) antibodies (mAb24955N, mAb24956N, mAb24958N, and mAb24959N) were reformatted into VL-VH or VH-VL single chain variable fragment chimeric antigen receptors (CARs) using a CD8α hinge and transmembrane domain, 4-1 BB costimulatory domain, and a CD3ξ stimulatory domain. The NY-ESO-1: 157-165 CARs were cloned into a lentiviral expression vector (Lenti-X™ Bicistronic Expression System (Neo), Clontech Cat #632181) and lentiviral particles were generated via the Lenti-X Packaging Single-Shot (VSV-G) system (Clontech Cat #631276) according to manufacturer protocols. Jurkat/NFATLuc cl. 3C7 cells (cells to express an NFAT-luciferase reporter) were then transduced with the 8 different CARs using RetroNectin Precoated Dishes (Clontech, Cat #T110a) according to manufacturer's protocols. Following selection for at least 2 weeks in 500 µg/ml G418 (Gibco, Cat #11811-098), the following CAR-T cell lines were generated: Jurkat/NFATLuc cl 3C7/NY-ESO CAR-T 24955N VH-VL; Jurkat/NFATLuc cl 3C7/NY-ESO CAR-T 24955N VL-VH; Jurkat/NFATLuc cl 3C7/NY-ESO CAR-T 24956N VH-VL; Jurkat/NFATLuc cl 3C7/NY-ESO CAR-T 24956N VL-VH; Jurkat/NFATLuc cl 3C7/NY-ESO CAR-T 24958N VH-VL; Jurkat/NFATLuc cl 3C7/NY-ESO CAR-T 24958N VL-VH; Jurkat/NFATLuc cl 3C7/NY-ESO CAR-T 24959N VH-VL; and Jurkat/NFATLuc cl 3C7/NY-ESO CAR-T 24959N VL-VH. Activity of the CAR-T cell lines was then assessed in a CAR-T/APC (Antigen presenting cell) bioassay. To perform the bioassay, 50,000 CAR-T cells were added to Thermo-Nunc 96 well white plates (Thermo Scientific, Cat #136101) in 50 ml of assay media (RPMI media with 10% FBS and 1% P/S/G) followed by the addition of a 3-fold serial dilution of APCs (200,000 cells to 274 cells) in 50 ml of assay media. The following APCs were utilized: 3T3/HLA.A2/hB2M/NY-ESO-1: 157-165 WT (NIH3T3 cells engineered to express human HLA.A2 (accession number P01892), human B2M (accession number NP_004039.1) and a ubiquitin peptide cassette comprising the NY-ESO-1: 157-165 peptide, 3T3/HLA.A2/hB2M/ HPV16E7:11-19 (as described above with a ubiquitin peptide cassette (Lévy F, et al. (1996) Proc. Nat. Acad. Sci. USA 93(10):4907-4912; Valmori D, et al. (1999) J Exp Med. 189(6):895-906) comprising the HPV16E7:11-19 peptide, IM9 (HLA.A2 positive, NY-ESO-1: 157-165 positive), and HEK293 (HLA.A2 positive and NY-ESO-1: 157-165 negative). The cell mixture was incubated in a 37° C., 5% $CO_2$, humidified incubator for 5 hours. NFAT-Luciferase activity was measured using Promega One-Glo (Cat #E6130) and a Perkin Elmer Envision plate reader. Relative luciferase units (RLU) were generated and plotted in Graphpad Prism using a four-parameter logistic equation over an 8-point response curve to calculate $EC_{50}$ values. The zero APC condition for each dose-response curve is also included in the analysis as a continuation of the three-fold serial dilution and is represented as the lowest dose. Max fold activation was determined by taking the ratio of the highest RLU on the curve to the lowest. All eight NY-ESO-1 CAR cell lines activated in the presence of 3T3/HLA.A2/hB2M/NY-ESO-1: 157-165 WT cells. As demonstrated in Table 10, three NY-ESO-1 CAR cell lines were activated in the presence of IM9 cells (Jurkat/NFATLuc cl 3C7/NY-ESO CAR-T 24955N VH-VL; Jurkat/NFATLuc cl 3C7/NY-ESO CAR-T 24955N VL-VH; and Jurkat/NFATLuc cl 3C7/NY-ESO CAR-T 24956N VL-VH).

binds. This Fab was centered on the bound peptide, with HCDR3 contacting the C terminal half of the bound peptide, and the light chain CDRs contacting the peptide's N terminal half. Peptide residues M160 and W161 were at the center of the Fab binding interface, making contacts with both heavy and light chain CDR residues, as described below. Other published peptide-in-groove antibody complex structures (e.g., PDB codes 1W72 and 4WUU) reveal that an antibody does not have to cover the entire HLA-displayed peptide; however, antibodies with only partial peptide coverage have poor specificity, tolerating extensive changes in the part of the peptide that is not contacted with little loss in binding affinity.

The structure showed that the mAb28105P Fab heavy chain was in contact with residues 160, 161, and 164 in the

TABLE 10

| Activation of NY-ESO-1:157-165 CAR-Ts in a CAR-T/APC Bioassay. | | | | | | | |
|---|---|---|---|---|---|---|---|
| | 3T3/HLA.A2/hB2M/NY-ESO-1 157-165 WT | | 3T3/HLA.A2/hB2M/ HPV16E7 11-19 | | IM9 | | HEK293 | |
| | EC50 (#of APC cells) | Max Fold (RLU) | EC50 (#of APC cells) | Max Fold (RLU) | EC50 (#of APC cells) | Max Fold (RLU) | EC50 (#of APC cells) | Max Fold (RLU) |
| Jurkat/NFATLuc cl 3C7 | N.D. | 1 | N.D. | 1 | N.D. | 1 | N.D. | 1 |
| Jurkat/NFATLuc cl 3C7/NY-ESO CAR-T 24955N VH-VL | 20306 | 39 | N.D. | 1 | 84852 | 3 | N.D. | 1 |
| Jurkat/NFATLuc cl 3C7/NY-ESO CAR-T 24955N VL-VH | 88656 | 30.5 | N.D. | 1 | 253190 | 4.1 | N.D. | 0.8 |
| Jurkat/NFATLuc cl 3C7/NY-ESO CAR-T 24956N VH-VL | 47635 | 30.1 | N.D. | 1 | N.D. | 1.2 | N.D. | 0.8 |
| Jurkat/NFATLuc cl 3C7/NY-ESO CAR-T 24956N VL-VH | 25855 | 38.1 | N.D. | 0.9 | 111502 | 4.4 | N.D. | 0.7 |
| Jurkat/NFATLuc cl 3C7/NY-ESO CAR-T 24958N VH-VL | 24506 | 6.7 | N.D. | 1.1 | N.D. | 1 | N.D. | 0.7 |
| Jurkat/NFATLuc cl 3C7/NY-ESO CAR-T 24958N VL-VH | 19871 | 6.4 | N.D. | 1 | N.D. | 0.9 | N.D. | 0.7 |
| Jurkat/NFATLuc cl 3C7/NY-ESO CAR-T 24959N VH-VL | 14233 | 13.3 | N.D. | 1.1 | N.D. | 1.1 | N.D. | 0.7 |
| Jurkat/NFATLuc cl 3C7/NY-ESO CAR-T 24959N VL-VH | 24009 | 28.6 | N.D. | 0.9 | N.D. | 0.8 | N.D. | 0.6 |

Example 7: Structural Analysis of Fab Binding to HLA2:NY-ESO-1_157-165 Peptide

To better understand the specific interactions between antibody and HLA-peptide complex, an X-ray crystal structure was determined for the Fab fragment of antibody mAb28105P bound to HLA-A2/hB2M displaying a peptide comprising residues 157-165 from cancer testis antigen 1 (CTAG1B; NY-ESO-1). This peptide was modified by substituting residue 165 from its native cysteine with a valine. All 9 residues of the HLA-displayed NY-ESO-1 (C165V) peptide were clearly visible in the electron density map of this structure, and the residues of HLA and Fab that surround the peptide were also well resolved. This structure was refined at a resolution of 3.3 Å, but newer crystallographic refinement techniques (deformable elastic network, or "jelly body" refinement) helped to prevent overfitting, ensuring accuracy of the resulting model.

The mAb28105P Fab was bound to the top of the HLA-peptide complex, in a manner similar to the way that a TCR HLA-bound NY-ESO-1 peptide, while the Fab light chain was in contact with residues 160 and 161. Peptide residues 157, 158, 159, 162, and 165 all pointed toward the HLA molecule. Residue 163 was completely screened from solvent by the Fab light chain, but did not make any direct contacts with the antibody residues. The bound peptide was numbered according to the residue positions in the SEQ ID NO: 271), as shown in SEQ ID NO: 291:

| | Amino Acid | | | | | | | |
|---|---|---|---|---|---|---|---|---|
| | S | L | L | M | W | I | T | Q | V |
| Position | 157 | 158 | 159 | 160 | 161 | 162 | 163 | 164 | 165 |

(SEQ ID NO: 291)

All Fab contacts were made with the side chains of the HLA-bound peptide, rather than its backbone.

Peptide contacts made by mAb28105P Fab were concentrated in HCDR3, with small contributions from LCDR1 and LCDR2. In particular, Fab heavy chain residues 100, 101, 104, 105, and 111 (SEQ ID NO:162) and light chain residues 32 and 49 (SEQ ID NO:170) interacted with the bound peptide, while Fab heavy chain residues 100, 101, 107, and 109 (SEQ ID NO:162) and light chain residue 92 (SEQ ID NO:170) interacted with the HLA. As used above, the term "interacted with" here can include direct or water-mediated hydrogen bonds, charge-charge interactions, or hydrophobic/van der Waals interactions.

Four of the NY-ESO-1_157-165 antibodies (mAb24955N, mAb24956N, mAb24958N, and mAb24959N) were all highly similar in light chain sequence, but the heavy chain sequences diverged in HCDR2 and HCDR3. The seven peptide-binding residues were generally conserved: three residues were identical in all four antibodies, and three more were identical in three out of four sequences, suggesting a common binding modality between the antibodies.

Example 8: Analysis of Vhimeric Antigen Receptor Signaling Domains

Chimeric antigen receptors containing either an anti-HLA-A2/NY-ESO-1$_{157-165}$ scFv in the $V_H$-$V_L$ orientation plus either 1) a human CD8 (huCD8) hinge/transmembrane domain, a 4-1 BB co-stimulatory domain, and a CD3zeta signaling domain (BB/z CAR) (full-length CAR sequence: SEQ ID NO: 301), or 2) huCD28 hinge/transmembrane/costimulatory domains and a CD3z signaling domain (28/z CAR) (full-length CAR sequence: SEQ ID NO: 302) were constructed using the $V_L$ and $V_H$ sequences of an anti-HLA-A2/NY-ESO-1$_{157-165}$ antibody, mAb28105P ($V_L$: SEQ ID NO: 294; $V_H$: SEQ ID NO: 293). As a non-binding control, a BB/z CAR was designed using an irrelevant scFv plus a huCD8 hinge/transmembrane domain, a 4-1 BB co-stimulatory domain, and a CD3z signaling domain. These CARs were cloned into a pLVX lentiviral vector with an EF1a promoter and P2A:eGFP sequence (SEQ ID NO: 300) for tracking CAR-transduced cells, and VSV-pseudotyped lentivirus was produced. See FIG. 1A for construct design and Table 11 for a summary of the constructs.

CD3+ T cells were isolated from human peripheral blood mononuclear cells (PBMCs) from a normal donor, stimulated with CD3/CD28 microbeads plus 100 U/ml recombinant human IL-2, and transduced with the lentivirus at an MOI=5. The transduced cells were expanded for 19 days with CD3/CD28 microbeads plus 100 U/ml recombinant human IL-2 before being cryopreserved until use during the in vivo experiment.

To determine the in vivo efficacy of anti-HLA-A2/NY-ESO-1$_{157-165}$-targeted chimeric antigen receptor (CAR) T cells, a xenogenic tumor study was performed. On day 0, immunodeficient NOD.Cg-Prkdcsc$^{scid}$II2rg$^{tm1\,Wjl}$/SzJ (NSG) mice were subcutaneously injected with $5\times10^6$ HLA-A2$^+$NY-ESO-1$^+$ A375 human melanoma tumor cells. On day 3 after tumors were established, the mice (n=5 per group) were intravenously injected with $20\times10^6$ T cells that express either the non-binding control BB/z CAR (Control CAR T), the anti-HLA-A2/NY-ESO-1$_{157-165}$ BB/z CAR, or the anti-HLA-A2/NY-ESO-1$_{157-165}$ 28/z CAR (as determined by the frequency of cells expressing GFP, which is a marker for those cells that have been transduced with CAR) from two different donors. Tumor growth was assessed through day 21 by measuring tumor volumes.

In order to determine tumor volume by external caliper, the greatest longitudinal diameter (length in mm) and the greatest transverse diameter (width in mm) were determined. Tumor volumes based on caliper measurements were calculated by the formula: Volume $(mm^3)=(length\times width^2)/2$.

TABLE 11

| CAR constructs | | |
|---|---|---|
| Parental mAb | Specificity | Description |
| Irrelevant | Non-binding control | Anti-HLA-A2/HPV16E7$_{11-19}$ scFv in VL-VH orientation with huCD8 hinge/transmembrane domain, a 4-1BB co-stimulatory domain, and a CD3z signaling domain (Control CAR) |
| mAb28105P | HLA-A2/NY-ESO-1$_{157-165}$ | anti-HLA-A2/NY-ESO-1$_{157-165}$ scFv mAb28105P in VH-VL orientation with huCD8 hinge/transmembrane domain, a 4-1 BB co-stimulatory domain, and a CD3z signaling domain (NY-ESO-1$_{157-165}$ BB/z CAR) |
| mAb28105P | HLA-A2/NY-ESO-1$_{157-165}$ | anti-HLA-A2/NY-ESO-1$_{157-165}$ scFv mAb28105P in VH-VL orientation with huCD28 hinge/transmembrane/costimulatory domains and a CD3z signaling domain (NY-ESO-1$_{157-165}$ 28/z CAR) |

Figure 1B:
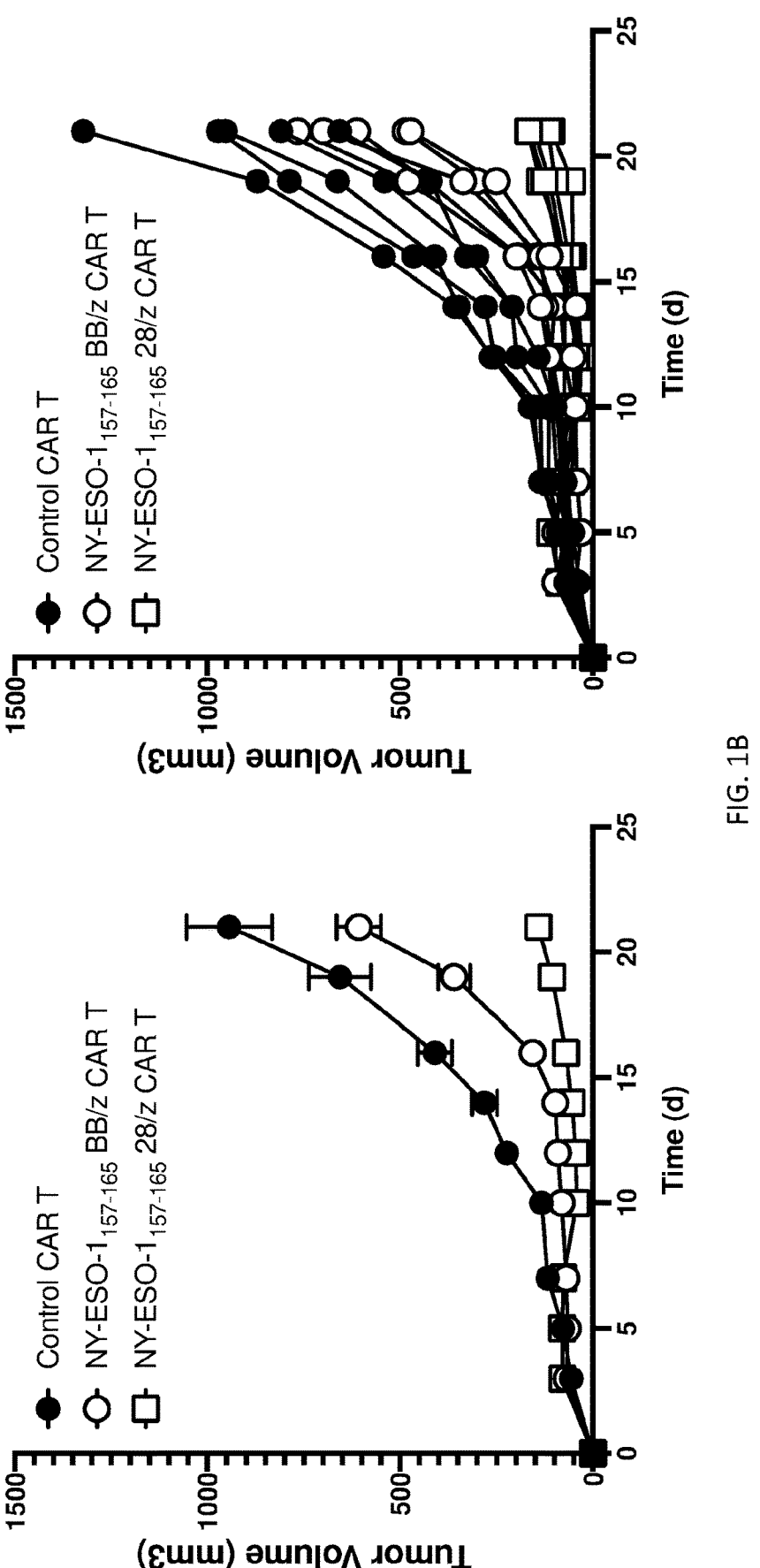
FIG. 1B depicts tumor volumes in mice treated with T cells that express either a non-binding control BB/z CAR (Control CAR T), the anti-HLA-A2/NY-ESO-1$_{157\text{-}165}$ BB/z CAR, or the anti-HLA-A2/NY-ESO-1$_{157\text{-}165}$ 28/z CAR over days 0 to 21. Left panel: average tumor volume; right panel: tumor volumes for individual mice.
Figure 1C:
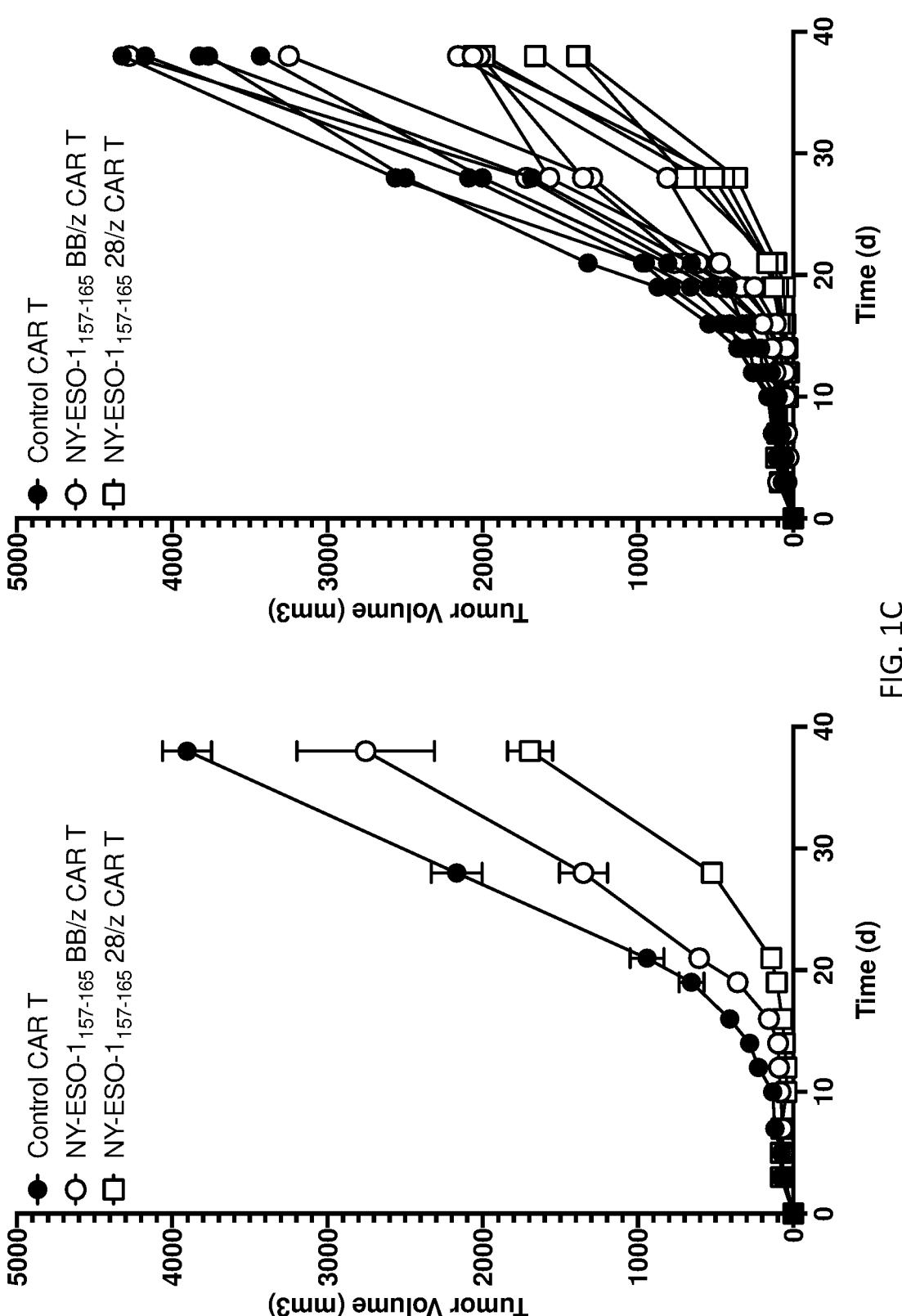
FIG. 1C depicts tumor volumes in mice treated with T cells that express either a non-binding control BB/z CAR (Control CAR T), the anti-HLA-A2/NY-ESO-1$_{157\text{-}165}$ BB/z CAR, or the anti-HLA-A2/NY-ESO-1$_{157\text{-}165}$ 28/z CAR over days 0 to 38. Left panel: average tumor volume; right panel: tumor volumes for individual mice.

Collectively, the results demonstrate that anti-HLA-A2/NY-ESO-1$_{157-165}$ 28/z CAR T cells demonstrate superior in vivo anti-tumor activity and anti-tumor kinetics compared to anti-HLA-A2/NY-ESO-1$_{157-165}$ BB/z CAR T cells, but that both types of CARs demonstrated anti-tumor activity as compared to the non-binding control. A375 tumors grew progressively in mice receiving Control CAR T cells. Mice receiving anti-HLA-A2/NY-ESO-1$_{157-165}$ BB/z CAR T cells demonstrated some tumor control, with reduced tumor growth compared to Control CAR T-treated mice on days 21 (p<0.04), 28 (p<0.0001), and 38 (p<0.0001) (statistics analyzed by 2-way ANOVA). Anti-HLA-A2/NY-ESO-1$_{157-165}$ 28/z CAR T treatment also led to suppression of established A375 tumor growth on days 16 (p=0.03), 19 (p=0.0002), 21 (p<0.0001), 28 (p<0.0001), and 38 (p<0.0001) (statistics analyzed by 2-way ANOVA). Enhanced efficacy of anti-HLA-A2/NY-ESO-1$_{157-165}$ 28/z CAR vs. anti-HLA-A2/NY-ESO-1$_{157-165}$ BB/z CAR is confirmed, as tumor sizes on days 21 (p=0.002), 28 (p<0.0001), and 38 (p<0.0001) are statistically significant, (p<0.0001 on both days) by 2-way ANOVA. See FIG. 1B and FIG. 1C, and Tables 12-22.

TABLE 12

| | CAR efficacy, day 3 | | |
|---|---|---|---|
| CAR T Treatment | Average Tumor Size $(mm^3)$ on Day 3 | Tumor size standard error of the mean (SEM) | Number of mice still alive (of 5) on day 3 |
| Control CAR T | 57.2 | 7.1 | 5 |
| NY-ESO-1$_{157-165}$ BB/z CAR T | 69.1 | 11.4 | 5 |
| NY-ESO-1$_{157-165}$ 28/z CAR T | 79.4 | 4.0 | 5 |

TABLE 13

| | CAR efficacy, day 5 | | |
|---|---|---|---|
| CAR T Treatment | Average Tumor Size (mm$^3$) on Day 5 | Tumor size standard error of the mean (SEM) | Number of mice still alive (of 5) on day 5 |
| Control CAR T | 78.8 | 7.0 | 5 |
| NY-ESO-1$_{157-165}$ BB/z CAR T | 65.9 | 10.9 | 5 |
| NY-ESO-1$_{157-165}$ 28/z CAR T | 80.7 | 8.0 | 5 |

TABLE 14

| | CAR efficacy, day 7 | | |
|---|---|---|---|
| CAR T Treatment | Average Tumor Size (mm$^3$) on Day 7 | Tumor size standard error of the mean (SEM) | Number of mice still alive (of 5) on day 7 |
| Control CAR T | 118.4 | 12.2 | 5 |
| NY-ESO-1$_{157-165}$ BB/z CAR T | 69.8 | 8.4 | 5 |
| NY-ESO-1$_{157-165}$ 28/z CAR T | 77.6 | 7.1 | 5 |

TABLE 15

| | CAR efficacy, day 10 | | |
|---|---|---|---|
| CAR T Treatment | Average Tumor Size (mm$^3$) on Day 10 | Tumor size standard error of the mean (SEM) | Number of mice still alive (of 5) on day 10 |
| Control CAR T | 134.0 | 12.1 | 5 |
| NY-ESO-1$_{157-165}$ BB/z CAR T | 81.8 | 10.4 | 5 |
| NY-ESO-1$_{157-165}$ 28/z CAR T | 43.7 | 2.5 | 5 |

TABLE 16

| | CAR efficacy, day 12 | | |
|---|---|---|---|
| CAR T Treatment | Average Tumor Size (mm$^3$) on Day 12 | Tumor size standard error of the mean (SEM) | Number of mice still alive (of 5) on day 12 |
| Control CAR T | 224.6 | 23.7 | 5 |
| NY-ESO-1$_{157-165}$ BB/z CAR T | 92.1 | 12.0 | 5 |
| NY-ESO-1$_{157-165}$ 28/z CAR T | 43.8 | 8.1 | 5 |

TABLE 17

| | CAR efficacy, day 14 | | |
|---|---|---|---|
| CAR T Treatment | Average Tumor Size (mm$^3$) on Day 14 | Tumor size standard error of the mean (SEM) | Number of mice still alive (of 5) on day 14 |
| Control CAR T | 281.8 | 31.8 | 5 |
| NY-ESO-1$_{157-165}$ BB/z CAR T | 98.3 | 16.4 | 5 |

TABLE 17-continued

| | CAR efficacy, day 14 | | |
|---|---|---|---|
| CAR T Treatment | Average Tumor Size (mm$^3$) on Day 14 | Tumor size standard error of the mean (SEM) | Number of mice still alive (of 5) on day 14 |
| NY-ESO-1$_{157-165}$ 28/z CAR T | 56.6 | 5.6 | 5 |

TABLE 18

| | CAR efficacy, day 16 | | |
|---|---|---|---|
| CAR T Treatment | Average Tumor Size (mm$^3$) on Day 16 | Tumor size standard error of the mean (SEM) | Number of mice still alive (of 5) on day 16 |
| Control CAR T | 409.8 | 44.5 | 5 |
| NY-ESO-1$_{157-165}$ BB/z CAR T | 157.9 | 16.7 | 5 |
| NY-ESO-1$_{157-165}$ 28/z CAR T | 70.5 | 6.0 | 5 |

TABLE 19

| | CAR efficacy, day 19 | | |
|---|---|---|---|
| CAR T Treatment | Average Tumor Size (mm$^3$) on Day 19 | Tumor size standard error of the mean (SEM) | Number of mice still alive (of 5) on day 19 |
| Control CAR T | 657.3 | 81.3 | 5 |
| NY-ESO-1$_{157-165}$ BB/z CAR T | 359.8 | 41.9 | 5 |
| NY-ESO-1$_{157-165}$ 28/z CAR T | 106.6 | 14.5 | 5 |

TABLE 20

| | CAR efficacy, day 21 | | |
|---|---|---|---|
| CAR T Treatment | Average Tumor Size (mm$^3$) on Day 21 | Tumor size standard error of the mean (SEM) | Number of mice still alive (of 5) on day 21 |
| Control CAR T | 943.1 | 110.5 | 5 |
| NY-ESO-1$_{157-165}$ BB/z CAR T | 607.6 | 57.8 | 5 |
| NY-ESO-1$_{157-165}$ 28/z CAR T | 142.7 | 12.6 | 5 |

TABLE 21

| | CAR efficacy, day 28 | | |
|---|---|---|---|
| CAR T Treatment | Average Tumor Size (mm$^3$) on Day 28 | Tumor size standard error of the mean (SEM) | Number of mice still alive (of 5) on day 28 |
| Control CAR T | 2168.4 | 162.9 | 5 |
| NY-ESO-1$_{157-165}$ BB/z CAR T | 1351.5 | 154.6 | 5 |

TABLE 21-continued

| | CAR efficacy, day 28 | | |
|---|---|---|---|
| CAR T Treatment | Average Tumor Size (mm$^3$) on Day 28 | Tumor size standard error of the mean (SEM) | Number of mice still alive (of 5) on day 28 |
| NY-ESO-1$_{157-165}$ 28/z CAR T | 523.8 | 57.7 | 5 |

TABLE 22

| | CAR efficacy, day 38 | | |
|---|---|---|---|
| CAR T Treatment | Average Tumor Size (mm$^3$) on Day 38 | Tumor size standard error of the mean (SEM) | Number of mice still alive (of 5) on day 38 |
| Control CAR T | 3904.3 | 157.4 | 5 |
| NY-ESO-1$_{157-165}$ BB/z CAR T | 2754.3 | 443.7 | 5 |

TABLE 22-continued

| | CAR efficacy, day 38 | | |
|---|---|---|---|
| CAR T Treatment | Average Tumor Size (mm$^3$) on Day 38 | Tumor size standard error of the mean (SEM) | Number of mice still alive (of 5) on day 38 |
| NY-ESO-1$_{157-165}$ 28/z CAR T | 1696.4 | 144.0 | 5 |

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims.

What is claimed is:

1. An antibody, or antigen-binding portion thereof, that binds specifically to at least one amino acid of an HLA-A2: New York esophageal squamous cell carcinoma 1 peptide (NY-ESO-1 peptide) complex, wherein the antibody, or antigen-binding portion thereof, comprises a heavy chain variable region (HCVR) comprising a heavy chain complementarity determining region (HCDR) 1 of SEQ ID NO: 4, an HCDR2 of SEQ ID NO: 6, an HCDR3 of SEQ ID NO: 8, and a light chain variable region (LCVR) comprising a light chain complementarity determining region (LCDR) 1 of SEQ ID NO: 12, an LCDR2 of SEQ ID NO: 14, and an LCDR3 of SEQ ID NO: 16.

2. The antibody, or antigen-binding portion thereof, of claim 1 that binds specifically to an HLA-A2: NY-ESO-1 157-165 peptide complex, wherein said antibody, or antigen-binding portion thereof, interacts with amino acids M160, W161, and Q164 of said NY-ESO-1 157-165 peptide as determined by X-ray crystallography at a resolution of 4.0 Å or higher.

3. The antibody, or antigen-binding portion thereof, of claim 1 that specifically binds to an HLA-A2: NY-ESO-1 157-165 peptide complex but does not specifically bind to one or more off-target peptides selected from the group consisting of BCL9L 1351-1359 (SEQ ID NO: 273), GRID1 7-15 (SEQ ID NO: 274), ZDHHC1 376-384 (SEQ ID NO: 276), ITCH 807-815 (SEQ ID NO: 277), and URB1 1853-1861 (SEQ ID NO: 280), wherein the ratio of i) said antibody, or antigen-binding portion thereof, binding to cells pulsed with said one or more off-target peptides to ii) unpulsed cells is less than about nine.

4. The antibody, or antigen-binding portion thereof, of claim 1, wherein said NY-ESO-1 peptide comprises the amino acid sequence of SLLMWITQC (SEQ ID NO: 269) or SLLMWITQV (SEQ ID NO: 291).

5. The antibody, or antigen-binding portion thereof, of claim 1, wherein the antibody, or antigen-binding portion thereof, is, a Fab, a Fab', a (Fab')2, an Fv, a single chain Fv (scFv), or a T-body construct.

6. The antibody, or antigen-binding portion thereof, of claim 1, further comprising a detectable moiety.

7. A pharmaceutical composition comprising the antibody, or antigen-binding portion thereof, that binds to HLA-A2: NY-ESO-1 according to claim 1 and a pharmaceutically acceptable carrier or diluent.

8. An isolated polynucleotide molecule comprising a polynucleotide sequence that encodes the HCVR of the antibody, or antigen-binding portion thereof, as set forth in claim 1 and the LCVR of the antibody, or antigen-binding portion thereof, as set forth in claim 1.

9. A vector comprising the polynucleotide molecule of claim 8.

10. A cell expressing the polynucleotide molecule of claim 8.

11. A method of treating a subject having an NY-ESO-1-associated disease or disorder, comprising administering to the subject a therapeutically effective amount of the antibody, or antigen-binding portion thereof, as set forth in claim 1, thereby treating the subject.

12. The method of claim 11, wherein the NY-ESO-1-associated disease or disorder is an NY-ESO-1-associated cancer.

13. An isolated nucleic acid molecule encoding a chimeric antigen receptor (CAR), wherein the CAR comprises an extracellular binding domain that specifically binds to a conformational epitope of an HLA-A2 presented New York esophageal squamous cell carcinoma 1 peptide (NY-ESO-1 peptide), a transmembrane domain, and an intracellular signaling domain,
  wherein the extracellular binding domain is an antibody, or antigen-binding portion thereof, comprising a heavy chain variable region (HCVR) comprising a heavy chain complementarity determining region (HCDR) 1 of SEQ ID NO: 4, an HCDR2 of SEQ ID NO: 6, an HCDR3 of SEQ ID NO: 8, and a light chain variable region (LCVR) comprising a light chain complementarity determining region (LCDR) 1 of SEQ ID NO: 12, an LCDR2 of SEQ ID NO: 14, and an LCDR3 of SEQ ID NO: 16.

14. A vector comprising the isolated nucleic acid molecule of claim 13.

15. An isolated immune effector cell comprising the isolated nucleic acid molecule of claim 13.

16. A method of treating a subject having an NY-ESO-1-associated disease or disorder, comprising administering to the subject the immune effector cell of claim 15.

17. The method of claim 16, wherein the NY-ESO-1-associated disease or disorder is NY-ESO-1-associated cancer.

18. The antibody, or antigen-binding portion thereof, of claim 1, wherein:
  (a) the amino acid sequence of the HCVR comprises at least 90% or at least 95% sequence identity to SEQ ID NO: 2; and
  (b) the amino acid sequence of the LCVR comprises at least 90% or at least 95% sequence identity to SEQ ID NO: 10.

19. The human monoclonal antibody, or antigen-binding portion thereof, of claim 18, wherein the amino acid sequence of the HCVR comprises SEQ ID NO:2 and the amino acid sequence of the LCVR comprises SEQ ID NO: 10.

20. The antibody, or antigen-binding portion thereof, of claim 5, wherein the antibody, or antigen-binding portion thereof, is a scFv.

21. A Chimeric Antigen Receptor (CAR), comprising the antibody, or antigen-binding portion thereof, of claim 1.

22. The isolated polynucleotide molecule of claim 8, wherein the antibody, or antigen-binding portion thereof, is an scFv.

23. The method of claim 12, wherein the NY-ESO-associated cancer is a liposarcoma, a neuroblastoma, a myeloma, a metastatic melanoma, a synovial sarcoma, a bladder cancer, an esophageal cancer, a hepatocellular cancer, a head and neck cancer, a non-small cell lung cancer, an ovarian cancer, a prostate cancer, a breast cancer, astrocytic tumor, glioblastoma multiforme, anaplastic astrocytoma, brain tumor, fallopian tube cancer, ovarian epithelial cancer, primary peritoneal cavity cancer, advanced solid tumors, soft tissue sarcoma, melanoma, a sarcoma, myelodysplastic syndrome, acute myeloid leukemia, Hodgkin lymphoma, non-Hodgkin lymphoma, Hodgkin disease, multiple myeloma, synovial sarcoma, metastatic solid tumors, esophageal cancer, rhabdomyosarcoma, advanced myxoid, round cell liposarcoma, metastatic melanoma, or recurrent non-small cell lung cancer.

24. The method of claim 11, further comprising administering a second therapeutic agent.

25. The method of claim 24, wherein the second therapeutic agent is a PD-1 inhibitor, a CTLA-4 inhibitor, an antibody to a tumor specific antigen, an antibody to a virally-infected-cell antigen, a PD-L1 inhibitor, a CD20 inhibitor, a bispecific antibody against CD20 and CD3, a dietary supplement such as an antioxidant, a VEGF antagonist, a chemotherapeutic agent, a cytotoxic agent, surgery, radiation, a NSAID, a corticosteroid, or any other therapy useful for ameliorating at least one symptom associated with the disease or disorder.

26. The method of claim 11, wherein the antibody, or antigen-binding portion thereof, is for subcutaneous, intravenous, intradermal, intraperitoneal, oral, intramuscular or intracranial administration.

27. The method of claim 11, wherein the antibody, or antigen-binding portion thereof, is for administration at a dose of about 0.1 mg/kg of body weight to about 100 mg/kg of body weight of the subject.

28. The isolated nucleic acid molecule of claim 13, wherein the antibody, or antigen-binding portion thereof, is an scFv.

29. The isolated nucleic acid molecule of claim 13, wherein the costimulatory domain is a 4-1BB costimulatory domain.

30. The isolated nucleic acid molecule of claim 13, wherein the costimulatory domain is a CD28 costimulatory domain.

31. The isolated immune effector cell of claim 15, which is a T-body.

32. A method of treating a subject having an NY-ESO-1-associated disease or disorder, comprising administering to the subject the immune effector cell of claim 15.

33. The method of claim 32, wherein the NY-ESO-1-associated disease or disorder is NY-ESO-1-associated cancer.

34. The method of claim 33, wherein the NY-ESO-associated cancer is a liposarcoma, a neuroblastoma, a myeloma, a metastatic melanoma, a synovial sarcoma, a bladder cancer, an esophageal cancer, a hepatocellular cancer, a head and neck cancer, a non-small cell lung cancer, an ovarian cancer, a prostate cancer, a breast cancer, astrocytic tumor, glioblastoma multiforme, anaplastic astrocytoma, brain tumor, fallopian tube cancer, ovarian epithelial cancer, primary peritoneal cavity cancer, advanced solid tumors, soft tissue sarcoma, melanoma, a sarcoma, myelodysplastic syndrome, acute myeloid leukemia, Hodgkin lymphoma, non-Hodgkin lymphoma, Hodgkin disease, multiple myeloma, synovial sarcoma, metastatic solid tumors, esophageal cancer, rhabdomyosarcoma, advanced myxoid, round cell liposarcoma, metastatic melanoma, or recurrent non-small cell lung cancer.

35. The method of claim 32, further comprising a second therapeutic agent.

36. The method of claim 35, wherein the second therapeutic agent is a PD-1 inhibitor, a CTLA-4 inhibitor, an antibody to a tumor specific antigen, an antibody to a virally-infected-cell antigen, a PD-L1 inhibitor, a CD20 inhibitor, a bispecific antibody against CD20 and CD3, a dietary supplement such as an antioxidant, a VEGF antagonist, a chemotherapeutic agent, a cytotoxic agent, surgery, radiation, a NSAID, a corticosteroid, or any other therapy useful for ameliorating at least one symptom associated with the disease or disorder.

37. The isolated polynucleotide molecule of claim 8, wherein the polynucleotide sequence that encodes the HCVR comprises the nucleotide sequence of SEQ ID NO: 1.

38. The isolated polynucleotide molecule of claim 8, wherein the polynucleotide sequence that encodes the LCVR comprises the nucleotide sequence of SEQ ID NO: 9.

39. A cell comprising a first polynucleotide molecule, wherein the first polynucleotide molecule comprises a polynucleotide sequence that encodes the HCVR as set forth in claim 1; and a second polynucleotide molecule, wherein the second polynucleotide molecule comprises a polynucleotide sequence that encodes the LCVR as set forth in claim 1.

40. The cell of claim 39, wherein the polynucleotide sequence that encodes the HCVR comprises the nucleotide sequence of SEQ ID NO: 1, and wherein the polynucleotide sequence that encodes the LCVR comprises the nucleotide sequence of SEQ ID NO: 9.

41. The cell of claim 39, wherein the first polynucleotide molecule is contained within a vector.

42. The cell of claim 39, wherein the second polynucleotide molecule is contained within a vector.

43. The cell of claim 39, wherein the first polynucleotide molecule and the second polynucleotide molecule are contained within a vector.

44. A cell expressing the vector of claim 9.

45. An isolated immune effector cell comprising the vector of claim 14.

46. A pharmaceutical composition comprising the isolated immune effector cell of claim 15.

\* \* \* \* \*

SEQUENCE LISTING

```
<160> NUMBER OF SEQ ID NOS: 305

<210> SEQ ID NO 1
<211> LENGTH: 396
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 1
gaagtgcagc tggtcgagtc tggggggaggc gtggtacagc ctggggggtc cctgagactc      60
tcctgtgtag cctctggatt cacctttgat gattatgcca tgtactgggt ccgacaagtt     120
ccagggaagg atctggagtg ggtctctctt ataagtgggg atggtgatat cacatattat     180
gtagactctg tgaagggccg attcaccgtc tccagagaca acaacaaaaa ctccctgtat     240
ctgcaaatga aaagtctgag agttgaggac accgccttgt attactgtgc aaaagatatg     300
atatattacg cttcttggag tggttacggg tcgtccgact actactacta cgttatggac     360
gtctggggcc aagggaccac ggtcaccgtc tcctca                                396

<210> SEQ ID NO 2
<211> LENGTH: 132
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Glu Val Gln Leu Val Glu Ser Gly Gly Gly Val Val Gln Pro Gly Gly
1               5                   10                  15

Ser Leu Arg Leu Ser Cys Val Ala Ser Gly Phe Thr Phe Asp Asp Tyr
            20                  25                  30

Ala Met Tyr Trp Val Arg Gln Val Pro Gly Lys Asp Leu Glu Trp Val
        35                  40                  45

Ser Leu Ile Ser Gly Asp Gly Asp Ile Thr Tyr Tyr Val Asp Ser Val
    50                  55                  60
```

```
Lys Gly Arg Phe Thr Val Ser Arg Asp Asn Asn Lys Asn Ser Leu Tyr
65                  70                  75                  80

Leu Gln Met Lys Ser Leu Arg Val Glu Asp Thr Ala Leu Tyr Tyr Cys
                85                  90                  95

Ala Lys Asp Met Ile Tyr Tyr Ala Ser Trp Ser Gly Tyr Gly Ser Ser
            100                 105                 110

Asp Tyr Tyr Tyr Tyr Val Met Asp Val Trp Gly Gln Gly Thr Thr Val
        115                 120                 125

Thr Val Ser Ser
    130
```

```
<210> SEQ ID NO 3
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
ggattcacct ttgatgatta tgcc                                          24
```

```
<210> SEQ ID NO 4
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Gly Phe Thr Phe Asp Asp Tyr Ala
1               5
```

```
<210> SEQ ID NO 5
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5
ataagtgggg atggtgatat caca                                          24
```

```
<210> SEQ ID NO 6
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Ile Ser Gly Asp Gly Asp Ile Thr
1               5
```

```
<210> SEQ ID NO 7
<211> LENGTH: 75
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7
```

```
gcaaaagata tgatatatta cgcttcttgg agtggttacg ggtcgtccga ctactactac    60
tacgttatgg acgtc                                                      75
```

<210> SEQ ID NO 8
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

```
Ala Lys Asp Met Ile Tyr Tyr Ala Ser Trp Ser Gly Tyr Gly Ser Ser
1               5                   10                  15

Asp Tyr Tyr Tyr Tyr Val Met Asp Val
            20                  25
```

<210> SEQ ID NO 9
<211> LENGTH: 324
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 9

```
gacatccaga tgacccagtc tccatcctcc ctgtctgcat ctgtaggaga cagagtcacc    60
atcacttgcc gggcaagtca gagcattagc agctatttaa attggtatca gcagaaacca   120
gggaaagccc ctaagctcct gatctatgct gcatccagtt tgcaaagtgg ggtcccgtca   180
aggttcagtg gcagtggatc tgggacagat ttcactctca ccatcagcag tctgcaacct   240
gaagattttg caacttacta ctgtcaacag agttacagta cccctccgat caccttcggc   300
caagggacac gactggagat taaa                                          324
```

<210> SEQ ID NO 10
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Pro
                85                  90                  95

Ile Thr Phe Gly Gln Gly Thr Arg Leu Glu Ile Lys
            100                 105
```

<210> SEQ ID NO 11

```
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11
cagagcatta gcagctat                                                        18

<210> SEQ ID NO 12
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Gln Ser Ile Ser Ser Tyr
1               5

<210> SEQ ID NO 13
<211> LENGTH: 9
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 13 gctgcatcc                                                                   9

<210> SEQ ID NO 14
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Ala Ala Ser
1

<210> SEQ ID NO 15
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 15
caacagagtt acagtaccccc tccgatcacc                                          30

<210> SEQ ID NO 16
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Gln Gln Ser Tyr Ser Thr Pro Pro Ile Thr
1               5                   10
```

-continued

```
<210> SEQ ID NO 17
<211> LENGTH: 1377
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 17
gaagtgcagc tggtcgagtc tgggggaggc gtggtacagc ctggggggtc cctgagactc      60
tcctgtgtag cctctggatt cacctttgat gattatgcca tgtactgggt ccgacaagtt     120
ccagggaagg atctggagtg ggtctctctt ataagtgggg atggtgatat cacatattat     180
gtagactctg tgaagggccg attcaccgtc tccagagaca acaacaaaaa ctccctgtat     240
ctgcaaatga aaagtctgag agttgaggac accgccttgt attactgtgc aaaagatatg     300
atatattacg cttcttggag tggttacggg tcgtccgact actactacta cgttatggac     360
gtctggggcc aagggaccac ggtcaccgtc tcctcagcct ccaccaaggg cccatcggtc     420
ttccccctgg cgccctgctc caggagcacc tccgagagca gccgccct gggctgcctg     480 gtcaaggact acttccccga accggtgacg gtgtcgtgga actcaggcgc cctgaccagc     540
ggcgtgcaca ccttcccggc tgtcctacag tcctcaggac tctactccct cagcagcgtg     600
gtgaccgtgc cctccagcag cttgggcacg aagacctaca cctgcaacgt agatcacaag     660
cccagcaaca ccaaggtgga caagagagtt gagtccaaat atggtccccc atgcccaccg     720
tgcccagcac cacctgtggc aggaccatca gtcttcctgt tccccccaaa acccaaggac     780
actctcatga tctcccggac ccctgaggtc acgtgcgtgg tggtggacgt gagccaggaa     840
gaccccgagg tccagttcaa ctggtacgtg gatggcgtgg aggtgcataa tgccaagaca     900
aagccgcggg aggagcagtt caacagcacg taccgtgtgg tcagcgtcct caccgtcctg     960
caccaggact ggctgaacgg caaggagtac aagtgcaagg tctccaacaa aggcctcccg    1020
tcctccatcg agaaaaccat ctccaaagcc aaagggcagc cccgagagcc acaggtgtac    1080
accctgcccc catcccagga ggagatgacc aagaaccagg tcagcctgac ctgcctggtc    1140
aaaggcttct accccagcga catcgccgtg gagtgggaga gcaatgggca gccggagaac    1200
aactacaaga ccacgcctcc cgtgctggac tccgacggct ccttcttcct ctacagcagg    1260
ctcaccgtgg acaagagcag gtggcaggag gggaatgtct tctcatgctc cgtgatgcat    1320
gaggctctgc acaaccacta cacacagaag tccctctccc tgtctctggg taaatga      1377

<210> SEQ ID NO 18
<211> LENGTH: 458
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 18

Glu Val Gln Leu Val Glu Ser Gly Gly Gly Val Val Gln Pro Gly Gly
1               5                   10                  15

Ser Leu Arg Leu Ser Cys Val Ala Ser Gly Phe Thr Phe Asp Asp Tyr
            20                  25                  30

Ala Met Tyr Trp Val Arg Gln Val Pro Gly Lys Asp Leu Glu Trp Val
        35                  40                  45

Ser Leu Ile Ser Gly Asp Gly Asp Ile Thr Tyr Tyr Val Asp Ser Val
    50                  55                  60
```

-continued

Lys Gly Arg Phe Thr Val Ser Arg Asp Asn Asn Lys Asn Ser Leu Tyr
65                  70                  75                  80

Leu Gln Met Lys Ser Leu Arg Val Glu Asp Thr Ala Leu Tyr Tyr Cys
                85                  90                  95

Ala Lys Asp Met Ile Tyr Tyr Ala Ser Trp Ser Gly Tyr Gly Ser Ser
            100                 105                 110

Asp Tyr Tyr Tyr Tyr Val Met Asp Val Trp Gly Gln Gly Thr Thr Val
            115                 120                 125

Thr Val Ser Ser Ala Ser Thr Lys Gly Pro Ser Val Phe Pro Leu Ala
        130                 135                 140

Pro Cys Ser Arg Ser Thr Ser Glu Ser Thr Ala Ala Leu Gly Cys Leu
145                 150                 155                 160

Val Lys Asp Tyr Phe Pro Glu Pro Val Thr Val Ser Trp Asn Ser Gly
                165                 170                 175

Ala Leu Thr Ser Gly Val His Thr Phe Pro Ala Val Leu Gln Ser Ser
            180                 185                 190

Gly Leu Tyr Ser Leu Ser Ser Val Val Thr Val Pro Ser Ser Ser Leu
            195                 200                 205

Gly Thr Lys Thr Tyr Thr Cys Asn Val Asp His Lys Pro Ser Asn Thr
        210                 215                 220

Lys Val Asp Lys Arg Val Glu Ser Lys Tyr Gly Pro Pro Cys Pro Pro
225                 230                 235                 240

Cys Pro Ala Pro Pro Val Ala Gly Pro Ser Val Phe Leu Phe Pro Pro
                245                 250                 255

Lys Pro Lys Asp Thr Leu Met Ile Ser Arg Thr Pro Glu Val Thr Cys
            260                 265                 270

Val Val Val Asp Val Ser Gln Glu Asp Pro Glu Val Gln Phe Asn Trp
            275                 280                 285

Tyr Val Asp Gly Val Glu Val His Asn Ala Lys Thr Lys Pro Arg Glu
        290                 295                 300

Glu Gln Phe Asn Ser Thr Tyr Arg Val Val Ser Val Leu Thr Val Leu
305                 310                 315                 320

His Gln Asp Trp Leu Asn Gly Lys Glu Tyr Lys Cys Lys Val Ser Asn
                325                 330                 335

Lys Gly Leu Pro Ser Ser Ile Glu Lys Thr Ile Ser Lys Ala Lys Gly
            340                 345                 350

Gln Pro Arg Glu Pro Gln Val Tyr Thr Leu Pro Pro Ser Gln Glu Glu
            355                 360                 365

Met Thr Lys Asn Gln Val Ser Leu Thr Cys Leu Val Lys Gly Phe Tyr
        370                 375                 380

Pro Ser Asp Ile Ala Val Glu Trp Glu Ser Asn Gly Gln Pro Glu Asn
385                 390                 395                 400

Asn Tyr Lys Thr Thr Pro Pro Val Leu Asp Ser Asp Gly Ser Phe Phe
                405                 410                 415

Leu Tyr Ser Arg Leu Thr Val Asp Lys Ser Arg Trp Gln Glu Gly Asn
            420                 425                 430

Val Phe Ser Cys Ser Val Met His Glu Ala Leu His Asn His Tyr Thr
            435                 440                 445

Gln Lys Ser Leu Ser Leu Ser Leu Gly Lys
        450                 455

<210> SEQ ID NO 19
<211> LENGTH: 648

<212> TYPE: DNA
<213> ORGANISM: Artificial Sequence
<220> FEATURE:
<223> OTHER INFORMATION: Description of Artificial Sequence: Synthetic
     polynucleotide

<400> SEQUENCE: 19
gacatccaga tgacccagtc tccatcctcc ctgtctgcat ctgtaggaga cagagtcacc        60
atcacttgcc gggcaagtca gagcattagc agctatttaa attggtatca gcagaaacca       120
gggaaagccc ctaagctcct gatctatgct gcatccagtt tgcaaagtgg ggtcccgtca       180
aggttcagtg gcagtggatc tgggacagat ttcactctca ccatcagcag tctgcaacct       240
gaagattttg caacttacta ctgtcaacag agttacagta cccctccgat caccttcggc       300
caagggacac gactggagat taaacgaact gtggctgcac catctgtctt catcttcccg       360
ccatctgatg agcagttgaa atctggaact gcctctgttg tgtgcctgct gaataacttc       420
tatcccagag aggccaaagt acagtggaag gtggataacg ccctccaatc gggtaactcc       480
caggagagtg tcacagagca ggacagcaag gacagcacct acagcctcag cagcaccctg       540
acgctgagca aagcagacta cgagaaacac aaagtctacg cctgcgaagt cacccatcag       600
ggcctgagct cgcccgtcac aaagagcttc aacaggggag agtgttag                    648

<210> SEQ ID NO 20
<211> LENGTH: 215
<212> TYPE: PRT
<213> ORGANISM: Artificial Sequence
<220> FEATURE:
<223> OTHER INFORMATION: Description of Artificial Sequence: Synthetic
     polypeptide

<400> SEQUENCE: 20

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Pro
                85                  90                  95

Ile Thr Phe Gly Gln Gly Thr Arg Leu Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

-continued

Ser Phe Asn Arg Gly Glu Cys
    210                 215

<210> SEQ ID NO 21
<211> LENGTH: 396
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 21
gaagtgcagc tggtggagtc tggggggaggc gtggttcagc ctggggggtc cctgagactc        60
tcctgtgcag cctctggatt caccttgat gattatgcca tgtactgggt ccgtcaagct         120
ccagggaagg gtctggagtg ggtctctctt attagtgggg atggtggtag tatgtactat        180
gcagactctg tgaagggccg attcaccatc tccagagaca acagcaaaaa ctccctgtat        240
ctgcaaatga acagtctgag aactgaggac accgccttgt attactgtgc aaaagatatg        300
atcttttacg cttttttggag tggttacggg tcgtccgact actactacta cgttatggac       360
gtctggggcc aagggaccac ggtcaccgtc tactca                                  396

<210> SEQ ID NO 22
<211> LENGTH: 132
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 22

Glu Val Gln Leu Val Glu Ser Gly Gly Gly Val Val Gln Pro Gly Gly
1               5                   10                  15

Ser Leu Arg Leu Ser Cys Ala Ala Ser Gly Phe Thr Phe Asp Asp Tyr
            20                  25                  30

Ala Met Tyr Trp Val Arg Gln Ala Pro Gly Lys Gly Leu Glu Trp Val
        35                  40                  45

Ser Leu Ile Ser Gly Asp Gly Gly Ser Met Tyr Tyr Ala Asp Ser Val
    50                  55                  60

Lys Gly Arg Phe Thr Ile Ser Arg Asp Asn Ser Lys Asn Ser Leu Tyr
65                  70                  75                  80

Leu Gln Met Asn Ser Leu Arg Thr Glu Asp Thr Ala Leu Tyr Tyr Cys
                85                  90                  95

Ala Lys Asp Met Ile Phe Tyr Ala Phe Trp Ser Gly Tyr Gly Ser Ser
            100                 105                 110

Asp Tyr Tyr Tyr Tyr Val Met Asp Val Trp Gly Gln Gly Thr Thr Val
        115                 120                 125

Thr Val Tyr Ser
    130

<210> SEQ ID NO 23
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 23
ggattcacct ttgatgatta tgcc                                                24

```
<210> SEQ ID NO 24
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Gly Phe Thr Phe Asp Asp Tyr Ala
1               5

<210> SEQ ID NO 25
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 25
attagtgggg atggtggtag tatg                                          24

<210> SEQ ID NO 26
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Ile Ser Gly Asp Gly Gly Ser Met
1               5

<210> SEQ ID NO 27
<211> LENGTH: 75
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 27
gcaaaagata tgatctttta cgcttttttgg agtggttacg ggtcgtccga ctactactac     60
tacgttatgg acgtc                                                        75

<210> SEQ ID NO 28
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Ala Lys Asp Met Ile Phe Tyr Ala Phe Trp Ser Gly Tyr Gly Ser Ser
1               5                   10                  15

Asp Tyr Tyr Tyr Tyr Val Met Asp Val
            20                  25

<210> SEQ ID NO 29
<211> LENGTH: 324
<212> TYPE: DNA
<213> ORGANISM: Artificial Sequence
```

<220> FEATURE:
<223> OTHER INFORMATION: Description of Artificial Sequence: Synthetic
      polynucleotide

<400> SEQUENCE: 29
gacatccaga tgacccagtc tccatcctcc ctgtctgcat ctgttggaga cagagtcacc      60
atcacttgcc gggcaagtca gcgcattagc acttatttaa attggtatca gcagaaacca     120
gggaaagccc ctaagctcct gatctatgct gcatccagtt tgcaaagtgg ggtcccatca     180
aggttcagtg gcagtggatc tgggacagat ttcactctca ccatcagcag tctgcaacct     240
gaagattttg caacttacta ctgtcaacag agttacagta cccctccgat caccttcggc     300
caagggacac gactggagat taaa                                             324

<210> SEQ ID NO 30
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 30

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Arg Ile Ser Thr Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Pro
                85                  90                  95

Ile Thr Phe Gly Gln Gly Thr Arg Leu Glu Ile Lys
            100                 105

<210> SEQ ID NO 31
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 31
cagcgcatta gcacttat                                                     18

<210> SEQ ID NO 32
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Gln Arg Ile Ser Thr Tyr
1               5

<210> SEQ ID NO 33

-continued

```
<211> LENGTH: 9
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 33 gctgcatcc                                                                9

<210> SEQ ID NO 34
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Ala Ala Ser
1

<210> SEQ ID NO 35
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 35
caacagagtt acagtacccc tccgatcacc                                          30

<210> SEQ ID NO 36
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Gln Gln Ser Tyr Ser Thr Pro Pro Ile Thr
1               5                   10

<210> SEQ ID NO 37
<211> LENGTH: 1377
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 37
gaagtgcagc tggtggagtc tggggggaggc gtggttcagc ctggggggtc cctgagactc      60
tcctgtgcag cctctggatt caccttttgat gattatgcca tgtactgggt ccgtcaagct     120
ccagggaagg gtctggagtg ggtctctctt attagtgggg atggtggtag tatgtactat     180
gcagactctg tgaagggccg attcaccatc tccagagaca acagcaaaaa ctccctgtat     240
ctgcaaatga acagtctgag aactgaggac accgccttgt attactgtgc aaaagatatg     300
atcttttacg cttttttggag tggttacggg tcgtccgact actactacta cgttatggac     360
gtctggggcc aagggaccac ggtcaccgtc tactcagcct ccaccaaggg cccatcggtc     420
ttccccctgg cgccctgctc caggagcacc tccgagagca gccgccctct gggctgcctg     480
```

-continued

```
gtcaaggact acttccccga accggtgacg gtgtcgtgga actcaggcgc cctgaccagc      540
ggcgtgcaca ccttcccggc tgtcctacag tcctcaggac tctactccct cagcagcgtg      600
gtgaccgtgc cctccagcag cttgggcacg aagacctaca cctgcaacgt agatcacaag      660
cccagcaaca ccaaggtgga caagagagtt gagtccaaat atggtccccc atgcccaccg      720
tgcccagcac cacctgtggc aggaccatca gtcttcctgt tccccccaaa acccaaggac      780
actctcatga tctcccggac ccctgaggtc acgtgcgtgg tggtggacgt gagccaggaa      840
gaccccgagg tccagttcaa ctggtacgtg gatggcgtgg aggtgcataa tgccaagaca      900
aagccgcggg aggagcagtt caacagcacg taccgtgtgg tcagcgtcct caccgtcctg      960
caccaggact ggctgaacgg caaggagtac aagtgcaagg tctccaacaa aggcctcccg     1020
tcctccatcg agaaaaccat ctccaaagcc aaagggcagc cccgagagcc acaggtgtac     1080
accctgcccc catcccagga ggagatgacc aagaaccagg tcagcctgac ctgcctggtc     1140
aaaggcttct accccagcga catcgccgtg gagtgggaga gcaatgggca gccggagaac     1200
aactacaaga ccacgcctcc cgtgctggac tccgacggct ccttcttcct ctacagcagg     1260
ctcaccgtgg acaagagcag gtggcaggag gggaatgtct tctcatgctc cgtgatgcat     1320
gaggctctgc acaaccacta cacacagaag tccctctccc tgtctctggg taaatga       1377
```

```
<210> SEQ ID NO 38
<211> LENGTH: 458
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 38

Glu Val Gln Leu Val Glu Ser Gly Gly Gly Val Val Gln Pro Gly Gly
1               5                   10                  15

Ser Leu Arg Leu Ser Cys Ala Ala Ser Gly Phe Thr Phe Asp Asp Tyr
            20                  25                  30

Ala Met Tyr Trp Val Arg Gln Ala Pro Gly Lys Gly Leu Glu Trp Val
        35                  40                  45

Ser Leu Ile Ser Gly Asp Gly Gly Ser Met Tyr Tyr Ala Asp Ser Val
    50                  55                  60

Lys Gly Arg Phe Thr Ile Ser Arg Asp Asn Ser Lys Asn Ser Leu Tyr
65                  70                  75                  80

Leu Gln Met Asn Ser Leu Arg Thr Glu Asp Thr Ala Leu Tyr Tyr Cys
                85                  90                  95

Ala Lys Asp Met Ile Phe Tyr Ala Phe Trp Ser Gly Tyr Gly Ser Ser
            100                 105                 110

Asp Tyr Tyr Tyr Tyr Val Met Asp Val Trp Gly Gln Gly Thr Thr Val
            115                 120                 125

Thr Val Tyr Ser Ala Ser Thr Lys Gly Pro Ser Val Phe Pro Leu Ala
        130                 135                 140

Pro Cys Ser Arg Ser Thr Ser Glu Ser Thr Ala Ala Leu Gly Cys Leu
145                 150                 155                 160

Val Lys Asp Tyr Phe Pro Glu Pro Val Thr Val Ser Trp Asn Ser Gly
                165                 170                 175

Ala Leu Thr Ser Gly Val His Thr Phe Pro Ala Val Leu Gln Ser Ser
            180                 185                 190

Gly Leu Tyr Ser Leu Ser Ser Val Val Thr Val Pro Ser Ser Ser Leu
            195                 200                 205
```

```
Gly Thr Lys Thr Tyr Thr Cys Asn Val Asp His Lys Pro Ser Asn Thr
    210                 215                 220

Lys Val Asp Lys Arg Val Glu Ser Lys Tyr Gly Pro Pro Cys Pro Pro
225                 230                 235                 240

Cys Pro Ala Pro Pro Val Ala Gly Pro Ser Val Phe Leu Phe Pro Pro
            245                 250                 255

Lys Pro Lys Asp Thr Leu Met Ile Ser Arg Thr Pro Glu Val Thr Cys
            260                 265                 270

Val Val Val Asp Val Ser Gln Glu Asp Pro Glu Val Gln Phe Asn Trp
        275                 280                 285

Tyr Val Asp Gly Val Glu Val His Asn Ala Lys Thr Lys Pro Arg Glu
    290                 295                 300

Glu Gln Phe Asn Ser Thr Tyr Arg Val Val Ser Val Leu Thr Val Leu
305                 310                 315                 320

His Gln Asp Trp Leu Asn Gly Lys Glu Tyr Lys Cys Lys Val Ser Asn
            325                 330                 335

Lys Gly Leu Pro Ser Ser Ile Glu Lys Thr Ile Ser Lys Ala Lys Gly
            340                 345                 350

Gln Pro Arg Glu Pro Gln Val Tyr Thr Leu Pro Pro Ser Gln Glu Glu
            355                 360                 365

Met Thr Lys Asn Gln Val Ser Leu Thr Cys Leu Val Lys Gly Phe Tyr
    370                 375                 380

Pro Ser Asp Ile Ala Val Glu Trp Glu Ser Asn Gly Gln Pro Glu Asn
385                 390                 395                 400

Asn Tyr Lys Thr Thr Pro Pro Val Leu Asp Ser Asp Gly Ser Phe Phe
            405                 410                 415

Leu Tyr Ser Arg Leu Thr Val Asp Lys Ser Arg Trp Gln Glu Gly Asn
            420                 425                 430

Val Phe Ser Cys Ser Val Met His Glu Ala Leu His Asn His Tyr Thr
            435                 440                 445

Gln Lys Ser Leu Ser Leu Ser Leu Gly Lys
    450                 455

<210> SEQ ID NO 39
<211> LENGTH: 645
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 39
gacatccaga tgacccagtc tccatcctcc ctgtctgcat ctgttggaga cagagtcacc      60
atcacttgcc gggcaagtca gcgcattagc acttatttaa attggtatca gcagaaacca     120
gggaaagccc ctaagctcct gatctatgct gcatccagtt tgcaaagtgg ggtcccatca     180
aggttcagtg gcagtggatc tgggacagat ttcactctca ccatcagcag tctgcaacct     240
gaagattttg caacttacta ctgtcaacag agttacagta cccctccgat caccttcggc     300
caagggacac gactggagat taaacgaact gtggctgcac catctgtctt catcttcccg     360
ccatctgatg agcagttgaa atctggaact gcctctgttg tgtgcctgct gaataacttc     420
tatcccagag aggccaaagt acagtggaag gtggataacg ccctccaatc gggtaactcc     480
caggagagtg tcacagagca ggacagcaag gacagcacct acagcctcag cagcaccctg     540
acgctgagca aagcagacta cgagaaacac aaagtctacg cctgcgaagt cacccatcag     600
```

-continued

```
ggcctgagct cgcccgtcac aaagagcttc aacaggggag agtgt                      645
```

<210> SEQ ID NO 40
<211> LENGTH: 215
<212> TYPE: PRT
<213> ORGANISM: Artificial Sequence
<220> FEATURE:
<223> OTHER INFORMATION: Description of Artificial Sequence: Synthetic
     polypeptide

<400> SEQUENCE: 40

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Arg Ile Ser Thr Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Pro
                85                  90                  95

Ile Thr Phe Gly Gln Gly Thr Arg Leu Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215
```

<210> SEQ ID NO 41
<211> LENGTH: 360
<212> TYPE: DNA
<213> ORGANISM: Artificial Sequence
<220> FEATURE:
<223> OTHER INFORMATION: Description of Artificial Sequence: Synthetic
     polynucleotide

<400> SEQUENCE: 41

```
caggtgcagc tgcaggagtc gggcccagga ctggtgaagc cttcacagac cctgtccctc      60
acctgtactg tgtctggtgg ctccatcatc agtgatggtt actactggag ttggattcgc     120
cagcacccag ggaagggcct ggagtggatt gggtacgtcg attacagtgg gaatacctac     180
tataatccgt ccctcaagag tcgaattatt atgtcagtag acacgtctaa gaaccagttc     240
tccctgaaat tgacctctgt gactgccgcg gacacggccg tgtatttctg tgtgagagaa     300 gggcccttc gggatgcttt tgaaatctgg gggcaaggga caatggtcac cgtctcttca     360
```

-continued

```
<210> SEQ ID NO 42
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 42

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ile Ser Asp
            20                  25                  30

Gly Tyr Tyr Trp Ser Trp Ile Arg Gln His Pro Gly Lys Gly Leu Glu
            35                  40                  45

Trp Ile Gly Tyr Val Asp Tyr Ser Gly Asn Thr Tyr Tyr Asn Pro Ser
        50                  55                  60

Leu Lys Ser Arg Ile Ile Met Ser Val Asp Thr Ser Lys Asn Gln Phe
65                  70                  75                  80

Ser Leu Lys Leu Thr Ser Val Thr Ala Ala Asp Thr Ala Val Tyr Phe
                85                  90                  95

Cys Val Arg Glu Gly Pro Leu Arg Asp Ala Phe Glu Ile Trp Gly Gln
            100                 105                 110

Gly Thr Met Val Thr Val Ser Ser
        115                 120

<210> SEQ ID NO 43
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 43
ggtggctcca tcatcagtga tggttactac                                        30

<210> SEQ ID NO 44
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

Gly Gly Ser Ile Ile Ser Asp Gly Tyr Tyr
1               5                   10

<210> SEQ ID NO 45
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 45
gtcgattaca gtgggaatac c                                                 21

<210> SEQ ID NO 46
<211> LENGTH: 7
<212> TYPE: PRT
```

-continued

```
<213> ORGANISM: Artificial Sequence
<220> FEATURE:
<223> OTHER INFORMATION: Description of Artificial Sequence: Synthetic
      peptide

<400> SEQUENCE: 46

Val Asp Tyr Ser Gly Asn Thr
1               5

<210> SEQ ID NO 47
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 47
gtgagagaag ggcccctttcg ggatgctttt gaaatc                              36

<210> SEQ ID NO 48
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

Val Arg Glu Gly Pro Leu Arg Asp Ala Phe Glu Ile
1               5                   10

<210> SEQ ID NO 49
<211> LENGTH: 324
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 49
gacatccaga tgacccagtc tccatcctcc ctgtctgcat ctgtaggaga cagagtcacc    60
atcacttgcc ggacaagtca gagcattagc agatatttaa attggtatca gcagaaacca   120
gggaaagccc ctaagctcct gatctttgct gcatccagtt tgcaaagtgg ggtcccatca   180
aggttcagtg gcagtggatc tgggggcagat ttcactctca ccatcagcag tctgcaacct   240
gaagattttg caacttacta ctgtcaacag agttacagta cccctccgat caccttcggc   300
caagggacac gactggagat taaa                                          324

<210> SEQ ID NO 50
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 50

Asp Ile Gln Met Thr Gln Ser Pro Ser Ser Leu Ser Ala Ser Val Gly
1               5                   10                  15

Asp Arg Val Thr Ile Thr Cys Arg Thr Ser Gln Ser Ile Ser Arg Tyr
                20                  25                  30

Leu Asn Trp Tyr Gln Gln Lys Pro Gly Lys Ala Pro Lys Leu Leu Ile
        35                  40                  45
```

```
Phe Ala Ala Ser Ser Leu Gln Ser Gly Val Pro Ser Arg Phe Ser Gly
    50                  55                  60

Ser Gly Ser Gly Ala Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Pro
                85                  90                  95

Ile Thr Phe Gly Gln Gly Thr Arg Leu Glu Ile Lys
            100                 105
```

```
<210> SEQ ID NO 51
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 51
cagagcatta gcagatat                                                  18
```

```
<210> SEQ ID NO 52
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52

Gln Ser Ile Ser Arg Tyr
1               5
```

```
<210> SEQ ID NO 53
<211> LENGTH: 9
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 53 gctgcatcc                                                             9
```

```
<210> SEQ ID NO 54
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54

Ala Ala Ser
1
```

```
<210> SEQ ID NO 55
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 55
caacagagtt acagtacccc tccgatcacc                                     30
```

<210> SEQ ID NO 56
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 56

Gln Gln Ser Tyr Ser Thr Pro Pro Ile Thr
1               5                   10

<210> SEQ ID NO 57
<211> LENGTH: 1341
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 57
caggtgcagc tgcaggagtc gggcccagga ctggtgaagc cttcacagac cctgtccctc        60
acctgtactg tgtctggtgg ctccatcatc agtgatggtt actactggag ttggattcgc       120
cagcacccag ggaagggcct ggagtggatt gggtacgtcg attacagtgg gaatacctac       180
tataatccgt ccctcaagag tcgaattatt atgtcagtag acacgtctaa gaaccagttc       240
tccctgaaat tgacctctgt gactgccgcg gacacggccg tgtatttctg tgtgagagaa       300 gggcccttc gggatgcttt tgaaatctgg ggcaaggga caatggtcac cgtctcttca        360
gcctccacca agggcccatc ggtcttcccc ctggcgccct gctccaggag cacctccgag       420
agcacagccg ccctgggctg cctggtcaag gactacttcc ccgaaccggt gacggtgtcg       480
tggaactcag gcgccctgac cagcggcgtg cacaccttcc cggctgtcct acagtcctca       540
ggactctact ccctcagcag cgtggtgacc gtgccctcca gcagcttggg cacgaagacc       600
tacacctgca acgtagatca caagcccagc aacaccaagg tggacaagag agttgagtcc       660
aaatatggtc ccccatgccc accgtgccca gcaccacctg tggcaggacc atcagtcttc       720
ctgttccccc caaaacccaa ggacactctc atgatctccc ggaccccctga ggtcacgtgc      780 gtggtggtgg acgtgagcca ggaagacccc gaggtccagt tcaactggta cgtggatggc       840
gtggaggtgc ataatgccaa gacaaagccg cgggaggagc agttcaacag cacgtaccgt       900
gtggtcagcg tcctcaccgt cctgcaccag gactggctga acggcaagga gtacaagtgc       960
aaggtctcca acaaaggcct cccgtcctcc atcgagaaaa ccatctccaa agccaaaggg      1020
cagccccgag agccacaggt gtacaccctg cccccatccc aggaggagat gaccaagaac      1080
caggtcagcc tgacctgcct ggtcaaaggc ttctacccca gcgacatcgc cgtggagtgg      1140
gagagcaatg ggcagccgga gaacaactac aagaccacgc ctcccgtgct ggactccgac      1200
ggctccttct tcctctacag caggctcacc gtggacaaga gcaggtggca ggaggggaat      1260
gtcttctcat gctccgtgat gcatgaggct ctgcacaacc actacacaca gaagtccctc      1320
tccctgtctc tgggtaaatg a                                              1341

<210> SEQ ID NO 58
<211> LENGTH: 446
<212> TYPE: PRT
<213> ORGANISM: Artificial Sequence
<220> FEATURE:
<223> OTHER INFORMATION: Description of Artificial Sequence: Synthetic

```
      polypeptide

<400> SEQUENCE: 58

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ile Ser Asp
            20                  25                  30

Gly Tyr Tyr Trp Ser Trp Ile Arg Gln His Pro Gly Lys Gly Leu Glu
        35                  40                  45

Trp Ile Gly Tyr Val Asp Tyr Ser Gly Asn Thr Tyr Tyr Asn Pro Ser
    50                  55                  60

Leu Lys Ser Arg Ile Ile Met Ser Val Asp Thr Ser Lys Asn Gln Phe
65                  70                  75                  80

Ser Leu Lys Leu Thr Ser Val Thr Ala Ala Asp Thr Ala Val Tyr Phe
                85                  90                  95

Cys Val Arg Glu Gly Pro Leu Arg Asp Ala Phe Glu Ile Trp Gly Gln
            100                 105                 110

Gly Thr Met Val Thr Val Ser Ser Ala Ser Thr Lys Gly Pro Ser Val
        115                 120                 125

Phe Pro Leu Ala Pro Cys Ser Arg Ser Thr Ser Glu Ser Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Lys Thr Tyr Thr Cys Asn Val Asp His Lys
        195                 200                 205

Pro Ser Asn Thr Lys Val Asp Lys Arg Val Glu Ser Lys Tyr Gly Pro
    210                 215                 220

Pro Cys Pro Pro Cys Pro Ala Pro Pro Val Ala Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser Gln Glu Asp Pro Glu Val
            260                 265                 270

Gln Phe Asn Trp Tyr Val Asp Gly Val Glu Val His Asn Ala Lys Thr
        275                 280                 285

Lys Pro Arg Glu Glu Gln Phe Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Gly Leu Pro Ser Ser Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Gln Glu Glu Met Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400
```

-continued

```
Gly Ser Phe Phe Leu Tyr Ser Arg Leu Thr Val Asp Lys Ser Arg Trp
            405                 410                 415

Gln Glu Gly Asn Val Phe Ser Cys Ser Val Met His Glu Ala Leu His
        420                 425                 430

Asn His Tyr Thr Gln Lys Ser Leu Ser Leu Ser Leu Gly Lys
    435                 440                 445
```

```
<210> SEQ ID NO 59
<211> LENGTH: 645
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 59
gacatccaga tgacccagtc tccatcctcc ctgtctgcat ctgtaggaga cagagtcacc        60
atcacttgcc ggacaagtca gagcattagc agatatttaa attggtatca gcagaaacca      120
gggaaagccc ctaagctcct gatctttgct gcatccagtt tgcaaagtgg ggtcccatca      180
aggttcagtg gcagtggatc tgggcagat ttcactctca ccatcagcag tctgcaacct       240
gaagattttg caacttacta ctgtcaacag agttacagta cccctccgat caccttcggc      300
caagggacac gactggagat taaacgaact gtggctgcac atctgtctt catcttcccg       360 ccatctgatg agcagttgaa atctggaact gcctctgttg tgtgcctgct gaataacttc      420
tatcccagag aggccaaagt acagtggaag gtggataacg ccctccaatc gggtaactcc      480
caggagagtg tcacagagca ggacagcaag gacagcacct acagcctcag cagcaccctg      540
acgctgagca aagcagacta cgagaaacac aaagtctacg cctgcgaagt cacccatcag      600
ggcctgagct cgcccgtcac aaagagcttc aacaggggag agtgt                      645
```

```
<210> SEQ ID NO 60
<211> LENGTH: 215
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 60

Asp Ile Gln Met Thr Gln Ser Pro Ser Ser Leu Ser Ala Ser Val Gly
1                 5                   10                  15

Asp Arg Val Thr Ile Thr Cys Arg Thr Ser Gln Ser Ile Ser Arg Tyr
            20                  25                  30

Leu Asn Trp Tyr Gln Gln Lys Pro Gly Lys Ala Pro Lys Leu Leu Ile
        35                  40                  45

Phe Ala Ala Ser Ser Leu Gln Ser Gly Val Pro Ser Arg Phe Ser Gly
    50                  55                  60

Ser Gly Ser Gly Ala Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Pro
                85                  90                  95

Ile Thr Phe Gly Gln Gly Thr Arg Leu Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140
```

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 61
<211> LENGTH: 369
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 61
cagttgcagc tgctggagtc gggcccagga ctggtgaagc cttcggagac cctgtccctc      60
atctgcactg tctctggtgg ctccatcaga ggaagtagtt attactgggg ctggatccgc     120
cagcccccag agaaggggct ggagtggatt gggagtatct attctagtgg gagtacctat     180
tacaatccgt ccctcaagag tcgagtcacc atatccgcag acacgtccaa gaaccagttc     240
tccctgaagc tgagctctgt gaccgccgca gacacggctg tgtattactg tgcgagacat     300 gggggggatta cagcagtcca actggagttc gaccctgggg ccagggaac cctggtcacc     360 gtctcctca                                                            369

<210> SEQ ID NO 62
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 62

Gln Leu Gln Leu Leu Glu Ser Gly Pro Gly Leu Val Lys Pro Ser Glu
1               5                   10                  15

Thr Leu Ser Leu Ile Cys Thr Val Ser Gly Gly Ser Ile Arg Gly Ser
            20                  25                  30

Ser Tyr Tyr Trp Gly Trp Ile Arg Gln Pro Pro Glu Lys Gly Leu Glu
        35                  40                  45

Trp Ile Gly Ser Ile Tyr Ser Ser Gly Ser Thr Tyr Tyr Asn Pro Ser
    50                  55                  60

Leu Lys Ser Arg Val Thr Ile Ser Ala Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg His Gly Gly Ile Thr Ala Val Gln Leu Glu Phe Asp Pro
            100                 105                 110

Trp Gly Gln Gly Thr Leu Val Thr Val Ser Ser
        115                 120

<210> SEQ ID NO 63
<211> LENGTH: 30

-continued

<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 63
ggtggctcca tcagaggaag tagttattac                                              30

<210> SEQ ID NO 64
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 64

Gly Gly Ser Ile Arg Gly Ser Ser Tyr Tyr
1               5                   10

<210> SEQ ID NO 65
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 65
atctattcta gtgggagtac c                                                       21

<210> SEQ ID NO 66
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 66

Ile Tyr Ser Ser Gly Ser Thr
1               5

<210> SEQ ID NO 67
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 67
gcgagacatg gggggattac agcagtccaa ctggagttcg acccc                             45

<210> SEQ ID NO 68
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 68

Ala Arg His Gly Gly Ile Thr Ala Val Gln Leu Glu Phe Asp Pro
1               5                   10                  15

<210> SEQ ID NO 69
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 69
gacatccaga tgacccagtc tccatcctcc ctgtctgcat ctgtaggaga cagagtcacc        60
atcacttgcc aggcgagtca ggacattagc aactatttaa aatggtatca gcagaaacca       120
gggaaagccc ctaagatcct gatccacgat gcatccaatt tggagatagg ggtcccatca       180
aggttcagtg gaagtggagc tgggacagat tttattttca ccatcagcag cctgcagcct       240
gaagatattg aacatatta ctgtcaacag tatgataatc tcccgatcac cttcggccaa       300
gggacacgac tggagattaa a                                                  321

<210> SEQ ID NO 70
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 70

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
            20                  25                  30

Leu Lys Trp Tyr Gln Gln Lys Pro Gly Lys Ala Pro Lys Ile Leu Ile
        35                  40                  45

His Asp Ala Ser Asn Leu Glu Ile Gly Val Pro Ser Arg Phe Ser Gly
    50                  55                  60

Ser Gly Ala Gly Thr Asp Phe Ile Phe Thr Ile Ser Ser Leu Gln Pro
65                  70                  75                  80

Glu Asp Ile Gly Thr Tyr Tyr Cys Gln Gln Tyr Asp Asn Leu Pro Ile
                85                  90                  95

Thr Phe Gly Gln Gly Thr Arg Leu Glu Ile Lys
            100                 105

<210> SEQ ID NO 71
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 71
caggacatta gcaactat                                                      18

<210> SEQ ID NO 72
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 72

Gln Asp Ile Ser Asn Tyr

-continued 1              5

<210> SEQ ID NO 73
<211> LENGTH: 9
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 73 gatgcatcc                                                                               9

<210> SEQ ID NO 74
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 74

Asp Ala Ser
1

<210> SEQ ID NO 75
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 75
caacagtatg ataatctccc gatcacc                                                           27

<210> SEQ ID NO 76
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 76

Gln Gln Tyr Asp Asn Leu Pro Ile Thr
1               5

<210> SEQ ID NO 77
<211> LENGTH: 1350
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 77
cagttgcagc tgctggagtc gggcccagga ctggtgaagc cttcggagac cctgtccctc      60
atctgcactg tctctggtgg ctccatcaga ggaagtagtt attactgggg ctggatccgc      120
cagcccccag agaaggggct ggagtggatt gggagtatct attctagtgg gagtacctat      180
tacaatccgt ccctcaagag tcgagtcacc atatccgcag acacgtccaa gaaccagttc      240
tccctgaagc tgagctctgt gaccgccgca gacacggctg tgtattactg tgcgagacat      300 gggggggatta cagcagtcca actggagttc gacccctggg gccagggaac cctggtcacc      360

-continued

```
gtctcctcag cctccaccaa gggcccatcg gtcttccccc tggcgccctg ctccaggagc   420
acctccgaga gcacagccgc cctgggctgc ctggtcaagg actacttccc cgaaccggtg   480
acggtgtcgt ggaactcagg cgccctgacc agcggcgtgc acaccttccc ggctgtccta   540
cagtcctcag gactctactc cctcagcagc gtggtgaccg tgccctccag cagcttgggc   600
acgaagacct acacctgcaa cgtagatcac aagcccagca acaccaaggt ggacaagaga   660
gttgagtcca aatatggtcc cccatgccca ccgtgcccag caccacctgt ggcaggacca   720
tcagtcttcc tgttcccccc aaaacccaag gacactctca tgatctcccg gacccctgag   780
gtcacgtgcg tggtggtgga cgtgagccag gaagaccccg aggtccagtt caactggtac   840
gtggatggcg tggaggtgca taatgccaag acaaagccgc gggaggagca gttcaacagc   900
acgtaccgtg tggtcagcgt cctcaccgtc ctgcaccagg actggctgaa cggcaaggag   960
tacaagtgca aggtctccaa caaaggcctc ccgtcctcca tcgagaaaac catctccaaa  1020
gccaaagggc agccccgaga gccacaggtg tacaccctgc ccccatccca ggaggagatg  1080
accaagaacc aggtcagcct gacctgcctg gtcaaaggct tctaccccag cgacatcgcc  1140
gtggagtggg agagcaatgg gcagccggag aacaactaca agaccacgcc tcccgtgctg  1200
gactccgacg gctccttctt cctctacagc aggctcaccg tggacaagag caggtggcag  1260
gaggggaatg tcttctcatg ctccgtgatg catgaggctc tgcacaacca ctacacacag  1320
aagtccctct ccctgtctct gggtaaatga                                   1350
```

```
<210> SEQ ID NO 78
<211> LENGTH: 449
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 78

Gln Leu Gln Leu Leu Glu Ser Gly Pro Gly Leu Val Lys Pro Ser Glu
1               5                   10                  15

Thr Leu Ser Leu Ile Cys Thr Val Ser Gly Gly Ser Ile Arg Gly Ser
            20                  25                  30

Ser Tyr Tyr Trp Gly Trp Ile Arg Gln Pro Pro Glu Lys Gly Leu Glu
        35                  40                  45

Trp Ile Gly Ser Ile Tyr Ser Ser Gly Ser Thr Tyr Tyr Asn Pro Ser
    50                  55                  60

Leu Lys Ser Arg Val Thr Ile Ser Ala Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg His Gly Gly Ile Thr Ala Val Gln Leu Glu Phe Asp Pro
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Cys Ser Arg Ser Thr Ser Glu Ser
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
```

-continued

```
                180              185              190
Thr Val Pro Ser Ser Ser Leu Gly Thr Lys Thr Tyr Thr Cys Asn Val
            195              200              205
Asp His Lys Pro Ser Asn Thr Lys Val Asp Lys Arg Val Glu Ser Lys
    210              215              220
Tyr Gly Pro Pro Cys Pro Cys Pro Ala Pro Pro Val Ala Gly Pro
225              230              235              240
Ser Val Phe Leu Phe Pro Pro Lys Pro Lys Asp Thr Leu Met Ile Ser
            245              250              255
Arg Thr Pro Glu Val Thr Cys Val Val Val Asp Val Ser Gln Glu Asp
            260              265              270
Pro Glu Val Gln Phe Asn Trp Tyr Val Asp Gly Val Glu Val His Asn
    275              280              285
Ala Lys Thr Lys Pro Arg Glu Glu Gln Phe Asn Ser Thr Tyr Arg Val
    290              295              300
Val Ser Val Leu Thr Val Leu His Gln Asp Trp Leu Asn Gly Lys Glu
305              310              315              320
Tyr Lys Cys Lys Val Ser Asn Lys Gly Leu Pro Ser Ser Ile Glu Lys
            325              330              335
Thr Ile Ser Lys Ala Lys Gly Gln Pro Arg Glu Pro Gln Val Tyr Thr
            340              345              350
Leu Pro Pro Ser Gln Glu Glu Met Thr Lys Asn Gln Val Ser Leu Thr
            355              360              365
Cys Leu Val Lys Gly Phe Tyr Pro Ser Asp Ile Ala Val Glu Trp Glu
    370              375              380
Ser Asn Gly Gln Pro Glu Asn Asn Tyr Lys Thr Thr Pro Pro Val Leu
385              390              395              400
Asp Ser Asp Gly Ser Phe Phe Leu Tyr Ser Arg Leu Thr Val Asp Lys
            405              410              415
Ser Arg Trp Gln Glu Gly Asn Val Phe Ser Cys Ser Val Met His Glu
            420              425              430
Ala Leu His Asn His Tyr Thr Gln Lys Ser Leu Ser Leu Ser Leu Gly
            435              440              445
Lys
```

```
<210> SEQ ID NO 79
<211> LENGTH: 642
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 79
gacatccaga tgacccagtc tccatcctcc ctgtctgcat ctgtaggaga cagagtcacc        60
atcacttgcc aggcgagtca ggacattagc aactatttaa atggtatca gcagaaacca       120 gggaaagccc ctaagatcct gatccacgat gcatccaatt ggagatagg ggtcccatca       180 aggttcagtg gaagtggagc tgggacagat tttatttttca ccatcagcag cctgcagcct      240
gaagatattg aacatatta ctgtcaacag tatgataatc tcccgatcac cttcggccaa       300
gggacacgac tggagattaa acgaactgtg gctgcaccat ctgtcttcat cttcccgcca      360
tctgatgagc agttgaaatc tggaactgcc tctgttgtgt gcctgctgaa taacttctat      420
cccagagagg ccaaagtaca gtggaaggtg gataacgccc tccaatcggg taactcccag      480
```

-continued

```
gagagtgtca cagagcagga cagcaaggac agcacctaca gcctcagcag caccctgacg      540
ctgagcaaag cagactacga gaaacacaaa gtctacgcct gcgaagtcac ccatcagggc      600
ctgagctcgc ccgtcacaaa gagcttcaac aggggagagt gt                         642
```

```
<210> SEQ ID NO 80
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 80

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
            20                  25                  30

Leu Lys Trp Tyr Gln Gln Lys Pro Gly Lys Ala Pro Lys Ile Leu Ile
        35                  40                  45

His Asp Ala Ser Asn Leu Glu Ile Gly Val Pro Ser Arg Phe Ser Gly
    50                  55                  60

Ser Gly Ala Gly Thr Asp Phe Ile Phe Thr Ile Ser Ser Leu Gln Pro
65                  70                  75                  80

Glu Asp Ile Gly Thr Tyr Tyr Cys Gln Gln Tyr Asp Asn Leu Pro Ile
                85                  90                  95

Thr Phe Gly Gln Gly Thr Arg Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

```
<210> SEQ ID NO 81
<211> LENGTH: 369
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 81
cagctgcagc tgcaggagtc ggacccaggc ctggtgaagc cttcggagac cctgtccctc      60
acctgcactg tctctggtga ctccatcaga aacagtaatt actactgggg ctggatccgc      120 cagcccccg ggaagggct ggagtggatt gggagtatct attttagtgg gaggaccat       180 ttcaacccgt ccctcaagag tcgagtcacc atccccgttg acatgtccaa gaaccagttc      240
tcccttatgt tgaactctgt gaccgccaca gacacggctg tgtattactg tgcgcgacat      300
```

```
gggggtataa cagcagctgg gggcttcttt gactactggg gccagggaac cctggtcacc    360
gtctcctca                                                           369
```

<210> SEQ ID NO 82
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 82

```
Gln Leu Gln Leu Gln Glu Ser Asp Pro Gly Leu Val Lys Pro Ser Glu
1               5                   10                  15

Thr Leu Ser Leu Thr Cys Thr Val Ser Gly Asp Ser Ile Arg Asn Ser
            20                  25                  30

Asn Tyr Tyr Trp Gly Trp Ile Arg Gln Pro Pro Gly Lys Gly Leu Glu
        35                  40                  45

Trp Ile Gly Ser Ile Tyr Phe Ser Gly Arg Thr Tyr Phe Asn Pro Ser
    50                  55                  60

Leu Lys Ser Arg Val Thr Ile Pro Val Asp Met Ser Lys Asn Gln Phe
65                  70                  75                  80

Ser Leu Met Leu Asn Ser Val Thr Ala Thr Asp Thr Ala Val Tyr Tyr
                85                  90                  95

Cys Ala Arg His Gly Gly Ile Thr Ala Ala Gly Gly Phe Phe Asp Tyr
            100                 105                 110

Trp Gly Gln Gly Thr Leu Val Thr Val Ser Ser
        115                 120
```

<210> SEQ ID NO 83
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 83

```
ggtgactcca tcagaaacag taattactac                                    30
```

<210> SEQ ID NO 84
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 84

```
Gly Asp Ser Ile Arg Asn Ser Asn Tyr Tyr
1               5                   10
```

<210> SEQ ID NO 85
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 85

```
atctatttta gtgggaggac c                                             21
```

```
<210> SEQ ID NO 86
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 86

Ile Tyr Phe Ser Gly Arg Thr
1               5

<210> SEQ ID NO 87
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 87
gcgcgacatg ggggtataac agcagctggg ggcttctttg actac                    45

<210> SEQ ID NO 88
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 88

Ala Arg His Gly Gly Ile Thr Ala Ala Gly Gly Phe Phe Asp Tyr
1               5                   10                  15

<210> SEQ ID NO 89
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 89
gacatccaga tgacccagtc tccatcctcc ctgtctgcat ctgtaggaga cagagtcacc     60
atcacttgcc aggcgagtca ggacattagc aactatttaa attggtatca acagaaacca    120
gggaaagccc ctaacgtcct gatctacgat gcatccaatt tggaaacagg ggtcccatca    180
aggttcagtg gaagtgggtc tgggacagat tttacgttca ccatcagcag tctacagcct    240
gaagattttg caacatatta ttgtcaacag aatgataatc tcccgctcac tttcggcgga    300
gggaccaagg tggagatcaa a                                              321

<210> SEQ ID NO 90
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 90

Asp Ile Gln Met Thr Gln Ser Pro Ser Ser Leu Ser Ala Ser Val Gly
1               5                   10                  15
```

```
Asp Arg Val Thr Ile Thr Cys Gln Ala Ser Gln Asp Ile Ser Asn Tyr
            20                  25                  30

Leu Asn Trp Tyr Gln Gln Lys Pro Gly Lys Ala Pro Asn Val Leu Ile
        35                  40                  45

Tyr Asp Ala Ser Asn Leu Glu Thr Gly Val Pro Ser Arg Phe Ser Gly
    50                  55                  60

Ser Gly Ser Gly Thr Asp Phe Thr Phe Thr Ile Ser Ser Leu Gln Pro
65              70                  75                  80

Glu Asp Phe Ala Thr Tyr Tyr Cys Gln Gln Asn Asp Asn Leu Pro Leu
                85                  90                  95

Thr Phe Gly Gly Gly Thr Lys Val Glu Ile Lys
            100                 105
```

```
<210> SEQ ID NO 91
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 91
caggacatta gcaactat                                                      18
```

```
<210> SEQ ID NO 92
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 92

Gln Asp Ile Ser Asn Tyr
1               5
```

```
<210> SEQ ID NO 93
<211> LENGTH: 9
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 93 gatgcatcc                                                                 9
```

```
<210> SEQ ID NO 94
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 94

Asp Ala Ser
1
```

```
<210> SEQ ID NO 95
<211> LENGTH: 27
<212> TYPE: DNA
<213> ORGANISM: Artificial Sequence
<220> FEATURE:
<223> OTHER INFORMATION: Description of Artificial Sequence: Synthetic
```

-continued oligonucleotide

<400> SEQUENCE: 95
caacagaatg ataatctccc gctcact                                             27

<210> SEQ ID NO 96
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 96

Gln Gln Asn Asp Asn Leu Pro Leu Thr
1               5

<210> SEQ ID NO 97
<211> LENGTH: 1350
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 97
cagctgcagc tgcaggagtc ggacccaggc ctggtgaagc cttcggagac cctgtccctc       60
acctgcactg tctctggtga ctccatcaga aacagtaatt actactgggg ctggatccgc      120
cagccccccg ggaaggggct ggagtggatt gggagtatct attttagtgg gaggacctat      180
ttcaacccgt ccctcaagag tcgagtcacc atccccgttg acatgtccaa gaaccagttc      240
tcccttatgt tgaactctgt gaccgccaca gacacggctg tgtattactg tgcgcgacat      300
gggggtataa cagcagctgg gggcttcttt gactactggg gccagggaac cctggtcacc      360
gtctcctcag cctccaccaa gggcccatcg gtcttccccc tggcgccctg ctccaggagc      420
acctccgaga gcacagccgc cctgggctgc ctggtcaagg actacttccc cgaaccggtg      480
acggtgtcgt ggaactcagg cgccctgacc agcggcgtgc acaccttccc ggctgtccta      540
cagtcctcag gactctactc cctcagcagc gtggtgaccg tgccctccag cagcttgggc      600
acgaagacct acacctgcaa cgtagatcac aagcccagca acaccaaggt ggacaagaga      660
gttgagtcca aatatggtcc cccatgccca ccgtgcccag caccacctgt ggcaggacca      720
tcagtcttcc tgttcccccc aaaacccaag gacactctca tgatctcccg gacccctgag      780
gtcacgtgcg tggtggtgga cgtgagccag gaagaccccg aggtccagtt caactggtac      840
gtggatggcg tggaggtgca taatgccaag acaaagccgc gggaggagca gttcaacagc      900
acgtaccgtg tggtcagcgt cctcaccgtc ctgcaccagg actggctgaa cggcaaggag      960
tacaagtgca aggtctccaa caaaggcctc ccgtcctcca tcgagaaaac catctccaaa     1020
gccaaagggc agccccgaga gccacaggtg tacaccctgc ccccatccca ggaggagatg     1080
accaagaacc aggtcagcct gacctgcctg gtcaaaggct tctaccccag cgacatcgcc     1140
gtggagtggg agagcaatgg gcagccggag aacaactaca agaccacgcc tcccgtgctg     1200
gactccgacg gctccttctt cctctacagc aggctcaccg tggacaagag caggtggcag     1260
gaggggaatg tcttctcatg ctccgtgatg catgaggctc tgcacaacca ctacacacag     1320
aagtccctct ccctgtctct gggtaaatga                                      1350

<210> SEQ ID NO 98

```
<211> LENGTH: 449
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 98

Gln Leu Gln Leu Gln Glu Ser Asp Pro Gly Leu Val Lys Pro Ser Glu
1               5                   10                  15

Thr Leu Ser Leu Thr Cys Thr Val Ser Gly Asp Ser Ile Arg Asn Ser
            20                  25                  30

Asn Tyr Tyr Trp Gly Trp Ile Arg Gln Pro Pro Gly Lys Gly Leu Glu
        35                  40                  45

Trp Ile Gly Ser Ile Tyr Phe Ser Gly Arg Thr Tyr Phe Asn Pro Ser
    50                  55                  60

Leu Lys Ser Arg Val Thr Ile Pro Val Asp Met Ser Lys Asn Gln Phe
65                  70                  75                  80

Ser Leu Met Leu Asn Ser Val Thr Ala Thr Asp Thr Ala Val Tyr Tyr
                85                  90                  95

Cys Ala Arg His Gly Gly Ile Thr Ala Ala Gly Gly Phe Phe Asp Tyr
                100                 105                 110

Trp Gly Gln Gly Thr Leu Val Thr Val Ser Ser Ala Ser Thr Lys Gly
            115                 120                 125

Pro Ser Val Phe Pro Leu Ala Pro Cys Ser Arg Ser Thr Ser Glu Ser
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Lys Thr Tyr Thr Cys Asn Val
            195                 200                 205

Asp His Lys Pro Ser Asn Thr Lys Val Asp Lys Arg Val Glu Ser Lys
    210                 215                 220

Tyr Gly Pro Pro Cys Pro Pro Cys Pro Ala Pro Val Ala Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser Gln Glu Asp
            260                 265                 270

Pro Glu Val Gln Phe Asn Trp Tyr Val Asp Gly Val Glu Val His Asn
            275                 280                 285

Ala Lys Thr Lys Pro Arg Glu Glu Gln Phe Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Gly Leu Pro Ser Ser Ile Glu Lys
                325                 330                 335

Thr Ile Ser Lys Ala Lys Gly Gln Pro Arg Glu Pro Gln Val Tyr Thr
                340                 345                 350

Leu Pro Pro Ser Gln Glu Glu Met Thr Lys Asn Gln Val Ser Leu Thr
            355                 360                 365

Cys Leu Val Lys Gly Phe Tyr Pro Ser Asp Ile Ala Val Glu Trp Glu
```

-continued

```
            370              375              380
Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Arg Leu Thr Val Asp Lys
                405                 410                 415

Ser Arg Trp Gln Glu Gly Asn Val Phe Ser Cys Ser Val Met His Glu
            420                 425                 430

Ala Leu His Asn His Tyr Thr Gln Lys Ser Leu Ser Leu Ser Leu Gly
        435                 440                 445

Lys
```

```
<210> SEQ ID NO 99
<211> LENGTH: 645
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 99
gacatccaga tgacccagtc tccatcctcc ctgtctgcat ctgtaggaga cagagtcacc      60
atcacttgcc aggcgagtca ggacattagc aactatttaa attggtatca acagaaacca     120
gggaaagccc ctaacgtcct gatctacgat gcatccaatt tggaaacagg ggtcccatca     180
aggttcagtg gaagtgggtc tgggacagat tttacgttca ccatcagcag tctacagcct     240
gaagattttg caacatatta ttgtcaacag aatgataatc tcccgctcac tttcggcgga     300
gggaccaagg tggagatcaa acgaactgtg gctgcaccat ctgtcttcat cttcccgcca     360
tctgatgagc agttgaaatc tggaactgcc tctgttgtgt gcctgctgaa taacttctat     420
cccagagagg ccaaagtaca gtggaaggtg gataacgccc tccaatcggg taactcccag     480
gagagtgtca cagagcagga cagcaaggac agcacctaca gcctcagcag caccctgacg     540
ctgagcaaag cagactacga gaaacacaaa gtctacgcct gcgaagtcac ccatcagggc     600
ctgagctcgc ccgtcacaaa gagcttcaac aggggagagt gttag                     645
```

```
<210> SEQ ID NO 100
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 100

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
                20                  25                  30

Leu Asn Trp Tyr Gln Gln Lys Pro Gly Lys Ala Pro Asn Val Leu Ile
            35                  40                  45

Tyr Asp Ala Ser Asn Leu Glu Thr Gly Val Pro Ser Arg Phe Ser Gly
        50                  55                  60

Ser Gly Ser Gly Thr Asp Phe Thr Phe Thr Ile Ser Ser Leu Gln Pro
65                  70                  75                  80

Glu Asp Phe Ala Thr Tyr Tyr Cys Gln Gln Asn Asp Asn Leu Pro Leu
                85                  90                  95

Thr Phe Gly Gly Gly Thr Lys Val Glu Ile Lys Arg Thr Val Ala Ala
```

```
                 100                 105                 110
Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

```
<210> SEQ ID NO 101
<211> LENGTH: 354
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 101
caggtgcagc tggtacagtc tggggctgag gtgatgaagc ctggggcctc agtgaaggtc      60
tcctgcaagg tttccggata caccctcagt gatttatcca tgcactgggt gcgacaggct     120
cctggaaaag gacttgagtg gatgggaggt tttgatttcg aacatggtaa aacaatctac     180
gcacagaagt tccagggcag agtcaccatg accgaggaca catctacaga cacaacctac     240
atggagctga gtagtctgag atctgaggac acggccgtgt attactgtgc aaaggtacct     300
aactggggat tctttgacta ctggggccag ggaaccctgg tcaccgtctc ctca           354
```

```
<210> SEQ ID NO 102
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 102

Gln Val Gln Leu Val Gln Ser Gly Ala Glu Val Met Lys Pro Gly Ala
1               5                   10                  15

Ser Val Lys Val Ser Cys Lys Val Ser Gly Tyr Thr Leu Ser Asp Leu
            20                  25                  30

Ser Met His Trp Val Arg Gln Ala Pro Gly Lys Gly Leu Glu Trp Met
        35                  40                  45

Gly Gly Phe Asp Phe Glu His Gly Lys Thr Ile Tyr Ala Gln Lys Phe
    50                  55                  60

Gln Gly Arg Val Thr Met Thr Glu Asp Thr Ser Thr Asp Thr Thr Tyr
65                  70                  75                  80

Met Glu Leu Ser Ser Leu Arg Ser Glu Asp Thr Ala Val Tyr Tyr Cys
                85                  90                  95

Ala Lys Val Pro Asn Trp Gly Phe Phe Asp Tyr Trp Gly Gln Gly Thr
            100                 105                 110

Leu Val Thr Val Ser Ser
```

-continued

```
        115

<210> SEQ ID NO 103
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 103 ggatacacccc tcagtgattt atcc                                        24

<210> SEQ ID NO 104
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 104

Gly Tyr Thr Leu Ser Asp Leu Ser
1               5

<210> SEQ ID NO 105
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 105
tttgatttcg aacatggtaa aaca                                         24

<210> SEQ ID NO 106
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 106

Phe Asp Phe Glu His Gly Lys Thr
1               5

<210> SEQ ID NO 107
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 107
gcaaaggtac ctaactgggg attctttgac tac                               33

<210> SEQ ID NO 108
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 108
```

```
Ala Lys Val Pro Asn Trp Gly Phe Phe Asp Tyr
1               5                   10

<210> SEQ ID NO 109
<211> LENGTH: 336
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 109
gatattgtga tgactcagtc tccactctcc ctgcccgtca cccctggaga gccggcctcc      60
atctcctgca ggtctagtca gagcctcctg catagtaatg gattcaacta tttggattgg     120
tacctgcaga ggccaggtca gtctccacaa ctcctgatct atttgggttc taatcgggcc     180 tccgggggtcc ctgacaggtt cagtggcagt ggatcaggca cagattttac actgaaaatc    240
agcagagtgg aggctgagga tgttggggtt tattactgca tgcaggctct acaaactcct     300
ctcactttcg gcggagggac caaggtggag atcaaa                               336

<210> SEQ ID NO 110
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 110

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Phe Asn Tyr Leu Asp Trp Tyr Leu Gln Arg Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Pro Leu Thr Phe Gly Gly Gly Thr Lys Val Glu Ile Lys
            100                 105                 110

<210> SEQ ID NO 111
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 111
cagagcctcc tgcatagtaa tggattcaac tat                                   33

<210> SEQ ID NO 112
<211> LENGTH: 11
<212> TYPE: PRT
<213> ORGANISM: Artificial Sequence
<220> FEATURE:
<223> OTHER INFORMATION: Description of Artificial Sequence: Synthetic
```

```
                  peptide

<400> SEQUENCE: 112

Gln Ser Leu Leu His Ser Asn Gly Phe Asn Tyr
1               5                   10

<210> SEQ ID NO 113
<211> LENGTH: 9
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 113 ttgggttct                                                              9

<210> SEQ ID NO 114
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 114

Leu Gly Ser
1

<210> SEQ ID NO 115
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 115
atgcaggctc tacaaactcc tctcact                                         27

<210> SEQ ID NO 116
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 116

Met Gln Ala Leu Gln Thr Pro Leu Thr
1               5

<210> SEQ ID NO 117
<211> LENGTH: 1335
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 117
caggtgcagc tggtacagtc tggggctgag gtgatgaagc ctggggcctc agtgaaggtc     60
tcctgcaagg tttccggata caccctcagt gatttatcca tgcactgggt gcgacaggct    120
cctggaaaag gacttgagtg gatgggaggt tttgatttcg aacatggtaa aacaatctac    180
gcacagaagt tccagggcag agtcaccatg accgaggaca catctacaga cacaacctac    240
```

```
atggagctga gtagtctgag atctgaggac acggccgtgt attactgtgc aaaggtacct      300
aactggggat tctttgacta ctggggccag ggaaccctgg tcaccgtctc ctcagcctcc      360
accaagggcc catcggtctt ccccctggcg ccctgctcca ggagcacctc cgagagcaca      420
gccgccctgg gctgcctggt caaggactac ttccccgaac cggtgacggt gtcgtggaac      480
tcaggcgccc tgaccagcgg cgtgcacacc ttcccggctg tcctacagtc ctcaggactc      540
tactccctca gcagcgtggt gaccgtgccc tccagcagct tgggcacgaa gacctacacc      600
tgcaacgtag atcacaagcc cagcaacacc aaggtggaca agagagttga gtccaaatat      660
ggtcccccat gcccaccgtg cccagcacca cctgtggcag gaccatcagt cttcctgttc      720 ccccaaaac ccaaggacac tctcatgatc tcccggaccc ctgaggtcac gtgcgtggtg       780
gtggacgtga gccaggaaga ccccgaggtc cagttcaact ggtacgtgga tggcgtggag      840
gtgcataatg ccaagacaaa gccgcgggag gagcagttca acagcacgta ccgtgtggtc      900
agcgtcctca ccgtcctgca ccaggactgg ctgaacggca aggagtacaa gtgcaaggtc      960
tccaacaaag gcctcccgtc ctccatcgag aaaaccatct ccaaagccaa agggcagccc     1020
cgagagccac aggtgtacac cctgcccca tcccaggagg agatgaccaa gaaccaggtc      1080
agcctgacct gcctggtcaa aggcttctac cccagcgaca tcgccgtgga gtgggagagc     1140
aatgggcagc cggagaacaa ctacaagacc acgcctcccg tgctggactc cgacggctcc     1200
ttcttcctct acagcaggct caccgtggac aagagcaggt ggcaggaggg gaatgtcttc     1260
tcatgctccg tgatgcatga ggctctgcac aaccactaca cacagaagtc cctctccctg     1320
tctctgggta aatga                                                     1335
```

<210> SEQ ID NO 118
<211> LENGTH: 444
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 118

```
Gln Val Gln Leu Val Gln Ser Gly Ala Glu Val Met Lys Pro Gly Ala
1               5                   10                  15

Ser Val Lys Val Ser Cys Lys Val Ser Gly Tyr Thr Leu Ser Asp Leu
            20                  25                  30

Ser Met His Trp Val Arg Gln Ala Pro Gly Lys Gly Leu Glu Trp Met
        35                  40                  45

Gly Gly Phe Asp Phe Glu His Gly Lys Thr Ile Tyr Ala Gln Lys Phe
    50                  55                  60

Gln Gly Arg Val Thr Met Thr Glu Asp Thr Ser Thr Asp Thr Thr Tyr
65                  70                  75                  80

Met Glu Leu Ser Ser Leu Arg Ser Glu Asp Thr Ala Val Tyr Tyr Cys
                85                  90                  95

Ala Lys Val Pro Asn Trp Gly Phe Phe Asp Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Cys Ser Arg Ser Thr Ser Glu Ser Thr Ala Ala Leu Gly
    130                 135                 140

Cys Leu Val Lys Asp Tyr Phe Pro Glu Pro Val Thr Val Ser Trp Asn
145                 150                 155                 160
```

-continued

```
Ser Gly Ala Leu Thr Ser Gly Val His Thr Phe Pro Ala Val Leu Gln
            165                 170                 175

Ser Ser Gly Leu Tyr Ser Leu Ser Ser Val Val Thr Val Pro Ser Ser
            180                 185                 190

Ser Leu Gly Thr Lys Thr Tyr Thr Cys Asn Val Asp His Lys Pro Ser
            195                 200                 205

Asn Thr Lys Val Asp Lys Arg Val Glu Ser Lys Tyr Gly Pro Pro Cys
        210                 215                 220

Pro Pro Cys Pro Ala Pro Pro Val Ala Gly Pro Ser Val Phe Leu Phe
225                 230                 235                 240

Pro Pro Lys Pro Lys Asp Thr Leu Met Ile Ser Arg Thr Pro Glu Val
            245                 250                 255

Thr Cys Val Val Val Asp Val Ser Gln Glu Asp Pro Glu Val Gln Phe
            260                 265                 270

Asn Trp Tyr Val Asp Gly Val Glu Val His Asn Ala Lys Thr Lys Pro
            275                 280                 285

Arg Glu Glu Gln Phe Asn Ser Thr Tyr Arg Val Val Ser Val Leu Thr
        290                 295                 300

Val Leu His Gln Asp Trp Leu Asn Gly Lys Glu Tyr Lys Cys Lys Val
305                 310                 315                 320

Ser Asn Lys Gly Leu Pro Ser Ser Ile Glu Lys Thr Ile Ser Lys Ala
            325                 330                 335

Lys Gly Gln Pro Arg Glu Pro Gln Val Tyr Thr Leu Pro Pro Ser Gln
            340                 345                 350

Glu Glu Met Thr Lys Asn Gln Val Ser Leu Thr Cys Leu Val Lys Gly
            355                 360                 365

Phe Tyr Pro Ser Asp Ile Ala Val Glu Trp Glu Ser Asn Gly Gln Pro
        370                 375                 380

Glu Asn Asn Tyr Lys Thr Thr Pro Pro Val Leu Asp Ser Asp Gly Ser
385                 390                 395                 400

Phe Phe Leu Tyr Ser Arg Leu Thr Val Asp Lys Ser Arg Trp Gln Glu
            405                 410                 415

Gly Asn Val Phe Ser Cys Ser Val Met His Glu Ala Leu His Asn His
            420                 425                 430

Tyr Thr Gln Lys Ser Leu Ser Leu Ser Leu Gly Lys
            435                 440
```

```
<210> SEQ ID NO 119
<211> LENGTH: 660
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 119
gatattgtga tgactcagtc tccactctcc ctgcccgtca cccctggaga gccggcctcc      60
atctcctgca ggtctagtca gagcctcctg catagtaatg gattcaacta tttggattgg     120
tacctgcaga ggccaggtca gtctccacaa ctcctgatct atttgggttc taatcgggcc     180
tccggggtcc ctgacaggtt cagtggcagt ggatcaggca cagattttac actgaaaatc     240
agcagagtgg aggctgagga tgttggggtt tattactgca tgcaggctct acaaactcct     300
ctcactttcg gcggagggac caaggtggag atcaaacgaa ctgtggctgc accatctgtc     360
ttcatcttcc cgccatctga tgagcagttg aaatctggaa ctgcctctgt tgtgtgcctg     420
```

-continued

```
ctgaataact tctatcccag agaggccaaa gtacagtgga aggtggataa cgccctccaa      480
tcgggtaact cccaggagag tgtcacagag caggacagca aggacagcac ctacagcctc      540
agcagcaccc tgacgctgag caaagcagac tacgagaaac acaaagtcta cgcctgcgaa      600
gtcacccatc agggcctgag ctcgcccgtc acaaagagct tcaacagggg agagtgttag      660
```

```
<210> SEQ ID NO 120
<211> LENGTH: 219
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 120

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Phe Asn Tyr Leu Asp Trp Tyr Leu Gln Arg Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Pro Leu Thr Phe Gly Gly Gly Thr Lys Val Glu Ile Lys
            100                 105                 110

Arg Thr Val Ala Ala Pro Ser Val Phe Ile Phe Pro Pro Ser Asp Glu
            115                 120                 125

Gln Leu Lys Ser Gly Thr Ala Ser Val Val Cys Leu Leu Asn Asn Phe
        130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215
```

```
<210> SEQ ID NO 121
<211> LENGTH: 366
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 121
caggtgcagc tgcaggagtc gggcccagga ctggtgaagc cttcggagac cctgtccctc      60
acttgcactg tctctggtga ctccatcagt gtttattatt ggacctggat ccggcagccc      120
ccagggaagg gactggagtg gattgggtat gtccattata ctgggtatac caactacaat      180
```

-continued

```
ccctccctca agagtcgagt caccatgtca gtcgacacgg ccaagaaaca gatctccctg    240
aaggtgaggt ctgtgaccgc tgcggacacg gccgtttact actgtgcgcg aacaattcca    300
gctgccgccc actactacca cggaacggac gtctggggcc cagggaccac ggtcaccgtc    360
tcctca                                                               366
```

```
<210> SEQ ID NO 122
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 122

Gln Val Gln Leu Gln Glu Ser Gly Pro Gly Leu Val Lys Pro Ser Glu
1               5                   10                  15

Thr Leu Ser Leu Thr Cys Thr Val Ser Gly Asp Ser Ile Ser Val Tyr
            20                  25                  30

Tyr Trp Thr Trp Ile Arg Gln Pro Pro Gly Lys Gly Leu Glu Trp Ile
        35                  40                  45

Gly Tyr Val His Tyr Thr Gly Tyr Thr Asn Tyr Asn Pro Ser Leu Lys
    50                  55                  60

Ser Arg Val Thr Met Ser Val Asp Thr Ala Lys Lys Gln Ile Ser Leu
65                  70                  75                  80

Lys Val Arg Ser Val Thr Ala Ala Asp Thr Ala Val Tyr Tyr Cys Ala
                85                  90                  95

Arg Thr Ile Pro Ala Ala Ala His Tyr Tyr His Gly Thr Asp Val Trp
            100                 105                 110

Gly Pro Gly Thr Thr Val Thr Val Ser Ser
        115                 120
```

```
<210> SEQ ID NO 123
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 123
ggtgactcca tcagtgttta ttat                                           24
```

```
<210> SEQ ID NO 124
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 124

Gly Asp Ser Ile Ser Val Tyr Tyr
1               5
```

```
<210> SEQ ID NO 125
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
```

```
<400> SEQUENCE: 125
gtccattata ctgggtatac c                                              21

<210> SEQ ID NO 126
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 126

Val His Tyr Thr Gly Tyr Thr
1               5

<210> SEQ ID NO 127
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 127
gcgcgaacaa ttccagctgc cgcccactac taccacggaa cggacgtc                 48

<210> SEQ ID NO 128
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 128

Ala Arg Thr Ile Pro Ala Ala Ala His Tyr Tyr His Gly Thr Asp Val
1               5                   10                  15

<210> SEQ ID NO 129
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 129
gacatccaga tgacccagtc tccatcctcc ctgtctgcat ctgtaggaga cagagtcacc     60
atcacttgcc aggcgaatca ggacattagg aaatatttaa attggtatca gcagaaatca    120
gggaaagccc ctacactcct gatctacgag gcgtccaatt tggagacagg ggccccatca    180
acgttcagtg gaagtggatc tgggacagaa tttactttca ctatcagcag tctgcggcct    240
gaagatattg caacatatta ctgtcaacag tatgagagtc ttccgctcac tttcggcgga    300
gggaccaagg tggagatcaa a                                             321

<210> SEQ ID NO 130
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 130
```

```
Asp Ile Gln Met Thr Gln Ser Pro Ser Ser Leu Ser Ala Ser Val Gly
1               5                   10                  15

Asp Arg Val Thr Ile Thr Cys Gln Ala Asn Gln Asp Ile Arg Lys Tyr
            20                  25                  30

Leu Asn Trp Tyr Gln Gln Lys Ser Gly Lys Ala Pro Thr Leu Leu Ile
        35                  40                  45

Tyr Glu Ala Ser Asn Leu Glu Thr Gly Ala Pro Ser Thr Phe Ser Gly
    50                  55                  60

Ser Gly Ser Gly Thr Glu Phe Thr Phe Thr Ile Ser Ser Leu Arg Pro
65                  70                  75                  80

Glu Asp Ile Ala Thr Tyr Tyr Cys Gln Gln Tyr Glu Ser Leu Pro Leu
                85                  90                  95

Thr Phe Gly Gly Gly Thr Lys Val Glu Ile Lys
            100                 105
```

```
<210> SEQ ID NO 131
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 131
caggacatta ggaaatat                                                     18
```

```
<210> SEQ ID NO 132
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 132

Gln Asp Ile Arg Lys Tyr
1               5
```

```
<210> SEQ ID NO 133
<211> LENGTH: 9
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 133 gaggcgtcc                                                               9
```

```
<210> SEQ ID NO 134
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 134

Glu Ala Ser
1
```

```
<210> SEQ ID NO 135
<211> LENGTH: 27
<212> TYPE: DNA
```

-continued

<213> ORGANISM: Artificial Sequence
<220> FEATURE:
<223> OTHER INFORMATION: Description of Artificial Sequence: Synthetic
      oligonucleotide

<400> SEQUENCE: 135
caacagtatg agagtcttcc gctcact                                            27

<210> SEQ ID NO 136
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 136

Gln Gln Tyr Glu Ser Leu Pro Leu Thr
1               5

<210> SEQ ID NO 137
<211> LENGTH: 1347
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 137
caggtgcagc tgcaggagtc gggcccagga ctggtgaagc cttcggagac cctgtccctc       60
acttgcactg tctctggtga ctccatcagt gtttattatt ggacctggat ccggcagccc      120
ccagggaagg gactggagtg gattgggtat gtccattata ctgggtatac caactacaat      180
ccctccctca agagtcgagt caccatgtca gtcgacacgg ccaagaaaca gatctccctg      240
aaggtgaggt ctgtgaccgc tgcggacacg gccgtttact actgtgcgcg aacaattcca      300
gctgccgccc actactacca cggaacggac gtctgggggcc cagggaccac ggtcaccgtc      360
tcctcagcct ccaccaaggg cccatcggtc ttcccccctgg cgccctgctc caggagcacc      420
tccgagagca gccgccct gggctgcctg gtcaaggact acttccccga accggtgacg      480
gtgtcgtgga actcaggcgc cctgaccagc ggcgtgcaca ccttcccggc tgtcctacag      540
tcctcaggac tctactccct cagcagcgtg gtgaccgtgc cctccagcag cttgggcacg      600
aagacctaca cctgcaacgt agatcacaag cccagcaaca ccaaggtgga caagagagtt      660
gagtccaaat atggtccccc atgcccaccg tgcccagcac cacctgtggc aggaccatca      720
gtcttcctgt tccccccaaa acccaaggac actctcatga tctcccggac ccctgaggtc      780
acgtgcgtgg tggtggacgt gagccaggaa gaccccgagg tccagttcaa ctggtacgtg      840
gatggcgtgg aggtgcataa tgccaagaca aagccgcggg aggagcagtt caacagcacg      900
taccgtgtgg tcagcgtcct caccgtcctg caccaggact ggctgaacgg caaggagtac      960
aagtgcaagg tctccaacaa aggcctcccg tcctccatcg agaaaaccat ctccaaagcc     1020
aaagggcagc cccgagagcc acaggtgtac accctgcccc catcccagga ggagatgacc     1080
aagaaccagg tcagcctgac ctgcctggtc aaaggcttct accccagcga catcgccgtg     1140
gagtgggaga gcaatgggca gccggagaac aactacaaga ccacgcctcc cgtgctggac     1200
tccgacggct ccttcttcct ctacagcagg ctcaccgtgg acaagagcag gtggcaggag     1260
gggaatgtct tctcatgctc cgtgatgcat gaggctctgc acaaccacta cacacagaag     1320
tccctctccc tgtctctggg taaatga                                         1347

-continued

```
<210> SEQ ID NO 138
<211> LENGTH: 448
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 138

Gln Val Gln Leu Gln Glu Ser Gly Pro Gly Leu Val Lys Pro Ser Glu
1               5                   10                  15

Thr Leu Ser Leu Thr Cys Thr Val Ser Gly Asp Ser Ile Ser Val Tyr
            20                  25                  30

Tyr Trp Thr Trp Ile Arg Gln Pro Pro Gly Lys Gly Leu Glu Trp Ile
        35                  40                  45

Gly Tyr Val His Tyr Thr Gly Tyr Thr Asn Tyr Asn Pro Ser Leu Lys
    50                  55                  60

Ser Arg Val Thr Met Ser Val Asp Thr Ala Lys Lys Gln Ile Ser Leu
65                  70                  75                  80

Lys Val Arg Ser Val Thr Ala Ala Asp Thr Ala Val Tyr Tyr Cys Ala
                85                  90                  95

Arg Thr Ile Pro Ala Ala Ala His Tyr Tyr His Gly Thr Asp Val Trp
            100                 105                 110

Gly Pro Gly Thr Thr Val Thr Val Ser Ser Ala Ser Thr Lys Gly Pro
        115                 120                 125

Ser Val Phe Pro Leu Ala Pro Cys Ser Arg Ser Thr Ser Glu Ser Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Lys Thr Tyr Thr Cys Asn Val Asp
            195                 200                 205

His Lys Pro Ser Asn Thr Lys Val Asp Lys Arg Val Glu Ser Lys Tyr
    210                 215                 220

Gly Pro Pro Cys Pro Pro Cys Pro Ala Pro Val Ala Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser Gln Glu Asp Pro
            260                 265                 270

Glu Val Gln Phe Asn Trp Tyr Val Asp Gly Val Glu Val His Asn Ala
        275                 280                 285

Lys Thr Lys Pro Arg Glu Glu Gln Phe Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Gly Leu Pro Ser Ser Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Gln Glu Glu Met Thr Lys Asn Gln Val Ser Leu Thr Cys
```

-continued 355                  360                  365

Leu Val Lys Gly Phe Tyr Pro Ser Asp Ile Ala Val Glu Trp Glu Ser
    370                  375                  380

Asn Gly Gln Pro Glu Asn Asn Tyr Lys Thr Thr Pro Pro Val Leu Asp
385                  390                  395                  400

Ser Asp Gly Ser Phe Phe Leu Tyr Ser Arg Leu Thr Val Asp Lys Ser
                405                  410                  415

Arg Trp Gln Glu Gly Asn Val Phe Ser Cys Ser Val Met His Glu Ala
                420                  425                  430

Leu His Asn His Tyr Thr Gln Lys Ser Leu Ser Leu Ser Leu Gly Lys
        435                  440                  445

<210> SEQ ID NO 139
<211> LENGTH: 645
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 139
gacatccaga tgacccagtc tccatcctcc ctgtctgcat ctgtaggaga cagagtcacc      60
atcacttgcc aggcgaatca ggacattagg aaatatttaa attggtatca gcagaaatca     120
gggaaagccc ctacactcct gatctacgag gcgtccaatt tggagacagg ggccccatca     180
acgttcagtg gaagtggatc tgggacagaa tttactttca ctatcagcag tctgcggcct     240
gaagatattg caacatatta ctgtcaacag tatgagagtc ttccgctcac tttcggcgga     300
gggaccaagg tggagatcaa acgaactgtg gctgcaccat ctgtcttcat cttcccgcca     360
tctgatgagc agttgaaatc tggaactgcc tctgttgtgt gcctgctgaa taacttctat     420
cccagagagg ccaaagtaca gtggaaggtg gataacgccc tccaatcggg taactcccag     480
gagagtgtca cagagcagga cagcaaggac agcacctaca gcctcagcag caccctgacg     540
ctgagcaaag cagactacga gaaacacaaa gtctacgcct gcgaagtcac ccatcagggc     600
ctgagctcgc ccgtcacaaa gagcttcaac aggggagagt gttag                     645

<210> SEQ ID NO 140
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 140

Asp Ile Gln Met Thr Gln Ser Pro Ser Ser Leu Ser Ala Ser Val Gly
1                5                   10                  15

Asp Arg Val Thr Ile Thr Cys Gln Ala Asn Gln Asp Ile Arg Lys Tyr
                20                  25                  30

Leu Asn Trp Tyr Gln Gln Lys Ser Gly Lys Ala Pro Thr Leu Leu Ile
        35                  40                  45

Tyr Glu Ala Ser Asn Leu Glu Thr Gly Ala Pro Ser Thr Phe Ser Gly
    50                  55                  60

Ser Gly Ser Gly Thr Glu Phe Thr Phe Thr Ile Ser Ser Leu Arg Pro
65                  70                  75                  80

Glu Asp Ile Ala Thr Tyr Tyr Cys Gln Gln Tyr Glu Ser Leu Pro Leu
                85                  90                  95

```
Thr Phe Gly Gly Gly Thr Lys Val Glu Ile Lys Arg Thr Val Ala Ala
        100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
                180                 185                 190

Ala Cys Glu Val Thr His Gln Gly Leu Ser Ser Pro Val Thr Lys Ser
        195                 200                 205

Phe Asn Arg Gly Glu Cys
    210
```

```
<210> SEQ ID NO 141
<211> LENGTH: 381
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 141
gaagtgcagc tggtggagtc tgggggaggc gtggtacagc ctggggggtc cctgagactc      60
tcctgtgcag cctctggatt cacctttgat gattatgcca tgcactgggt ccgtcaagct     120
ccagggaagg gtctggagtg ggtctctctg attagtgggg atggtgataa tacatactat     180
gcagactctg tgaagggccg attcaccatc tccagagaca acaacaaaaa ctccctatat     240
ctgcaaatga acagtctgag aactgaggac accgccttct attactgtgc aaaagaactc     300
atttttggaa aggttctcca tgactttttac tactacgtta tggacgtctg gggccaaggg     360
accacggtca ccgtctcctc a                                               381
```

```
<210> SEQ ID NO 142
<211> LENGTH: 127
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 142
```

```
Glu Val Gln Leu Val Glu Ser Gly Gly Gly Val Val Gln Pro Gly Gly
1               5                   10                  15

Ser Leu Arg Leu Ser Cys Ala Ala Ser Gly Phe Thr Phe Asp Asp Tyr
                20                  25                  30

Ala Met His Trp Val Arg Gln Ala Pro Gly Lys Gly Leu Glu Trp Val
        35                  40                  45

Ser Leu Ile Ser Gly Asp Gly Asp Asn Thr Tyr Tyr Ala Asp Ser Val
        50                  55                  60

Lys Gly Arg Phe Thr Ile Ser Arg Asp Asn Asn Lys Asn Ser Leu Tyr
65                  70                  75                  80

Leu Gln Met Asn Ser Leu Arg Thr Glu Asp Thr Ala Phe Tyr Tyr Cys
                85                  90                  95

Ala Lys Glu Leu Ile Phe Gly Lys Val Leu His Asp Phe Tyr Tyr Tyr
```

-continued

```
          100               105               110
Val Met Asp Val Trp Gly Gln Gly Thr Thr Val Thr Val Ser Ser
        115               120               125

<210> SEQ ID NO 143
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 143
ggattcacct ttgatgatta tgcc                                        24

<210> SEQ ID NO 144
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 144

Gly Phe Thr Phe Asp Asp Tyr Ala
1               5

<210> SEQ ID NO 145
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 145
attagtgggg atggtgataa taca                                        24

<210> SEQ ID NO 146
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 146

Ile Ser Gly Asp Gly Asp Asn Thr
1               5

<210> SEQ ID NO 147
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 147
gcaaaagaac tcattttttgg aaaggttctc catgactttt actactacgt tatggacgtc    60

<210> SEQ ID NO 148
<211> LENGTH: 20
<212> TYPE: PRT
<213> ORGANISM: Artificial Sequence
<220> FEATURE:
<223> OTHER INFORMATION: Description of Artificial Sequence: Synthetic
```

-continued peptide

<400> SEQUENCE: 148

Ala Lys Glu Leu Ile Phe Gly Lys Val Leu His Asp Phe Tyr Tyr Tyr
1               5                   10                  15

Val Met Asp Val
            20

<210> SEQ ID NO 149
<211> LENGTH: 324
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 149
gacatccaga tgacccagtc tccatcctcc ctgtctgcat ctgtaggaga cagagtcacc      60
atcacttgcc gggcaagtca gagcattagc agctatttaa attggtatca gcagaaacca     120
gggaaagccc ctaagctcct gatctatgct gcatccagtt tgcaaagtgg ggtcccgtca     180
aggttcagtg gcagtggatc tgggacagat ttcactctca ccatcagcag tctgcaacct     240
gaagattttg caacttacta ctgtcaacag agttacagta cccctccgat caccttcggc     300
caagggacac gactggagat taaa                                            324

<210> SEQ ID NO 150
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 150

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
                20                  25                  30

Leu Asn Trp Tyr Gln Gln Lys Pro Gly Lys Ala Pro Lys Leu Leu Ile
            35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Pro
                85                  90                  95

Ile Thr Phe Gly Gln Gly Thr Arg Leu Glu Ile Lys
            100                 105

<210> SEQ ID NO 151
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 151
cagagcatta gcagctat                                                    18

```
<210> SEQ ID NO 152
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 152

Gln Ser Ile Ser Ser Tyr
1               5

<210> SEQ ID NO 153
<211> LENGTH: 9
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 153 gctgcatcc                                                                      9

<210> SEQ ID NO 154
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 154

Ala Ala Ser
1

<210> SEQ ID NO 155
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 155
caacagagtt acagtacccc tccgatcacc                                              30

<210> SEQ ID NO 156
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 156

Gln Gln Ser Tyr Ser Thr Pro Pro Ile Thr
1               5                   10

<210> SEQ ID NO 157
<211> LENGTH: 1362
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 157
gaagtgcagc tggtggagtc tgggggaggc gtggtacagc ctgggggtc cctgagactc      60
```

-continued

```
tcctgtgcag cctctggatt cacctttgat gattatgcca tgcactgggt ccgtcaagct   120
ccagggaagg gtctggagtg ggtctctctg attagtgggg atggtgataa tacatactat   180
gcagactctg tgaagggccg attcaccatc tccagagaca acaacaaaaa ctccctatat   240
ctgcaaatga acagtctgag aactgaggac accgccttct attactgtgc aaaagaactc   300 attttttggaa aggttctcca tgactttttac tactacgtta tggacgtctg gggccaaggg   360
accacggtca ccgtctcctc agcctccacc aagggcccat cggtcttccc cctggcgccc   420
tgctccagga gcacctccga gagcacagcc gccctgggct gcctggtcaa ggactacttc   480
cccgaaccgg tgacggtgtc gtggaactca ggcgccctga ccagcggcgt gcacaccttc   540
ccggctgtcc tacagtcctc aggactctac tccctcagca gcgtggtgac cgtgccctcc   600
agcagcttgg gcacgaagac ctacacctgc aacgtagatc acaagcccag caacaccaag   660
gtggacaaga gagttgagtc caaatatggt cccccatgcc caccgtgccc agcaccacct   720
gtggcaggac catcagtctt cctgttcccc ccaaaaccca aggacactct catgatctcc   780
cggacccctg aggtcacgtg cgtggtggtg gacgtgagcc aggaagaccc cgaggtccag   840
ttcaactggt acgtggatgg cgtggaggtg cataatgcca agacaaagcc gcgggaggag   900
cagttcaaca gcacgtaccg tgtggtcagc gtcctcaccg tcctgcacca ggactggctg   960
aacggcaagg agtacaagtg caaggtctcc aacaaaggcc tcccgtcctc catcgagaaa  1020
accatctcca aagccaaagg gcagccccga gagccacagg tgtacaccct gcccccatcc  1080
caggaggaga tgaccaagaa ccaggtcagc ctgacctgcc tggtcaaagg cttctacccc  1140
agcgacatcg ccgtggagtg ggagagcaat gggcagccgg agaacaacta caagaccacg  1200
cctcccgtgc tggactccga cggctccttc ttcctctaca gcaggctcac cgtggacaag  1260
agcaggtggc aggaggggaa tgtcttctca tgctccgtga tgcatgaggc tctgcacaac  1320
cactacacac agaagtccct ctccctgtct ctgggtaaat ga                     1362
```

```
<210> SEQ ID NO 158
<211> LENGTH: 453
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 158

Glu Val Gln Leu Val Glu Ser Gly Gly Gly Val Val Gln Pro Gly Gly
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Leu Ile Ser Gly Asp Gly Asp Asn Thr Tyr Tyr Ala Asp Ser Val
    50                  55                  60

Lys Gly Arg Phe Thr Ile Ser Arg Asp Asn Asn Lys Asn Ser Leu Tyr
65                  70                  75                  80

Leu Gln Met Asn Ser Leu Arg Thr Glu Asp Thr Ala Phe Tyr Tyr Cys
                85                  90                  95

Ala Lys Glu Leu Ile Phe Gly Lys Val Leu His Asp Phe Tyr Tyr Tyr
            100                 105                 110

Val Met Asp Val Trp Gly Gln Gly Thr Thr Val Thr Val Ser Ser Ala
            115                 120                 125
```

```
Ser Thr Lys Gly Pro Ser Val Phe Pro Leu Ala Pro Cys Ser Arg Ser
    130             135             140

Thr Ser Glu Ser Thr Ala Ala Leu Gly Cys Leu Val Lys Asp Tyr Phe
145             150             155             160

Pro Glu Pro Val Thr Val Ser Trp Asn Ser Gly Ala Leu Thr Ser Gly
                165             170             175

Val His Thr Phe Pro Ala Val Leu Gln Ser Ser Gly Leu Tyr Ser Leu
            180             185             190

Ser Ser Val Val Thr Val Pro Ser Ser Ser Leu Gly Thr Lys Thr Tyr
        195             200             205

Thr Cys Asn Val Asp His Lys Pro Ser Asn Thr Lys Val Asp Lys Arg
    210             215             220

Val Glu Ser Lys Tyr Gly Pro Pro Cys Pro Pro Cys Pro Ala Pro Pro
225             230             235             240

Val Ala Gly Pro Ser Val Phe Leu Phe Pro Pro Lys Pro Lys Asp Thr
                245             250             255

Leu Met Ile Ser Arg Thr Pro Glu Val Thr Cys Val Val Val Asp Val
            260             265             270

Ser Gln Glu Asp Pro Glu Val Gln Phe Asn Trp Tyr Val Asp Gly Val
        275             280             285

Glu Val His Asn Ala Lys Thr Lys Pro Arg Glu Glu Gln Phe Asn Ser
    290             295             300

Thr Tyr Arg Val Val Ser Val Leu Thr Val Leu His Gln Asp Trp Leu
305             310             315             320

Asn Gly Lys Glu Tyr Lys Cys Lys Val Ser Asn Lys Gly Leu Pro Ser
                325             330             335

Ser Ile Glu Lys Thr Ile Ser Lys Ala Lys Gly Gln Pro Arg Glu Pro
            340             345             350

Gln Val Tyr Thr Leu Pro Pro Ser Gln Glu Glu Met Thr Lys Asn Gln
        355             360             365

Val Ser Leu Thr Cys Leu Val Lys Gly Phe Tyr Pro Ser Asp Ile Ala
    370             375             380

Val Glu Trp Glu Ser Asn Gly Gln Pro Glu Asn Asn Tyr Lys Thr Thr
385             390             395             400

Pro Pro Val Leu Asp Ser Asp Gly Ser Phe Phe Leu Tyr Ser Arg Leu
                405             410             415

Thr Val Asp Lys Ser Arg Trp Gln Glu Gly Asn Val Phe Ser Cys Ser
            420             425             430

Val Met His Glu Ala Leu His Asn His Tyr Thr Gln Lys Ser Leu Ser
    435             440             445

Leu Ser Leu Gly Lys
    450
```

```
<210> SEQ ID NO 159
<211> LENGTH: 648
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 159
gacatccaga tgacccagtc tccatcctcc ctgtctgcat ctgtaggaga cagagtcacc      60
atcacttgcc gggcaagtca gagcattagc agctatttaa attggtatca gcagaaacca     120
```

```
gggaaagccc ctaagctcct gatctatgct gcatccagtt tgcaaagtgg ggtcccgtca      180
aggttcagtg gcagtggatc tgggacagat ttcactctca ccatcagcag tctgcaacct      240
gaagattttg caacttacta ctgtcaacag agttacagta cccctccgat caccttcggc      300
caagggacac gactggagat taaacgaact gtggctgcac catctgtctt catcttcccg      360
ccatctgatg agcagttgaa atctggaact gcctctgttg tgtgcctgct gaataacttc      420
tatcccagag aggccaaagt acagtggaag gtggataacg ccctccaatc gggtaactcc      480
caggagagtg tcacagagca ggacagcaag gacagcacct acagcctcag cagcaccctg      540
acgctgagca aagcagacta cgagaaacac aaagtctacg cctgcgaagt cacccatcag      600
ggcctgagct cgcccgtcac aaagagcttc aacagggggag agtgttag              648
```

```
<210> SEQ ID NO 160
<211> LENGTH: 215
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 160

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Pro
                85                  90                  95

Ile Thr Phe Gly Gln Gly Thr Arg Leu Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 161
<211> LENGTH: 381
<212> TYPE: DNA
<213> ORGANISM: Artificial Sequence
<220> FEATURE:
<223> OTHER INFORMATION: Description of Artificial Sequence: Synthetic
      polynucleotide
```

<400> SEQUENCE: 161

```
gaagtgcagc tggtggagtc tggggggggc gtggtacagc cgggggggtc cctgagactc        60
tcctgtgaag cctctggatt tattttttgat gattatgcca tgcactgggt ccgtcaagct       120
ccagggaagg gtctggagtg ggtctctctc attagtgggg atggtgatat catatactat       180
gcagactctg tgaagggccg attcaccatc tccagagaca acagcaaaaa ctccctgtat       240
cttcaaatga acagtctgat aattgaggac accgccttgt attactgtgc aaaggattgg       300
gtctttggcg tggttatgac ccactactgg tacttcggat tggacgtctg gggccaaggg       360
accacggtca ccgtctcctc a                                                  381
```

<210> SEQ ID NO 162
<211> LENGTH: 127
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 162

```
Glu Val Gln Leu Val Glu Ser Gly Gly Gly Val Val Gln Pro Gly Gly
1               5                   10                  15

Ser Leu Arg Leu Ser Cys Glu Ala Ser Gly Phe Ile Phe Asp Asp Tyr
            20                  25                  30

Ala Met His Trp Val Arg Gln Ala Pro Gly Lys Gly Leu Glu Trp Val
        35                  40                  45

Ser Leu Ile Ser Gly Asp Gly Asp Ile Ile Tyr Tyr Ala Asp Ser Val
    50                  55                  60

Lys Gly Arg Phe Thr Ile Ser Arg Asp Asn Ser Lys Asn Ser Leu Tyr
65                  70                  75                  80

Leu Gln Met Asn Ser Leu Ile Ile Glu Asp Thr Ala Leu Tyr Tyr Cys
                85                  90                  95

Ala Lys Asp Trp Val Phe Gly Val Val Met Thr His Tyr Trp Tyr Phe
            100                 105                 110

Gly Leu Asp Val Trp Gly Gln Gly Thr Thr Val Thr Val Ser Ser
        115                 120                 125
```

<210> SEQ ID NO 163
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 163

```
ggatttattt ttgatgatta tgcc                                               24
```

<210> SEQ ID NO 164
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 164

```
Gly Phe Ile Phe Asp Asp Tyr Ala
1               5
```

-continued

```
<210> SEQ ID NO 165
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 165
attagtgggg atggtgatat cata                                              24

<210> SEQ ID NO 166
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 166

Ile Ser Gly Asp Gly Asp Ile Ile
1               5

<210> SEQ ID NO 167
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 167
gcaaaggatt gggtctttgg cgtggttatg acccactact ggtacttcgg attggacgtc       60

<210> SEQ ID NO 168
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 168

Ala Lys Asp Trp Val Phe Gly Val Val Met Thr His Tyr Trp Tyr Phe
1               5                   10                  15

Gly Leu Asp Val
            20

<210> SEQ ID NO 169
<211> LENGTH: 324
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 169
gacatccaga tgacccagtc tccatcctcc ctgtctgcat ctgaaggaga cagagtcacc       60
atcacttgcc gggcaagtca gagcattagc acctatttaa attggtatca gcagaaacca      120
gggaaagccc ctaaactcct gatctatggt gcatccagtt tgcaaagtgg ggtcccatca      180
aggttcagtg gcagtggatc tgggacagat ttcactctca ccatcagcag tctgcaacct      240
gaagattttg caacttacta ctgtcaacag agttacagta cccctccgat caccttcggc      300
caagggacca aggtggaaat caaa                                             324
```

-continued

```
<210> SEQ ID NO 170
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 170

Asp Ile Gln Met Thr Gln Ser Pro Ser Ser Leu Ser Ala Ser Glu Gly
1               5                   10                  15

Asp Arg Val Thr Ile Thr Cys Arg Ala Ser Gln Ser Ile Ser Thr Tyr
                20                  25                  30

Leu Asn Trp Tyr Gln Gln Lys Pro Gly Lys Ala Pro Lys Leu Leu Ile
            35                  40                  45

Tyr Gly Ala Ser Ser Leu Gln Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Pro
                85                  90                  95

Ile Thr Phe Gly Gln Gly Thr Lys Val Glu Ile Lys
            100                 105

<210> SEQ ID NO 171
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 171
cagagcatta gcacctat                                               18

<210> SEQ ID NO 172
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 172

Gln Ser Ile Ser Thr Tyr
1               5

<210> SEQ ID NO 173
<211> LENGTH: 9
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 173 ggtgcatcc                                                          9

<210> SEQ ID NO 174
<211> LENGTH: 3
<212> TYPE: PRT
<213> ORGANISM: Artificial Sequence
<220> FEATURE:
```

<223> OTHER INFORMATION: Description of Artificial Sequence: Synthetic
      peptide

<400> SEQUENCE: 174

Gly Ala Ser
1

<210> SEQ ID NO 175
<211> LENGTH: 1362
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 175
gaagtgcagc tggtggagtc tggggggaggc gtggtacagc cggggggggtc cctgagactc      60 tcctgtgaag cctctggatt tattttttgat gattatgcca tgcactgggt ccgtcaagct     120
ccagggaagg gtctggagtg ggtctctctc attagtgggg atggtgatat catatactat     180
gcagactctg tgaagggccg attcaccatc tccagagaca acagcaaaaa ctccctgtat     240
cttcaaatga acagtctgat aattgaggac accgccttgt attactgtgc aaaggattgg     300
gtctttggcg tggttatgac ccactactgg tacttcggat tggacgtctg gggccaaggg     360
accacggtca ccgtctcctc agcctccacc aagggcccat cggtcttccc cctggcgccc     420
tgctccagga gcacctccga gagcacagcc gccctgggct gcctggtcaa ggactacttc     480
cccgaaccgg tgacggtgtc gtggaactca ggcgccctga ccagcggcgt gcacaccttc     540
ccggctgtcc tacagtcctc aggactctac tccctcagca gcgtggtgac cgtgccctcc     600
agcagcttgg gcacgaagac ctacacctgc aacgtagatc acaagcccag caacaccaag     660
gtggacaaga gagttgagtc caaatatggt cccccatgcc caccgtgccc agcaccacct     720
gtggcaggac catcagtctt cctgttcccc ccaaaaccca aggacactct catgatctcc     780
cggacccctg aggtcacgtg cgtggtggtg gacgtgagcc aggaagaccc cgaggtccag     840
ttcaactggt acgtggatgg cgtggaggtg cataatgcca agacaaagcc gcgggaggag     900
cagttcaaca gcacgtaccg tgtggtcagc gtcctcaccg tcctgcacca ggactggctg     960
aacggcaagg agtacaagtg caaggtctcc aacaaaggcc tcccgtcctc catcgagaaa    1020
accatctcca aagccaaagg gcagccccga gagccacagg tgtacaccct gcccccatcc    1080
caggaggaga tgaccaagaa ccaggtcagc ctgacctgcc tggtcaaagg cttctacccc    1140
agcgacatcg ccgtggagtg ggagagcaat gggcagccgg agaacaacta caagaccacg    1200
cctcccgtgc tggactccga cggctccttc ttcctctaca gcaggctcac cgtggacaag    1260
agcaggtggc aggaggggaa tgtcttctca tgctccgtga tgcatgaggc tctgcacaac    1320
cactacacac agaagtccct ctccctgtct ctgggtaaat ga                       1362

<210> SEQ ID NO 176
<211> LENGTH: 453
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 176

Glu Val Gln Leu Val Glu Ser Gly Gly Gly Val Val Gln Pro Gly Gly
1               5                   10                  15

-continued

```
Ser Leu Arg Leu Ser Cys Glu Ala Ser Gly Phe Ile Phe Asp Asp Tyr
         20              25                  30

Ala Met His Trp Val Arg Gln Ala Pro Gly Lys Gly Leu Glu Trp Val
         35              40                  45

Ser Leu Ile Ser Gly Asp Gly Asp Ile Ile Tyr Tyr Ala Asp Ser Val
         50              55                  60

Lys Gly Arg Phe Thr Ile Ser Arg Asp Asn Ser Lys Asn Ser Leu Tyr
65              70              75                  80

Leu Gln Met Asn Ser Leu Ile Ile Glu Asp Thr Ala Leu Tyr Tyr Cys
             85              90                  95

Ala Lys Asp Trp Val Phe Gly Val Val Met Thr His Tyr Trp Tyr Phe
         100             105                 110

Gly Leu Asp Val Trp Gly Gln Gly Thr Thr Val Thr Val Ser Ser Ala
         115             120                 125

Ser Thr Lys Gly Pro Ser Val Phe Pro Leu Ala Pro Cys Ser Arg Ser
     130             135                 140

Thr Ser Glu Ser Thr Ala Ala Leu Gly Cys Leu Val Lys Asp Tyr Phe
145             150                 155                 160

Pro Glu Pro Val Thr Val Ser Trp Asn Ser Gly Ala Leu Thr Ser Gly
             165             170                 175

Val His Thr Phe Pro Ala Val Leu Gln Ser Ser Gly Leu Tyr Ser Leu
             180             185                 190

Ser Ser Val Val Thr Val Pro Ser Ser Ser Leu Gly Thr Lys Thr Tyr
         195             200                 205

Thr Cys Asn Val Asp His Lys Pro Ser Asn Thr Lys Val Asp Lys Arg
     210             215                 220

Val Glu Ser Lys Tyr Gly Pro Pro Cys Pro Pro Cys Pro Ala Pro Pro
225             230                 235                 240

Val Ala Gly Pro Ser Val Phe Leu Phe Pro Pro Lys Pro Lys Asp Thr
             245             250                 255

Leu Met Ile Ser Arg Thr Pro Glu Val Thr Cys Val Val Val Asp Val
         260             265                 270

Ser Gln Glu Asp Pro Glu Val Gln Phe Asn Trp Tyr Val Asp Gly Val
         275             280                 285

Glu Val His Asn Ala Lys Thr Lys Pro Arg Glu Glu Gln Phe Asn Ser
     290             295                 300

Thr Tyr Arg Val Val Ser Val Leu Thr Val Leu His Gln Asp Trp Leu
305             310                 315                 320

Asn Gly Lys Glu Tyr Lys Cys Lys Val Ser Asn Lys Gly Leu Pro Ser
             325             330                 335

Ser Ile Glu Lys Thr Ile Ser Lys Ala Lys Gly Gln Pro Arg Glu Pro
         340             345                 350

Gln Val Tyr Thr Leu Pro Pro Ser Gln Glu Glu Met Thr Lys Asn Gln
         355             360                 365

Val Ser Leu Thr Cys Leu Val Lys Gly Phe Tyr Pro Ser Asp Ile Ala
     370             375                 380

Val Glu Trp Glu Ser Asn Gly Gln Pro Glu Asn Asn Tyr Lys Thr Thr
385             390                 395                 400

Pro Pro Val Leu Asp Ser Asp Gly Ser Phe Phe Leu Tyr Ser Arg Leu
             405             410                 415

Thr Val Asp Lys Ser Arg Trp Gln Glu Gly Asn Val Phe Ser Cys Ser
             420             425                 430

Val Met His Glu Ala Leu His Asn His Tyr Thr Gln Lys Ser Leu Ser
```

-continued

```
                435                    440                    445

Leu Ser Leu Gly Lys
        450

<210> SEQ ID NO 177
<211> LENGTH: 648
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 177
gacatccaga tgacccagtc tccatcctcc ctgtctgcat ctgaaggaga cagagtcacc        60
atcacttgcc gggcaagtca gagcattagc acctatttaa attggtatca gcagaaacca       120
gggaaagccc ctaaactcct gatctatggt gcatccagtt tgcaaagtgg ggtcccatca       180
aggttcagtg gcagtggatc tgggacagat ttcactctca ccatcagcag tctgcaacct       240
gaagattttg caacttacta ctgtcaacag agttacagta cccctccgat caccttcggc       300
caagggacca aggtggaaat caaacgaact gtggctgcac catctgtctt catcttcccg       360
ccatctgatg agcagttgaa atctggaact gcctctgttg tgtgcctgct gaataacttc       420
tatcccagag aggccaaagt acagtggaag gtggataacg ccctccaatc gggtaactcc       480
caggagagtg tcacagagca ggacagcaag gacagcacct acagcctcag cagcaccctg       540
acgctgagca aagcagacta cgagaaacac aaagtctacg cctgcgaagt cacccatcag       600
ggcctgagct cgcccgtcac aaagagcttc aacaggggag agtgttag                    648

<210> SEQ ID NO 178
<211> LENGTH: 215
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 178

Asp Ile Gln Met Thr Gln Ser Pro Ser Ser Leu Ser Ala Ser Glu Gly
1               5                   10                  15

Asp Arg Val Thr Ile Thr Cys Arg Ala Ser Gln Ser Ile Ser Thr Tyr
            20                  25                  30

Leu Asn Trp Tyr Gln Gln Lys Pro Gly Lys Ala Pro Lys Leu Leu Ile
        35                  40                  45

Tyr Gly Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Pro
                85                  90                  95

Ile Thr Phe Gly Gln Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160
```

```
Gln Glu Ser Val Thr Glu Gln Asp Ser Lys Asp Ser Thr Tyr Ser Leu
            165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215
```

<210> SEQ ID NO 179
<211> LENGTH: 378
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 179

```
gaagtgcagc tggtggagtc tgggggaggc gtggtacagc ctggggggtc cctgagactc      60
tcctgtgcag cctctggatt cacctttgat gattatgcca tgcactgggt ccgtcaagct     120
ccagggaagg gtctggagtg ggtctctctt attagtgggg gtggtggtgg cacatactat     180
tcagactctg tgaagggccg attcaccatc tccagagaca ccagcaaaga ctccctgtat     240
ctgcaaatga acagtctgag aactgaggac accgccttgt attactgtgc aaaagatatg     300
gtttttggag tggttacccc ctactactac ttcgctttgg acgtctgggg ccaagggacc     360
acggtcaccg tctcctca                                                    378
```

<210> SEQ ID NO 180
<211> LENGTH: 126
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 180

```
Glu Val Gln Leu Val Glu Ser Gly Gly Gly Val Val Gln Pro Gly Gly
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Leu Ile Ser Gly Gly Gly Gly Gly Thr Tyr Tyr Ser Asp Ser Val
    50                  55                  60

Lys Gly Arg Phe Thr Ile Ser Arg Asp Thr Ser Lys Asp Ser Leu Tyr
65                  70                  75                  80

Leu Gln Met Asn Ser Leu Arg Thr Glu Asp Thr Ala Leu Tyr Tyr Cys
                85                  90                  95

Ala Lys Asp Met Val Phe Gly Val Val Thr Pro Tyr Tyr Tyr Phe Ala
            100                 105                 110

Leu Asp Val Trp Gly Gln Gly Thr Thr Val Thr Val Ser Ser
        115                 120                 125
```

<210> SEQ ID NO 181
<211> LENGTH: 24
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 181
attagtgggg gtggtggtgg caca                                                              24

<210> SEQ ID NO 182
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 182

Ile Ser Gly Gly Gly Gly Gly Thr
1               5

<210> SEQ ID NO 183
<211> LENGTH: 57
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 183
gcaaaagata tggtttttgg agtggttacc ccctactact acttcgcttt ggacgtc         57

<210> SEQ ID NO 184
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 184

Ala Lys Asp Met Val Phe Gly Val Val Thr Pro Tyr Tyr Tyr Phe Ala
1               5                   10                  15

Leu Asp Val

<210> SEQ ID NO 185
<211> LENGTH: 324
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 185
gacatccaga tgacccagtc tccatcctcc ctgtctgcat ctgtaggaga cagagtcacc      60
atcacttgcc gggcaagtca gagcattaac agctatttaa attggtatca gcagaaacca     120
gggaaagccc ctaagctcct gatctatgct gcatccagtt tgcaaagtgg ggtcccatca     180
aggttcagtg gcagtggatc tgggacagat ttcactctca ccatcagcag tctgcaacct     240
gaagattttg caacttacta ctgtcaacag agttacagtg cccctccgat caccttcggc     300
caagggacac gactggagat taaa                                             324

<210> SEQ ID NO 186
<211> LENGTH: 108
<212> TYPE: PRT
<213> ORGANISM: Artificial Sequence
<220> FEATURE:
<223> OTHER INFORMATION: Description of Artificial Sequence: Synthetic

```
    polypeptide

<400> SEQUENCE: 186

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Asn Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Ala Pro Pro
                85                  90                  95

Ile Thr Phe Gly Gln Gly Thr Arg Leu Glu Ile Lys
            100                 105

<210> SEQ ID NO 187
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 187
cagagcatta acagctat                                                  18

<210> SEQ ID NO 188
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 188

Gln Ser Ile Asn Ser Tyr
1               5

<210> SEQ ID NO 189
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 189
caacagagtt acagtgcccc tccgatcacc                                     30

<210> SEQ ID NO 190
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 190

Gln Gln Ser Tyr Ser Ala Pro Pro Ile Thr
1               5                   10
```

-continued

```
<210> SEQ ID NO 191
<211> LENGTH: 1359
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 191
gaagtgcagc tggtggagtc tggggggaggc gtggtacagc ctggggggtc cctgagactc      60
tcctgtgcag cctctggatt caccttgat gattatgcca tgcactgggt ccgtcaagct    120
ccagggaagg gtctggagtg ggtctctctt attagtgggg gtggtggtgg cacatactat    180
tcagactctg tgaagggccg attcaccatc tccagagaca ccagcaaaga ctccctgtat    240
ctgcaaatga acagtctgag aactgaggac accgccttgt attactgtgc aaaagatatg    300 gttttttggag tggttacccc ctactactac ttcgctttgg acgtctgggg ccaagggacc    360
acggtcaccg tctcctcagc ctccaccaag ggcccatcgg tcttcccct ggcgccctgc    420 tccaggagca cctccgagag cacagccgcc ctgggctgcc tggtcaagga ctacttcccc    480
gaaccggtga cggtgtcgtg gaactcaggc gccctgacca gcggcgtgca cacctttcccg    540 gctgtcctac agtcctcagg actctactcc ctcagcagcg tggtgaccgt gccctccagc    600
agcttgggca cgaagaccta cacctgcaac gtagatcaca gcccagcaa caccaaggtg    660 gacaagagag ttgagtccaa atatggtccc ccatgccac cgtgcccagc accacctgtg    720
gcaggaccat cagtcttcct gttccccca aaacccaagg acactctcat gatctcccgg    780
acccctgagg tcacgtgcgt ggtggtggac gtgagccagg aagaccccga ggtccagttc    840
aactggtacg tggatggcgt ggaggtgcat aatgccaaga caaagccgcg ggaggagcag    900
ttcaacagca cgtaccgtgt ggtcagcgtc ctcaccgtcc tgcaccagga ctggctgaac    960
ggcaaggagt acaagtgcaa ggtctccaac aaaggcctcc cgtcctccat cgagaaaacc   1020
atctccaaag ccaaagggca gccccgagag ccacaggtgt acaccctgcc cccatcccag   1080
gaggagatga ccaagaacca ggtcagcctg acctgcctgg tcaaaggctt ctaccccagc   1140
gacatcgccg tggagtggga gagcaatggg cagccggaga caactacaa gaccacgcct   1200 cccgtgctgg actccgacgg ctccttcttc ctctacagca ggctcaccgt ggacaagagc   1260
aggtggcagg aggggaatgt cttctcatgc tccgtgatgc atgaggctct gcacaaccac   1320
tacacacaga gtccctctc cctgtctctg ggtaaatga                           1359

<210> SEQ ID NO 192
<211> LENGTH: 452
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 192

Glu Val Gln Leu Val Glu Ser Gly Gly Gly Val Val Gln Pro Gly Gly
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Leu Ile Ser Gly Gly Gly Gly Gly Thr Tyr Tyr Ser Asp Ser Val
    50                  55                  60
```

Lys Gly Arg Phe Thr Ile Ser Arg Asp Thr Ser Lys Asp Ser Leu Tyr
65                  70                  75                  80

Leu Gln Met Asn Ser Leu Arg Thr Glu Asp Thr Ala Leu Tyr Tyr Cys
                85                  90                  95

Ala Lys Asp Met Val Phe Gly Val Val Thr Pro Tyr Tyr Tyr Phe Ala
                100                 105                 110

Leu Asp Val Trp Gly Gln Gly Thr Thr Val Thr Val Ser Ser Ala Ser
                115                 120                 125

Thr Lys Gly Pro Ser Val Phe Pro Leu Ala Pro Cys Ser Arg Ser Thr
    130                 135                 140

Ser Glu Ser Thr Ala Ala Leu Gly Cys Leu Val Lys Asp Tyr Phe Pro
145                 150                 155                 160

Glu Pro Val Thr Val Ser Trp Asn Ser Gly Ala Leu Thr Ser Gly Val
                165                 170                 175

His Thr Phe Pro Ala Val Leu Gln Ser Ser Gly Leu Tyr Ser Leu Ser
                180                 185                 190

Ser Val Val Thr Val Pro Ser Ser Ser Leu Gly Thr Lys Thr Tyr Thr
                195                 200                 205

Cys Asn Val Asp His Lys Pro Ser Asn Thr Lys Val Asp Lys Arg Val
    210                 215                 220

Glu Ser Lys Tyr Gly Pro Pro Cys Pro Pro Cys Pro Ala Pro Pro Val
225                 230                 235                 240

Ala Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
                260                 265                 270

Gln Glu Asp Pro Glu Val Gln Phe Asn Trp Tyr Val Asp Gly Val Glu
                275                 280                 285

Val His Asn Ala Lys Thr Lys Pro Arg Glu Glu Gln Phe Asn Ser Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Gly Leu Pro Ser Ser
                325                 330                 335

Ile Glu Lys Thr Ile Ser Lys Ala Lys Gly Gln Pro Arg Glu Pro Gln
                340                 345                 350

Val Tyr Thr Leu Pro Pro Ser Gln Glu Glu Met Thr Lys Asn Gln Val
                355                 360                 365

Ser Leu Thr Cys Leu Val Lys Gly Phe Tyr Pro Ser Asp Ile Ala Val
    370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Arg Leu Thr
                405                 410                 415

Val Asp Lys Ser Arg Trp Gln Glu Gly Asn Val Phe Ser Cys Ser Val
                420                 425                 430

Met His Glu Ala Leu His Asn His Tyr Thr Gln Lys Ser Leu Ser Leu
                435                 440                 445

Ser Leu Gly Lys
    450

<210> SEQ ID NO 193
<211> LENGTH: 648

<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 193
gacatccaga tgacccagtc tccatcctcc ctgtctgcat ctgtaggaga cagagtcacc        60
atcacttgcc gggcaagtca gagcattaac agctatttaa attggtatca gcagaaacca       120
gggaaagccc ctaagctcct gatctatgct gcatccagtt tgcaaagtgg ggtcccatca       180
aggttcagtg gcagtggatc tgggacagat ttcactctca ccatcagcag tctgcaacct       240
gaagattttg caacttacta ctgtcaacag agttacagtg cccctccgat caccttcggc       300
caagggacac gactggagat taaacgaact gtggctgcac catctgtctt catcttcccg       360
ccatctgatg agcagttgaa atctggaact gcctctgttg tgtgcctgct gaataacttc       420
tatcccagag aggccaaagt acagtggaag gtggataacg ccctccaatc gggtaactcc       480
caggagagtg tcacagagca ggacagcaag gacagcacct acagcctcag cagcaccctg       540
acgctgagca aagcagacta cgagaaacac aaagtctacg cctgcgaagt cacccatcag       600
ggcctgagct cgcccgtcac aaagagcttc aacaggggag agtgttag                    648

<210> SEQ ID NO 194
<211> LENGTH: 215
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 194

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Asn Ser Tyr
                20                  25                  30

Leu Asn Trp Tyr Gln Gln Lys Pro Gly Lys Ala Pro Lys Leu Leu Ile
            35                  40                  45

Tyr Ala Ala Ser Ser Leu Gln Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Ala Pro Pro
                85                  90                  95

Ile Thr Phe Gly Gln Gly Thr Arg Leu Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
            195                 200                 205

-continued

```
Ser Phe Asn Arg Gly Glu Cys
    210                 215

<210> SEQ ID NO 195
<211> LENGTH: 378
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 195
gaagtgcagc tggtggagtc tggggggaggc gtggtacagc ctggggggtc cctgagactc        60
tcctgtgcag cctctggatt catttttgat gattatgcca tgcactgggt ccgtcaagtt       120
ccagggaagg gtctggagtg gatctctctt agtagtgggg gtggtggtgg cacatactat       180
gcagaccctg tgaagggccg attcaccatc tccagagaca acagcaaaaa ctccctgcat       240
cttcaaatga atagtctgag agctgaggac accgcctcat attattgtgc aaaagacatg       300 gttttttgggg tggttacccc cgacttcttt tttgctatgg acgtctgggg ccaagggacc       360
acggtcaccg tctcctca                                                    378

<210> SEQ ID NO 196
<211> LENGTH: 126
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 196

Glu Val Gln Leu Val Glu Ser Gly Gly Gly Val Val Gln Pro Gly Gly
1               5                   10                  15

Ser Leu Arg Leu Ser Cys Ala Ala Ser Gly Phe Ile Phe Asp Asp Tyr
            20                  25                  30

Ala Met His Trp Val Arg Gln Val Pro Gly Lys Gly Leu Glu Trp Ile
        35                  40                  45

Ser Leu Ser Ser Gly Gly Gly Gly Gly Thr Tyr Tyr Ala Asp Pro Val
    50                  55                  60

Lys Gly Arg Phe Thr Ile Ser Arg Asp Asn Ser Lys Asn Ser Leu His
65                  70                  75                  80

Leu Gln Met Asn Ser Leu Arg Ala Glu Asp Thr Ala Ser Tyr Tyr Cys
                85                  90                  95

Ala Lys Asp Met Val Phe Gly Val Val Thr Pro Asp Phe Phe Phe Ala
            100                 105                 110

Met Asp Val Trp Gly Gln Gly Thr Thr Val Thr Val Ser Ser
        115                 120                 125

<210> SEQ ID NO 197
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 197
ggattcattt ttgatgatta tgcc                                              24

<210> SEQ ID NO 198
```

```
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 198
agtagtgggg gtggtggtgg caca                                          24

<210> SEQ ID NO 199
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 199

Ser Ser Gly Gly Gly Gly Gly Thr
1               5

<210> SEQ ID NO 200
<211> LENGTH: 57
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 200
gcaaaagaca tggtttttgg ggtggttacc cccgacttct tttttgctat ggacgtc       57

<210> SEQ ID NO 201
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 201

Ala Lys Asp Met Val Phe Gly Val Val Thr Pro Asp Phe Phe Phe Ala
1               5                   10                  15

Met Asp Val

<210> SEQ ID NO 202
<211> LENGTH: 324
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 202
gacatccaga tgacccagtc tccatcctcc ctgtctgcat ctgtaggaga cagagtcacc       60
atcacttgcc gggcaagtca gagcattagc acctatttaa attggtatca gcagaaacca      120
gggaaagccc ctaagctcct gatctatggt gcatccagtt tgcaaagggg ggtcccatca      180
aggttcagtg gcagtggatc tgggacagat ttcactctca ccatcagcag tctgcaacct      240
gaagattttg caacttacta ctgtcaacag acttacagta cccctccgat caccttcggc      300
caagggacac gactggagat taaa                                            324

<210> SEQ ID NO 203
```

<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 203

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Thr Tyr
            20                  25                  30

Leu Asn Trp Tyr Gln Gln Lys Pro Gly Lys Ala Pro Lys Leu Leu Ile
        35                  40                  45

Tyr Gly Ala Ser Ser Leu Gln Arg Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Thr Tyr Ser Thr Pro Pro
                85                  90                  95

Ile Thr Phe Gly Gln Gly Thr Arg Leu Glu Ile Lys
            100                 105

<210> SEQ ID NO 204
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 204
caacagactt acagtacccc tccgatcacc                                        30

<210> SEQ ID NO 205
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 205

Gln Gln Thr Tyr Ser Thr Pro Pro Ile Thr
1               5                   10

<210> SEQ ID NO 206
<211> LENGTH: 1359
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 206
gaagtgcagc tggtggagtc tgggggaggc gtggtacagc ctgggggggtc cctgagactc        60 tcctgtgcag cctctggatt cattttttgat gattatgcca tgcactgggt ccgtcaagtt       120
ccagggaagg gtctggagtg gatctctctt agtagtgggg gtggtggtgg cacatactat       180
gcagaccctg tgaagggccg attcaccatc tccagagaca acagcaaaaa ctccctgcat       240
cttcaaatga atagtctgag agctgaggac accgcctcat attattgtgc aaaagacatg       300 gttttttgggg tggttacccc cgacttcttt tttgctatgg acgtctgggg ccaagggacc       360

-continued

```
acggtcaccg tctcctcagc ctccaccaag ggcccatcgg tcttcccct ggcgccctgc      420 tccaggagca cctccgagag cacagccgcc ctgggctgcc tggtcaagga ctacttcccc      480
gaaccggtga cggtgtcgtg gaactcaggc gccctgacca gcggcgtgca caccttcccg      540
gctgtcctac agtcctcagg actctactcc ctcagcagcg tggtgaccgt gccctccagc      600
agcttgggca cgaagaccta cacctgcaac gtagatcaca agcccagcaa caccaaggtg      660
gacaagagag ttgagtccaa atatggtccc ccatgcccac cgtgcccagc accacctgtg      720
gcaggaccat cagtcttcct gttcccccca aaacccaagg acactctcat gatctcccgg      780
acccctgagg tcacgtgcgt ggtggtggac gtgagccagg aagaccccga ggtccagttc      840
aactggtacg tggatggcgt ggaggtgcat aatgccaaga caaagccgcg ggaggagcag      900
ttcaacagca cgtaccgtgt ggtcagcgtc ctcaccgtcc tgcaccagga ctggctgaac      960
ggcaaggagt acaagtgcaa ggtctccaac aaaggcctcc cgtcctccat cgagaaaacc     1020
atctccaaag ccaaagggca gccccgagag ccacaggtgt acaccctgcc cccatcccag     1080
gaggagatga ccaagaacca ggtcagcctg acctgcctgg tcaaaggctt ctaccccagc     1140
gacatcgccg tggagtggga gagcaatggg cagccggaga acaactacaa gaccacgcct     1200
cccgtgctgg actccgacgg ctccttcttc ctctacagca ggctcaccgt ggacaagagc     1260
aggtggcagg aggggaatgt cttctcatgc tccgtgatgc atgaggctct gcacaaccac     1320
tacacacaga gtccctctc cctgtctctg ggtaaatga                              1359
```

<210> SEQ ID NO 207
<211> LENGTH: 452
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 207

```
Glu Val Gln Leu Val Glu Ser Gly Gly Gly Val Val Gln Pro Gly Gly
1               5                   10                  15

Ser Leu Arg Leu Ser Cys Ala Ala Ser Gly Phe Ile Phe Asp Asp Tyr
            20                  25                  30

Ala Met His Trp Val Arg Gln Val Pro Gly Lys Gly Leu Glu Trp Ile
        35                  40                  45

Ser Leu Ser Ser Gly Gly Gly Gly Thr Tyr Tyr Ala Asp Pro Val
    50                  55                  60

Lys Gly Arg Phe Thr Ile Ser Arg Asp Asn Ser Lys Asn Ser Leu His
65                  70                  75                  80

Leu Gln Met Asn Ser Leu Arg Ala Glu Asp Thr Ala Ser Tyr Tyr Cys
                85                  90                  95

Ala Lys Asp Met Val Phe Gly Val Val Thr Pro Asp Phe Phe Phe Ala
            100                 105                 110

Met Asp Val Trp Gly Gln Gly Thr Thr Val Thr Val Ser Ser Ala Ser
        115                 120                 125

Thr Lys Gly Pro Ser Val Phe Pro Leu Ala Pro Cys Ser Arg Ser Thr
    130                 135                 140

Ser Glu Ser Thr Ala Ala Leu Gly Cys Leu Val Lys Asp Tyr Phe Pro
145                 150                 155                 160

Glu Pro Val Thr Val Ser Trp Asn Ser Gly Ala Leu Thr Ser Gly Val
                165                 170                 175
```

```
His Thr Phe Pro Ala Val Leu Gln Ser Ser Gly Leu Tyr Ser Leu Ser
            180                 185                 190

Ser Val Val Thr Val Pro Ser Ser Leu Gly Thr Lys Thr Tyr Thr
            195                 200                 205

Cys Asn Val Asp His Lys Pro Ser Asn Thr Lys Val Asp Lys Arg Val
    210                 215                 220

Glu Ser Lys Tyr Gly Pro Pro Cys Pro Pro Cys Pro Ala Pro Pro Val
225                 230                 235                 240

Ala Gly Pro Ser Val Phe Leu Phe Pro Pro Lys Pro Lys Asp Thr Leu
            245                 250                 255

Met Ile Ser Arg Thr Pro Glu Val Thr Cys Val Val Val Asp Val Ser
            260                 265                 270

Gln Glu Asp Pro Glu Val Gln Phe Asn Trp Tyr Val Asp Gly Val Glu
            275                 280                 285

Val His Asn Ala Lys Thr Lys Pro Arg Glu Glu Gln Phe Asn Ser Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Gly Leu Pro Ser Ser
            325                 330                 335

Ile Glu Lys Thr Ile Ser Lys Ala Lys Gly Gln Pro Arg Glu Pro Gln
            340                 345                 350

Val Tyr Thr Leu Pro Pro Ser Gln Glu Glu Met Thr Lys Asn Gln Val
            355                 360                 365

Ser Leu Thr Cys Leu Val Lys Gly Phe Tyr Pro Ser Asp Ile Ala Val
    370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Arg Leu Thr
            405                 410                 415

Val Asp Lys Ser Arg Trp Gln Glu Gly Asn Val Phe Ser Cys Ser Val
            420                 425                 430

Met His Glu Ala Leu His Asn His Tyr Thr Gln Lys Ser Leu Ser Leu
            435                 440                 445

Ser Leu Gly Lys
    450
```

```
<210> SEQ ID NO 208
<211> LENGTH: 648
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 208
gacatccaga tgacccagtc tccatcctcc ctgtctgcat ctgtaggaga cagagtcacc      60
atcacttgcc gggcaagtca gagcattagc acctatttaa attggtatca gcagaaacca     120
gggaaagccc ctaagctcct gatctatggt gcatccagtt tgcaaagggg ggtcccatca     180
aggttcagtg gcagtggatc tgggacagat ttcactctca ccatcagcag tctgcaacct     240
gaagattttg caacttacta ctgtcaacag acttacagta cccctccgat caccttcggc     300
caagggacac gactggagat taaacgaact gtggctgcac catctgtctt catcttcccg     360
ccatctgatg agcagttgaa atctggaact gcctctgttg tgtgcctgct gaataacttc     420
```

```
tatcccagag aggccaaagt acagtggaag gtggataacg ccctccaatc gggtaactcc      480
caggagagtg tcacagagca ggacagcaag gacagcacct acagcctcag cagcaccctg      540
acgctgagca aagcagacta cgagaaacac aaagtctacg cctgcgaagt cacccatcag      600
ggcctgagct cgcccgtcac aaagagcttc aacagggggag agtgttag              648
```

<210> SEQ ID NO 209
<211> LENGTH: 215
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 209

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Thr Tyr
            20                  25                  30

Leu Asn Trp Tyr Gln Gln Lys Pro Gly Lys Ala Pro Lys Leu Leu Ile
        35                  40                  45

Tyr Gly Ala Ser Ser Leu Gln Arg Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Thr Tyr Ser Thr Pro Pro
                85                  90                  95

Ile Thr Phe Gly Gln Gly Thr Arg Leu Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215
```

<210> SEQ ID NO 210
<211> LENGTH: 375
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 210

```
caggtgcagc tggtggagtc tggggggaggc gtggtccagc ctgggaggtc cctgagactc       60
tcctgtgtag cgtctggatt caccttcagt agttatggca tgcactgggt ccgccaggct      120
ccaggcaagg ggctggaatg ggtggcagtt atatggtatg ttggaagtaa taaatattat      180
ggagactccg tgaagggccg attcaccatc tccagagaca attccaagaa cacgctgtat      240
```

-continued

```
ctgcaaatga acagcctgag agccgaggac acggctgtct attactgtgc gagagatctg      300
atagcagatc gtccgggcta ctactataac ggtatggacg tctggggcca agggaccacg      360
gtcaccgtct cctca                                                      375
```

```
<210> SEQ ID NO 211
<211> LENGTH: 125
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 211

Gln Val Gln Leu Val Glu Ser Gly Gly Gly Val Val Gln Pro Gly Arg
1               5                   10                  15

Ser Leu Arg Leu Ser Cys Val Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Trp Tyr Val Gly Ser Asn Lys Tyr Tyr Gly Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Leu Ile Ala Asp Arg Pro Gly Tyr Tyr Tyr Asn Gly Met
            100                 105                 110

Asp Val Trp Gly Gln Gly Thr Thr Val Thr Val Ser Ser
        115                 120                 125
```

```
<210> SEQ ID NO 212
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 212
ggattcacct tcagtagtta tggc                                             24
```

```
<210> SEQ ID NO 213
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 213

Gly Phe Thr Phe Ser Ser Tyr Gly
1               5
```

```
<210> SEQ ID NO 214
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 214
```

-continued

```
atatggtatg ttggaagtaa taaa                                                24

<210> SEQ ID NO 215
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 215

Ile Trp Tyr Val Gly Ser Asn Lys
1               5

<210> SEQ ID NO 216
<211> LENGTH: 54
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 216
gcgagagatc tgatagcaga tcgtccgggc tactactata acggtatgga cgtc             54

<210> SEQ ID NO 217
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 217

Ala Arg Asp Leu Ile Ala Asp Arg Pro Gly Tyr Tyr Tyr Asn Gly Met
1               5                   10                  15

Asp Val

<210> SEQ ID NO 218
<211> LENGTH: 324
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 218
gaaattgtga tgacgcagtc tccagtcacc ctgtttgtgt ctccagggga aagagccacc       60
ctctcctgca gggccagtca gagtgtgaac accaacttag cctggtacca acagcaacct      120
ggccaggctc ccaggctcct catccatgga gcatccacca ggcccactgg tgtcccagcc      180
aggttcagtg gcagtgggtc tgggacagag ttcactctca tcatcagcag cctgcagtct      240
gaagattttg cagtttatta ctgtcagcaa tataataatt ggccccgtg gacgttcggc      300 caagggacca aggtggaaat caaa                                             324

<210> SEQ ID NO 219
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 219
```

```
Glu Ile Val Met Thr Gln Ser Pro Val Thr Leu Phe Val Ser Pro Gly
1               5                   10                  15

Glu Arg Ala Thr Leu Ser Cys Arg Ala Ser Gln Ser Val Asn Thr Asn
            20                  25                  30

Leu Ala Trp Tyr Gln Gln Gln Pro Gly Gln Ala Pro Arg Leu Leu Ile
        35                  40                  45

His Gly Ala Ser Thr Arg Pro Thr Gly Val Pro Ala Arg Phe Ser Gly
    50                  55                  60

Ser Gly Ser Gly Thr Glu Phe Thr Leu Ile Ile Ser Ser Leu Gln Ser
65                  70                  75                  80

Glu Asp Phe Ala Val Tyr Tyr Cys Gln Gln Tyr Asn Asn Trp Pro Pro
                85                  90                  95

Trp Thr Phe Gly Gln Gly Thr Lys Val Glu Ile Lys
            100                 105
```

```
<210> SEQ ID NO 220
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 220
cagagtgtga acaccaac                                                       18

<210> SEQ ID NO 221
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 221

Gln Ser Val Asn Thr Asn
1               5

<210> SEQ ID NO 222
<211> LENGTH: 9
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 222 ggagcatcc                                                                  9

<210> SEQ ID NO 223
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 223
cagcaatata ataattggcc cccgtggacg                                          30

<210> SEQ ID NO 224
<211> LENGTH: 10
<212> TYPE: PRT
```

-continued

```
<213> ORGANISM: Artificial Sequence
<220> FEATURE:
<223> OTHER INFORMATION: Description of Artificial Sequence: Synthetic
      peptide

<400> SEQUENCE: 224

Gln Gln Tyr Asn Asn Trp Pro Pro Trp Thr
1               5                   10

<210> SEQ ID NO 225
<211> LENGTH: 1356
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 225
caggtgcagc tggtggagtc tggggggaggc gtggtccagc ctggggaggtc cctgagactc        60 tcctgtgtag cgtctggatt caccttcagt agttatggca tgcactgggt ccgccaggct       120
ccaggcaagg ggctggaatg ggtggcagtt atatggtatg ttggaagtaa taaatattat       180
ggagactccg tgaagggccg attcaccatc tccagagaca attccaagaa cacgctgtat       240
ctgcaaatga acagcctgag agccgaggac acggctgtct attactgtgc gagagatctg       300
atagcagatc gtccgggcta ctactataac ggtatggacg tctggggcca agggaccacg       360
gtcaccgtct cctcagcctc caccaagggc ccatcggtct tccccctggc gccctgctcc       420
aggagcacct ccgagagcac agccgccctg ggctgcctgg tcaaggacta cttccccgaa       480
ccggtgacgg tgtcgtggaa ctcaggcgcc ctgaccagcg gcgtgcacac cttcccggct       540
gtcctacagt cctcaggact ctactccctc agcagcgtgg tgaccgtgcc ctccagcagc       600
ttgggcacga gacctacac ctgcaacgta gatcacaagc ccagcaacac caaggtggac       660
aagagagttg agtccaaata tggtcccccca tgcccaccgt gcccagcacc acctgtggca       720
ggaccatcag tcttcctgtt ccccccaaaa cccaaggaca ctctcatgat ctcccggacc       780
cctgaggtca cgtgcgtggt ggtggacgtg agccaggaag accccgaggt ccagttcaac       840
tggtacgtgg atggcgtgga ggtgcataat gccaagacaa agccgcggga ggagcagttc       900
aacagcacgt accgtgtggt cagcgtcctc accgtcctgc accaggactg gctgaacggc       960
aaggagtaca agtgcaaggt ctccaacaaa ggcctcccgt cctccatcga gaaaaccatc      1020
tccaaagcca aagggcagcc ccgagagcca caggtgtaca ccctgcccccc atcccaggag      1080 gagatgacca gaaccaggt cagcctgacc tgcctggtca aaggcttcta ccccagcgac      1140
atcgccgtgg agtgggagag caatgggcag ccggagaaca actacaagac cacgcctccc      1200
gtgctggact ccgacggctc cttcttcctc tacagcaggc tcaccgtgga caagagcagg      1260
tggcaggagg ggaatgtctt ctcatgctcc gtgatgcatg aggctctgca caaccactac      1320
acacagaagt ccctctcccct gtctctgggt aaatga                               1356

<210> SEQ ID NO 226
<211> LENGTH: 451
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 226

Gln Val Gln Leu Val Glu Ser Gly Gly Gly Val Val Gln Pro Gly Arg
```

```
1              5              10             15
Ser Leu Arg Leu Ser Cys Val Ala Ser Gly Phe Thr Phe Ser Ser Tyr
            20             25             30

Gly Met His Trp Val Arg Gln Ala Pro Gly Lys Gly Leu Glu Trp Val
            35             40             45

Ala Val Ile Trp Tyr Val Gly Ser Asn Lys Tyr Tyr Gly Asp Ser Val
      50             55             60

Lys Gly Arg Phe Thr Ile Ser Arg Asp Asn Ser Lys Asn Thr Leu Tyr
65             70             75             80

Leu Gln Met Asn Ser Leu Arg Ala Glu Asp Thr Ala Val Tyr Tyr Cys
            85             90             95

Ala Arg Asp Leu Ile Ala Asp Arg Pro Gly Tyr Tyr Tyr Asn Gly Met
            100            105            110

Asp Val Trp Gly Gln Gly Thr Thr Val Thr Val Ser Ser Ala Ser Thr
            115            120            125

Lys Gly Pro Ser Val Phe Pro Leu Ala Pro Cys Ser Arg Ser Thr Ser
      130            135            140

Glu Ser Thr Ala Ala Leu Gly Cys Leu Val Lys Asp Tyr Phe Pro Glu
145            150            155            160

Pro Val Thr Val Ser Trp Asn Ser Gly Ala Leu Thr Ser Gly Val His
            165            170            175

Thr Phe Pro Ala Val Leu Gln Ser Ser Gly Leu Tyr Ser Leu Ser Ser
            180            185            190

Val Val Thr Val Pro Ser Ser Ser Leu Gly Thr Lys Thr Tyr Thr Cys
            195            200            205

Asn Val Asp His Lys Pro Ser Asn Thr Lys Val Asp Lys Arg Val Glu
      210            215            220

Ser Lys Tyr Gly Pro Pro Cys Pro Pro Cys Pro Ala Pro Pro Val Ala
225            230            235            240

Gly Pro Ser Val Phe Leu Phe Pro Pro Lys Pro Lys Asp Thr Leu Met
            245            250            255

Ile Ser Arg Thr Pro Glu Val Thr Cys Val Val Val Asp Val Ser Gln
            260            265            270

Glu Asp Pro Glu Val Gln Phe Asn Trp Tyr Val Asp Gly Val Glu Val
            275            280            285

His Asn Ala Lys Thr Lys Pro Arg Glu Glu Gln Phe Asn Ser Thr Tyr
      290            295            300

Arg Val Val Ser Val Leu Thr Val Leu His Gln Asp Trp Leu Asn Gly
305            310            315            320

Lys Glu Tyr Lys Cys Lys Val Ser Asn Lys Gly Leu Pro Ser Ser Ile
            325            330            335

Glu Lys Thr Ile Ser Lys Ala Lys Gly Gln Pro Arg Glu Pro Gln Val
            340            345            350

Tyr Thr Leu Pro Pro Ser Gln Glu Glu Met Thr Lys Asn Gln Val Ser
            355            360            365

Leu Thr Cys Leu Val Lys Gly Phe Tyr Pro Ser Asp Ile Ala Val Glu
      370            375            380

Trp Glu Ser Asn Gly Gln Pro Glu Asn Asn Tyr Lys Thr Thr Pro Pro
385            390            395            400

Val Leu Asp Ser Asp Gly Ser Phe Phe Leu Tyr Ser Arg Leu Thr Val
            405            410            415

Asp Lys Ser Arg Trp Gln Glu Gly Asn Val Phe Ser Cys Ser Val Met
            420            425            430
```

His Glu Ala Leu His Asn His Tyr Thr Gln Lys Ser Leu Ser Leu Ser
        435                 440                 445

Leu Gly Lys
    450

<210> SEQ ID NO 227
<211> LENGTH: 648
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 227
gaaattgtga tgacgcagtc tccagtcacc ctgtttgtgt ctccagggga aagagccacc      60
ctctcctgca gggccagtca gagtgtgaac accaacttag cctggtacca acagcaacct     120
ggccaggctc ccaggctcct catccatgga gcatccacca ggcccactgg tgtcccagcc     180
aggttcagtg gcagtgggtc tgggacagag ttcactctca tcatcagcag cctgcagtct     240
gaagattttg cagtttatta ctgtcagcaa tataataatt ggcccccgtg gacgttcggc     300
caagggacca aggtggaaat caaacgaact gtggctgcac catctgtctt catcttcccg     360
ccatctgatg agcagttgaa atctggaact gcctctgttg tgtgcctgct gaataacttc     420
tatcccagag aggccaaagt acagtggaag gtggataacg ccctccaatc gggtaactcc     480
caggagagtg tcacagagca ggacagcaag gacagcacct acagcctcag cagcaccctg     540
acgctgagca agcagacta cgagaaacac aaagtctacg cctgcgaagt cacccatcag     600
ggcctgagct cgcccgtcac aaagagcttc aacaggggag agtgttag                  648

<210> SEQ ID NO 228
<211> LENGTH: 215
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 228

Glu Ile Val Met Thr Gln Ser Pro Val Thr Leu Phe Val Ser Pro Gly
1               5                   10                  15

Glu Arg Ala Thr Leu Ser Cys Arg Ala Ser Gln Ser Val Asn Thr Asn
            20                  25                  30

Leu Ala Trp Tyr Gln Gln Gln Pro Gly Gln Ala Pro Arg Leu Leu Ile
        35                  40                  45

His Gly Ala Ser Thr Arg Pro Thr Gly Val Pro Ala Arg Phe Ser Gly
    50                  55                  60

Ser Gly Ser Gly Thr Glu Phe Thr Leu Ile Ile Ser Ser Leu Gln Ser
65                  70                  75                  80

Glu Asp Phe Ala Val Tyr Tyr Cys Gln Gln Tyr Asn Asn Trp Pro Pro
                85                  90                  95

Trp Thr Phe Gly Gln Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser

-continued

```
145               150               155               160

Gln Glu Ser Val Thr Glu Gln Asp Ser Lys Asp Ser Thr Tyr Ser Leu
                  165               170               175

Ser Ser Thr Leu Thr Leu Ser Lys Ala Asp Tyr Glu Lys His Lys Val
                  180               185               190

Tyr Ala Cys Glu Val Thr His Gln Gly Leu Ser Ser Pro Val Thr Lys
                  195               200               205

Ser Phe Asn Arg Gly Glu Cys
    210               215

<210> SEQ ID NO 229
<211> LENGTH: 396
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 229
gaaatacagc tggtcgagtc tgggggaggc gtggtacagc ctggggggtc cctgagactc        60
tcctgtgtag cctctggatt cacctttgat gattatgcca tgtactgggt ccgacaagtt       120
ccagggaagg atctggagtg ggtctctctt ataagtgggg atggtgatat cacatattat       180
gtagactctg tgaagggccg attcaccgtc tccagagaca acaacaaaaa ctccctgtat       240
ctgcaaatga aaagtctgag agttgaggac accgccttgt attactgtgc aaaagatatg       300
atatattacg cttcttggag tggttacggg tcgtccgact actactacta cgttatggac       360
gtctggggcc aagggaccac ggtcaccgtc tcctca                                396

<210> SEQ ID NO 230
<211> LENGTH: 132
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 230

Glu Ile Gln Leu Val Glu Ser Gly Gly Gly Val Val Gln Pro Gly Gly
1               5               10               15

Ser Leu Arg Leu Ser Cys Val Ala Ser Gly Phe Thr Phe Asp Asp Tyr
            20               25               30

Ala Met Tyr Trp Val Arg Gln Val Pro Gly Lys Asp Leu Glu Trp Val
            35               40               45

Ser Leu Ile Ser Gly Asp Gly Asp Ile Thr Tyr Tyr Val Asp Ser Val
        50               55               60

Lys Gly Arg Phe Thr Val Ser Arg Asp Asn Asn Lys Asn Ser Leu Tyr
65               70               75               80

Leu Gln Met Lys Ser Leu Arg Val Glu Asp Thr Ala Leu Tyr Tyr Cys
                85               90               95

Ala Lys Asp Met Ile Tyr Tyr Ala Ser Trp Ser Gly Tyr Gly Ser Ser
            100               105               110

Asp Tyr Tyr Tyr Tyr Val Met Asp Val Trp Gly Gln Gly Thr Thr Val
            115               120               125

Thr Val Ser Ser
    130

<210> SEQ ID NO 231
```

-continued

```
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 231
ggattcacct ttgatgatta tgcc                                              24

<210> SEQ ID NO 232
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 232

Gly Phe Thr Phe Asp Asp Tyr Ala
1               5

<210> SEQ ID NO 233
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 233
ataagtgggg atggtgatat caca                                              24

<210> SEQ ID NO 234
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 234

Ile Ser Gly Asp Gly Asp Ile Thr
1               5

<210> SEQ ID NO 235
<211> LENGTH: 75
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 235
gcaaaagata tgatatatta cgcttcttgg agtggttacg ggtcgtccga ctactactac     60
tacgttatgg acgtc                                                        75

<210> SEQ ID NO 236
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 236

Ala Lys Asp Met Ile Tyr Tyr Ala Ser Trp Ser Gly Tyr Gly Ser Ser
```

-continued

```
1               5                   10                  15

Asp Tyr Tyr Tyr Tyr Val Met Asp Val
                20                  25
```

```
<210> SEQ ID NO 237
<211> LENGTH: 324
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 237
gacatccaga tgacccagtc tccatcctcc ctgtctgcat ctgtaggaga cagagtcacc      60
atcacttgcc gggcaagtca gagcattagc agctatttaa attggtatca gcagaaaccc     120
gggaaagccc ctaaactcct gatctatgct gcatccagtt tgcaaagtgg ggtcccatca     180
aggttcagtg gcagtggatc tgggacagat ttcactctca ccatcagcag tctgcaacct     240
gaagattttg caacttacta ctgtcaacag agttacagta tgtttccgat taccttcggc     300
caagggacac gactggagat taaa                                            324
```

```
<210> SEQ ID NO 238
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 238

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
                20                  25                  30

Leu Asn Trp Tyr Gln Gln Lys Pro Gly Lys Ala Pro Lys Leu Leu Ile
            35                  40                  45

Tyr Ala Ala Ser Ser Leu Gln Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Met Phe Pro
                85                  90                  95

Ile Thr Phe Gly Gln Gly Thr Arg Leu Glu Ile Lys
            100                 105
```

```
<210> SEQ ID NO 239
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 239
cagagcatta gcagctat                                                    18
```

```
<210> SEQ ID NO 240
<211> LENGTH: 6
<212> TYPE: PRT
<213> ORGANISM: Artificial Sequence
<220> FEATURE:
```

-continued

<223> OTHER INFORMATION: Description of Artificial Sequence: Synthetic
      peptide

<400> SEQUENCE: 240

Gln Ser Ile Ser Ser Tyr
1               5

<210> SEQ ID NO 241
<211> LENGTH: 9
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 241 gctgcatcc                                                                 9

<210> SEQ ID NO 242
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 242

Ala Ala Ser
1

<210> SEQ ID NO 243
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 243
caacagagtt acagtatgtt tccgattacc                                          30

<210> SEQ ID NO 244
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 244

Gln Gln Ser Tyr Ser Met Phe Pro Ile Thr
1               5                   10

<210> SEQ ID NO 245
<211> LENGTH: 1389
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 245
gaaatacagc tggtcgagtc tggggggaggc gtggtacagc ctggggggtc cctgagactc        60
tcctgtgtag cctctggatt caccttttgat gattatgcca tgtactgggt ccgacaagtt       120
ccagggaagg atctggagtg ggtctctctt ataagtgggg atggtgatat cacatattat       180

-continued

```
gtagactctg tgaagggccg attcaccgtc tccagagaca acaacaaaaa ctccctgtat       240
ctgcaaatga aaagtctgag agttgaggac accgccttgt attactgtgc aaaagatatg       300
atatattacg cttcttggag tggttacggg tcgtccgact actactacta cgttatggac       360
gtctggggcc aagggaccac ggtcaccgtc tcctcagcca aaacaacagc cccatcggtc       420
tatccactgg cccctgtgtg tggagataca actggctcct cggtgactct aggatgcctg       480
gtcaagggtt atttccctga gccagtgacc ttgacctgga actctggatc cctgtccagt       540
ggtgtgcaca ccttcccagc tgtcctgcag tctgacctct acaccctcag cagctcagtg       600
actgtaacct cgagcaccctg gcccagccag tccatcacct gcaatgtggc caccccggca       660
agcagcacca aggtggacaa gaaaattgag cccagagggc cacaatcaa gccctgtcct       720 ccatgcaaat gcccagcacc taacctcttg ggtggaccat ccgtcttcat cttccctcca       780
aagatcaagg atgtactcat gatctccctg agccccatag tcacatgtgt ggtggtggat       840
gtgagcgagg atgacccaga tgtccagatc agctggtttg tgaacaacgt ggaagtacac       900
acagctcaga cacaaaccca tagagaggat tacaacagta ctctccgggt ggtcagtgcc       960
ctccccatcc agcaccagga ctggatgagt ggcaaggagt tcaaatgcaa ggtcaacaac       1020
aaagacctcc cagcgcccat cgagagaacc atctcaaaac ccaaagggtc agtaagagct       1080
ccacaggtat atgtcttgcc tccaccagaa gaagagatga ctaagaaaca ggtcactctg       1140
acctgcatgg tcacagactt catgcctgaa gacatttacg tggagtggac caacaacggg       1200
aaaacagagc taaactacaa gaacactgaa ccagtcctgg actctgatgg ttcttacttc       1260
atgtacagca gctgagagt ggaaaagaag aactgggtgg aaagaaatag ctactcctgt       1320
tcagtggtcc acgagggtct gcacaatcac cacacgacta gagcttctc ccggactccg       1380 ggtaaatga                                                              1389
```

<210> SEQ ID NO 246
<211> LENGTH: 462
<212> TYPE: PRT
<213> ORGANISM: Artificial Sequence
<220> FEATURE:
<223> OTHER INFORMATION: Description of Artificial Sequence: Synthetic
     polypeptide

<400> SEQUENCE: 246

```
Glu Ile Gln Leu Val Glu Ser Gly Gly Gly Val Val Gln Pro Gly Gly
1               5                   10                  15

Ser Leu Arg Leu Ser Cys Val Ala Ser Gly Phe Thr Phe Asp Asp Tyr
            20                  25                  30

Ala Met Tyr Trp Val Arg Gln Val Pro Gly Lys Asp Leu Glu Trp Val
        35                  40                  45

Ser Leu Ile Ser Gly Asp Gly Asp Ile Thr Tyr Tyr Val Asp Ser Val
    50                  55                  60

Lys Gly Arg Phe Thr Val Ser Arg Asp Asn Asn Lys Asn Ser Leu Tyr
65                  70                  75                  80

Leu Gln Met Lys Ser Leu Arg Val Glu Asp Thr Ala Leu Tyr Tyr Cys
                85                  90                  95

Ala Lys Asp Met Ile Tyr Tyr Ala Ser Trp Ser Gly Tyr Gly Ser Ser
            100                 105                 110

Asp Tyr Tyr Tyr Tyr Val Met Asp Val Trp Gly Gln Gly Thr Thr Val
        115                 120                 125

Thr Val Ser Ser Ala Lys Thr Thr Ala Pro Ser Val Tyr Pro Leu Ala
    130                 135                 140
```

```
Pro Val Cys Gly Asp Thr Thr Gly Ser Ser Val Thr Leu Gly Cys Leu
145                 150                 155                 160

Val Lys Gly Tyr Phe Pro Glu Pro Val Thr Leu Thr Trp Asn Ser Gly
                165                 170                 175

Ser Leu Ser Ser Gly Val His Thr Phe Pro Ala Val Leu Gln Ser Asp
                180                 185                 190

Leu Tyr Thr Leu Ser Ser Ser Val Thr Val Thr Ser Ser Thr Trp Pro
            195                 200                 205

Ser Gln Ser Ile Thr Cys Asn Val Ala His Pro Ala Ser Ser Thr Lys
    210                 215                 220

Val Asp Lys Lys Ile Glu Pro Arg Gly Pro Thr Ile Lys Pro Cys Pro
225                 230                 235                 240

Pro Cys Lys Cys Pro Ala Pro Asn Leu Leu Gly Gly Pro Ser Val Phe
                245                 250                 255

Ile Phe Pro Pro Lys Ile Lys Asp Val Leu Met Ile Ser Leu Ser Pro
                260                 265                 270

Ile Val Thr Cys Val Val Val Asp Val Ser Glu Asp Asp Pro Asp Val
            275                 280                 285

Gln Ile Ser Trp Phe Val Asn Asn Val Glu Val His Thr Ala Gln Thr
    290                 295                 300

Gln Thr His Arg Glu Asp Tyr Asn Ser Thr Leu Arg Val Val Ser Ala
305                 310                 315                 320

Leu Pro Ile Gln His Gln Asp Trp Met Ser Gly Lys Glu Phe Lys Cys
                325                 330                 335

Lys Val Asn Asn Lys Asp Leu Pro Ala Pro Ile Glu Arg Thr Ile Ser
                340                 345                 350

Lys Pro Lys Gly Ser Val Arg Ala Pro Gln Val Tyr Val Leu Pro Pro
            355                 360                 365

Pro Glu Glu Glu Met Thr Lys Lys Gln Val Thr Leu Thr Cys Met Val
    370                 375                 380

Thr Asp Phe Met Pro Glu Asp Ile Tyr Val Glu Trp Thr Asn Asn Gly
385                 390                 395                 400

Lys Thr Glu Leu Asn Tyr Lys Asn Thr Glu Pro Val Leu Asp Ser Asp
                405                 410                 415

Gly Ser Tyr Phe Met Tyr Ser Lys Leu Arg Val Glu Lys Lys Asn Trp
                420                 425                 430

Val Glu Arg Asn Ser Tyr Ser Cys Ser Val Val His Glu Gly Leu His
            435                 440                 445

Asn His His Thr Thr Lys Ser Phe Ser Arg Thr Pro Gly Lys
    450                 455                 460
```

```
<210> SEQ ID NO 247
<211> LENGTH: 648
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 247
gacatccaga tgacccagtc tccatcctcc ctgtctgcat ctgtaggaga cagagtcacc      60
atcacttgcc gggcaagtca gagcattagc agctatttaa attggtatca gcagaaaccc     120
gggaaagccc ctaaactcct gatctatgct gcatccagtt tgcaaagtgg ggtcccatca     180
aggttcagtg gcagtggatc tgggacagat ttcactctca ccatcagcag tctgcaacct     240
```

-continued

```
gaagatttg  caacttacta  ctgtcaacag  agttacagta  tgtttccgat  taccttcggc      300
caagggacac  gactggagat  taaacgagct  gatgctgcac  caactgtatc  catcttccca      360
ccatccagtg  agcagttaac  atctggaggt  gcctcagtcg  tgtgcttctt  gaacaacttc      420 tacccccaaag  acatcaatgt  caagtggaag  attgatggca  gtgaacgaca  aaatggcgtc      480
ctgaacagtt  ggactgatca  ggacagcaaa  gacagcacct  acagcatgag  cagcaccctc      540
acgttgacca  aggacgagta  tgaacgacat  aacagctata  cctgtgaggc  cactcacaag      600
acatcaactt  cacccattgt  caagagcttc  aacaggggag  agtgttga                   648
```

<210> SEQ ID NO 248
<211> LENGTH: 215
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 248

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Met Phe Pro
                85                  90                  95

Ile Thr Phe Gly Gln Gly Thr Arg Leu Glu Ile Lys Arg Ala Asp Ala
            100                 105                 110

Ala Pro Thr Val Ser Ile Phe Pro Pro Ser Ser Glu Gln Leu Thr Ser
        115                 120                 125

Gly Gly Ala Ser Val Val Cys Phe Leu Asn Asn Phe Tyr Pro Lys Asp
    130                 135                 140

Ile Asn Val Lys Trp Lys Ile Asp Gly Ser Glu Arg Gln Asn Gly Val
145                 150                 155                 160

Leu Asn Ser Trp Thr Asp Gln Asp Ser Lys Asp Ser Thr Tyr Ser Met
                165                 170                 175

Ser Ser Thr Leu Thr Leu Thr Lys Asp Glu Tyr Glu Arg His Asn Ser
            180                 185                 190

Tyr Thr Cys Glu Ala Thr His Lys Thr Ser Thr Ser Pro Ile Val Lys
        195                 200                 205

Ser Phe Asn Arg Gly Glu Cys
    210                 215
```

<210> SEQ ID NO 249
<211> LENGTH: 381
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 249

```
gaagtgcagc tggtggagtc tgggggaggc gtggtacagc ctggggggtc cctgagactc      60
tcctgtgcag tctctggatt caccttgat gattatgcca tgcactgggt ccgtcaagct      120
ccagggaagg gtctggagtg ggtctctctt attagtgggg atggtggtag tacacactat      180
gcagactctg tgaagggccg attcaccatc tccagagaca acagcaaaaa ctccctgtat      240
ctgcaaatga acagtctgag aactggggac accgccttgt attactgtgc aaaagacatg      300
atttttgcag tggttattac tgactaccac tactacggta tggacgtctg gggccaaggg      360
accacggtca ccgtctcctc a                                               381
```

```
<210> SEQ ID NO 250
<211> LENGTH: 127
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 250

Glu Val Gln Leu Val Glu Ser Gly Gly Gly Val Val Gln Pro Gly Gly
1               5                   10                  15

Ser Leu Arg Leu Ser Cys Ala Val Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Leu Ile Ser Gly Asp Gly Gly Ser Thr His Tyr Ala Asp Ser Val
    50                  55                  60

Lys Gly Arg Phe Thr Ile Ser Arg Asp Asn Ser Lys Asn Ser Leu Tyr
65                  70                  75                  80

Leu Gln Met Asn Ser Leu Arg Thr Gly Asp Thr Ala Leu Tyr Tyr Cys
                85                  90                  95

Ala Lys Asp Met Ile Phe Ala Val Val Ile Thr Asp Tyr His Tyr Tyr
            100                 105                 110

Gly Met Asp Val Trp Gly Gln Gly Thr Thr Val Thr Val Ser Ser
        115                 120                 125
```

```
<210> SEQ ID NO 251
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 251
ggattcacct ttgatgatta tgcc                                             24
```

```
<210> SEQ ID NO 252
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 252

Gly Phe Thr Phe Asp Asp Tyr Ala
1               5
```

```
<210> SEQ ID NO 253
<211> LENGTH: 24
```

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 253
attagtgggg atggtggtag taca                                            24

<210> SEQ ID NO 254
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 254

Ile Ser Gly Asp Gly Gly Ser Thr
1               5

<210> SEQ ID NO 255
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 255
gcaaaagaca tgatttttgc agtggttatt actgactacc actactacgg tatggacgtc    60

<210> SEQ ID NO 256
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 256

Ala Lys Asp Met Ile Phe Ala Val Val Ile Thr Asp Tyr His Tyr Tyr
1               5                   10                  15

Gly Met Asp Val
            20

<210> SEQ ID NO 257
<211> LENGTH: 324
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 257
gacatccaga tgacccagtc tccatcctcc ctgtctgcat ctgtaggaga cagagtcacc    60
atcacttgcc gggcaagtca gagcattagc agctatttaa attggtatca gcagaaacca    120
gggaaagccc ctaagctcct gatctatgct gcatccagtt tgcaaagtgg ggtcccgtca    180
aggttcagtg gcagtggatc tgggacagat ttcactctca ccatcagcag tctgcaacct    240
gaagattttg caacttacta ctgtcaacag agttacagta cccctccgat caccttcggc    300
caagggacac gactggagat taaa                                           324

<210> SEQ ID NO 258
```

<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 258

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Pro
                85                  90                  95

Ile Thr Phe Gly Gln Gly Thr Arg Leu Glu Ile Lys
            100                 105
```

<210> SEQ ID NO 259
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 259

```
cagagcatta gcagctat                                             18
```

<210> SEQ ID NO 260
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 260

```
Gln Ser Ile Ser Ser Tyr
1               5
```

<210> SEQ ID NO 261
<211> LENGTH: 9
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 261

```
gctgcatcc                                                        9
```

<210> SEQ ID NO 262
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 262

Ala Ala Ser
1

<210> SEQ ID NO 263
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 263
caacagagtt acagtaccccc tccgatcacc                                            30

<210> SEQ ID NO 264
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 264

Gln Gln Ser Tyr Ser Thr Pro Pro Ile Thr
1               5                   10

<210> SEQ ID NO 265
<211> LENGTH: 1362
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 265
gaagtgcagc tggtggagtc tgggggaggc gtggtacagc ctggggggtc cctgagactc     60
tcctgtgcag tctctggatt caccttttgat gattatgcca tgcactgggt ccgtcaagct   120
ccagggaagg gtctggagtg ggtctctctt attagtgggg atggtggtag tacacactat   180
gcagactctg tgaagggccg attcaccatc tccagagaca acagcaaaaa ctccctgtat   240
ctgcaaatga acagtctgag aactggggac accgccttgt attactgtgc aaaagacatg   300
atttttgcag tggttattac tgactaccac tactacggta tggacgtctg gggccaaggg   360
accacggtca ccgtctcctc agcctccacc aagggcccat cggtcttccc cctggcgccc   420
tgctccagga gcacctccga gagcacagcc gccctgggct gcctggtcaa ggactacttc   480
cccgaaccgg tgacggtgtc gtggaactca ggcgccctga ccagcggcgt gcacaccttc   540
ccggctgtcc tacagtcctc aggactctac tccctcagca gcgtggtgac cgtgccctcc   600
agcagcttgg gcacgaagac ctacacctgc aacgtagatc acaagcccag caacaccaag   660
gtggacaaga gagttgagtc caaatatggt cccccatgcc caccgtgccc agcaccacct   720
gtggcaggac catcagtctt cctgttcccc ccaaaaccca aggacactct catgatctcc   780
cggacccctg aggtcacgtg cgtggtggtg gacgtgagcc aggaagaccc cgaggtccag   840
ttcaactggt acgtggatgg cgtggaggtg cataatgcca agacaaagcc gcgggaggag   900
cagttcaaca gcacgtaccg tgtggtcagc gtcctcaccg tcctgcacca ggactggctg   960
aacggcaagg agtacaagtg caaggtctcc aacaaaggcc tcccgtcctc catcgagaaa  1020
accatctcca aagccaaagg gcagccccga gagccacagg tgtacaccct gcccccatcc  1080
```

-continued

```
caggaggaga tgaccaagaa ccaggtcagc ctgacctgcc tggtcaaagg cttctacccc   1140
agcgacatcg ccgtggagtg gagagcaat gggcagccgg agaacaacta caagaccacg   1200
cctcccgtgc tggactccga cggctccttc ttcctctaca gcaggctcac cgtggacaag   1260
agcaggtggc aggagggaa tgtcttctca tgctccgtga tgcatgaggc tctgcacaac   1320
cactacacac agaagtccct ctccctgtct ctgggtaaat ga                     1362
```

<210> SEQ ID NO 266
<211> LENGTH: 453
<212> TYPE: PRT
<213> ORGANISM: Artificial Sequence
<220> FEATURE:
<223> OTHER INFORMATION: Description of Artificial Sequence: Synthetic
     polypeptide

<400> SEQUENCE: 266

```
Glu Val Gln Leu Val Glu Ser Gly Gly Gly Val Val Gln Pro Gly Gly
1               5                   10                  15

Ser Leu Arg Leu Ser Cys Ala Val Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Leu Ile Ser Gly Asp Gly Gly Ser Thr His Tyr Ala Asp Ser Val
    50                  55                  60

Lys Gly Arg Phe Thr Ile Ser Arg Asp Asn Ser Lys Asn Ser Leu Tyr
65                  70                  75                  80

Leu Gln Met Asn Ser Leu Arg Thr Gly Asp Thr Ala Leu Tyr Tyr Cys
                85                  90                  95

Ala Lys Asp Met Ile Phe Ala Val Val Ile Thr Asp Tyr His Tyr Tyr
            100                 105                 110

Gly Met Asp Val Trp Gly Gln Gly Thr Thr Val Thr Val Ser Ser Ala
        115                 120                 125

Ser Thr Lys Gly Pro Ser Val Phe Pro Leu Ala Pro Cys Ser Arg Ser
    130                 135                 140

Thr Ser Glu Ser Thr Ala Ala Leu Gly Cys Leu Val Lys Asp Tyr Phe
145                 150                 155                 160

Pro Glu Pro Val Thr Val Ser Trp Asn Ser Gly Ala Leu Thr Ser Gly
                165                 170                 175

Val His Thr Phe Pro Ala Val Leu Gln Ser Ser Gly Leu Tyr Ser Leu
            180                 185                 190

Ser Ser Val Val Thr Val Pro Ser Ser Ser Leu Gly Thr Lys Thr Tyr
        195                 200                 205

Thr Cys Asn Val Asp His Lys Pro Ser Asn Thr Lys Val Asp Lys Arg
    210                 215                 220

Val Glu Ser Lys Tyr Gly Pro Pro Cys Pro Pro Cys Pro Ala Pro Pro
225                 230                 235                 240

Val Ala Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser Gln Glu Asp Pro Glu Val Gln Phe Asn Trp Tyr Val Asp Gly Val
        275                 280                 285

Glu Val His Asn Ala Lys Thr Lys Pro Arg Glu Glu Gln Phe Asn Ser
    290                 295                 300

Thr Tyr Arg Val Val Ser Val Leu Thr Val Leu His Gln Asp Trp Leu
```

```
305            310            315            320

Asn Gly Lys Glu Tyr Lys Cys Lys Val Ser Asn Lys Gly Leu Pro Ser
            325            330            335

Ser Ile Glu Lys Thr Ile Ser Lys Ala Lys Gly Gln Pro Arg Glu Pro
            340            345            350

Gln Val Tyr Thr Leu Pro Pro Ser Gln Glu Glu Met Thr Lys Asn Gln
            355            360            365

Val Ser Leu Thr Cys Leu Val Lys Gly Phe Tyr Pro Ser Asp Ile Ala
    370            375            380

Val Glu Trp Glu Ser Asn Gly Gln Pro Glu Asn Asn Tyr Lys Thr Thr
385            390            395            400

Pro Pro Val Leu Asp Ser Asp Gly Ser Phe Phe Leu Tyr Ser Arg Leu
            405            410            415

Thr Val Asp Lys Ser Arg Trp Gln Glu Gly Asn Val Phe Ser Cys Ser
            420            425            430

Val Met His Glu Ala Leu His Asn His Tyr Thr Gln Lys Ser Leu Ser
    435            440            445

Leu Ser Leu Gly Lys
    450
```

<210> SEQ ID NO 267
<211> LENGTH: 648
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 267

```
gacatccaga tgacccagtc tccatcctcc ctgtctgcat ctgtaggaga cagagtcacc      60
atcacttgcc gggcaagtca gagcattagc agctatttaa attggtatca gcagaaacca     120
gggaaagccc ctaagctcct gatctatgct gcatccagtt tgcaaagtgg ggtcccgtca     180
aggttcagtg gcagtggatc tgggacagat ttcactctca ccatcagcag tctgcaacct     240
gaagattttg caacttacta ctgtcaacag agttacagta cccctccgat caccttcggc     300
caagggacac gactggagat taaacgaact gtggctgcac catctgtctt catcttcccg     360
ccatctgatg agcagttgaa atctggaact gcctctgttg tgtgcctgct gaataacttc     420
tatcccagag aggccaaagt acagtggaag gtggataacg ccctccaatc gggtaactcc     480
caggagagtg tcacagagca ggacagcaag gacagcacct acagcctcag cagcaccctg     540
acgctgagca aagcagacta cgagaaacac aaagtctacg cctgcgaagt cacccatcag     600
ggcctgagct cgcccgtcac aaagagcttc aacaggggag agtgttag                  648
```

<210> SEQ ID NO 268
<211> LENGTH: 215
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 268

```
Asp Ile Gln Met Thr Gln Ser Pro Ser Ser Leu Ser Ala Ser Val Gly
1               5               10              15

Asp Arg Val Thr Ile Thr Cys Arg Ala Ser Gln Ser Ile Ser Ser Tyr
            20              25              30
```

-continued

```
Leu Asn Trp Tyr Gln Gln Lys Pro Gly Lys Ala Pro Lys Leu Leu Ile
    35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Pro
                85                  90                  95

Ile Thr Phe Gly Gln Gly Thr Arg Leu Glu Ile Lys Arg Thr Val Ala
                100                 105                 110

Ala Pro Ser Val Phe Ile Phe Pro Pro Ser Asp Glu Gln Leu Lys Ser
                115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
                180                 185                 190

Tyr Ala Cys Glu Val Thr His Gln Gly Leu Ser Ser Pro Val Thr Lys
                195                 200                 205

Ser Phe Asn Arg Gly Glu Cys
    210                 215

<210> SEQ ID NO 269
<211> LENGTH: 9
<212> TYPE: PRT
<213> ORGANISM: Homo sapiens

<400> SEQUENCE: 269

Ser Leu Leu Met Trp Ile Thr Gln Cys
1               5

<210> SEQ ID NO 270
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 270

Ser Leu Met Met Trp Ile Thr Gln Val
1               5

<210> SEQ ID NO 271
<211> LENGTH: 180
<212> TYPE: PRT
<213> ORGANISM: Homo sapiens

<400> SEQUENCE: 271

Met Gln Ala Glu Gly Arg Gly Thr Gly Gly Ser Thr Gly Asp Ala Asp
1               5                   10                  15

Gly Pro Gly Gly Pro Gly Ile Pro Asp Gly Pro Gly Gly Asn Ala Gly
                20                  25                  30

Gly Pro Gly Glu Ala Gly Ala Thr Gly Gly Arg Gly Pro Arg Gly Ala
    35                  40                  45

Gly Ala Ala Arg Ala Ser Gly Pro Gly Gly Gly Ala Pro Arg Gly Pro
```

-continued

```
        50                  55                  60

His Gly Gly Ala Ala Ser Gly Leu Asn Gly Cys Cys Arg Cys Gly Ala
65                  70                  75                  80

Arg Gly Pro Glu Ser Arg Leu Leu Glu Phe Tyr Leu Ala Met Pro Phe
                85                  90                  95

Ala Thr Pro Met Glu Ala Glu Leu Ala Arg Arg Ser Leu Ala Gln Asp
                100                 105                 110

Ala Pro Pro Leu Pro Val Pro Gly Val Leu Leu Lys Glu Phe Thr Val
            115                 120                 125

Ser Gly Asn Ile Leu Thr Ile Arg Leu Thr Ala Ala Asp His Arg Gln
            130                 135                 140

Leu Gln Leu Ser Ile Ser Ser Cys Leu Gln Gln Leu Ser Leu Leu Met
145                 150                 155                 160

Trp Ile Thr Gln Cys Phe Leu Pro Val Phe Leu Ala Gln Pro Pro Ser
                165                 170                 175

Gly Gln Arg Arg
            180

<210> SEQ ID NO 272
<211> LENGTH: 447
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 272

Ser Leu Leu Met Trp Ile Thr Gln Val Gly Cys Gly Gly Ser Gly Gly
1                   5                   10                  15

Gly Gly Ser Gly Gly Gly Gly Ser Ile Gln Arg Thr Pro Lys Ile Gln
                20                  25                  30

Val Tyr Ser Arg His Pro Ala Glu Asn Gly Lys Ser Asn Phe Leu Asn
            35                  40                  45

Cys Tyr Val Ser Gly Phe His Pro Ser Asp Ile Glu Val Asp Leu Leu
        50                  55                  60

Lys Asn Gly Glu Arg Ile Glu Lys Val Glu His Ser Asp Leu Ser Phe
65                  70                  75                  80

Ser Lys Asp Trp Ser Phe Tyr Leu Leu Tyr Tyr Thr Glu Phe Thr Pro
                85                  90                  95

Thr Glu Lys Asp Glu Tyr Ala Cys Arg Val Asn His Val Thr Leu Ser
                100                 105                 110

Gln Pro Lys Ile Val Lys Trp Asp Arg Asp Met Gly Gly Gly Gly Ser
            115                 120                 125

Gly Gly Gly Gly Ser Gly Gly Gly Gly Ser Gly Gly Gly Gly Ser Gly
            130                 135                 140

Ser His Ser Met Arg Tyr Phe Phe Thr Ser Val Ser Arg Pro Gly Arg
145                 150                 155                 160

Gly Glu Pro Arg Phe Ile Ala Val Gly Tyr Val Asp Asp Thr Gln Phe
                165                 170                 175

Val Arg Phe Asp Ser Asp Ala Ala Ser Gln Arg Met Glu Pro Arg Ala
                180                 185                 190

Pro Trp Ile Glu Gln Glu Gly Pro Glu Tyr Trp Asp Gly Glu Thr Arg
            195                 200                 205

Lys Val Lys Ala His Ser Gln Thr His Arg Val Asp Leu Gly Thr Leu
            210                 215                 220
```

```
Arg Gly Cys Tyr Asn Gln Ser Glu Ala Gly Ser His Thr Val Gln Arg
225                 230                 235                 240

Met Tyr Gly Cys Asp Val Gly Ser Asp Trp Arg Phe Leu Arg Gly Tyr
                245                 250                 255

His Gln Tyr Ala Tyr Asp Gly Lys Asp Tyr Ile Ala Leu Lys Glu Asp
                260                 265                 270

Leu Arg Ser Trp Thr Ala Ala Asp Met Ala Ala Gln Thr Thr Lys His
            275                 280                 285

Lys Trp Glu Ala Ala His Val Ala Glu Gln Leu Arg Ala Tyr Leu Glu
        290                 295                 300

Gly Thr Cys Val Glu Trp Leu Arg Arg Tyr Leu Glu Asn Gly Lys Glu
305                 310                 315                 320

Thr Leu Gln Arg Thr Asp Ala Pro Lys Thr His Met Thr His His Ala
                325                 330                 335

Val Ser Asp His Glu Ala Thr Leu Arg Cys Trp Ala Leu Ser Phe Tyr
                340                 345                 350

Pro Ala Glu Ile Thr Leu Thr Trp Gln Arg Asp Gly Glu Asp Gln Thr
                355                 360                 365

Gln Asp Thr Glu Leu Val Glu Thr Arg Pro Ala Gly Asp Gly Thr Phe
        370                 375                 380

Gln Lys Trp Ala Ala Val Val Val Pro Ser Gly Gln Glu Gln Arg Tyr
385                 390                 395                 400

Thr Cys His Val Gln His Glu Gly Leu Pro Lys Pro Leu Thr Leu Arg
                405                 410                 415

Trp Glu Pro Glu Gln Lys Leu Ile Ser Glu Glu Asp Leu Gly Gly Glu
                420                 425                 430

Gln Lys Leu Ile Ser Glu Glu Asp Leu His His His His His His
        435                 440                 445

<210> SEQ ID NO 273
<211> LENGTH: 9
<212> TYPE: PRT
<213> ORGANISM: Unknown
<220> FEATURE:
<223> OTHER INFORMATION: Description of Unknown:
      BCL9L off-target sequence

<400> SEQUENCE: 273

Ser Leu Leu Met Trp Leu Thr Pro Leu
1               5

<210> SEQ ID NO 274
<211> LENGTH: 9
<212> TYPE: PRT
<213> ORGANISM: Unknown
<220> FEATURE:
<223> OTHER INFORMATION: Description of Unknown:
      GRID1 off-target sequence

<400> SEQUENCE: 274

Trp Leu Leu Pro Trp Ile Cys Gln Cys
1               5

<210> SEQ ID NO 275
<211> LENGTH: 9
<212> TYPE: PRT
<213> ORGANISM: Unknown
<220> FEATURE:
<223> OTHER INFORMATION: Description of Unknown:
      EARS2 off-target sequence
```

```
<400> SEQUENCE: 275

Ser Leu Leu Asp Ile Ile Thr Asn Cys
1               5

<210> SEQ ID NO 276
<211> LENGTH: 9
<212> TYPE: PRT
<213> ORGANISM: Unknown
<220> FEATURE:
<223> OTHER INFORMATION: Description of Unknown:
      ZDHHC1 off-target sequence

<400> SEQUENCE: 276

Leu Leu Ala Met Trp Gly Pro Gln Ala
1               5

<210> SEQ ID NO 277
<211> LENGTH: 9
<212> TYPE: PRT
<213> ORGANISM: Unknown
<220> FEATURE:
<223> OTHER INFORMATION: Description of Unknown:
      ITCH off-target sequence

<400> SEQUENCE: 277

Lys Gln Ile Met Trp Phe Trp Gln Phe
1               5

<210> SEQ ID NO 278
<211> LENGTH: 9
<212> TYPE: PRT
<213> ORGANISM: Unknown
<220> FEATURE:
<223> OTHER INFORMATION: Description of Unknown:
      MAGEH1 off-target sequence

<400> SEQUENCE: 278

Ser Leu Leu Met Ser Ile Leu Ala Leu
1               5

<210> SEQ ID NO 279
<211> LENGTH: 9
<212> TYPE: PRT
<213> ORGANISM: Unknown
<220> FEATURE:
<223> OTHER INFORMATION: Description of Unknown:
      FBXL22 off-target sequence

<400> SEQUENCE: 279

Leu Leu Thr Met His Ile Thr Gln Leu
1               5

<210> SEQ ID NO 280
<211> LENGTH: 9
<212> TYPE: PRT
<213> ORGANISM: Unknown
<220> FEATURE:
<223> OTHER INFORMATION: Description of Unknown:
      URB1 off-target sequence

<400> SEQUENCE: 280

Ser Leu Leu Thr Trp Ile Leu His Ile
1               5

<210> SEQ ID NO 281
<211> LENGTH: 9
<212> TYPE: PRT
```

<213> ORGANISM: Artificial Sequence
<220> FEATURE:
<223> OTHER INFORMATION: Description of Artificial Sequence: Synthetic
      peptide

<400> SEQUENCE: 281

Ser Leu Leu Met Trp Ile Thr Gln Val
1               5

<210> SEQ ID NO 282
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 282

Ala Leu Leu Met Trp Ile Thr Gln Val
1               5

<210> SEQ ID NO 283
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 283

Ser Ala Leu Met Trp Ile Thr Gln Val
1               5

<210> SEQ ID NO 284
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 284

Ser Leu Ala Met Trp Ile Thr Gln Val
1               5

<210> SEQ ID NO 285
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 285

Ser Leu Leu Ala Trp Ile Thr Gln Val
1               5

<210> SEQ ID NO 286
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 286

Ser Leu Leu Met Ala Ile Thr Gln Val
1               5

<210> SEQ ID NO 287
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 287

Ser Leu Leu Met Trp Ala Thr Gln Val
1               5

<210> SEQ ID NO 288
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 288

Ser Leu Leu Met Trp Ile Ala Gln Val
1               5

<210> SEQ ID NO 289
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 289

Ser Leu Leu Met Trp Ile Thr Ala Val
1               5

<210> SEQ ID NO 290
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 290

Ser Leu Leu Met Trp Ile Thr Gln Ala
1               5

<210> SEQ ID NO 291
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 291

Ser Leu Leu Met Trp Ile Thr Gln Val
1               5

<210> SEQ ID NO 292
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 292

His His His His His His
1               5

<210> SEQ ID NO 293
<211> LENGTH: 127
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 293

Glu Val Gln Leu Val Glu Ser Gly Gly Gly Val Val Gln Pro Gly Gly
1               5                   10                  15

Ser Leu Arg Leu Ser Cys Glu Ala Ser Gly Phe Ile Phe Asp Asp Tyr
                20                  25                  30

Ala Met His Trp Val Arg Gln Ala Pro Gly Lys Gly Leu Glu Trp Val
            35                  40                  45

Ser Leu Ile Ser Gly Asp Gly Asp Ile Ile Tyr Tyr Ala Asp Ser Val
        50                  55                  60

Lys Gly Arg Phe Thr Ile Ser Arg Asp Asn Ser Lys Asn Ser Leu Tyr
65                  70                  75                  80

Leu Gln Met Asn Ser Leu Ile Ile Glu Asp Thr Ala Leu Tyr Tyr Cys
                85                  90                  95

Ala Lys Asp Trp Val Phe Gly Val Val Met Thr His Tyr Trp Tyr Phe
                100                 105                 110

Gly Leu Asp Val Trp Gly Gln Gly Thr Thr Val Thr Val Ser Ser
            115                 120                 125

<210> SEQ ID NO 294
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 294

Asp Ile Gln Met Thr Gln Ser Pro Ser Ser Leu Ser Ala Ser Glu Gly
1               5                   10                  15

Asp Arg Val Thr Ile Thr Cys Arg Ala Ser Gln Ser Ile Ser Thr Tyr
                20                  25                  30

Leu Asn Trp Tyr Gln Gln Lys Pro Gly Lys Ala Pro Lys Leu Leu Ile
            35                  40                  45

Tyr Gly Ala Ser Ser Leu Gln Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Pro
                85                  90                  95

Ile Thr Phe Gly Gln Gly Thr Lys Val Glu Ile Lys
                100                 105

<210> SEQ ID NO 295
<211> LENGTH: 5
<212> TYPE: PRT
<213> ORGANISM: Artificial Sequence
<220> FEATURE:

```
<223> OTHER INFORMATION: Description of Artificial Sequence: Synthetic
      peptide

<400> SEQUENCE: 295

Gly Gly Gly Gly Ser
1               5

<210> SEQ ID NO 296
<211> LENGTH: 69
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 296

Thr Thr Thr Pro Ala Pro Arg Pro Pro Thr Pro Ala Pro Thr Ile Ala
1               5                   10                  15

Ser Gln Pro Leu Ser Leu Arg Pro Glu Ala Cys Arg Pro Ala Ala Gly
                20                  25                  30

Gly Ala Val His Thr Arg Gly Leu Asp Phe Ala Cys Asp Ile Tyr Ile
            35                  40                  45

Trp Ala Pro Leu Ala Gly Thr Cys Gly Val Leu Leu Leu Ser Leu Val
        50                  55                  60

Ile Thr Leu Tyr Cys
65

<210> SEQ ID NO 297
<211> LENGTH: 42
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 297

Lys Arg Gly Arg Lys Lys Leu Leu Tyr Ile Phe Lys Gln Pro Phe Met
1               5                   10                  15

Arg Pro Val Gln Thr Thr Gln Glu Glu Asp Gly Cys Ser Cys Arg Phe
                20                  25                  30

Pro Glu Glu Glu Glu Gly Gly Cys Glu Leu
            35                  40

<210> SEQ ID NO 298
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 298

Arg Val Lys Phe Ser Arg Ser Ala Asp Ala Pro Ala Tyr Gln Gln Gly
1               5                   10                  15

Gln Asn Gln Leu Tyr Asn Glu Leu Asn Leu Gly Arg Arg Glu Glu Tyr
                20                  25                  30

Asp Val Leu Asp Lys Arg Arg Gly Arg Asp Pro Glu Met Gly Gly Lys
            35                  40                  45

Pro Arg Arg Lys Asn Pro Gln Glu Gly Leu Tyr Asn Glu Leu Gln Lys
        50                  55                  60

Asp Lys Met Ala Glu Ala Tyr Ser Glu Ile Gly Met Lys Gly Glu Arg
65                  70                  75                  80
```

-continued

```
Arg Arg Gly Lys Gly His Asp Gly Leu Tyr Gln Gly Leu Ser Thr Ala
            85                  90                  95

Thr Lys Asp Thr Tyr Asp Ala Leu His Met Gln Ala Leu Pro Pro Arg
            100                 105                 110

<210> SEQ ID NO 299
<211> LENGTH: 41
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 299

Arg Ser Lys Arg Ser Arg Leu Leu His Ser Asp Tyr Met Asn Met Thr
1               5                   10                  15

Pro Arg Arg Pro Gly Pro Thr Arg Lys His Tyr Gln Pro Tyr Ala Pro
            20                  25                  30

Pro Arg Asp Phe Ala Ala Tyr Arg Ser
            35                  40

<210> SEQ ID NO 300
<211> LENGTH: 261
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 300

Gly Ser Gly Ala Thr Asn Phe Ser Leu Leu Lys Gln Ala Gly Asp Val
1               5                   10                  15

Glu Glu Asn Pro Gly Pro Met Val Ser Lys Gly Glu Glu Leu Phe Thr
            20                  25                  30

Gly Val Val Pro Ile Leu Val Glu Leu Asp Gly Asp Val Asn Gly His
            35                  40                  45

Lys Phe Ser Val Ser Gly Glu Gly Glu Gly Asp Ala Thr Tyr Gly Lys
    50                  55                  60

Leu Thr Leu Lys Phe Ile Cys Thr Thr Gly Lys Leu Pro Val Pro Trp
65                  70                  75                  80

Pro Thr Leu Val Thr Thr Leu Thr Tyr Gly Val Gln Cys Phe Ser Arg
            85                  90                  95

Tyr Pro Asp His Met Lys Gln His Asp Phe Phe Lys Ser Ala Met Pro
            100                 105                 110

Glu Gly Tyr Val Gln Glu Arg Thr Ile Phe Phe Lys Asp Asp Gly Asn
            115                 120                 125

Tyr Lys Thr Arg Ala Glu Val Lys Phe Glu Gly Asp Thr Leu Val Asn
    130                 135                 140

Arg Ile Glu Leu Lys Gly Ile Asp Phe Lys Glu Asp Gly Asn Ile Leu
145                 150                 155                 160

Gly His Lys Leu Glu Tyr Asn Tyr Asn Ser His Asn Val Tyr Ile Met
            165                 170                 175

Ala Asp Lys Gln Lys Asn Gly Ile Lys Val Asn Phe Lys Ile Arg His
            180                 185                 190

Asn Ile Glu Asp Gly Ser Val Gln Leu Ala Asp His Tyr Gln Gln Asn
            195                 200                 205

Thr Pro Ile Gly Asp Gly Pro Val Leu Leu Pro Asp Asn His Tyr Leu
    210                 215                 220
```

-continued

```
Ser Thr Gln Ser Ala Leu Ser Lys Asp Pro Asn Glu Lys Arg Asp His
225                 230                 235                 240

Met Val Leu Leu Glu Phe Val Thr Ala Ala Gly Ile Thr Leu Gly Met
                245                 250                 255

Asp Glu Leu Tyr Lys
            260

<210> SEQ ID NO 301
<211> LENGTH: 739
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 301

Glu Val Gln Leu Val Glu Ser Gly Gly Gly Val Val Gln Pro Gly Gly
1               5                   10                  15

Ser Leu Arg Leu Ser Cys Glu Ala Ser Gly Phe Ile Phe Asp Asp Tyr
            20                  25                  30

Ala Met His Trp Val Arg Gln Ala Pro Gly Lys Gly Leu Glu Trp Val
        35                  40                  45

Ser Leu Ile Ser Gly Asp Gly Asp Ile Ile Tyr Tyr Ala Asp Ser Val
    50                  55                  60

Lys Gly Arg Phe Thr Ile Ser Arg Asp Asn Ser Lys Asn Ser Leu Tyr
65                  70                  75                  80

Leu Gln Met Asn Ser Leu Ile Ile Glu Asp Thr Ala Leu Tyr Tyr Cys
                85                  90                  95

Ala Lys Asp Trp Val Phe Gly Val Val Met Thr His Tyr Trp Tyr Phe
            100                 105                 110

Gly Leu Asp Val Trp Gly Gln Gly Thr Thr Val Thr Val Ser Ser Gly
        115                 120                 125

Gly Gly Gly Ser Gly Gly Gly Gly Ser Gly Gly Gly Gly Ser Asp Ile
        130                 135                 140

Gln Met Thr Gln Ser Pro Ser Ser Leu Ser Ala Ser Glu Gly Asp Arg
145                 150                 155                 160

Val Thr Ile Thr Cys Arg Ala Ser Gln Ser Ile Ser Thr Tyr Leu Asn
                165                 170                 175

Trp Tyr Gln Gln Lys Pro Gly Lys Ala Pro Lys Leu Leu Ile Tyr Gly
            180                 185                 190

Ala Ser Ser Leu Gln Ser Gly Val Pro Ser Arg Phe Ser Gly Ser Gly
        195                 200                 205

Ser Gly Thr Asp Phe Thr Leu Thr Ile Ser Ser Leu Gln Pro Glu Asp
    210                 215                 220

Phe Ala Thr Tyr Tyr Cys Gln Gln Ser Tyr Ser Thr Pro Pro Ile Thr
225                 230                 235                 240

Phe Gly Gln Gly Thr Lys Val Glu Ile Lys Gly Gly Gly Gly Ser Thr
                245                 250                 255

Thr Thr Pro Ala Pro Arg Pro Pro Thr Pro Ala Pro Thr Ile Ala Ser
            260                 265                 270

Gln Pro Leu Ser Leu Arg Pro Glu Ala Cys Arg Pro Ala Ala Gly Gly
            275                 280                 285

Ala Val His Thr Arg Gly Leu Asp Phe Ala Cys Asp Ile Tyr Ile Trp
    290                 295                 300

Ala Pro Leu Ala Gly Thr Cys Gly Val Leu Leu Leu Ser Leu Val Ile
```

-continued

```
305              310              315              320

Thr Leu Tyr Cys Lys Arg Gly Arg Lys Lys Leu Leu Tyr Ile Phe Lys
                325              330              335

Gln Pro Phe Met Arg Pro Val Gln Thr Thr Gln Glu Glu Asp Gly Cys
                340              345              350

Ser Cys Arg Phe Pro Glu Glu Glu Glu Gly Gly Cys Glu Leu Arg Val
                355              360              365

Lys Phe Ser Arg Ser Ala Asp Ala Pro Ala Tyr Gln Gln Gly Gln Asn
        370              375              380

Gln Leu Tyr Asn Glu Leu Asn Leu Gly Arg Arg Glu Glu Tyr Asp Val
385              390              395              400

Leu Asp Lys Arg Arg Gly Arg Asp Pro Glu Met Gly Gly Lys Pro Arg
                405              410              415

Arg Lys Asn Pro Gln Glu Gly Leu Tyr Asn Glu Leu Gln Lys Asp Lys
                420              425              430

Met Ala Glu Ala Tyr Ser Glu Ile Gly Met Lys Gly Glu Arg Arg Arg
                435              440              445

Gly Lys Gly His Asp Gly Leu Tyr Gln Gly Leu Ser Thr Ala Thr Lys
        450              455              460

Asp Thr Tyr Asp Ala Leu His Met Gln Ala Leu Pro Pro Arg Gly Ser
465              470              475              480

Gly Ala Thr Asn Phe Ser Leu Leu Lys Gln Ala Gly Asp Val Glu Glu
                485              490              495

Asn Pro Gly Pro Met Val Ser Lys Gly Glu Glu Leu Phe Thr Gly Val
                500              505              510

Val Pro Ile Leu Val Glu Leu Asp Gly Asp Val Asn Gly His Lys Phe
                515              520              525

Ser Val Ser Gly Glu Gly Glu Gly Asp Ala Thr Tyr Gly Lys Leu Thr
        530              535              540

Leu Lys Phe Ile Cys Thr Thr Gly Lys Leu Pro Val Pro Trp Pro Thr
545              550              555              560

Leu Val Thr Thr Leu Thr Tyr Gly Val Gln Cys Phe Ser Arg Tyr Pro
                565              570              575

Asp His Met Lys Gln His Asp Phe Phe Lys Ser Ala Met Pro Glu Gly
                580              585              590

Tyr Val Gln Glu Arg Thr Ile Phe Phe Lys Asp Asp Gly Asn Tyr Lys
                595              600              605

Thr Arg Ala Glu Val Lys Phe Glu Gly Asp Thr Leu Val Asn Arg Ile
        610              615              620

Glu Leu Lys Gly Ile Asp Phe Lys Glu Asp Gly Asn Ile Leu Gly His
625              630              635              640

Lys Leu Glu Tyr Asn Tyr Asn Ser His Asn Val Tyr Ile Met Ala Asp
                645              650              655

Lys Gln Lys Asn Gly Ile Lys Val Asn Phe Lys Ile Arg His Asn Ile
        660              665              670

Glu Asp Gly Ser Val Gln Leu Ala Asp His Tyr Gln Gln Asn Thr Pro
        675              680              685

Ile Gly Asp Gly Pro Val Leu Leu Pro Asp Asn His Tyr Leu Ser Thr
        690              695              700

Gln Ser Ala Leu Ser Lys Asp Pro Asn Glu Lys Arg Asp His Met Val
705              710              715              720

Leu Leu Glu Phe Val Thr Ala Ala Gly Ile Thr Leu Gly Met Asp Glu
                725              730              735
```

Leu Tyr Lys

<210> SEQ ID NO 302
<211> LENGTH: 735
<212> TYPE: PRT
<213> ORGANISM: Artificial Sequence
<220> FEATURE:
<223> OTHER INFORMATION: Description of Artificial Sequence: Synthetic
     polypeptide

<400> SEQUENCE: 302

Glu Val Gln Leu Val Glu Ser Gly Gly Gly Val Val Gln Pro Gly Gly
1               5                   10                  15

Ser Leu Arg Leu Ser Cys Glu Ala Ser Gly Phe Ile Phe Asp Asp Tyr
            20                  25                  30

Ala Met His Trp Val Arg Gln Ala Pro Gly Lys Gly Leu Glu Trp Val
        35                  40                  45

Ser Leu Ile Ser Gly Asp Gly Asp Ile Ile Tyr Tyr Ala Asp Ser Val
    50                  55                  60

Lys Gly Arg Phe Thr Ile Ser Arg Asp Asn Ser Lys Asn Ser Leu Tyr
65                  70                  75                  80

Leu Gln Met Asn Ser Leu Ile Ile Glu Asp Thr Ala Leu Tyr Tyr Cys
                85                  90                  95

Ala Lys Asp Trp Val Phe Gly Val Val Met Thr His Tyr Trp Tyr Phe
            100                 105                 110

Gly Leu Asp Val Trp Gly Gln Gly Thr Thr Val Thr Val Ser Ser Gly
            115                 120                 125

Gly Gly Gly Ser Gly Gly Gly Gly Ser Gly Gly Gly Gly Ser Asp Ile
    130                 135                 140

Gln Met Thr Gln Ser Pro Ser Ser Leu Ser Ala Ser Glu Gly Asp Arg
145                 150                 155                 160

Val Thr Ile Thr Cys Arg Ala Ser Gln Ser Ile Ser Thr Tyr Leu Asn
                165                 170                 175

Trp Tyr Gln Gln Lys Pro Gly Lys Ala Pro Lys Leu Leu Ile Tyr Gly
            180                 185                 190

Ala Ser Ser Leu Gln Ser Gly Val Pro Ser Arg Phe Ser Gly Ser Gly
            195                 200                 205

Ser Gly Thr Asp Phe Thr Leu Thr Ile Ser Ser Leu Gln Pro Glu Asp
    210                 215                 220

Phe Ala Thr Tyr Tyr Cys Gln Gln Ser Tyr Ser Thr Pro Pro Ile Thr
225                 230                 235                 240

Phe Gly Gln Gly Thr Lys Val Glu Ile Lys Gly Gly Gly Gly Ser Ile
            245                 250                 255

Glu Val Met Tyr Pro Pro Pro Tyr Leu Asp Asn Glu Lys Ser Asn Gly
            260                 265                 270

Thr Ile Ile His Val Lys Gly Lys His Leu Cys Pro Ser Pro Leu Phe
            275                 280                 285

Pro Gly Pro Ser Lys Pro Phe Trp Val Leu Val Val Val Gly Gly Val
    290                 295                 300

Leu Ala Cys Tyr Ser Leu Leu Val Thr Val Ala Phe Ile Ile Phe Trp
305                 310                 315                 320

Val Arg Ser Lys Arg Ser Arg Leu Leu His Ser Asp Tyr Met Asn Met
            325                 330                 335

Thr Pro Arg Arg Pro Gly Pro Thr Arg Lys His Tyr Gln Pro Tyr Ala
            340                 345                 350

-continued

```
Pro Pro Arg Asp Phe Ala Ala Tyr Arg Ser Arg Val Lys Phe Ser Arg
        355                 360                 365

Ser Ala Asp Ala Pro Ala Tyr Gln Gln Gly Gln Asn Gln Leu Tyr Asn
        370                 375                 380

Glu Leu Asn Leu Gly Arg Arg Glu Glu Tyr Asp Val Leu Asp Lys Arg
385                 390                 395                 400

Arg Gly Arg Asp Pro Glu Met Gly Gly Lys Pro Arg Arg Lys Asn Pro
                405                 410                 415

Gln Glu Gly Leu Tyr Asn Glu Leu Gln Lys Asp Lys Met Ala Glu Ala
                420                 425                 430

Tyr Ser Glu Ile Gly Met Lys Gly Glu Arg Arg Arg Gly Lys Gly His
        435                 440                 445

Asp Gly Leu Tyr Gln Gly Leu Ser Thr Ala Thr Lys Asp Thr Tyr Asp
        450                 455                 460

Ala Leu His Met Gln Ala Leu Pro Pro Arg Gly Ser Gly Ala Thr Asn
465                 470                 475                 480

Phe Ser Leu Leu Lys Gln Ala Gly Asp Val Glu Glu Asn Pro Gly Pro
                485                 490                 495

Met Val Ser Lys Gly Glu Glu Leu Phe Thr Gly Val Val Pro Ile Leu
                500                 505                 510

Val Glu Leu Asp Gly Asp Val Asn Gly His Lys Phe Ser Val Ser Gly
        515                 520                 525

Glu Gly Glu Gly Asp Ala Thr Tyr Gly Lys Leu Thr Leu Lys Phe Ile
        530                 535                 540

Cys Thr Thr Gly Lys Leu Pro Val Pro Trp Pro Thr Leu Val Thr Thr
545                 550                 555                 560

Leu Thr Tyr Gly Val Gln Cys Phe Ser Arg Tyr Pro Asp His Met Lys
                565                 570                 575

Gln His Asp Phe Phe Lys Ser Ala Met Pro Glu Gly Tyr Val Gln Glu
                580                 585                 590

Arg Thr Ile Phe Phe Lys Asp Asp Gly Asn Tyr Lys Thr Arg Ala Glu
        595                 600                 605

Val Lys Phe Glu Gly Asp Thr Leu Val Asn Arg Ile Glu Leu Lys Gly
        610                 615                 620

Ile Asp Phe Lys Glu Asp Gly Asn Ile Leu Gly His Lys Leu Glu Tyr
625                 630                 635                 640

Asn Tyr Asn Ser His Asn Val Tyr Ile Met Ala Asp Lys Gln Lys Asn
                645                 650                 655

Gly Ile Lys Val Asn Phe Lys Ile Arg His Asn Ile Glu Asp Gly Ser
                660                 665                 670

Val Gln Leu Ala Asp His Tyr Gln Gln Asn Thr Pro Ile Gly Asp Gly
        675                 680                 685

Pro Val Leu Leu Pro Asp Asn His Tyr Leu Ser Thr Gln Ser Ala Leu
        690                 695                 700

Ser Lys Asp Pro Asn Glu Lys Arg Asp His Met Val Leu Leu Glu Phe
705                 710                 715                 720

Val Thr Ala Ala Gly Ile Thr Leu Gly Met Asp Glu Leu Tyr Lys
                725                 730                 735
```

```
<210> SEQ ID NO 303
<211> LENGTH: 15
<212> TYPE: PRT
<213> ORGANISM: Artificial Sequence
<220> FEATURE:
```

```
<223> OTHER INFORMATION: Description of Artificial Sequence: Synthetic
      peptide

<400> SEQUENCE: 303

Gly Gly Gly Gly Ser Gly Gly Gly Gly Ser Gly Gly Gly Gly Ser
1               5                   10                  15

<210> SEQ ID NO 304
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 304

Phe Trp Val Leu Val Val Val Gly Gly Val Leu Ala Cys Tyr Ser Leu
1               5                   10                  15

Leu Val Thr Val Ala Phe Ile Ile Phe Trp Val
            20                  25

<210> SEQ ID NO 305
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 305

Ile Glu Val Met Tyr Pro Pro Pro Tyr Leu Asp Asn Glu Lys Ser Asn
1               5                   10                  15

Gly Thr Ile Ile His Val Lys Gly Lys His Leu Cys Pro Ser Pro Leu
            20                  25                  30

Phe Pro Gly Pro Ser Lys Pro
            35
```